US011034931B2

(12) United States Patent
Solodovnikova et al.

(10) Patent No.: US 11,034,931 B2
(45) Date of Patent: Jun. 15, 2021

(54) YEAST FOR PREPARING ALCOHOLIC BEVERAGES

(71) Applicant: Carlsberg Breweries A/S, Copenhagen V (DK)

(72) Inventors: Natalia Y. Solodovnikova, Copenhagen NV (DK); Jeppe Frank Andersen, Kgs. Lyngby (DK); Rosa Garcia Sanchez, Malmö (SE); Zoran Gojkovic, Holte (DK)

(73) Assignee: Carlsberg Breweries A/S, Copenhagen V (DK)

( * ) Notice: Subject to any disclaimer, the term of this patent is extended or adjusted under 35 U.S.C. 154(b) by 643 days.

(21) Appl. No.: 15/537,031

(22) PCT Filed: Dec. 22, 2015

(86) PCT No.: PCT/DK2015/050413
§ 371 (c)(1),
(2) Date: Jun. 16, 2017

(87) PCT Pub. No.: WO2016/101960
PCT Pub. Date: Jun. 30, 2016

(65) Prior Publication Data
US 2018/0163168 A1 Jun. 14, 2018

(30) Foreign Application Priority Data

Dec. 23, 2014 (DK) .......................... PA 2014 70825
Jun. 8, 2015 (DK) .......................... PA 2015 70351

(51) Int. Cl.
*C12N 1/16* (2006.01)
*C12N 1/19* (2006.01)
*C12N 9/44* (2006.01)
*C12N 1/18* (2006.01)
*C12C 11/02* (2006.01)
*C12N 15/01* (2006.01)
*C12N 15/04* (2006.01)
*C07K 14/395* (2006.01)
*A61K 38/00* (2006.01)

(52) U.S. Cl.
CPC .............. *C12N 1/18* (2013.01); *C07K 14/395* (2013.01); *C12C 11/02* (2013.01); *C12N 9/2451* (2013.01); *C12N 15/01* (2013.01); *C12N 15/04* (2013.01); *C12Y 302/0101* (2013.01); *C12C 2200/05* (2013.01)

(58) Field of Classification Search
CPC ........................ C12N 9/2451; C12C 11/02
See application file for complete search history.

(56) References Cited

U.S. PATENT DOCUMENTS

| 6,433,154 B1* | 8/2002 | Ostrander | B01J 2/006 435/235.1 |
| 2011/0091598 A1* | 4/2011 | Hsu | A23G 4/10 426/3 |
| 2014/0004526 A1* | 1/2014 | Dauner | C12Y 401/02009 435/6.13 |
| 2017/0073754 A1* | 3/2017 | He | C07K 16/18 |

FOREIGN PATENT DOCUMENTS

| WO | WO 2005/121337 A1 | 12/2005 |
| WO | WO 2012/177854 A2 | 12/2012 |
| WO | WO 2015/195934 A2 | 12/2015 |
| WO | WO 2017/106739 A1 | 6/2017 |

OTHER PUBLICATIONS

Teste et al. (2010) Characterization of a New Multigene Family Encoding Isomaltases in the Yeast Saccharomyces cerevisiae, the IMA Family*, J. Biol. Chem., vol. 285, p. 26815-26824.*
Reference "YMDB02304" (2019 updated) "Isomaltose (YMDB02304)", pp. 1-10.*
Pan et al. (2005) Production of high-purity isomalto-oligosaccharides syrup by the enzymatic conversion of transglucosidase and fermentation of yeast cells, Biotechnol. Bioeng., vol. 89, issue 7, pp. 797-804.*
Homann et al. (2005) Harnessing Natural Diversity to Probe Metabolic Pathways, PLos Genetics, vol. 1, issue 6, pp. 715-729.*
Rai et al (1988) Structure and Transcription of the Allantoate Permease Gene (DAL5) from Saccharomyces cerevisiae, J. Bacteriol., vol. 170, pp. 266-271.*
Damon et al. (2011) A novel fungal family of oligopeptide transporters identified by functional metatranscriptomics of soil eukaryotes, ISME J., vol. 5, pp. 1871-1880.*
Bartel et al. (1990) The recognition component of the N-end rule pathway, EMBO J., vol. 9, pp. 3179-3189.*
Han et al. (1995) Characterization of AGT1 encoding a general alpha-glucoside transporter from Saccharomyces, Mol. Microbiol., vol. 17, pp. 1093-1107.*
Galibert et al. (1996) Complete nucleotide sequence of Saccharomyces cerevisiae chromosome X, EMBO J., vol. 15, pp. 2031-2049.*
PubChem (2020, updated) Melibiose, pp. 1-4.*
Ito, K. et al., "Effect of Soy Peptides on the Recombinant Protein Production in Yeast," Soy Protein Research 15(33): 156-159 (2012).
Mukai, N. et al., "Comparison of the Brewing Properties of Beer Yeasts and Other Yeats Used in Alcohol Beverage Production," J. Brew. Soc. Japan, 93(12): 967-975 (1998).

(Continued)

*Primary Examiner* — Manjunath N Rao
*Assistant Examiner* — Samuel W Liu
(74) *Attorney, Agent, or Firm* — McNeill Baur PLLC

(57) ABSTRACT

The invention relates to yeast cells with useful characteristics, including being capable of utilizing panose as sole carbon source and/or capable of utilizing one or more dipeptidesas sole nitrogen source. The invention also relates to yeast cells with useful genotypes including comprising at least 4 allelic genes encoding IMA1p and/or at least two allelic genes encoding IMA5p.

17 Claims, 21 Drawing Sheets

Specification includes a Sequence Listing.

(56) References Cited

OTHER PUBLICATIONS

Third Party Observation filed at the Japanese Patent Office for Application No. 2017-533846 on Jan. 19, 2018 (2 pages), with English translation (3 pages).
Baert, J.J. et al., "On the Origin of Free and Bound Staling Aldehydes in Beer", J. of Agric. Food Chem., 2012, 60, p. 11449-11472.
Deng, X. et al., "Similarities and differences in the biochemical and enzymological properties of the four isomaltases from *Saccharomyces cerevisiae*", FEBS Open Bio 4, 2014, p. 200-212.
Hahn-Hägerdal, B. et al., "Role of cultivation media in the development of yeast strains for large scale industrial use", Microbial Cell Factories, BioMed Central, 2005, p. 1-16.
Lekkas, C. et al., "The Role of Small Wort Peptides in Brewing Fermentations", Journ. of the Institute of Brewing, vol. 115, No. 2, 2009, p. 134-139.
Annaluru, N. et al., "Total synthesis of a Functional Designer Eukaryotic Chomosome", Science, vol. 344, No. 6179, Apr. 4, 2014, p. 55-58.
Clapperton et al., "Fermentation of Minor Wort Carbohydrates by Brewing Yeasts", Journ. of the Institute of Brewing, vol. 77, No. 6, Nov. 12, 1971, p. 519-522.
Cosseau et al., "Characterization of maltotriose transporters from the *Saccharomyces eubayanus* subgenome of the hybrid *Saccharomyces pastorianus* lager brewing yeast strain Weihenstephan 34/70", Letters in Applied Microbiology, vol. 56, No. 1, Nov. 21, 2012, p. 21-29.
Han, E.K. et al., "Characterization of AGT1 encoding a general alpha-glucoside transporter from *Saccharomyces*", Molecular Microbiology, vol. 17, No. 6, Sep. 1, 1995 p. 1093-1107.
Hebly, Marit et al., "*S. cerevisiae*× *S. eubayanus* interspecific hybrid, the best of both worlds and beyond", Fems Yeast Research, vol. 15, No. 3, Mar. 5, 2015, p.
Krogerus et al., "New lager yeast strains generated by interspecific hybridization", Journ. of Industrial Microbiology and Biotechnology, vol. 42, No. 5, May 15, 2015, p. 769-778.
Naumov et al., "Molecular genetic differentiation of yeast alpha-glucosidases: Maltase and isomaltase", Microbiology, vol. 81, No. 3, Jun. 5, 2012, p. 276-280.
Saerens et al., "Genetic improvement of brewer's yeast: current state, perspectives and limits", Applied Microbiology and biotechnology, vol. 86, No. 5, Feb. 2, 2010, p. 1195-1212.
Sanchez et al.,"Breeding of lager yeast with *Saccharomyces cerevisiae* improves stress resistance and fermentation performance", Yeast, vol. 29, No. 8, Aug. 7, 2012, p. 343-355.
Stewart, G.G. et al.,"125th Anniversary Review: Developments in brewing and distilling yeast strains", Journ. of the Institute of Brewing, vol. 119, No. 4, Nov. 13, 2013, p. 202-220.
Teste et al., "Characterization of a New Multigene Family Encoding Isomaltases in the Yeasst *Saccharomyces cerevisiae*, the IMA Family" Journ. of Biological Chemistry, vol. 285, No. 35, Jun. 18, 2010, p. 26815-26824.
Voordeckers et al., "Reconstruction of Ancestral Metabolic Enzymes Reveals Molecurlar Mechanisms Underlying Evolutionary Innovation through Gene Duplication", Plos Biology, vol. 10, No. 12, Dec. 11, 2012, p. 1-17.
Hiraoka et al., "Inner nuclear membrane protein Ima1 is dispensable for intranuclear positioning of centromeres", Genes to Cells, vol. 16, No. 10, p. 1000-1011.
Nakao et al.,"Genome sequence of the lager brewing yeast, an interspecies hybrid", DNA Research, vol. 16, No. 2, Mar. 4, 2009, p. 115-129.
H. Cai et al., "Differential Regulation and Substrate Preference in Two Peptide Transporters of *Saccharomyces cerevisiae*," Eukaryotic Cell, 6(10): 1805-1813 (2007).

\* cited by examiner

A)
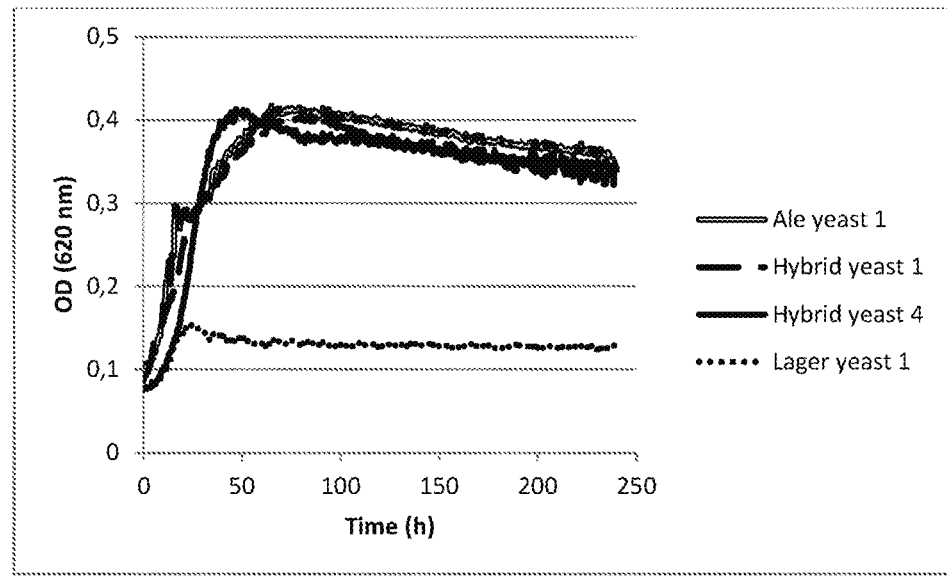
B)
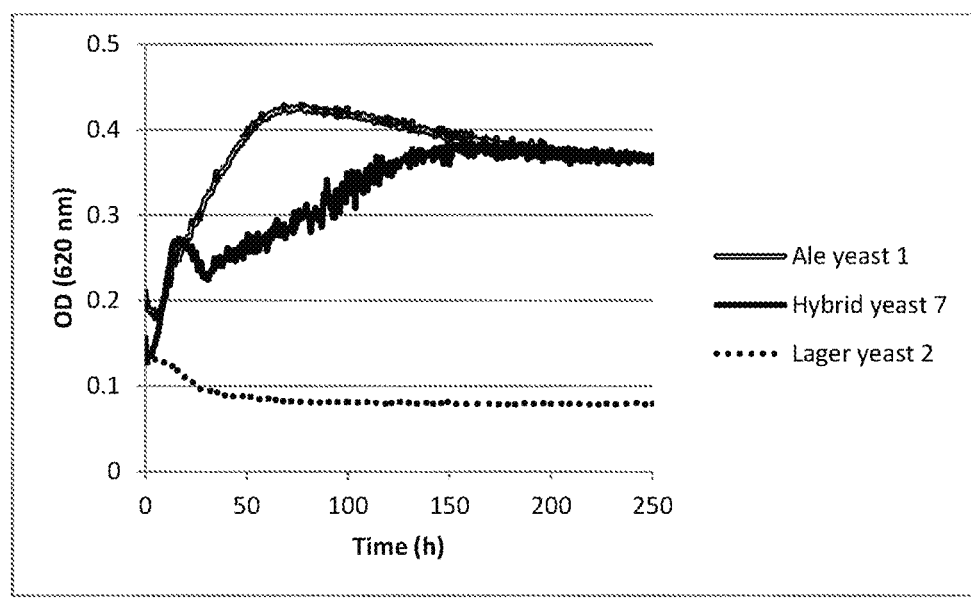
Fig. 1

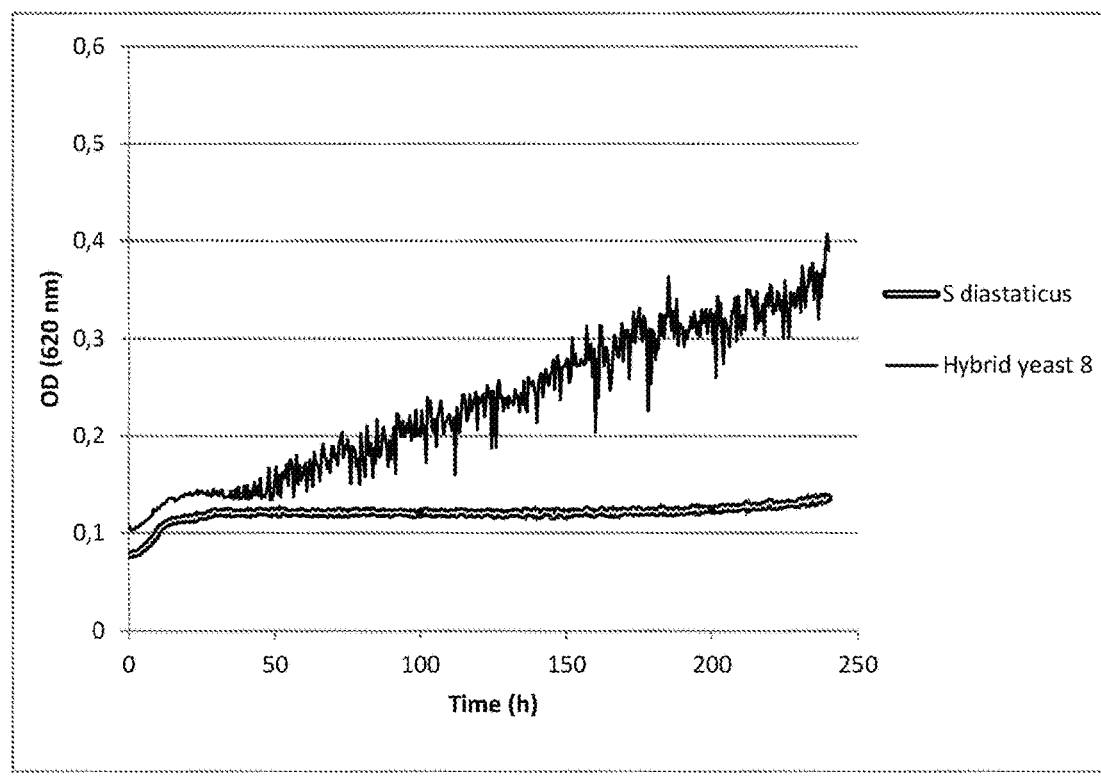
Fig. 1 - continued

A)
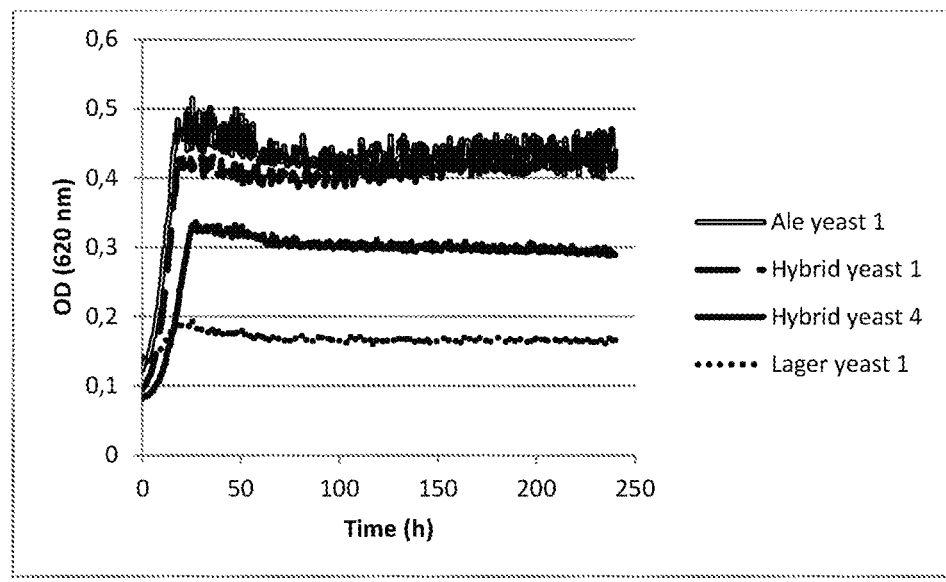
B)
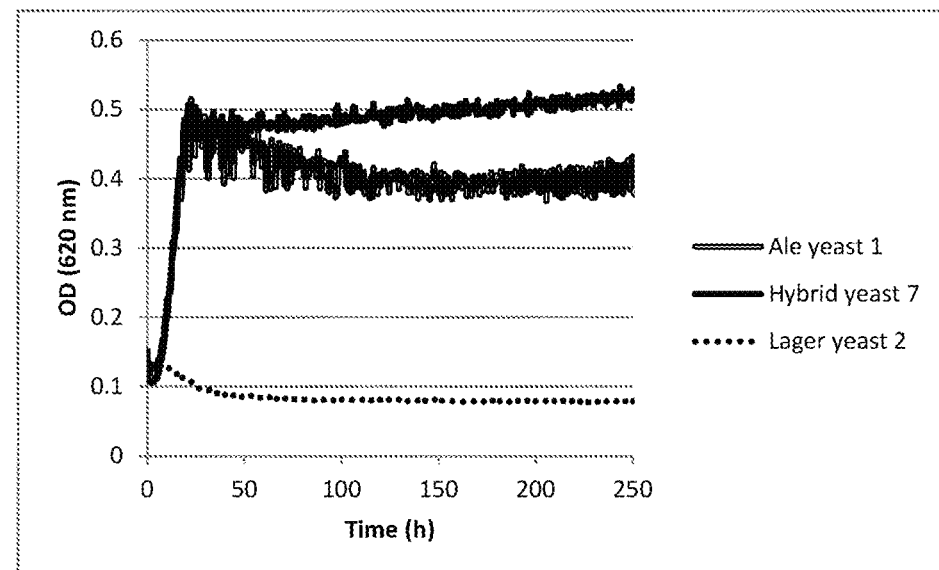
Fig. 2

C)
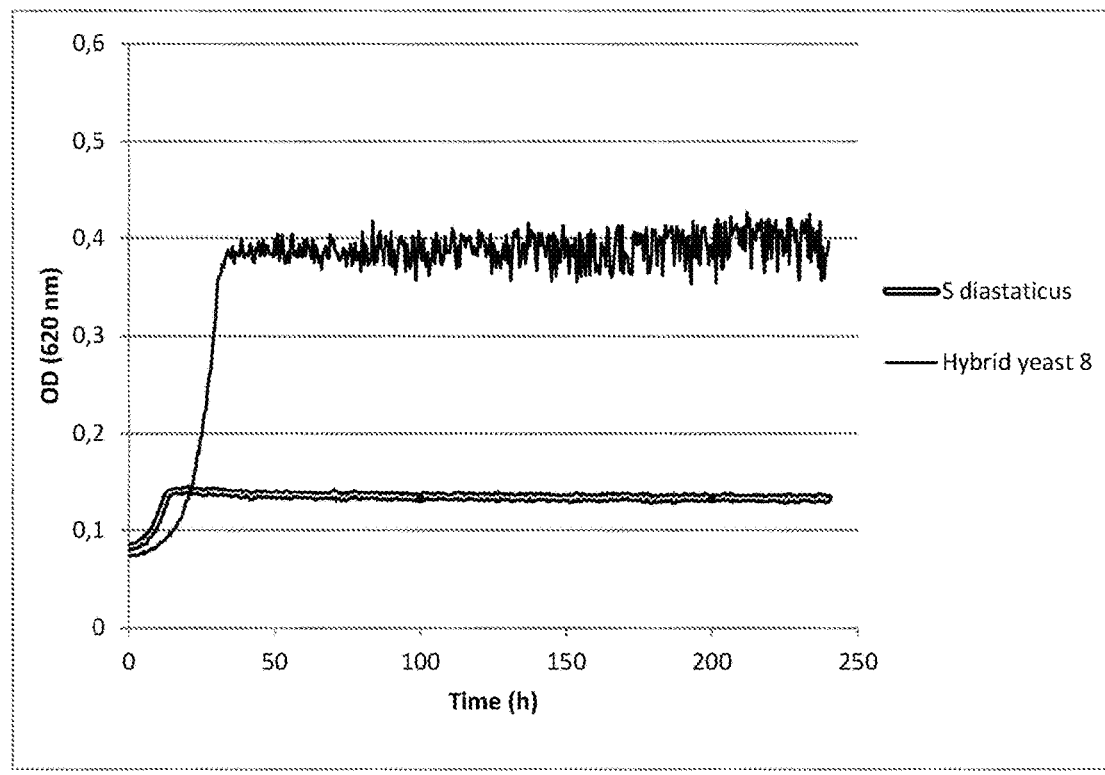
Figure 2 - continued

A)
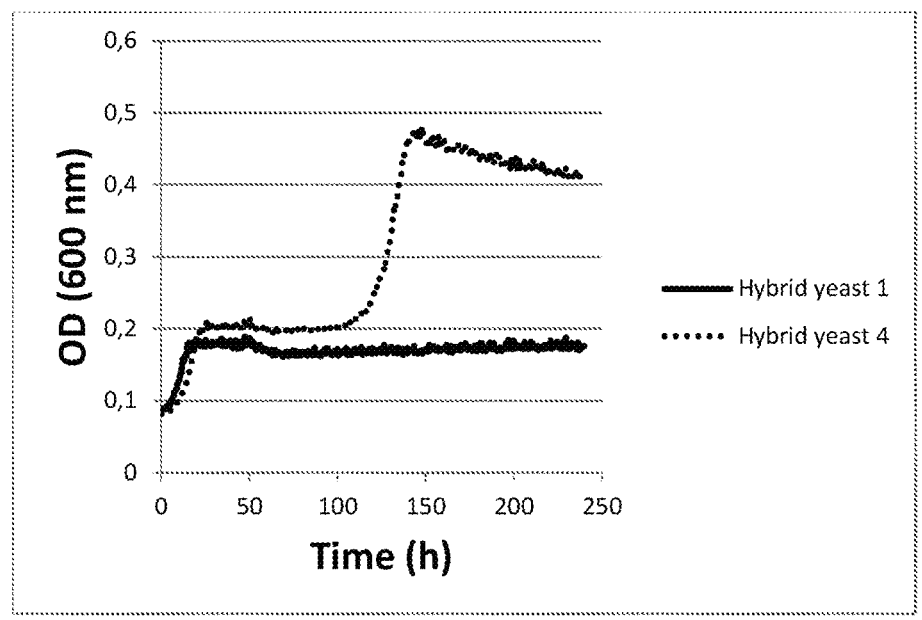
B)
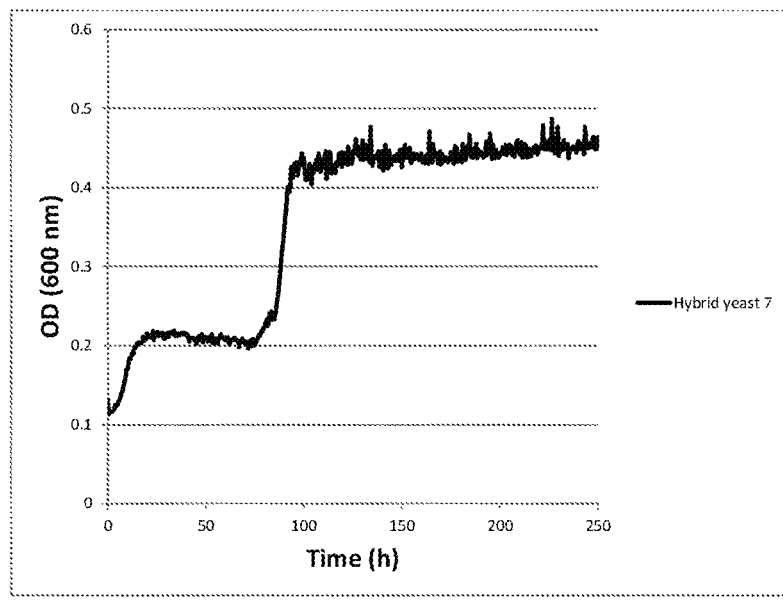
Fig. 3

| | | |
|---|---|---|
| ScDAL5_Ale_1 | MSADASTNSNASLDEKNLNI TSEAEI KNEDVTAEPVLSTVLSPNGKI VYI SDKVDEAMKLAEEAKEI EVTPEEDRKLRWK | 80 |
| nonSc_DAL5_Lager_1 | MSGGASTNSNASLDEKNLNI TSEAEI KNEDVYAEPVLSTVLSPNGKMVYI SDKVDEAMKLAEEAKEI EVTPEEDRKLRWK | 80 |
| Sc_DAL5_Hybrid_1 | MSADASTNSNASLDEKNLNI TSEAEI KNEDVTAEPVLSTVLSPNGKI VYI SDKVDEAMKLAEEAKEI EVTPEEDRKLRWK | 80 |
| ScDAL5_Ale_1 | IDYCMFPLMCI LYAVQFMDKI STSSAAVMGLRTDLKMHGDQYSWTSAFYFGYLFMNLGPVQFI FQRTSHMSKMLAVFI V | 160 |
| nonSc_DAL5_Lager_1 | IDYCMFPLMCI LYAVQFMDKI STSSAAVMGLRTDLKMHGDQYSWTSAFYFGYLFMNLGPVQLI FQKSKHMSKMLALFI L | 160 |
| Sc_DAL5_Hybrid_1 | IDYCMFPLMCI LYAVQFMDKI STSSAAVMGLRTDLKMHGDQYSWTSAFYFGYLFMNLGPVQFI FQRTSHMSKMLAVFI V | 160 |
| ScDAL5_Ale_1 | IWGMLLALHAAPTVKYPSFI VLRVLLGCAESVVTPCFTI I TAQYWKTEEQFTRVSI WFGMNGLGSI LI NAI AYGVYI HQD | 240 |
| nonSc_DAL5_Lager_1 | VWGLLLALHAYPSVKYSSFI ALRVLLGCAESVVTPCFTI I TAQYWKTEEQFTRLSI WFGMNGLGSI LI NAI AYGVYI HQE | 240 |
| Sc_DAL5_Hybrid_1 | IWGMLLALHAAPTVKYPSFI VLRVLLGCAESVVTPCFTI I TAQYWKTEEQFTRVSI WFGMNGLGSI LI NAI AYGVYI HQD | 240 |
| ScDAL5_Ale_1 | SYAI KGWRTLFVI TGVI TI FI GI LI FLWI PDDPSKARFLSKREKLMVVQRI RSNQQGFGNHEI KKYQI I EALKDVRTWLY | 320 |
| nonSc_DAL5_Lager_1 | SYAI KGWRALFVI TGVI TI FYGALI FLWI PDDPSKARFLSKREKLMVVQRI RSNQQGFGNHEI KKYQI MEALKDVRTWLY | 320 |
| Sc_DAL5_Hybrid_1 | SYAI KGWRTLFVI TGVI TI FI GI LI FLWI PDDPSKARFLSKREKLMVVQRI RSNQQGFGNHEI KKYQI I EALKDVRTWLY | 320 |
| ScDAL5_Ale_1 | FLFTVSSNI PNGGI SSFMSI LLNSDFGYSSKETLLMGLPTGAVELVGCPLFGI LAVYAANKKI PFWKYKLSWAI FAAVLA | 400 |
| nonSc_DAL5_Lager_1 | FLFTVSSNI PNGGI SSFMSI LLNSDFGYLSKETLLMGLPTGAVELVGCPLFGI LAVYAANKKI PFWKYKLAWAI FAAVLA | 400 |
| Sc_DAL5_Hybrid_1 | FLFTVSSNI PNGGI SSFMSI LLNSDFGYSSKETLLMGLPTGAVELVGCPLFGI LAVYAANKKI PFWKYKLSWAI FAAVLA | 400 |
| ScDAL5_Ale_1 | LI ASCMLGFATNSKKARLAGAYLWYI SPVSFI CVLSNI SANSSGYSKKWTVSSI NLVAYAAANLAGPQTFI AKQAPKYHG | 480 |
| nonSc_DAL5_Lager_1 | LI ASCMLGFATSKKARLAGAYLWYI SPVSFI CVLSNI SANSSGYSKKWTVSSI NLAAYAAANLAGPQTFI AKQAPKYHG | 480 |
| Sc_DAL5_Hybrid_1 | LI ASCMLGFATNSKKARLAGAYLWYI SPVSFI CVLSNI SANSSGYSKKWTVSSI NLVAYAAANLAGPQTFI AKQAPKYHG | 480 |
| ScDAL5_Ale_1 | AKVAMVVCYAVMI VLLSI LLI VNLRENKRRDKI AAERGFPEETENLEFSDLTDFENPNFRYTL | 544 |
| nonSc_DAL5_Lager_1 | AKVAMVVCYAVMI VLLSALLLI NMRENKRRDKI AAERGYPEETANLEFSDLTDFENPNFRYTL | 544 |
| Sc_DAL5_Hybrid_1 | AKVAMVVCYAVMI VLLSI LLI VNLRENKRRDKI AAERGFPEETENLEFSDLTDFENPNFRYTL | 544 |

Fig. 5

| | | |
|---|---|---|
| Sc_UBR1_Ale_1 | FKEFCKVEGGVLIWQRVQKSNLTKSYSISFKQGLYTVETXLSKVHDPNIPLRPKEIISLLTLCKLFNGAWKIKRKEGEHV | 679 |
| Sc_UBR1_Lager_1 | FKEFCKVEGGVLIWQRVQKSNLTKSYSISFKQGLYTVETLLSKVHDPNIPLRPKEIISLLTLCKLFNGAWKIKRKEGEHV | 679 |
| Sc_UBR1_Hybrid_1 | FKEFCKVEGGVLIWQRVQKSNLTKSYSISFKQGLYTVETLLSKVHDPNIPLRPKEIISLLTLCKLFNGAWKIKRKEGEHV | 80 |
| | | |
| Sc_UBR1_Ale_1 | LHEDQNFISYLEYTTSIYSIIQTAEKVSEKSKDSIDSKLFLNAIRIISSFLGNRSLTYKLIYDSHEVIKFSVSHERVAFM | 759 |
| Sc_UBR1_Lager_1 | LHEDQNFISYLEYTTSIYSIIQTAEKVSEKSKDSIDSKLFLNAIRIISSFLGNRSLTYKLIYDSHEVIKFSVSHERVAFM | 759 |
| Sc_UBR1_Hybrid_1 | LHEDQNFISYLEYTTSIYSIIQTAEKVSEKSKDSIDSKLFLNAIRIISSFLGNRSLTYKLIYDSHEVIKFSVSHERVAFM | 160 |
| | | |
| Sc_UBR1_Ale_1 | NPLQTMLSFLIEKVSLKDAYEALEDCSDFLKISDFSLRSVVLCSQIDVGFWRNGMSVLHQASYYKNNPELGSYSRDIHL | 839 |
| Sc_UBR1_Lager_1 | NPLQTMLSFLIEKVSLKDAYEALEDCSDFLKISDFSLRSVVLCSQIDVGFWRNGMSVLHQASYYKNNPELXSYSRDIHL | 839 |
| Sc_UBR1_Hybrid_1 | NPLQTMLSFLIEKVSLKDAYEALEDCSDFLKISDFSLRSVVLCSQIDVGFWRNGMSVLHQASYYKNNPELGSYSRDIHL | 240 |
| | | |
| Sc_UBR1_Ale_1 | NQLAILWERDDIPRIIYNILDRWELLDWFTGEVDYQHTVYEDKISFIIQQFIAFIYQXXSLX | 901 |
| Sc_UBR1_Lager_1 | NQLAILWERDDIPRIIYNILDRWELLDWFTGEVDYQHTVYEDKISFIIQQFIAFIYQILTERQYFKTFSSLKDRRMDQIK | 919 |
| Sc_UBR1_Hybrid_1 | NQLAILWERDDIPRIIYNILDRWELLDWFTGEVDYQHTVYEDKISFIIQQFIAFIYQILTERQYFKTFSSLKDRRMDQIK | 320 |
| | | |
| Sc_UBR1_Ale_1 | | 901 |
| Sc_UBR1_Lager_1 | NSIIYNLYMKPLSYSKLLRSVPDYLTEDTTEFDEALEEVSVFVEPKGXADNGVFKLKASLYAKVDPLKLLNLENEFESS | 998 |
| Sc_UBR1_Hybrid_1 | NSIIYNLYMKPLSYSKLLRSVPDYLTEDTTEFDEALEEVSVFVEPKGLADNGVFKLKASLYAKVDPLKLLNLENEFESS | 399 |

```
                                         10        20        30        40        50        60        70        80
                                         |         |         |         |         |         |         |         |
IMA1_Sc_allele_short_Ale_1      MGYDIANYEKVWPTYGTNEDCFALIEKTHKLGMKFITDLVINHCSSEHEWFKESRSSKTNPKRDWFFWRPPKGYDAEGKP  80
IMA1_Sc_allele_short_A_Hybrid_1 MGYDIANYEKVWPTYGTNEDCFALIEKTHKLGMKFITDLVINHCSSEHEWFKESRSSKTNPKRDWFFWRPPKGYDAEGKP  80
IMA1_Sc_allele_short_B_Hybrid_1 MGYDIANYEKVWPTYGTNEDCFALIEKTHKLGMKFITDLVINHCSSEHEWFKESRSSKTNPKRDWFFWRPPKGYDAEGKP  80

90       100       110       120       130       140       150       160
                                         |         |         |         |         |         |         |         |
IMA1_Sc_allele_short_Ale_1      IPPNNWKSYFGGSAWAFDEKTQEFYLRLFCSTQPDLNWENEDCRKAIYESAVGYWLDHGVDGFRIDVGSLYSKVVGLPDA 160
IMA1_Sc_allele_short_A_Hybrid_1 IPPNNWKSYFGGSAWAFDEKTQEFYLRLFCSTQPDLNWENEDCRKAIYESAVGYWLDHGVDGFRIDVGSLYSKVVGLPDA 160
IMA1_Sc_allele_short_B_Hybrid_1 IPPNNWKSYFGGSAWAFDEKTQEFYLRLFCSTQPDLNWENEDCRKAIYESAVGYWLDHGVDGFRIDVGSLYSKVVGLPDA 160

170       180       190       200       210       220       230       240
                                         |         |         |         |         |         |         |         |
IMA1_Sc_allele_short_Ale_1      PVVDKNSTWQSSDPYTLNGPRIHEFHQEMNQFIRNRVKDGREIMTVGEMQHASDETKRLYTSASRHELSELFNFSHTDVG 240
IMA1_Sc_allele_short_A_Hybrid_1 PVVDKNSTWQSSDPYTLNGPRIHEFHQEMNQFIRNRVKDGREIMTVGEMQHASDETKRLYTSASRHELSELFNFSHTDVG 240
IMA1_Sc_allele_short_B_Hybrid_1 PVVDKNSTWQSSDPYTLNGPRIHEFHQEMNQFIRNRVKSGREIMTVGEMQHASDETKRLYTSASRHELSELFNFSHTDVG 240

250       260       270       280       290       300       310       320
                                         |         |         |         |         |         |         |         |
IMA1_Sc_allele_short_Ale_1      TSPLFRYNLVPFELKDWKIALAELFRINGTDCWSTIYLENHDQPRSITRFGDDSPKNRVISGKLLSVLLSALTGTLYVV 320
IMA1_Sc_allele_short_A_Hybrid_1 TSPLFRYNLVPFELKDWKIALAELFRINGTDCWSTIYLENHDQPRSITRFGDDSPKNRVISGKLLSVLLSALTGTLYVV 320
IMA1_Sc_allele_short_B_Hybrid_1 TSPLFRYNLVPFELKDWKIALAELFRINGTDCWSTIYLENHDQPRSITRFGDDSPKNRVISGKLLSVLLSALTGTLYVV 320

330       340       350       360       370       380       390       400
                                         |         |         |         |         |         |         |         |
IMA1_Sc_allele_short_Ale_1      QGQELGQINFKNWSVEKYEDVEIRNNYRLIKEEGGENSEEMKKFLEGIALVSRDHARTPMPWTPNEPNAGFSGPNTKPWF 400
IMA1_Sc_allele_short_A_Hybrid_1 QGQELGQINFKNWSVEKYEDVEIRNNYRLIKEEGGENSEEMKKFLEGIALVSRDHARTPMPWTPNEPNAGFSGPNTKPWF 400
IMA1_Sc_allele_short_B_Hybrid_1 QGQELGQINFKNWSVEKYEDVEIRNNYRLIKEEGGENSEEMKKFLEGIALVSRDHARTPMPWTPNEPNAGFSGPNTKPWF 400

410       420       430       440       450       460       470       480
                                         |         |         |         |         |         |         |         |
IMA1_Sc_allele_short_Ale_1      YLNESFRQGINVEEEQKNSDSVLAFWKKALEFRKNHKDIAVYGFDFKFIDLDNKKLFSFTKRYNNKTLFAALNFSSDATD 480
IMA1_Sc_allele_short_A_Hybrid_1 YLNESFRQGINVEEEQKNSDSVLAFWKKALEFRKNHKDIAVYGFDFKFIDLDNKKLFSFTKRYNNKTLFAALNFSSDATD 480
IMA1_Sc_allele_short_B_Hybrid_1 YLNESFRQGINVEEEQKNSDSVLAFWKKALEFRKNHKDIAVYGFDFKFIDLDNKKLFSFTKRYNNKTLFAALNFSSDATD 480

490       500       510       520
                                         |         |         |         |
IMA1_Sc_allele_short_Ale_1      FKIPNDGSSFKLEFGNYPKNEVDASSRTLKPWEGRIHINE                                         521
IMA1_Sc_allele_short_A_Hybrid_1 FKIPNDGSSFKLEFGNYPKNEVDASSRTLKPWEGRIHINE                                         521
IMA1_Sc_allele_short_B_Hybrid_1 FKIPNDGSSFKLEFGNYPKNEVDASSRTLKPWEGRIHINE                                         521
```

Fig. 8

```
LONG_IMA1_Alo1        MTISSAHPETEPKWWKEATFYQIYPASFKDSNDDGWGDMKGISSKLEYIKELGVDAIWSPFYDSPQDDMGYDIANYEKV  80
LONG_IMA1_Alo1_pl27   MTISSAHPETEPKWWKEATFQQIYPASFKDSNDDGWGDMEGISSKLEYIKELGVDAIWSPFYDSPQDDMGYDIANYEKV  80
LONG_IMA1_Lager1_pS1  MTISSAHPETEPKWWKEATFYQIYPASFKDSNDDGWGDMKGISSKLEYIKELGVDAIWSPFYDSPQDDMGYDIANYEKV  80
LONG_IMA1_A_Hyb1_pl17 MTISSAHPETEPKWWKEATFYQIYPASFKDSNDDGWGDMKGISSKLEYIKELGVDAIWSPLYDSPQDDMGYDIANYEKV  80
LONG_IMA1_B_Hyb1_pl18 MTISSAHPEAEPKWWKEATFYQIYPASFKDSNDDGWGDMKGISSKLEYIKELGADAIWSPFYDSPQDDMGYDIANYEKV  80

LONG_IMA1_Alo1        WPTYGTNEDCFALIEKTHKLGMKFITDLVINHCSSEHEWFKESRSSKTNPKRDWFFWRPPKGYDAEGKPIPPNNWKSYFG 160
LONG_IMA1_Alo1_pl27   WPTYGTNEDCFALIEKTHKLGMKFITDLVINHCSSEHEWFKESRSSKTNPKRDWFFWRPPKGYDAEGKPIPPNNWKSYFG 160
LONG_IMA1_Lager1_pS1  WPTYGTNEDCFALIEKTHKLGMKFITDLVINHCSSEHEWFKESRSSKTNPKRDWFFWRPPKGYDAEGKPIPPNNWKSYFG 160
LONG_IMA1_A_Hyb1_pl17 WPTYGTNEDCFALIEKTHKLGMKFITDLVINHCSSEHEWFKESRSSKTNPKRDWFFWRPPKGYDAEGKPIPPNNWKSYFG 160
LONG_IMA1_B_Hyb1_pl18 WPTYGTNEDCFALIEKTHKLGMKFITDLVINHCSSEHEWLKESRSSKTNPKRDWFFWRPPKGYDAEGKPIPPNNWKSYFG 160

LONG_IMA1_Alo1        GSAWXFDEKTQEFYLRLFCSTQPDLNWENEDCRKAIYESAVGYWLDHGVDGFRIDVGSLYSKVXGLPDAPVVDKNSTWQS 240
LONG_IMA1_Alo1_pl27   GSAWIFDEKTQEFLRLFCSTQPDLNWENEDCRKAIYESAVGYWLDHGVDGFRIDVGSLYSKVVGLPDAPVVDKNSTWQS  240
LONG_IMA1_Lager1_pS1  GSAWIFDEKTQEFYLRLFCSTQPDLNWENEDCRKAIYESAVGYWLDHGVDGFRIDVGSLYSKVVGLPDAPVVDKNSTWQS 240
LONG_IMA1_A_Hyb1_pl17 GSAWIFDEKTQEFYLRLFCSTQPDLNWENEDCRKAIYESAVGYWLDHGVDGFRIDVGSLYSKVVGLPDAPVVDKNSTWQS 240
LONG_IMA1_B_Hyb1_pl18 GSAWIFDEKTQEFYLRLFCSTQPDLNWENEDCRKAIYESAVGYWLDHGVDGFRIDVGSLYSKVVGLPDAPVVDKNSTWQS 240

LONG_IMA1_Alo1        SDPYTLNGPRIHEFHQEMNQFIRNRVKDGREIMTVGEMQHASDETKXLYTSASRHELSELFNFSHTDVGTSPLFRYNLVP 320
LONG_IMA1_Alo1_pl27   SDPYTLNGPRIHEFVQEMNQFIRNRVKDGREIMTVGEMQHASDETKLYTSASRHELSELFNFSHTDVGTSPLFRYNLVP  320
LONG_IMA1_Lager1_pS1  SDPYTLNGPRIHEFHQEMNQFIRNRVKDGREIMTVGEMQHASDETKRLYTSASRHELSELFNFSHTDVGTSPLFRYNLVP 320
LONG_IMA1_A_Hyb1_pl17 SDPYTLNGPRIHEFHQEMNQFIRNRVKDGREIMTVGEMQHASDETKRLYTSASRHELSELFNFSHTDVGTSPLFRYNLVP 320
LONG_IMA1_B_Hyb1_pl18 SDPYTLNGPRIHEFHQEMNQFIRNRVKDGREIMTVGEMQHASDETKLYTSASRHELSELFNFSHTDVGTSPLFRYNLVP  320

LONG_IMA1_Alo1        FELKDWKIALAELFRXNGTDCWSTIYLENHDQPRSITRFGDDSPKNRVISGKLLSVLLSALTGTLYVYQGQELGQINFK  400
LONG_IMA1_Alo1_pl27   FELKDWKIALAELFRINGTDCWSTIYLENHDQPRSITRFGDDSPKNRVISGKLLSVLLSALTGTLYVYQGQELGQINFK  400
LONG_IMA1_Lager1_pS1  FELKDWKIALAELFRYNGTDCWSTIYLENHDQPRSITRFGDDSPKNRVISGKLLSVLLSALTGTLYVYQGQELGQINFK  400
LONG_IMA1_A_Hyb1_pl17 FELKDWKIALAELFRINGTDCWSTIYLENHDQPRSITRFGDDSPKNRVISGKLLSVLLSALTGTLYVYQGQELGQINFK  400
LONG_IMA1_B_Hyb1_pl18 FELKDWKIALAELFRRNGTDCWSTIYLENHDQPRSITRFGDDSPKNRVISGKLLSVLLSALTGTLYVYQGQELGQINFK  400

LONG_IMA1_Alo1        NWPVEKYEDVEIRNNYNAIKEEHGENSEEMKKFLEAIAXISRDHARTPMQWSREEPNAGFSGPSAKPWFYLNDSFREGIN 480
LONG_IMA1_Alo1_pl27   NWPVEKYEDVEIRNNYNAIKEEHGENSEEMKKFLEAIAXISRDHARTPMQWSREEPNAGFSGPSAKPWFYLNDSFREGIN 480
LONG_IMA1_Lager1_pS1  NWPVEKYEDVEIRNNYNAIKEEHGENSEEMKKFLEEIALVSRDHARTPMVWXXEPNAGFSGPSAKPWFYLNDSFREGIN  480
LONG_IMA1_A_Hyb1_pl17 NWPVEKYEDVEIRNNYNAIKEEHGENSEEMKKFLEEIALVSRDHARTPMVWXXEPNAGFSGPSAKPWFYLNDSFREGIN  480
LONG_IMA1_B_Hyb1_pl18 NWPVEKYEDVEIRNNYNAIKEEHGENSEEMKKFLEAIAXISRDHARTPMQWSREEPNAGFSGPSAKPWFYLNDSFREGIN 480

LONG_IMA1_Alo1        VEDEIKDPNSVLNFWKEALKFRKAHKDITVYGYDFEPIDLDNKKLFSFTKKYNNKTLFAALNFSSDATDFKIPNDDSFK  560
LONG_IMA1_Alo1_pl27   VEDEIKDPNSVLNFWKEALKFRKAHKDITVYGYDFEPIDLDNKKLFSFTKKYNNKTLFAALNFSSDATDFKIPNDDSFK  560
LONG_IMA1_Lager1_pS1  VEDEIKDPNSVLNFWKEALKFRKAHKDITVYGYDFEPIDLDNKKLFSFTKKYNNKTLFAALNFSSDATDFKIPNDDSFK  560
LONG_IMA1_A_Hyb1_pl17 VEDEIKDPNSVLNFWKEALKFRKAHKDITVYGYDFEPIDLDNKKLFSFTKKYNNKTLFAALNFSSDATDFKIPNDDSFK  560
LONG_IMA1_B_Hyb1_pl18 VEDEIKDPNSVLNFWKEALKFRKAHKDITVYGYDFEPIDLDNKKLFSFTKKYNNKTLFAALNFSSDATDFKIPNDDSFK  560

LONG_IMA1_Alo1        LEFGNYPKKEVDASSRTLKPWEGRIYISE   590
LONG_IMA1_Alo1_pl27   LEFGNYPKKEVDASSRTLKPWEGRIYISE   590
LONG_IMA1_Lager1_pS1  LEFGNYPKKEVDASSRTLKPWEGRIYISE   590
LONG_IMA1_A_Hyb1_pl17 LEFGNYPKKEVDASSRTLKPWEGRIYISE   590
LONG_IMA1_B_Hyb1_pl18 LEFGNYPKKEVDASSRTLKPWEGRIYISE   589
```

```
ScIMA5_Ale1           MTIIHNPKWWKEATVYQIYPASNKDSNNDGWGDLAGITSKLDYVKELGVDAIWWCLFYDSPQEDMGYDIANYEKVWPRYG  80
ScIMA5_Lager1         MTIIHNPKWWKEATVYQIYPASFKDSNNDGWGDLAGITSKLDYVKELGVDAIWWCFFYDSPQEDMGYDIANYEKVWPRYG  80
ScIMA5_Hybrid1_pI11   MTIIHNPKWWKEATVYQIYPASFKDSNNDGWGDLAGITSKLDYVKELGVDAIWWCLFYDSPQEDMGYDIANYEKVWPRYG  80
non-ScIMA5_Lager1     MTIIHNPKWWKEATIYQIYPASFKDSNNDGWGDLAGITSKLDYIKELGVDAIWWCFFYDSPQEDMGYDIANYEKVWPRYG  80
non-ScIMA5_Hybrid1    MTIIHNPKWWKEATIYQIYPASFKDSNNDGWGDLAGITSKLDYIKELGVDAIWWCFFYDSPQEDMGYDIANYEKVWPRYG  80

ScIMA5_Ale1           TNEDCFQMIEEAHKRGIKVIVDLVINHCSEEHEWFKESKSSKTNPKRDWFFWRPPKGFDEKGNPIPPNNWRSFFGGSAWR 160
ScIMA5_Lager1         TNEDCFQMIEEAHKRGIKVIVDLVINHCSEEHEWFKESKSSKTNPKRDWFFWRPPKGFDEKGNPIPPNNWRSFFGGSAWR 160
ScIMA5_Hybrid1_pI11   TNEDCFQMIEEAHKRGIKVIVDLVINHCSEEHEWFKESKSSKTNPKRDWFFWRPPKGFDEKGNPIPPNNWRSFFGGSAWR 160
non-ScIMA5_Lager1     TSEDCFQMIEESHKRGIKVIVDLVINHCSEEHEWFKESESSKTNQKRDWFFWKPPKCYEIECTPIPPNNWRSFFGGSAWS 160
non-ScIMA5_Hybrid1    TSEDCFQMIEESHKRGIKVIVDLVINHCSEEHEWFKESESSKTNQKRDWFFWKPPKCYEIECTPIPPNNWRSFFGGSAWS 160

ScIMA5_Ale1           YDEKTGEFFLHVFAPGQPDFNWENEECRKAIYDSSVGYWLRHNVDGFRIDVGSMYSKVEGLPDAPITDPTVPYQKGTEFF 240
ScIMA5_Lager1         YDEKTGEFFLHVFAPGQPDFNWENEECRKAIYDSSVGYWLRHNVDGFRIDVGSMYSKVEGLPDAPITDPTVPYQKGTEFF 240
ScIMA5_Hybrid1_pI11   YDEKTGEFFLHVFAPGQPDFNWENEECRKAIYDSSVGYWLRHNVDGFRIDVGSMYSKVEGLPDAPITDPTVPYQKGTEFF 240
non-ScIMA5_Lager1     YDEKTEEFFLHVFAPGQPDFNWENKECRKAIYDSSVGWLRHNVDGFRIDVGSMYSKVEGLPDASITDPTVPYQGTEFF 240
non-ScIMA5_Hybrid1    YDEKTEEFFLHVFAPGQPDFNWENKECRKAIYDSSVGWLRHNVDGFRIDVGSMYSKVEGLPDASITDPTVPYQGTEFF 240

ScIMA5_Ale1           INGPRIHEYHKEMRKYMLSQIPEGKEIMTVGEVGVGNEEDFRDYTSAKEGELNMMFNFKHTSVGESPECKYELIPFTLKD 320
ScIMA5_Lager1         INGPRIHEYHKEMRKYMLSQIPEGKEIMTVGEVGVGNEEDFRDYTSAKEGELNMMFNFKHTSVGESPECKYELIPFTLKD 320
ScIMA5_Hybrid1_pI11   INGSRIHEYHKEMRKYMLSQIPEGKEIMTVGEVGVGNEEDFRDYTSAKEGELNMMFNFKHTSVGESPECKYELIPFTLKD 320
non-ScIMA5_Lager1     VNGPRIHEYHKEMRQYMVIQIPEGKEIMTVGEVGIGNERDFKDYTSSKEFENMMFNFKHTSVGESPEFKYELIPFTLKD 320
non-ScIMA5_Hybrid1    VNGPRIHEYHKEMRQYMVIQIPEGKEIMTVGEVGIGNERDFKDYTSSKEFENMMFNFKHTSVGESPEFKYELIPFTLKD 320

ScIMA5_Ale1           FKLALAESFLFIENTDCWSTIYLENHDQPRSVSRFGSDSPKWRAISSKMLATLIISLTGTVFIYQGQELGMSNFKNRRIE 400
ScIMA5_Lager1         FKLALAESFLFIENTDCWSTIYLENHDQPRSVSRFGSDSPKWRAISSKMLATLIISLTGTVFIYQGQELGMSNFKNRRIE 400
ScIMA5_Hybrid1_pI11   FKLALAESFLFIENTDCWSTIYLENHDQPRSVSRFGSDSPKWRAISSKMLATLIISLTGTVFIYQGQELGMSNFKNRRIE 400
non-ScIMA5_Lager1     FKLALAESFLFIESTDCWSTIYLENHDQPRSVSRFGSDSPEWRFISSKMLATLIISLTGTVFIYQGQELGMENFKNRXIE 400
non-ScIMA5_Hybrid1    FKLALAESFLFIESTDCWSTIYLENHDQPRSVSRFGSDSPEWRFISSKMLATLIISLTGTVFIYQGQELGMENFKNRXIE 400

ScIMA5_Ale1           QIKCVEGTGTYAAIKRDYGEDSEKMKKFFEALALISRDHGRTPFPWSADEPSAGFSKDAKPWIDMNESFRDGINAEAELK 480
ScIMA5_Lager1         QIKCVEGTGTYAAIKRDYGEDSEKMKKFFEALALISRDHGRTPFPWSADEPSAGFSKDAKPWIDMNESFRDGINAEAELK 480
ScIMA5_Hybrid1_pI11   QIKCVEGTGTYAAIKRDYGEDSEKMKKFFEALALISRDHGRTPFPWSADEPSAGFSKDAKPHIDMNESFRDGINAEAELK 480
non-ScIMA5_Lager1     QIKCVEGTGTYEAIKRDYGEDSEKMKKFFEALALISRDHGRTPFPWSEERPYAGFSKDAKPWIDNESFVEGINAEAELN 480
non-ScIMA5_Hybrid1    QIKCVEGTGTYEAIKRDYGEDSEKMKKFFEALALISRDHGRTPFPWSEERPYAGFSKDAKPWIDNESFVEGINAEAELN 480

ScIMA5_Ale1           DKNSVFFFWKKALQVRKEHKDILVYGHNFQFIDLDNDKLFMFTKDTDNKKMFAVENFSSDNTDFSVPDNEASYTMFFGNY 560
ScIMA5_Lager1         DKNSVFFFWKKALQVRKEHKDILVYGHNFQFIDLDNDKLFMFTKDTDNKKMFAVENFSSDNTDFSVPDNEASYTMFFGNY 560
ScIMA5_Hybrid1_pI11   DKNSVFFFWKKALQVRKEHKDILVYGHNFQFIDLDNDKLFMFTKDTDNKKMFAVENFSSDNTDFSVPDNEASYTMFFGNY 560
non-ScIMA5_Lager1     DENSVFFFWKEALQVRKEHKNLVYGDNFQFYDLDNEKLFMFTKDSEKKMFAVENFSDSTDFSVPDNRASYDMFFGNY 560
non-ScIMA5_Hybrid1    DENSVFFFWKEALQVRKEHKNLVYGDNFQFYDLDNEKLFMFTKDSEKKMFAVENFSDSTDFSVPDNRASYDMFFGNY 560

ScIMA5_Ale1           ANSNGDSRTLQPWEGRLYLLK  582
ScIMA5_Lager1         ANSNGDSRTLQPWEGRLYLLK  582
ScIMA5_Hybrid1_pI11   ANSNGDSRTLQPWEGRLYLLK  582
non-ScIMA5_Lager1     ANSEGKSYTLKPWEGRLYMSV  582
non-ScIMA5_Hybrid1    ANSEGKSYTLKPWEGRLYMSV  582
```

```
Non-Sc_AGT1_Lager1    MKNILSLVGRKENTPEDVTANLADTSSTTVMQAKDLVIEDFEERKKNDAFELNHLELTTNATQLSDSDEDKENVIRVAEA  80
Non-Sc_AGT1_Hybrid1   MKNILSLVGRKENTPEDVTANLADTSSTTVMQAKDLVIEDFEERKKNDAFELNHLELTTNATQLSDSDEDKENVIRVAEA  80

Non-Sc_AGT1_Lager1    TDDANEANNEEKSMTLRQALRKYPKAALWSILVSTTLVMEGYDTALLSALYALPVFQRKFGTMNAEGSYEITSQWQIGLN  160
Non-Sc_AGT1_Hybrid1   TDDANEANNEEKSMTLRQALRKYPKAALWSILVSTTLVMEGYDTALLSALYALPVFQRKFGTMNAEGSYEITSQWQIGLN  160

Non-Sc_AGT1_Lager1    MCVLCGEMIGLQITTYMVEFMGNRYTMITALSLLTAYIFILYYCKSLAMIAVGQILSAMPWGCFQSLAVTYASEVCPLAL  240
Non-Sc_AGT1_Hybrid1   MCVLCGEMIGLQITTYMVEFMGNRYTMITALSLLTAYIFILYYCKSLAMIAVGQILSAMPWGCFQSLAVTYASEVCPLAL  240

Non-Sc_AGT1_Lager1    RYYMTSYSNICWLFGQIFASGIMKNSQENLGNSDLGYKLPFALQWIWPAPLIIGIFFAPESPWWLVRKNKIVEAKKSLNR  320
Non-Sc_AGT1_Hybrid1   RYYMTSYSNICWLFGQIFASGIMKNSQENLGNSDLGYKLPFALQWIWPAPLIIGIFFAPESPWWLVRKNKIVEAKKSLNR  320

Non-Sc_AGT1_Lager1    ILSGTVTEKEIQVDITLKQIEMTIEKERLRASKSGSFFSCFKGVDGRRTRLACLTWAQNSSGAVLLGYSTYFFERAGMA   400
Non-Sc_AGT1_Hybrid1   ILSGTVTEKEIQVDITLKQIEMTIEKERLRASKSGSFFSCFKGVDGRRTRLACLTWAQNSSGAVLLGYSTYFFERAGMA   400

Non-Sc_AGT1_Lager1    TDKAFTFSLIQYCLGLAGTLGSWWISGRVGRWTILTYGLSFQMVCLFIIGGMGFASGSSASNAAGGLLLALSFFYNAGIG  480
Non-Sc_AGT1_Hybrid1   TDKAFTFSLIQYCLGLAGTLGSWWISGRVGRWTILTYGLSFQMVCLFIIGGMGFASGSSASNAAGGLLLALSFFYNAGIG  480

Non-Sc_AGT1_Lager1    AVVYCIVAEIPSAELRTKTIVLARICYNLMAVFNAILTPYMLNVSDWNWGAKTGLYWGGFTALTLAWIIDLPETTGRTF   560
Non-Sc_AGT1_Hybrid1   AVVYCIVAEIPSAELRTKTIVLARICYNLMAVFNAILTPYMLNVSDWNWGAKTGLYWGGFTALTLAWIIDLPETTGRTF   560

Non-Sc_AGT1_Lager1    SEINELFSQGVPARKFASTVVDPFGKRGLQNRPQVDNIIDRFSSASQQAL■                               611
Non-Sc_AGT1_Hybrid1   SEINELFSQGVPARKFASTVVDPFGKRGLQNRPQVDNIIDRFSSASQQAL                                610
```

Decoration ": Shade (with solid black) residues that differ from the Consensus.

A)
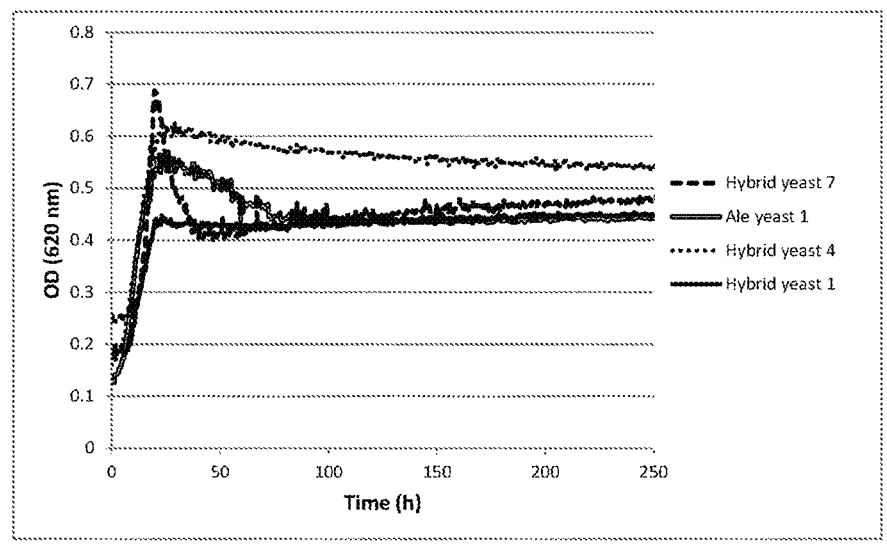
B)
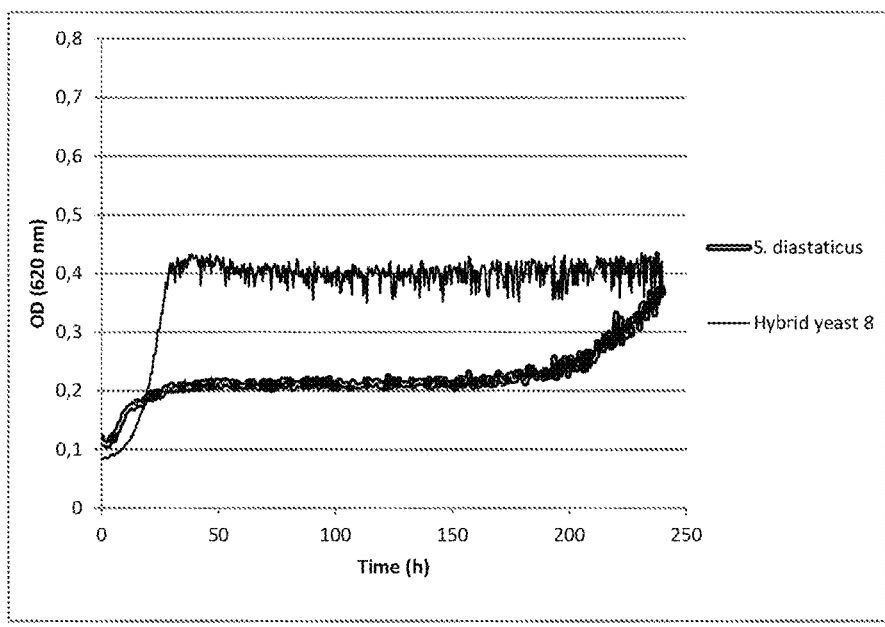
Fig. 14

A)
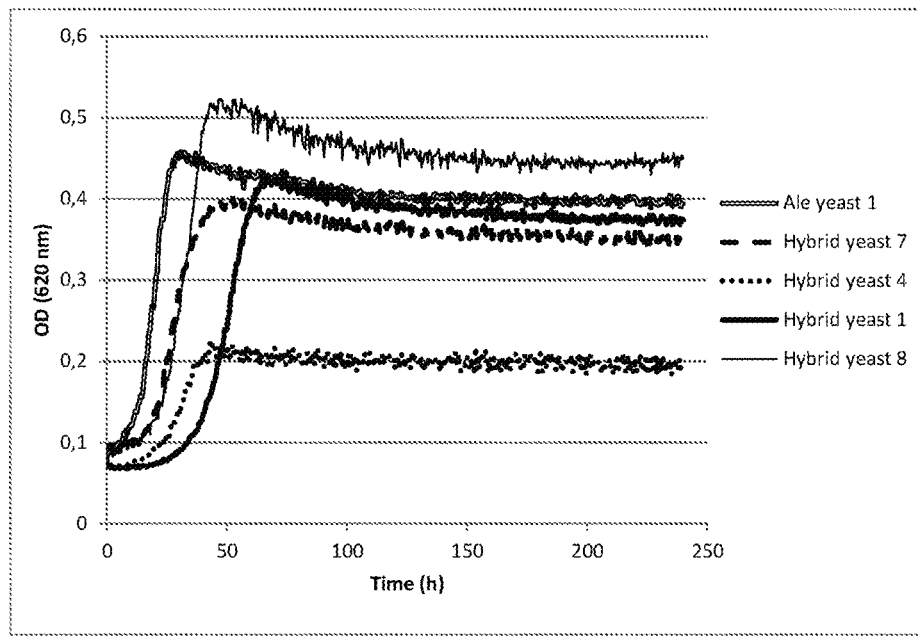
B)
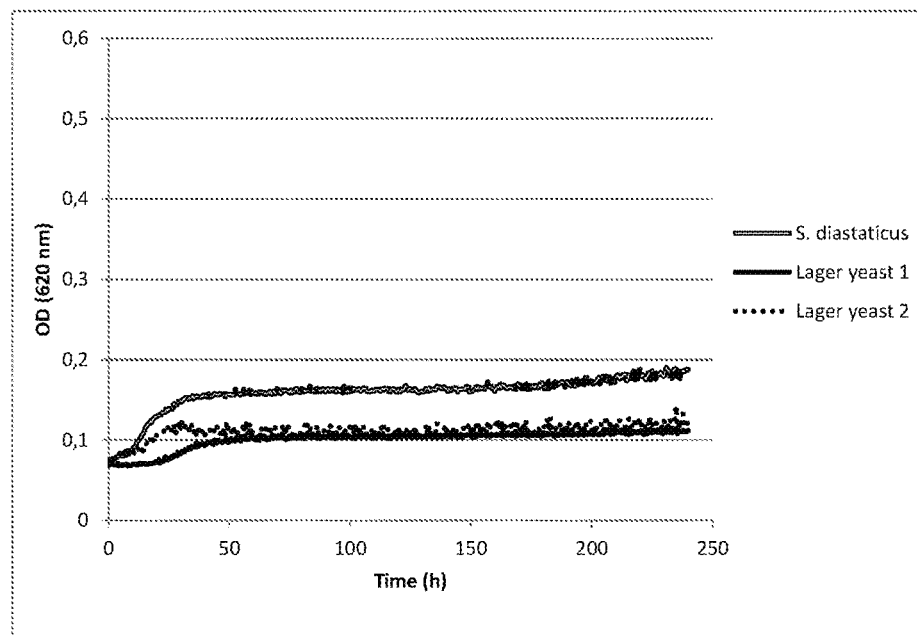
Fig. 15

YEAST FOR PREPARING ALCOHOLIC BEVERAGES

CROSS-REFERENCE TO RELATED APPLICATIONS

This application is a national phase entry pursuant to 35 U.S.C. § 371 of International Application No. PCT/DK2015/050413, filed Dec. 22, 2015, which claims the benefit of priority of Denmark Application No. PA 2014 70825, filed Dec. 23, 2014, and Denmark Application No. PA 2015 70351, filed Jun. 8, 2015, the contents of each of which is incorporated by reference herein in their entirety for any purpose.

BACKGROUND OF THE INVENTION

Alcoholic beverages are frequently prepared by fermentation of a carbohydrate rich liquid with yeast. For example, beer is prepared by fermenting wort with yeast. Wort contains a number of compounds, which can be utilized by yeast. For example wort is rich in sugars, in particular maltose and as well as in amino acids and small peptides. Conventional yeast can utilize maltose and thus conventional yeast can ferment maltose to produce ethanol. However, wort also contain other carbohydrates in addition to maltose, some of which cannot be utilized by conventional yeast, and in particular not by lager yeast.

Lager yeast in general differs from ale yeast in several ways. Lager yeast belong to the species *S. pastorianus*. Frequently, lager yeast is also referred to as "bottom-Fermenting Yeast" because they settle at the bottom during fermentation. Furthermore, lager yeast strains are best used at temperatures ranging from 7 to 15° C. In addition lager yeast is capable of using melibiose as the sole carbon source and cannot grow at 37° C.

In contrast, ale yeast belong to the species *S. cerevisiae*. Frequently, ale yeast is also referred to as "top-Fermenting Yeast", because they often rise to the surface during fermentation. Furthermore, Ale yeast strains are best used at temperatures ranging from 10 to 25° C., though some strains will not actively ferment below 12° C. In addition ale yeast is not capable of using melibiose as the sole carbon source and can grow at 37° C.

Other yeast can also be employed in beer brewing, e.g. *Saccharomyces diastaticus*. *Saccharomyces diastaticus* belongs to the *Saccharomyces cerevisiae* specie variety (var.) *diastaticus* and has the particularity of having glucoamylase enzyme activity encoded by at least one of the following genes STA1, STA2 or STA3 enabling the yeast to utilize starch as sole carbon source. The STA genes are in general absent in *S. cerevisiae* or *S. pastorianus* or other *Saccharomyces* species strains analyzed, but are present in the subgroup of *S. cerevisiae* var. *diastaticus*.

SUMMARY OF THE INVENTION

There is a need for improved yeast strains, which have characteristics of both lager beer (e.g. *S. pastorianus*) as well as of ale yeast (e.g. *S. cerevisiae*). In addition, there is a need for yeast strains, which can utilize as many different energy sources as possible. In particular, there is a need for yeast, which can utilizes sugars present in wort, which are not maltose and yeast which can utilize amino acids and peptides to a high degree.

Interestingly, the invention provides a hybrid yeast, which has several important characteristics of lager yeast, but which as the same time can utilize a lot of different energy sources present in wort.

Accordingly, it is an aspect of the invention to provide a yeast cell having at least one of the following characteristics:
I. Capable of utilizing isomaltose as sole carbon source;
II. Capable of utilizing panose as sole carbon source.

In addition to abovementioned characteristics I and II the yeast cell according to the invention may have additional characteristics, for example one or more of the following characteristics:
III. Capable of utilizing one or more dipeptides as sole nitrogen source;
IV. capable of utilizing one or more tri-peptides as sole nitrogen source;
V. capable of reducing the level of one or more amino acids to no more than 10% of the starting concentration after incubation for 5 days under conditions allowing growth of said yeast cells;
VI. Capable of generating at least 4.7 promille ethanol per ° Plato, when said yeast cell is added to a wort composition having a sugar content of at least 10° Plato and incubated until level of diacetyl is in spec; and/or
VII. Capable of fermenting sugar with a real degree of fermentation of at least 70, when said yeast cell is added to a wort composition having a sugar content of at least 10° Plato and incubated until level of diacetyl is in spec.

It is also an aspect of the invention to provide a yeast cell having at least one of the following characteristics:
II. Capable of utilizing panose as sole carbon source;
III. Capable of utilizing one or more dipeptides as sole nitrogen source.

It is also an aspect of the invention to provide a yeast cell having at the characteristic:
II. Capable of Capable of utilizing panose as sole carbon source In addition to abovementioned characteristics II and/or III the yeast cell according to the invention may have additional characteristics, for example one or more of the following characteristics:
I. Capable of utilizing isomaltose as sole carbon source;
IV. capable of utilizing one or more tri-peptides as sole nitrogen source;
V. capable of reducing the level of one or more amino acids to no more than 10% of the starting concentration after incubation for 5 days under conditions allowing growth of said yeast cells;
VI. Capable of generating at least 4.7 promille ethanol per ° Plato, when said yeast cell is added to a wort composition having a sugar content of at least 10° Plato and incubated until level of diacetyl is in spec; and/or
VII. Capable of fermenting sugar with a real degree of fermentation of at least 70, when said yeast cell is added to a wort composition having a sugar content of at least 10° Plato and incubated until level of diacetyl is in spec.

It is also an aspect of the invention to provide methods for producing a beverage, said methods comprising the steps of
I. Providing a starting liquid
II. Providing a yeast cell according to the invention
III. Fermenting said starting liquid with said yeast cell.

DESCRIPTION OF DRAWINGS

FIG. 1 shows growth of various yeast strains in defined medium with 2 g/L panose as sole carbon source. The data shown is representative of biological replicates. Panel A) shows growth of Ale yeast 1, Hybrid yeast 1, Hybrid yeast 4 and Lager yeast 1. Panel B) shows growth of Ale yeast 1, Hybrid yeast 7 and Lager yeast 2. Panel C) shows growth of S. diastaticus and Hybrid yeast 8.

FIG. 2 shows growth of yeast in defined medium with 2 g/L isomaltose as sole carbon source. The data shown is representative of biological replicates. Panel A) shows growth of Ale yeast 1, Hybrid yeast 1, Hybrid yeast 4 and Lager yeast 2. Panel B) shows growth of Ale yeast 1, Hybrid yeast 7 and Lager yeast 1. Panel C) shows growth of S. diastaticus and Hybrid yeast 8.

FIG. 3 shows growth of yeast cells in Bioscreen C MBR in defined medium with 2 g/L melibiose as sole carbon source. Panel A shows growth of Hybrid yeast 1 and Hybrid yeast 4. Panel B shows growth of Hybrid yeast 7.

FIG. 5 shows a protein alignment of DAL5 from Ale Yeast 1, Lager yeast 1 and Hybrid yeast 1. The sequence of DAL5 of Hybrid yeast 1 is denoted Sc_DAL5_Hybrid_1 (SEQ ID NO:6), the sequence of DAL5 of Ale Yeast 1 is denoted ScDAL5-Ale_1 (SEQ ID NO:46), and the sequence of DAL 5 of Lager yeast 1 is denoted nonSc_DAL5_Lager_1 (SEQ ID NO:47).

FIG. 6 shows a protein alignment of UBR1 encoded by Sc alleles of UBR1 illustrating the presence of Lager yeast 1 Sc allele in Hybrid yeast 1 while Ale yeast 1 is truncated. Only part of the alignment is shown; residues in black shade differ from Hybrid yeast 1 sequence. Sequences shown: Sc_UBR1_Ale_1 (SEQ ID NO:48), Sc_UBR1_Lager_1 (SEQ ID NO:49), and Sc_UBR1_Hybrid_1 (SEQ ID NO:10).

FIG. 7 shows a protein alignment of UBR1 encoded by nonSc alleles of UBR1 illustrating the presence of Lager yeast 1 Sc allele in Hybrid yeast 1. Sequences shown: nonSc_UBR1_Lager_1 (SEQ ID NO:50) and nonSc_UBR1_Hybrid_1 (SEQ ID NO:11).

FIG. 8 shows a protein alignment of IMA1p encoded by IMA1 short alleles. The IMA1p encoded by the IMA1 short alleles found in Hybrid yeast 1 are denoted IMA1_Sc_allele_short_A_Hybrid_1 and IMA1_Sc_allele_short_B_Hybrid_1, respectively. Sequences shown: IMA1_Sc_allene_short_Ale_1 (SEQ ID NO:51), IMA1_Sc_allene_short_A_Hybrid_1 (SEQ ID NO:12) and IMA1_Sc_allene_short_B_Hybrid_1 (SEQ ID NO:13).

Figure 9B:
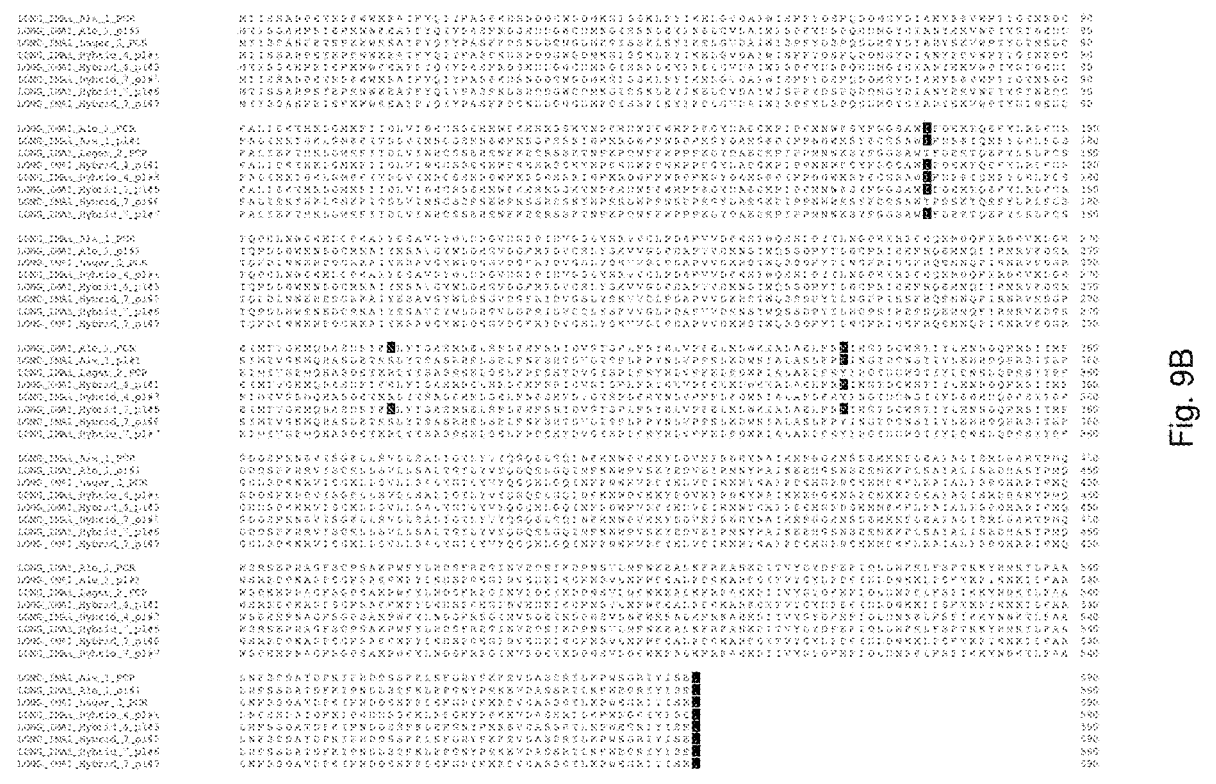

FIG. 9 shows a protein alignment of IMA1p encoded by IMA1 long alleles. FIG. 9A shows an alignment of IMA1p encoded by long alleles from Ale yeast 1, Lager yeast 1 and Hybrid yeast 1. The IMA1p encoded by the IMA1 long alleles found in Hybrid yeast 1 are denoted LONG_IMA1_A_Hyb1_pl17 and LONG_IMA1_B_Hyb1_pl18, respectively. FIG. 9B shows an alignment of IMA1p encoded by long alleles from Ale yeast 1, Lager yeast 2, Hybrid yeast 4 and Hybrid yeast 7. Sequences shown: LONG_IMA1_Ale1 (SEQ ID NO:52), LONG_IMA1_Ale1_pl27 (SEQ ID NO:53), LONG_IMA1_Lager1_pl31 (SEQ ID NO:54), LONG_IMA1_A_Hyb1_pl17 (SEQ ID NO:14), LONG_IMA1_B_Hyb1_pl18 (SEQ ID NO:15), LONG_IMA1_Ale_1_PCR (SEQ ID NO:55), LONG_IMA1_Ale_1_pl#1 (SEQ ID NO:56), LONG_IMA1_Lager_2_PCR (SEQ ID NO:57), LONG_IMA1_Hybrid_4_pl#1 (SEQ ID NO:21), LONG_IMA1_Hybrid_4_pl#3 (SEQ ID NO:22), LONG_IMA1_Hybrid_7_pl#5 (SEQ ID NO:23), LONG_IMA1_Hybrid_7_pl#6 (SEQ ID NO:24), and LONG_IMA1_Hybrid_7_pl#7 (SEQ ID NO:25).

FIG. 10 shows a protein alignment of IMA5p encoded by IMA5-like. The IMA5p encoded by the IMA5-like found in Hybrid yeast 1 are denoted ScIMA5_Hybrid1_pl1 and non-ScIMA5_Hybrid1, respectively. Sequences shown: ScIMA5_Ale1 (SEQ ID NO:58), ScIMA5_Lager1 (SEQ ID NO:59), ScIMA5_Hybrid1_pl11 (SEQ ID NO:17), non-ScIMA5_Lager1 (SEQ ID NO:60), and non-ScIMA5_Hybrid1 (SEQ ID NO:16).

Figure 11A:
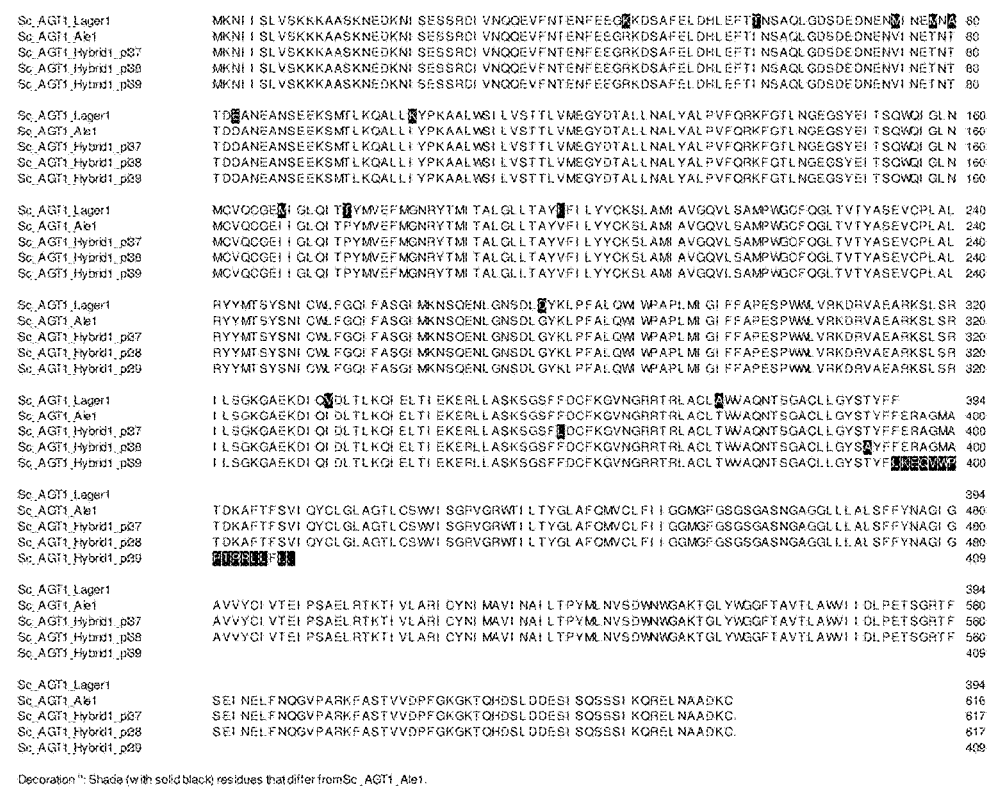

FIG. 11 shows a protein alignment of AGT1 encoded by Sc alleles of AGT1. FIG. 11A shows an alignment of AGT1 encoded by Sc alleles of AGT1 from Lager yeast 1, Ale yeast 1 and Hybrid yeast 1. The AGT1 encoded by the AGT1 found in Hybrid yeast 1 are denoted Sc_AGT1_Hybrid1_pl37, Sc_AGT1_Hybrid1_pl38 and Sc_AGT1_Hybrid1_pl39, respectively. FIG. 11B shows an alignment of AGT1 encoded by Sc alleles of AGT1 from Lager yeast 2, Ale yeast 1, Hybrid yeast 4 and Hybrid yeast 7. Sequences shown: Sc_AGT1_Lager1 (SEQ ID NO:61), Sc_AGT1_Ale1 (SEQ ID NO:62), Sc_AGT1_Hybrid1_pl37 (SEQ ID NO:19), Sc_AGT1_Hybrid1_pl38 (SEQ ID NO:20), Sc_AGT1_Hybrid1_pl39 (SEQ ID NO:63), Sc_AGT1_Lager_2 (SEQ ID NO:64), Sc_AGT1_Ale_1 (SEQ ID NO:65), Sc_AGT1_Hybrid_4_pl#2 (SEQ ID NO: 26), Sc_AGT1_Hybrid_7_pl#11 (SEQ ID NO:29), and Sc_AGT1_Hybrid_7_pl#12 (SEQ ID NO: 30).

Figure 12B:
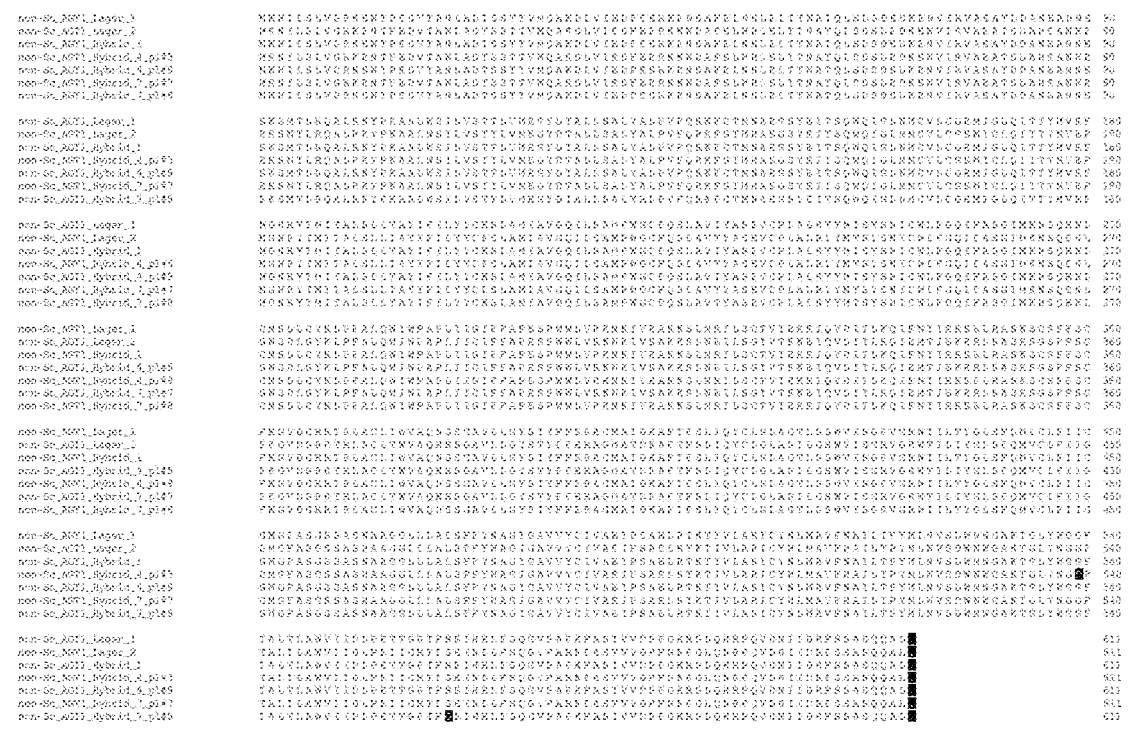

FIG. 12 shows a protein alignment of AGT1 encoded by non-Sc alleles of AGT1. FIG. 12A shows an alignment of AGT1 encoded by non-Sc alleles of AGT1 from Lager yeast 1 and Hybrid yeast 1. The AGT1 encoded by the AGT1 found in Hybrid yeast 1 is denoted Non-Sc_AGT1_Hybrid1. FIG. 12A shows an alignment of AGT1 encoded by non-Sc alleles of AGT1 from Lager yeast 1, Lager yeast 2, Hybrid yeast 1, Hybrid yeast 4 and Hybrid yeast 7. Sequences shown: Non-Sc_AGT1_Lager1 (SEQ ID NO:66), Non-Sc_AGT1_Hybrid1 (SEQ ID NO:18), non-Sc_AGT1_Lager_1 (SEQ ID NO:67), non-Sc_AGT1_Lager_2 (SEQ ID NO:68), non-Sc_AGT1_Hybrid_1 (SEQ ID NO:69), non-Sc_AGT1_Hybrid_4_pl#5 (SEQ ID NO:27), non-Sc_AGT1_Hybrid_4_pl#9 (SEQ ID NO: 28), non-Sc_AGT1_Hybrid_7_pl#7 (SEQ ID NO:31), and non-Sc_AGT1_Hybrid_7_pl#8 (SEQ ID NO:32).

FIG. 14 shows growth of yeast in defined medium with 2 g/L maltulose as sole carbon source. The data shown is representative of biological replicates.

FIG. 15 shows growth of yeast in defined medium with 2 g/L kojibiose as sole carbon source. The data shown is representative of biological replicates.

DETAILED DESCRIPTION OF THE INVENTION

Definitions

Figure 4:
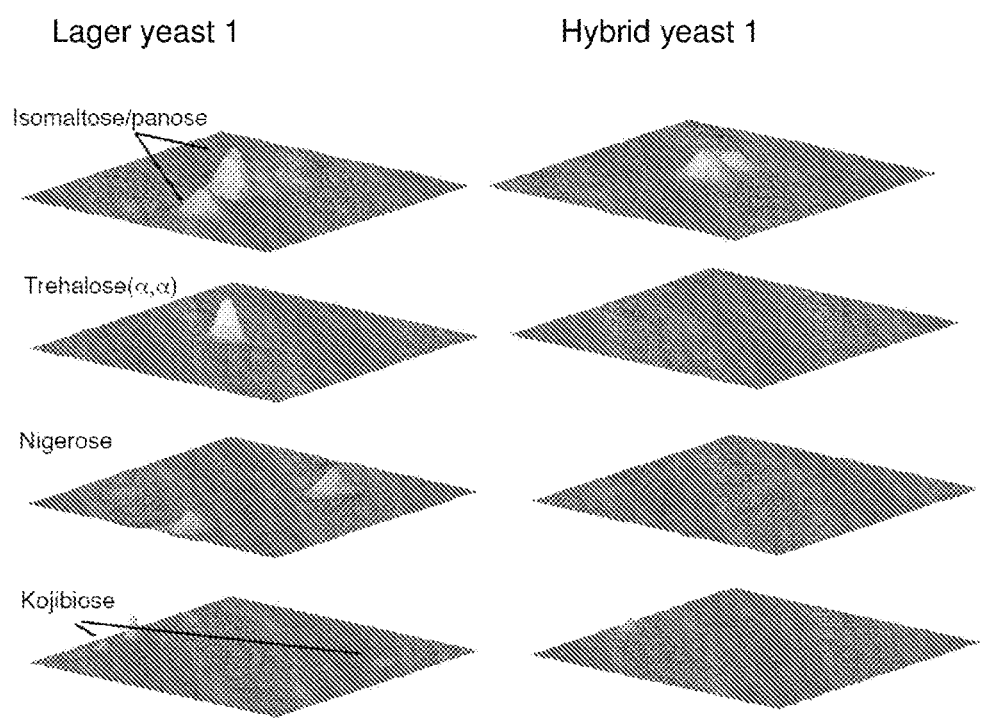
FIG. 4 shows an NMR analysis of single sugars in final bottled beer brew comparing beer made with Lager yeast 1 and Hybrid yeast 1.

As used herein, "a" can mean one or more, depending on the context in which it is used.

The term "AE" as used herein is an abbreviation of "Apparent Extract". The "apparent extract" is a measure of the density of beer wort in terms of the percentage of extract by weight and is expressed in the Plato scale. It is the final gravity or specific gravity measured at the end of beer fermentation. Gravity in the context of alcoholic beverages refers to the relative density of the liquid compared to water. The more sugars dissolved in the wort the higher the density of the wort.

Amino acids may be named herein using the IUPAC one-letter and three-letter codes.

The term "beer" as used herein refers to a beverage prepared by fermentation of wort. Preferably, said fermentation is done by yeast.

The term "carbon source" as used herein refers to any organic molecule, which can provide energy to yeast and provide carbon for cellular biosynthesis. In particular, said carbon source may be carbohydrates, and more preferably, the carbon source may be mono- and/or disaccharides.

The term "cells in suspension" is used herein in relation to incubation of cells in a liquid medium in a container. "Cells in suspension" are cells, which have not sedimented to the bottom of the container after incubation, but which float freely in the liquid medium. Cells in suspension can be determined by taking a sample of the liquid medium from the upper part of the container, and counting the cells therein.

The term "diacetyl in spec." refers to the level of diacetyl being below a predefined threshold, which is set at a level below the threshold considered off-flavor in lager beer. Preferably, the diacetyl is considered to be in spec when the level of diacetyl is at the most 30 ppb.

By "encoding" or "encoded", in the context of a specified nucleic acid, is meant comprising the information for translation into the specified protein. A nucleic acid or polynucleotide encoding a protein may comprise non-translated sequences, e.g. introns, within translated regions of the nucleic acid, or may lack such intervening non-translated sequences, e.g. in cDNA. The information by which a protein is encoded is specified by the use of codons.

As used herein, "expression" in the context of nucleic acids is to be understood as the transcription and accumulation of sense mRNA or antisense RNA derived from a nucleic acid fragment. "Expression" used in the context of proteins refers to translation of mRNA into a polypeptide.

The term "gene" means the segment of DNA involved in producing a polypeptide chain; it includes regions preceding and following the coding region (promoter and terminator). Furthermore, some yeast genes also comprise introns although only 5% of the genes in the S. cerevisae genome comprise introns. After transcription into RNA, the introns are removed by splicing to generate a mature messenger RNA (mRNA).

The term "growth" as used herein in relation to yeast, refers to the process by which a yeast cells multiply. Thus, when yeast cells are growing, the number of yeast cells increases. The number of yeast cells may be determined by any useful method, e.g. by determining the OD (620 nm). Increase in OD (620 nm) corresponds to an increase in the number of yeast cells. Conditions allowing growth of yeast are conditions allowing yeast cells to increase in number. Such conditions in general require the presence of adequate nutrients, e.g. a carbon source and an nitrogen source as well as an adequate temperature, which typically is in the range of 5 to 40° C.

The term "nitrogen source" as used herein refers to any organic nitrogen containing molecule and/or to ammonium containing molecules. In particular, said nitrogen source may be an organic nitrogen source, for example peptides, amino acids, and/or other amines. The nitrogen source may also be ammonium. Thus, N2 is not considered a "nitrogen source" herein.

The term "malt" refers to cereal grains, which have been malted. Malting is a special form of germination of cereal kernels (e.g. barley kernels) taking place under controlled environmental conditions—including, but not limited to steep tanks and germination boxes of the malting factory. In general malting involves steeping said kernels, followed by germination. The malting process may be stopped by drying of the cereal kernels (e.g. barley kernels), for example, in a kiln drying process, which is usually performed at elevated temperatures. Malt may be processed, for example, by milling and thus referred to as "milled malt" or "flour".

"Mashing" is the incubation of milled malt in water. Mashing is preferably performed at a specific temperature, and in a specific volume of water. The temperature and volume of water are of importance, as these affect the rate of decrease of enzyme activity derived from the malt, and hence especially the amount of starch hydrolysis that can occur; protease action may also be of importance. Mashing can occur in the presence of adjuncts, which is understood to comprise any carbohydrate source other than malt, such as, but not limited to, barley, barley syrups, or maize, or rice—either as whole kernels or processed products like grits, syrups or starch. All of the aforementioned adjuncts may be used principally as an additional source of extract (syrups are typically dosed during wort heating). The requirements for processing of the adjunct in the brewery depend on the state and type of adjunct used, and in particular on the starch gelatinization or liquefaction temperatures. If the gelatinization temperature is above that for normal malt saccharification, then starch is gelatinized and liquefied before addition to the mash.

The term "° Plato" as used herein refers to density as measured on the Plato scale. The Plato scale is an empirically derived hydrometer scale to measure density of beer or wort in terms of percentage of extract by weight. The scale expresses the density as the percentage of sugar by weight.

By the term "wort" is meant a liquid extract of malt, such as milled malt, or green malt, or milled green malt. In barley brewing, wort may also be prepared by incubating an extract of un-malted barley with an enzyme mixture that hydrolyzes the barley components. In addition to said malt or barley-derived extracts, the liquid extract may be prepared from malt and additional components (e.g. adjuncts), such as additional starch-containing material partly converted into fermentable sugars. The wort is in general obtained by mashing, optionally followed by "sparging", in a process of extracting residual sugars and other compounds from spent grains after mashing with hot water. Sparging is typically conducted in a lauter tun, a mash filter, or another apparatus to allow separation of the extracted water from spent grains. The wort obtained after mashing is generally referred to as "first wort", while the wort obtained after sparging is generally referred to as the "second wort". If not specified, the term wort may be first wort, second wort, or a combination of both. During conventional beer production, wort is boiled together with hops, however the present invention provides methods for reducing boiling or avoiding boiling of wort. Wort without hops, may also be referred to as "sweet wort", whereas wort boiled/heated with hops may be referred to as "boiled wort".

The term "yeast cell capable of utilizing XX" as used herein refers to a yeast cell, which can take up and degrade XX.

The term "yeast cell capable of utilizing XX as sole carbon source" as used herein refers to a yeast cell, which can grow on a medium containing XX as the only carbon source. Thus, said medium preferably does not contain any other carbohydrates apart from XX.

Yeast Cell

The present invention relates to a yeast cell having at least one of the characteristics I, II, III, IV, V, VI, VII and XI described herein below.

In particular it is preferred that said yeast cell at least has characteristics I and II described herein below.

It is also preferred that said yeast cell has at least characteristic II described below. It is also preferred that the yeast cell has at least characteristics II and III described below.

Characteristic I may be any of the characteristics I described in the section "Characteristic I" herein below. In particular characteristic I may be that the yeast cell is capable of utilizing isomaltose as sole carbon source.

Characteristic II may be any of the characteristics V described in the section "Characteristic II" herein below. In particular characteristic II may be that the yeast cell is capable of utilizing panose as sole carbon source.

Characteristic III may be any of the characteristics III described in the section "Characteristic III" herein below. In particular characteristic III may be that the yeast cell is capable of utilizing dipeptides as sole nitrogen source.

Characteristic IV may be any of the characteristics IV described in the section "Characteristic IV" herein below. In particular characteristic IV may be that the yeast cell is capable of utilizing tripeptides as sole nitrogen source.

Characteristic V may be any of the characteristics V described in the section "Characteristic III" herein below. In particular characteristic III may be that the yeast cell is capable of reducing the level of one or more amino acids to no more than 10% of the starting concentration after incubation for 5 days under conditions allowing growth of said yeast cells.

Characteristic VI may be any of the characteristics VI described in the section "Characteristic VI" herein below. In particular characteristic VI may be that the yeast cell is capable of generating at least 4.7 promille ethanol per ° Plato, when said yeast cell is added to a wort composition having a sugar content of at least 10° Plato and incubated until level of diacetyl is in spec.

Characteristic VII may be any of the characteristics VII described in the section "Characteristic VII" herein below. In particular characteristic VII may be that the yeast cell is capable of fermenting sugar with a real degree of fermentation of at least 70, when said yeast cell is added to a wort composition having a sugar content of at least 10° Plato and incubated until level of diacetyl is in spec.

Characteristic XI may be any of the characteristics XI described in the section "Characteristic XI" herein below. In particular characteristic XI may be that the yeast cell is capable of fermenting wort with a time of primary fermentation of at the most 4 days.

The yeast cell according to the invention may have one or more of the characteristics. Thus, the yeast cell may have at least two, preferably at least three, more preferably at least four, yet more preferably at least five, such as at least 6, such as all of the characteristics I, II, III, IV, V, VI and VII. The yeast cell may also have at least two, preferably at least three, more preferably at least four, yet more preferably at least five, such as at least 6, such as all of the characteristics I, II, III, IV, V, VI, VII and XI.

Thus, the yeast cell of the invention may have the characteristics I and II. The yeast cell of the invention may also have characteristics I and III. The yeast cell of the invention may also have characteristics I and IV. The yeast cell of the invention may also have characteristics I and V. The yeast cell of the invention may also have characteristics I and VI. The yeast cell may also have characteristics I and VII. The yeast cell may also have characteristics I and XI. The yeast cell of the invention may also have characteristics I, II, and III. The yeast cell of the invention may also have characteristics I, II and IV. The yeast cell of the invention may also have characteristics I, II and V. The yeast cell of the invention may also have characteristics I, II and VI. The yeast cell may also have characteristics I, II and VII. The yeast cell may also have characteristics I, II and XI. The yeast cell of the invention may also have characteristics I, II, III and IV. The yeast cell of the invention may also have characteristics I, II, III and V. The yeast cell of the invention may also have characteristics I, II, III and VI. The yeast cell may also have characteristics I, II, III and VII. The yeast cell may also have characteristics I, II, III and XI. The yeast cell of the invention may also have characteristics I, II, III, IV and V. The yeast cell of the invention may also have characteristics I, II, III, IV and VI. The yeast cell may also have characteristics I, II, III, IV and VII. The yeast cell may also have characteristics I, II, III, IV and XI. The yeast cell of the invention may also have characteristics I, II, III, IV, V and VI. The yeast cell may also have characteristics I, II, III, IV, V and VII. The yeast cell may also have characteristics I, II, III, IV, V and XI. The yeast cell may also have characteristics I, II, III, IV, V, VI and VII. The yeast cell may also have characteristics I, II, III, IV, V, VI and XI. The yeast cell may also have characteristics I, III and IV. The yeast cell may also have characteristics I, III and V. The yeast cell may also have characteristics I, III and VI. The yeast cell may also have characteristics I, III and VII. The yeast cell may also have characteristics I, III and XI. The yeast cell may also have characteristics I, III, IV and V. The yeast cell may also have characteristics I, III, IV and VI. The yeast cell may also have characteristics I, III, IV and VII. The yeast cell may also have characteristics I, III, IV and XI. The yeast cell may also have characteristics I, III, V and VI. The yeast cell may also have characteristics I, III, IV, V and VII. The yeast cell may also have characteristics I, III, IV, V and XI. The yeast cell may also have characteristics I, III, IV, V, VI and VII. The yeast cell may also have characteristics I, III, V and VI. The yeast cell may also have characteristics I, III, V and VII. The yeast cell may also have characteristics I, III, V and XI. The yeast cell may also have characteristics I, III, VI and VII. The yeast cell may also have characteristics I, III, VI and XI. The yeast cell may also have characteristics I, III, VII and XI. The yeast cell may also have characteristics I, IV and V. The yeast cell may also have characteristics I, IV and VI. The yeast cell may also have characteristics I, IV and VII. The yeast cell may also have characteristics I, IV and XI. The yeast cell may also have characteristics I, IV, V and VI. The yeast cell may also have characteristics I, IV, V and VII. The yeast cell may also have characteristics I, IV, V and XI. The yeast cell may also have characteristics I, IV, VI and VII. The yeast cell may also have characteristics I, IV, VI and XI. The yeast cell may also have characteristics I, IV, V, VI and VII. The yeast cell may also have characteristics I, IV, V, VI and XI. The yeast cell may also have characteristics I, IV, V, VI, VII and XI. The yeast cell may also have characteristics I, V and VI. The yeast cell may also have characteristics I, V and VII. The yeast cell may also have characteristics I, V and XI. The yeast cell may also have characteristics I, V, VI and VII. The yeast cell may also have characteristics I, V, VI and XI. The yeast cell may also have characteristics I, V, VI, VII and XI. The yeast cell may also have characteristics I, VI and VII. The yeast cell may also have characteristics I, VI and XI. The yeast cell may also have characteristics I, VI, VII and XI. The yeast cell may also have characteristics I, VII and XI. The yeast cell of the invention may also have characteristics II and III. The yeast cell of the invention may also have characteristics II and IV. The yeast cell of the invention may also have characteristics II and V. The yeast cell of the invention may also have characteristics II and VI. The yeast cell may also have characteristics II and VII. The yeast cell may also have characteristics II, and XI. The yeast cell of the invention may also have characteristics II, III and IV. The yeast cell of the invention may also have characteristics II, III and V. The yeast cell of the invention may also have characteristics II, III and VI. The yeast cell may also have characteristics II, III and VII. The yeast cell may also have characteristics II, III and XI. The yeast cell of the invention may also have characteristics II, III, IV and V. The yeast cell of the invention may also have characteristics II, III, IV and VI. The yeast cell may also have characteristics II, III, IV and VII. The yeast cell may also have characteristics II, III, IV and XI. The yeast cell of the invention may also have characteristics II, III, IV, V and VI. The yeast cell may also have characteristics II, III, IV, V and VII. The yeast cell may also have characteristics II, III, IV, V and XI. The yeast cell may also have characteristics II, III, IV, V, VI and VII. The yeast cell may also have characteristics II, III, IV, V, VI and XI. The yeast cell may also have characteristics II, III, IV, V, VI, VII and XI. The yeast cell may also have characteristics II, IV and V. The yeast cell may also have characteristics II, IV and VI. The yeast cell may also have characteristics II, IV and VII. The yeast cell may also have characteristics II, IV and XI. The yeast cell may also have characteristics II, IV, V and VI. The yeast cell may also have characteristics II, IV, V and VII. The yeast cell may also have characteristics II, IV, V and XI. The yeast cell may also have characteristics II, IV, V, VI and VII. The yeast cell may also have characteristics II, IV, V, VI and XI. The yeast cell may also have characteristics II, IV, V, VI, VII and XI. The yeast cell may also have characteristics II, V and VI. The yeast cell may also have characteristics II, V and VII. The yeast cell may also have characteristics II, V and XI. The yeast cell may also have characteristics II, V, VI and VII. The yeast cell may also have characteristics II, V, VI and XI. The yeast cell may also have characteristics II, V, VI, VII and XI. The yeast cell may also have characteristics II, VI and VII. The yeast cell may also have characteristics II, VI and XI. The yeast cell may also have characteristics II, VI, VII and XI. The yeast cell may also have characteristics II, VII and XI. The yeast cell of the invention may also have characteristics III and IV. The yeast cell of the invention may also have characteristics III and V. The yeast cell of the invention may also have characteristics III and VI. The yeast cell may also have characteristics III and VII. The yeast cell may also have characteristics III and XI. The yeast cell of the invention may also have characteristics III, IV and V. The yeast cell of the invention may also have characteristics III, IV and VI. The yeast cell may also have characteristics III, IV and VII. The yeast cell may also have characteristics III, IV and XI. The yeast cell of the invention may also have characteristics III, IV, V and VI. The yeast cell may also have characteristics III, IV, V and VII. The yeast cell may also have characteristics III, IV, V and XI. The yeast cell may also have characteristics III, IV, V, VI and VII. The yeast cell may also have characteristics III, IV, V, VI and XI. The yeast cell may also have characteristics III, IV, V; VI, VII and XI. The yeast cell may also have characteristics III, V and VI. The yeast cell may also have characteristics III, V and VII. The yeast cell may also have characteristics III, V and XI. The yeast cell may also have characteristics III, VI and VII. The yeast cell may also have characteristics III, VI and XI. The yeast cell may also have characteristics III, VI, VII and XI. The yeast cell may also have characteristics III, VII and XI. The yeast cell of the invention may also have characteristics IV and V. The yeast cell of the invention may also have characteristics IV and VI. The yeast cell may also have characteristics IV and VII. The yeast cell of the invention may also have characteristics IV, V and VI. The yeast cell may also have characteristics IV, V and VII. The yeast cell may also have characteristics IV, V, VI and VII. The yeast cell may also have characteristics IV, VI and VII. The yeast cell may also have characteristics IV, VI and XI. The yeast cell may also have characteristics IV, VI, VII and XI. The yeast cell of the invention may also have characteristics V and VI. The yeast cell may also have characteristics V and VII. The yeast cell may also have characteristics V and XI. The yeast cell may also have characteristics V, VI and VII. The yeast cell may also have characteristics V, VII and XI. The yeast cell may also have characteristics VI and VII. The yeast cell may also have characteristics VI and XI. The yeast cell may also have characteristics VI, VII and XI. The yeast cell may also have characteristics VII and XI.

In a preferred embodiment of the invention the yeast cell has all of characteristics I, II, III, IV, V, VI and VII. In a preferred embodiment of the invention the yeast cell has all of characteristics I, II, III, IV, V, VI, VII and XI.

In addition to the characteristics outlined above, the yeast cells of the invention may have one or more additional characteristics.

Thus, in addition to one or more of characteristics I, II, III, IV, V, VI, VII and/or XI, then the yeast cell may also have characteristic VIII. Characteristic VIII may be any of the characteristics VIII described in the section "Characteristic VIII" herein below. In particular characteristic VIII may be that the yeast cell is capable of utilizing melibiose as the sole carbon source.

In addition to one or more of characteristics I, II, III, IV, V, VI, VII, VIII and/or XI, then the yeast cell may also have characteristic IX. Characteristic IX may be any of the characteristics IX described in the section "Characteristic IX" herein below. In particular characteristic IX may be that the yeast cell is capable of utilizing disaccharides and/or trisaccharides as the sole carbon source.

In addition to one or more of characteristics I, II, III, IV, V, VI, VII, VIII, IX and/or XI, then the yeast cell may also have characteristic X. Characteristic X may be any of the characteristics X described in the section "Characteristic X" herein below. In particular characteristic X may be that the yeast cell only has a low number of cells in suspension.

In a preferred embodiment of the invention, the yeast cell may have all of characteristics I, II, III, IV, V, VI, VII, VIII, IX, X and XI.

The yeast cell may be a yeast cell of any suitable species. In a preferred embodiment of the invention the yeast cell is a hybrid between a yeast cell of the species *S. pastorianus* and a yeast cell of the species *S. cerevisiae*.

Characteristic I

The yeast cell according to the invention may have the characteristic I, wherein characteristic I is that the yeast cell is capable of utilizing isomaltose. Thus, upon incubation in a medium containing isomaltose, then said yeast cell is capable of removing at least part of said isomaltose.

More preferably the characteristic I is that the yeast cell is capable of utilizing isomaltose as the sole carbon source. Thus, the yeast cell is capable of growing in a medium containing isomaltose as the sole carbon source. Such medium preferably do not contain any mono- and/or disaccharides apart from isomaltose, and more preferably such medium does not contain any carbohydrates apart from isomaltose.

Even if a yeast cell is capable of fermenting isomaltose, this does not necessarily mean that said yeast cell is capable of utilizing isomaltose as the sole carbon source. Thus, it is preferred that the yeast cell is capable both of utilizing isomaltose, and of utilizing isomaltose as the sole carbon source.

In particular the characteristic I may be that the yeast cell is capable of growing in a medium containing in the range of 1 to 5 g/L, for example in the range of 1 to 3 g/L, such as 2 g/L isomaltose as the sole carbon source. Such medium preferably do not contain any carbohydrates apart from said concentration of isomaltose.

One useful method for determining whether a yeast cell is capable of utilizing isomaltose as sole carbon source is described herein below in Example 5.

Yeast cells having characteristic I, preferably also have one or more of genotypes IV, V and VI, more preferably all of genotypes IV, V and VI described below.

Characteristic II

The yeast cell according to the invention may have the characteristic II, wherein characteristic II is that the yeast cell is capable of utilizing panose. Thus, upon incubation in a medium containing panose, then said yeast cell is capable of removing at least part of said panose. Preferably, said yeast cell is capable of removing (e.g. capable of fermenting) at least 45%, such as at least 50%, for example at least 60% of the panose in said medium. Said medium may in particular be wort. Preferably, said yeast cell is capable of removing aforementioned amount of panose when incubated in said wort until diacetyl is in spec, e.g. for 4 to 6 days, e.g. for 5 days. Incubation may for example be at 16 to 18° C. Thus, said yeast cell may be capable of removing at least 45%, such as at least 50%, for example at least 60% of the panose present in wort when determined by fermenting wort as described herein below in Example 5.

More preferably the characteristic II is that the yeast cell is capable of utilizing panose as the sole carbon source. Thus, the yeast cell is capable of growing in a medium containing panose as the sole carbon source. Such medium preferably do not contain any mono-, di- and/or trisaccharides apart from panose, and more preferably such medium does not contain any carbohydrates apart from panose.

Even if a yeast cell is capable of fermenting panose, this does not necessarily mean that said yeast cell is capable of utilizing panose as the sole carbon source. In one embodiment the yeast cell is capable both of utilizing panose, and of utilizing panose as the sole carbon source.

In particular the characteristic II may be that the yeast cell is capable of growing in a medium containing in the range of 1 to 5 g/L, for example in the range of 1 to 3 g/L, such as 2 g/L panose as the sole carbon source. Such medium preferably do not contain any carbohydrates apart from said concentration of panose.

One useful method for determining whether a yeast cell is capable of utilizing panose as sole carbon source is described herein below in Example 5.

Yeast cells having characteristic II, preferably also have one or more of genotypes IV, V and VI, more preferably all of genotypes IV, V and VI described below.

Characteristic III

The yeast cell according to the invention may have the characteristic III, wherein characteristic III is that the yeast cell is capable of utilizing dipeptides. Thus, upon incubation in a medium containing dipeptides, then said yeast cell is capable of removing at least part of said dipeptides.

More preferably the characteristic III is that the yeast cell is capable of utilizing dipeptides as the sole nitrogen source. Thus, the yeast cell is capable of growing in a medium containing dipeptides as the sole nitrogen source. Such medium preferably do not contain any amino acids and peptides apart from dipeptides, and more preferably such medium does not contain any amino acids, peptides and ammonium apart from dipeptides.

The characteristic III may be that the yeast cell is capable of utilizing any dipeptide as the sole nitrogen source. However, it is also possible that said yeast is capable of utilizing only one or more specific dipeptides as the sole nitrogen source.

It is preferred that characteristic III is that the yeast cell is capable of utilizing at least one, such as at least two, for example at least three, such as at least 4, for example at least 5, such as all of the following dipeptides:
Met-Tyr
Leu-Tyr
Val-Met
Phe-Tyr
Ile-Leu
Ile-Asn.

In one embodiment, the characteristic III is that the yeast cell is capable of utilizing at least one, such as at least 3, for example at least 5, such as at least 7, for example at least 9, such as all of the following dipeptides:
Gly-Arg
Ile-Asn
Lys-Tyr
Met-Lys
Val-Ala
Val-Asn
Val-Gly
Val-Gln
Val-Met
Val-Ser The characteristic III may also be that the yeast cell is capable of utilizing one or more dipeptides of the formula Val-Xaa, wherein Xaa denotes any amino acid. For example, the characteristic III may be that the yeast cell is capable of utilizing at least 3, such as at least 4, for example at least t6 different dipeptides of the formula Val-Xaa. In particular, Xaa may be an amino acid selected from the group consisting of Ala, Asn, Gly, Gln, Met and Ser.

Characteristic III may also be that the yeast cell is capable of utilizing one or more dipeptides of the formula Ala-Xaa, wherein Xaa denotes any amino acid. In particular, Xaa may be an amino acid selected from the group consisting of Glu, Gly, His and Thr. Frequently, the capability of utilizing a dipeptide of the formula Ala-Xaa is connected with the capability of utilizing allantoate that is an intermediate of allantoine catabolism. Thus, it is preferred that the yeast cell furthermore is capable of utilizing allantoine as sole nitrogen source.

The characteristic III may also be that the yeast cell is capable of utilizing one or more of the following dipeptides, for example at least 3 of the following dipeptides, such as at least 5 of the following dipeptides, such as all of the following dipeptides:

Met-Tyr
Leu-Tyr
Val-Met
Phe-Tyr
Ile-Leu
Ile-Asn
Ala-Xaa, wherein Xaa is any amino acid and preferably Xaa is Glu, Gly, His or Thr.

One useful method for determining whether a yeast cell is capable of utilizing dipeptides as sole nitrogen source is described herein below in Example 6. The skilled person will understand that the methods described in Example 6 can be used to test whether any dipeptide can be utilized as sole nitrogen source by exchanging the tested dipeptides.

Yeast cells having characteristic III, preferably also have one or more of genotypes I, II and III, more preferably all of genotypes I, II and III described below.

Characteristic IV

The yeast cell according to the invention may have the characteristic IV, wherein characteristic IV is that the yeast cell is capable of utilizing tripeptides. Thus, upon incubation in a medium containing tripeptides, then said yeast cell is capable of removing at least part of said tripeptides.

More preferably the characteristic IV is that the yeast cell is capable of utilizing tripeptides as the sole nitrogen source. Thus, the yeast cell is capable of growing in a medium containing tripeptides as the sole nitrogen source. Such medium preferably do not contain any amino acids and peptides apart from tripeptides, and more preferably such medium does not contain any amino acids, peptides and ammonium apart from tripeptides.

The characteristic IV may be that the yeast cell is capable of utilizing any tripeptide as the sole nitrogen source. However, it is also possible that said yeast is capable of utilizing only one or more specific tripeptides as the sole nitrogen source.

It is preferred that characteristic IV is that the yeast cell is capable of utilizing the tripeptide Gly-Gly-Gly as the sole nitrogen source.

One useful method for determining whether a yeast cell is capable of utilizing tripeptides as sole nitrogen source is described herein below in Example 6. The skilled person will understand that the methods described in Example 6 can be used to test whether any tripeptide can be utilized as sole nitrogen source by exchanging the tested tripeptides. Yeast cells having characteristic IV, preferably also have one or more of genotypes I, II and III, more preferably at least genotypes II and III described below.

Characteristic V

The yeast cell according to the invention may have the characteristic V, wherein characteristic V is a high utilization of amino acids.

In general it is preferred that the yeast cell of the invention is capable of utilizing amino acids to a high degree. This both ensures that energy stored in amino acids can be utilized as well as ensuring a low level of amino acids after fermentation. Thus, if said yeast is used for preparation of beer, then the final beer will have a low level of amino acids. Strecker aldehydes are important constituents of the "aged" flavor in beer that partly originate from the amino acids of the bottled beer itself. Amino acids that have been shown to be involved in formation of Strecker aldehydes with a low sensory threshold include valine, isoleucine, leucine, methionine and phenylalanine (Table 2). Strecker aldehyde formation plays a crucial role because an increase in their concentration, gives an increasing sensory perception of "aged flavours".

Accordingly, it is an advantage of the yeast according to the present invention that the yeast cell is capable of utilizing amino acids to a higher degree than both conventional lager yeast and ale yeasts.

Thus, it is preferred that the yeast cells of the invention have characteristic V, wherein the characteristic V is that said yeast cells are capable of reducing the level of one or more amino acids to no more than 10% of the starting concentration after incubation for 5 days under conditions allowing growth of said yeast cells. In particular, characteristic V may be that the yeast cell is capable of reducing the level of at least 12, such as at least 13, for example of at least 14 different amino acids to less than 10% of the starting concentration after incubation for 5 days under conditions allowing growth of said yeast cells. For example the yeast cell may be able to reduce in the range of 12 to 20, such as in the range of 14 to 20 amino to no more than 10% of the starting concentration after incubation for 5 days under conditions allowing growth of said yeast cells.

The characteristic V may also be that the yeast cell is capable of reducing the total level of amino acids to less than 30%, such as less than 25% of the starting concentration after incubation for 5 days under conditions allowing growth of said yeast cells.

The characteristic V may also be that the yeast cell is capable of reducing the level of one or more amino acids to no more than 5% of the starting concentration after incubation for 5 days under conditions allowing growth of said yeast cells. In particular, characteristic V may be that the yeast cell is capable of reducing the level of at least 10, such as at least 11, for example of at least 13 different amino acids to less than 5% of the starting concentration after incubation for 5 days under conditions allowing growth of said yeast cells.

The characteristic V may also be that the yeast cell is capable of reducing the level of one or more amino acids to no more than 1% of the starting concentration after incubation for 5 days under conditions allowing growth of said yeast cells. In particular, characteristic V may be that the yeast cell is capable of reducing the level of at least 5, such as at least 6, for example of at least 7 different amino acids to less than 1% of the starting concentration after incubation for 5 days under conditions allowing growth of said yeast cells.

The characteristic V may also be that the yeast cell is capable of reducing the level of one or more of the Strecker aldehyde forming amino acids. Thus, characteristic V may be that the yeast cell is capable of reducing the level of Met to less than 10%, preferably less than 5%, even more preferably to at the most 2%, yet more preferably to less than 1% of the starting concentration after incubation for 5 days under conditions allowing growth of said yeast cells. In particular, the yeast cell may be capable of removing essentially all Met after incubation for 5 days under conditions allowing growth of said yeast cells. Characteristic V may also be that the yeast cell is capable of reducing the level of Val to less than 10%, preferably less than 5%, even more preferably to at the most 2% of the starting concentration after incubation for 5 days under conditions allowing growth of said yeast cells. The characteristic V may also be that the yeast cell is capable of reducing the level of Ile to less than 10%, preferably less than 5%, even more preferably to at the most 2%, yet more preferably to less than 1% of the starting concentration after incubation for 5 days under conditions allowing growth of said yeast cells. In particular, the yeast cell may be capable of removing essentially all Ile after incubation for 5 days under conditions allowing growth of said yeast cells. The characteristic V may also be that the yeast cell is capable of reducing the level of Leu to less than 10%, preferably less than 5%, even more preferably to at the most 2% of the starting concentration after incubation for 5 days under conditions allowing growth of said yeast cells. The characteristic V may also be that the yeast cell is capable of reducing the level of Phe to less than 10%, preferably less than 5%, even more preferably to at the most 2%, yet more preferably to less than 1% of the starting concentration after incubation for 5 days under conditions allowing growth of said yeast cells. In particular, the yeast cell may be capable of removing essentially all Phe after incubation for 5 days under conditions allowing growth of said yeast cells.

The term "removing essentially all" is used herein to denote that the amino acid is removed to a level, which is below the detection level, when the detection is performed by UPLC.

It is also comprised within the present invention that characteristic V is that the yeast cell is capable of reducing the level of at least 2, preferably of at least 3, more preferably of at least 4, yet more preferably of all of the amino acids Met, Val, Ile, Leu and Phe to less than 10%, preferably less than 5%, even more preferably to at the most 2% of the starting concentration after incubation for 5 days under conditions allowing growth of said yeast cells.

The characteristic V may also be that the yeast cells are capable of utilizing at least 80% of at least one of the amino acids Met, Val, Ile, Leu and Phe, when said yeast cell is added to a wort composition having a sugar content of at least 10° Plato and incubated until level of diacetyl is in spec.

It is also preferred that the yeast cells of the invention have the characteristic V, wherein said characteristic V is that the yeast cells are capable of reducing the total level of the amino acids Met, Val, Ile, Leu and/or Phe to at the most 400 mg/L, such as at the most 100 mg/L, such as at the most 50 mg/L, for example to at the most 10 mg/L after incubation for 6 days under conditions allowing growth of said yeast cell.

The characteristic V may also be a combination of any of the aforementioned characteristic Vs described in this section. Thus for example, the characteristic V may be that the yeast cell is capable of reducing the level of at least 12, such as at least 13, for example of at least 14 different amino acids to less than 10% and is capable of reducing the total level of amino acids to less than 30%, such as less than 25% of the starting concentration after incubation for 5 days under conditions allowing growth of said yeast cells. The characteristic V may also be that the yeast cell is capable of reducing the level of at least 10 amino acids to less than 5% and is capable of reducing the total level of amino acids to less than 30%, such as less than 25% of the starting concentration after incubation for 5 days under conditions allowing growth of said yeast cells. The characteristic V may also be that the yeast cell is capable of reducing the level of at least 5 amino acids to less than 1% and is capable of reducing the total level of amino acids to less than 30%, such as less than 25% of the starting concentration after incubation for 5 days under conditions allowing growth of said yeast cells. Conditions allowing growth of said yeast cells are described herein below in the section "Method for producing a beverage". Said conditions may be any of the fermentation conditions described in that section. E.g. said conditions may be incubation at a temperature in the range of 10 to 20° C. in wort. The level of amino acids may be determined by any useful method, e.g. using HPLC or UPLC. Useful methods for determining whether a yeast cell has a high utilization of amino acids are described herein below in Examples 4 and 9.

Characteristic VI

The yeast cell according to the invention may have the characteristic VI, wherein characteristic VI is high production of alcohol. Since the amount of alcohol produced by a given yeast cell is highly influenced by the starting material, it is preferred that the characteristic I is that the yeast cell is capable of generating at least 4.7 promille ethanol per ° Plato. ° Plato is a measure for the density of a liquid, and thus indicates the level of sugars and other fermentable nutrients.

In particular, it is preferred that the yeast cell is capable of generating at least 4.7 promille ethanol per ° Plato, when said yeast cell is added to a wort composition having a sugar content of at least 10° Plato and incubated until level of diacetyl is in spec.

Preferably, the diacetyl is considered to be in spec when the level of diacetyl is at the most 30 ppb.

Characteristic VII

The yeast cell according to the invention may have the characteristic VII, wherein characteristic VII is a high real degree of fermentation (RDF).

The RDF measures the degree to which sugar in the starting liquid has been fermented into alcohol. Thus, if the starting liquid is a wort the RDF measures the degree to which sugar in the wort has been fermented into alcohol in the resulting beer.

It is preferred that the yeast cell according to the invention has characteristic VII, wherein characteristic VII is that the yeast cell is capable of fermenting sugar with an RDF of at least 68%, such as at least 69%, for example at least 70%, and more preferably with an RDF of at least 71%.

In particular it is preferred that the yeast cell is capable of fermenting sugar with an RDF, which is higher than the RDF of at least one of the parental strains. Thus, the yeast cell according to the invention may be a hybrid yeast cell, which is capable of fermenting sugar with an RDF which is at least 1% higher, for example at least 2% higher than the RDF of one of the parental strains. In particular the yeast cell according to the invention may be a hybrid between a parent S. pastorianus strain and a parent S. cerevisiae strain. In such embodiments, the yeast cell may be capable of fermenting sugar with an RDF at least 1 higher than the RDF of the parent S. pastorianus strain. The yeast cell according to the invention may also be a hybrid between a parent S. diastaticus strain and a parent S. cerevisiae strain. In such embodiments, the yeast cell may be capable of fermenting sugar with an RDF at least 1% higher, preferably at least 2% higher than the RDF of the parent S. diastaticus strain.

Characteristic VIII

The yeast cell according to the invention may have the characteristic VIII, wherein characteristic VIII is that the yeast cell is capable of utilizing meliobiose. Thus, upon incubation in a medium containing melibiose, then said yeast cell is capable of removing at least part of said melibiose.

More preferably the characteristic VIII is that the yeast cell is capable of utilizing melibiose as the sole carbon source. Thus, the yeast cell is capable of growing in a medium containing melibiose as the sole carbon source. Such medium preferably do not contain any mono- and/or di saccharides apart from melibiose, and more preferably such medium does not contain any carbohydrates apart from melibiose.

One useful method for determining whether a yeast cell is capable of utilizing melibiose as sole carbon source is described herein below in Example 7.

Characteristic IX

The yeast cell according to the invention may have the characteristic IX, wherein characteristic IX is that the yeast cell is capable of utilizing disaccharides and/or trisaccharides. Thus, upon incubation in a medium containing disaccharides and/or trisaccharides, then said yeast cell is capable of removing at least part of said disaccharides and/or trisaccharides.

More preferably the characteristic IX is that the yeast cell is capable of utilizing disaccharides and/or trisaccharides as the sole carbon source. Thus, the yeast cell is capable of growing in a medium containing disaccharides and/or trisaccharides as the sole carbon source. Such medium preferably do not contain any saccharides apart from the disaccharides and/or trisaccharides.

The characteristic IX may be that the yeast cell is capable of utilizing any disaccharide and trisaccharide as the sole carbon source. However, it is also possible that said yeast is capable of utilizing only one or more specific disaccharides and/trisaccharides as the sole carbon source. As described above it is preferred that the yeast cells are capable of utilizing isomaltose (characteristic I), panose (characteristic II), and/or melibiose (characteristic VIII).

Thus, the characteristic IX is preferably that the yeast cell is capable of utilizing one or more disaccharide and/or trisaccharide, which is not isomaltose, panose, or melibiose. Thus, characteristic IX may be that the yeast cell is capable of utilizing one or more disaccharides and/or trisaccharides in addition to isomaltose, panose, or melibiose. The yeast cell may thus be capable of utilizing one or more disaccharide and/or trisaccharide, which is not isomaltose, panose, or melibiose as sole carbon source, and in addition said yeast cell may have one or more of characteristics I, II or VIII.

It is preferred that characteristic IX is that the yeast cell is capable of utilizing at least one, such as at least two, for example at least three, such as at least 4, for example at least 5, such as all disaccharides selected from the group consisting of kojibiose, nigerose, sucrose, turanose, leucrose, and palatinose as sole carbon source.

It is also preferred that characteristic IX is that the yeast cell is capable of utilizing maltotriose and/or isomaltotriose as sole carbon source.

Thus, the yeast cells may be capable of utilizing maltotriose as the sole carbon source. Thus, the yeast cell may be capable of growing in a medium containing maltotriose as the sole carbon source. Such medium preferably do not contain any mono- and/or disaccharides and/or trisaccharides apart from maltotriose, and more preferably such medium does not contain any carbohydrates apart from maltotriose.

In particular the characteristic IX may be that the yeast cell is capable of growing in a medium containing in the range of 1 to 5 g/L, for example in the range of 1 to 3 g/L, such as 2 g/L maltotriose as the sole carbon source. Such medium preferably do not contain any carbohydrates apart from said concentration of maltotriose.

Many yeast cells, e.g. many lager yeast cells are not capable of utilizing maltotriose as sole carbon source, in particular many lager yeast cells are not capable of utilizing maltotriose as sole carbon source, when maltotriose is present only at low levels.

The yeast cells may be capable of utilizing maltulose as the sole carbon source. Thus, the yeast cell may be capable of growing in a medium containing maltulose as the sole carbon source. Such medium preferably do not contain any mono- and/or disaccharides apart from maltulose, and more preferably such medium does not contain any carbohydrates apart from maltulose.

In particular the characteristic IX may be that the yeast cell is capable of growing in a medium containing in the range of 1 to 5 g/L, for example in the range of 1 to 3 g/L, such as 2 g/L maltulose as the sole carbon source. Such medium preferably do not contain any carbohydrates apart from said concentration of maltulose.

Many yeast cells, e.g. many lager yeast cells are not capable of utilizing maltulose as sole carbon source.

The yeast cells may be capable of utilizing kojibiose as the sole carbon source. Thus, the yeast cell may be capable of growing in a medium containing kojibiose as the sole carbon source. Such medium preferably do not contain any mono- and/or disaccharides apart from kojibiose, and more preferably such medium does not contain any carbohydrates apart from kojibiose.

In particular the characteristic IX may be that the yeast cell is capable of growing in a medium containing in the range of 1 to 5 g/L, for example in the range of 1 to 3 g/L, such as 2 g/L kojibiose as the sole carbon source. Such medium preferably do not contain any carbohydrates apart from said concentration of kojibiose.

Many yeast cells, e.g. many lager yeast cells are not capable of utilizing kojibiose as sole carbon source.

Thus, the yeast cells according to the invention may be capable of utilizing one or more of the disaccharides and/or trisaccharides described in Table 13.

TABLE 13

| Substrate | Linkage |
|---|---|
| Disaccharides (Glc → Glu) | |
| Kojibiose | O-α-D-glucosyl-(1→2)-α-D-glucose |
| Nigerose | O-α-D-glucosyl-(1→3)-α-D-glucose |
| Isomaltose | O-α-D-glucosyl-(1→6)-α-D-glucose |
| Disaccharides (Glc → Fru) | |
| Sucrose | O-α-D-glucosyl-(1→2)-β-D-fructose |
| Turanose | O-α-D-glucosyl-(1→3)-D-fructose |
| Maltulose | O-α-D-glucosyl-(1→4)-D-fructose |
| Leucrose | O-α-D-glucosyl-(1→5)-D-fructose |
| Palatinose | O-α-D-glucosyl-(1→6)-D-fructose |
| Trisaccharides | |
| Maltotriose | O-α-D-glucosyl-(1→4)-α-D-glucosyl-(1→4)-D-glucose |
| Isomaltotriose | O-α-D-glucosyl-(1→6)-α-D-glucosyl-(1→6)-D-glucose |
| Panose | O-α-D-glucosyl-(1→6)-α-D-glucosyl-(1→4)-D-glucose |

Useful methods for determining whether a yeast cell is capable of utilizing disaccharides and/or trisaccharides are described herein below in Examples 8 and 11. A useful method for determining whether a yeast cell is capable of utilizing disaccharides and/or trisaccharides as sole carbon source is described herein below in Example 5. The skilled person will understand that the methods described in Example 5 can be used to test whether any disaccharide and/or trisaccharide can be utilized as sole carbon source by exchanging panose/isomaltose, with the disaccharide and/or trisaccharide to be tested.

Yeast cells having characteristic IX, preferably also have one or more of genotypes IV, V and VI, more preferably all of genotypes IV, V and VI described below.

Characteristic X

The yeast cell according to the invention may have the characteristic X, wherein characteristic X is that the yeast cell only has a low number of cells in suspension, in particular the yeast cell has a low number of cells in suspension after incubation in a liquid medium in a container. Said incubation is preferably incubation for 1 to 14 days, such as from 2 to 10 days, for example from 4 to 8 days, for example from 4 to 6 days.

In particular it is preferred that characteristic X is that at the most 12 million, such as at the most 10 million cells/ml are in suspension after incubation for 4 days under conditions allowing growth of said yeast cell. Thus, characteristic X may be that at the most 12 million, such as at the most 10 million cells/ml are in suspension, when said yeast cell is added to a wort composition having a sugar content of at least 10° Plato and incubated for 4 days. Characteristic X may also be that at the most 12 million, such as at the most 10 million cells/ml are in suspension, when said yeast cell is added to a wort composition having a sugar content of at least 10° Plato and incubated for 5 days. Characteristic X may also be that at the most 12 million, such as at the most 10 million cells/ml are in suspension, when said yeast cell is added to a wort composition having a sugar content of at least 10° Plato and incubated for 6 days. Said incubation may for example be at a temperature in the range of 10 to 20° C., such as in the range of 10 to 18° C., for example at 16° C. or 18° C. The starting concentration of yeast cells may for example be in the range of 10 to 20 mill cells/ml, e.g. in the range of 14 to 15 mill cells/ml.

It may also be preferred that characteristic X may be that the yeast cell has a number of cells in suspension per ml which is at the most 80%, such as at the most 70%, for example at the most 60%, such as at the most 50%, for example at the most 40% of the starting number of cells per ml after 4 to 6 days, such as for 5 days incubation under conditions allowing growth of said cells.

For example, characteristic X may be that the yeast cell has a number of cells in suspension per ml which is at the most 80%, such as at the most 70%, for example at the most 60%, such as at the most 50%, for example at the most 40% of the starting number of cells per ml after 4 to 6 days, such as for 5 days incubation in a wort composition having a sugar content of at least 10° Plato. Characteristic X may also be that the yeast cell has a number of cells in suspension per ml which is at the most 80%, such as at the most 70%, for example at the most 60%, such as at the most 50%, for example at the most 40% of the starting number of cells per ml after 6 days incubation in a wort composition having a sugar content of at least 10° Plato. Said incubation may for example be at a temperature in the range of 15 to 20° C., such as in the range of 10 to 18° C., for example at 16° C. or 18° C.

In one embodiment characteristic X is that at the most 25 million, preferably at the most 20 million cells/ml are in suspension after incubation for 7 days under conditions allowing growth of said yeast cell. Thus, characteristic X may be that at the most 25 million, such as at the most 20 million cells/ml are in suspension, when said yeast cell is added to a wort composition having a sugar content of at least 10° Plato and incubated for 7 days at 18° C.

One useful method for determining cells in suspension is described herein below in Example 2.

Characteristic XI

The yeast cell according to the invention may have the characteristic XI, wherein characteristic XI is that the yeast cell is capable of fermenting wort with a time of primary fermentation of at the most 4 days.

In a preferred embodiment of the invention the characteristic XI is that the yeast cell is capable of fermenting wort with a time primary fermentation of at the most 3.5 days.

In another embodiment of the invention the characteristic XI is that the yeast cell is capable of fermenting wort with a time of primary fermentation of at the most 3 days.

The characteristic XI may also be that the yeast cell is capable of fermenting wort with a time of primary fermentation, which is at least one day shorter than the time of primary fermention by at least one of the parental strains under the same conditions. Thus, the yeast cell according to the invention may be a hybrid yeast cell, which is capable of fermenting wort with a time of primary fermentation, which is at least one day shorter than the time of primary fermentation by at least one of the parental strains under the same conditions. In particular the yeast cell according to the invention may be a hybrid between a parent *S. pastorianus* strain and a parent *S. cerevisiae* strain. In such embodiments, the yeast cell may be capable of fermenting wort with a time of primary fermentation, which is at least one day shorter than the time primary fermentation by the parent *S. pastorianus* strain under the same conditions. Said wort may be any standard wort, but is preferably a wort with having a sugar content of at least 10° Plato. Thus, said wort may in particular be a wort having a sugar content of in the range of 10° Plato to 20° Plato. In particular, said wort may be wort having a sugar content of 14 to 16° Plato.

The term "time of primary fermentation" is the time from pitching wort with yeast until the primary fermentation is completed. The primary fermentation is considered completed when the apparent extract is stable and/or when there is no longer active $CO_2$ release. The apparent extract is considered to be stable when the apparent extract between two measurements does not alter by more than +/−15%, preferably by not more than +/−10%.

Yeast may be pitched at any useful level, for example at 10 to 20 mill viable cells/ml, such as 13 to 16 mill viable cells/ml, for example 14-15 mill viable cells/ml.

The time of primary fermentation may be determined at a temperature at which the yeast cell is capable of growing. Thus, the time of primary fermentation may be determined at a temperature of in the range of 10 to 25° C., preferably at a temperature in the range of 12 to 20° C., for example in the range of 14 to 18° C.

One method of determining the time of primary fermentation is described in Example 3 herein below.

Genetic Background

The yeast cells according to the invention may have one or more of characteristics I to XI described herein above.

In addition to said characteristics, the yeast cell according to the invention may have one or more of the genotypes I to VI described herein below. Said genotypes may be linked to the characteristics outlined above.

In one embodiment, the yeast cell according to the invention at least has the genotype IV described herein below. In addition to having the genotype IV said yeast may also have one or more of the genotypes I, II, III, V, VI and one or more of the characteristics I to XI.

Thus, in one embodiment of the invention, the yeast cell has at least the genotype IV described below, and the genotype V described below. In addition to having the genotypes IV and V, said yeast may also have one or more of the genotypes I, II, III, VI and one or more of the characteristics I to XI.

Thus, the yeast cell of the invention may have the genotypes I and II. The yeast cell of the invention may also have genotypes I and III. The yeast cell of the invention may also have genotypes I and IV. The yeast cell of the invention may also have genotypes I and V. The yeast cell of the invention may also have genotypes I and VI. The yeast cell of the invention may also have genotypes I, II, and III. The yeast cell of the invention may also have genotypes I, II and IV. The yeast cell of the invention may also have genotypes I, II and V. The yeast cell of the invention may also have genotypes I, II and VI. The yeast cell of the invention may also have genotypes I, II, III and IV. The yeast cell of the invention may also have genotypes I, II, III and V. The yeast cell of the invention may also have genotypes I, II, III and VI. The yeast cell of the invention may also have genotypes I, II, III, IV and V. The yeast cell of the invention may also have genotypes I, II, III, IV and VI. The yeast cell of the invention may also have genotypes I, II, III, IV, V and VI. The yeast cell of the invention may also have genotypes II and III. The yeast cell of the invention may also have genotypes II and IV. The yeast cell of the invention may also have genotypes II and V. The yeast cell of the invention may also have genotypes II and VI. The yeast cell of the invention may also have genotypes II, III and IV. The yeast cell of the invention may also have genotypes II, III and V. The yeast cell of the invention may also have genotypes II, III and VI. The yeast cell of the invention may also have genotypes II, III, IV and V. The yeast cell of the invention may also have genotypes II, III, IV and VI. The yeast cell of the invention may also have genotypes II, III, IV, V and VI. The yeast cell of the invention may also have genotypes III and IV. The yeast cell of the invention may also have genotypes III and V. The yeast cell of the invention may also have genotypes III and VI. The yeast cell of the invention may also have genotypes III, IV and V. The yeast cell of the invention may also have genotypes III, IV and VI. The yeast cell of the invention may also have genotypes III, IV, V and VI. The yeast cell of the invention may also have genotypes IV and V. The yeast cell of the invention may also have genotypes IV and VI. The yeast cell of the invention may also have genotypes IV, V and VI. The yeast cell of the invention may also have genotypes V and VI.

In a preferred embodiment of the invention the yeast cells have all of genotypes I, II, III, IV, V and VI.

In one embodiment of the invention, the yeast cell according to the invention may be a yeast cell comprising the genomic DNA sequence available under DDBJ/EMBL/GenBank accession number LOQJ00000000, in particular the DNA sequence available under DDBJ/EMBL/GenBank the accession number LOQJ00000000, version no. LOQJ01000000. This sequence is provided as a whole Genome Shotgun project and more details on this sequence are provided herein below in the Examples.

In another embodiment of the invention, the yeast cell according to the invention may be a yeast cell comprising the genomic DNA sequence available under DDBJ/EMBL/GenBank accession number LOQJ00000000, in particular the DNA sequence available under DDBJ/EMBL/GenBank the accession number LOQJ00000000, version no. LOQJ01000000. This sequence is provided as a Whole Genome Shotgun project, and more details on this sequence are provided herein below in the Examples.

Based on the genomic sequences provided herein, synthetic yeast chromosomes may be prepared. This may for example be performed as described by Callaway in Nature in 2014 (Nature DOI: doi:10.1038/nature.2014.14941), or by Annaluru et al., Science 4 Apr. 2014: Vol. 344 no, 6179 pp. 55-58 (DOI: 10.1126/science.1249252). Also "Synthetic Yeast 2.0" provides information on how to prepare synthetic yeast chromosomes (see e.g., syntheticyeast.org/). Yeast cells comprising said synthetic yeast chromosomes can be prepared using conventional recombinant technology.

Genotype I

The yeast cell according to the invention may have the genotype I, wherein the genotype I is the presence of a gene encoding DAL5. In particular, it is preferred that the yeast cell according to the invention comprises a gene encoding DAL5 of SEQ ID NO:6 or a functional homologue thereof sharing at least 80%, preferably at least 90%, yet more preferably at least 95%, such as at least 98% sequence identity therewith. Preferably, the genotype I is the presence of a gene encoding DAL5 of SEQ ID NO:6.

In one embodiment of the invention, the genotype I is the presence of at least one allelic gene encoding DAL5, wherein the allelic gene encoding DAL5 encodes DAL5 selected from the group consisting of DAL5 of SEQ ID NO:6, DAL5 of SEQ ID NO:39, DAL5 of SEQ ID NO:40 and functional homologues thereof sharing at least 80%, preferably at least 90%, yet more preferably at least 95%, such as at least 98% sequence identity with any of the aforementioned.

In one embodiment, the genotype I may be the presence of the following 2 allelic genes:
1) a gene encoding DAL5 of SEQ ID NO:39 or a functional homologue thereof sharing at least 80%, preferably at least 90%, yet more preferably at least 95%, such as at least 98% sequence identity therewith; and
2) a gene encoding DAL5 of SEQ ID NO:40 or a functional homologue thereof sharing at least 80%, preferably at least 90%, yet more preferably at least 95%, such as at least 98% sequence identity therewith.

DAL5 is a di-peptide transporter that is transporting di-peptides by non-N-end rule. The yeast cell may for example have genotype I in embodiments of the invention, where the yeast cell has characteristics III, IV and/or VI, in particular when the yeast cell has characteristic III.

Genotype II

The yeast cell according to the invention may have the genotype II, wherein the genotype II is the presence of at least 3 genes encoding PTR2. In particular, it is preferred that the yeast cell according to the invention comprises at least 3 genes encoding PTR2, wherein PTR2 may be selected from the group consisting PTR2 of SEQ ID NO:7, PTR2 of SEQ ID:8, PRT2 of SEQ ID NO:9 and functional homologues of each of the aforementioned sharing at least 80%, preferably at least 90%, yet more preferably at least 95%, such as at least 98% sequence identity therewith.

Thus, the genotype II may be that the yeast cell comprises 3 genes selected from the group consisting of:
1) a gene encoding PRT2 of SEQ ID NO:7 or a functional homologues of each of the aforementioned sharing at least 80%, preferably at least 90%, yet more preferably at least 95%, such as at least 98% sequence identity;
2) a gene encoding PRT2 of SEQ ID NO:8 or a functional homologues of each of the aforementioned sharing at least 80%, preferably at least 90%, yet more preferably at least 95%, such as at least 98% sequence identity; and
3) a gene encoding PRT2 of SEQ ID NO:9 or a functional homologues of each of the aforementioned sharing at least 80%, preferably at least 90%, yet more preferably at least 95%, such as at least 98% sequence identity.

Thus, the genotype II may be that the yeast cell comprises the following 3 genes:
1) a gene encoding PRT2 of SEQ ID NO:7 or a functional homologue thereof sharing at least 80%, preferably at least 90%, yet more preferably at least 95%, such as at least 98% sequence identity therewith;
2) a gene encoding PRT2 of SEQ ID NO:8 or a functional homologue thereof sharing at least 80%, preferably at least 90%, yet more preferably at least 95%, such as at least 98% sequence identity therewith; and
3) a gene encoding PRT2 of SEQ ID NO:9 or a functional homologue thereof sharing at least 80%, preferably at least 90%, yet more preferably at least 95%, such as at least 98% sequence identity therewith.

Thus, the genotype II may be that the yeast cell comprises 3 genes selected from the group consisting of:
1) a gene encoding PRT2 of SEQ ID NO:7;
2) a gene encoding PRT2 of SEQ ID NO:8; and
3) a gene encoding PRT2 of SEQ ID NO:9.

In one embodiment genotype II may be that the yeast cell comprises at least 2 allelic genes encoding PTR2. For example, genotype II may be that the yeast cell comprises at least two allelic genes encoding PTR2 individually selected from the group consisting of genes encoding PTR2 of SEQ ID NO:7, PTR2 of SEQ ID:8, PRT2 of SEQ ID NO:9, PRT2 of SEQ ID NO:37, PRT2 of SEQ ID NO:38, PRT2 of SEQ ID NO:43, PRT2 of SEQ ID NO:44 and functional homologues of each of the aforementioned sharing at least 80%, preferably at least 90%, yet more preferably at least 95%, such as at least 98% sequence identity therewith.

In one embodiment the genotype II may be that the yeast cell comprises the following 2 allelic genes:
1) a gene encoding PRT2 of SEQ ID NO:37 or a functional homologue thereof sharing at least 80%, preferably at least 90%, yet more preferably at least 95%, such as at least 98% sequence identity therewith;
2) a gene encoding PRT2 of SEQ ID NO:38 or a functional homologue thereof sharing at least 80%, preferably at least 90%, yet more preferably at least 95%, such as at least 98% sequence identity therewith.

In one embodiment the genotype II may be that the yeast cell comprises the following 2 allelic genes:
1) a gene encoding PRT2 of SEQ ID NO:43 or a functional homologue thereof sharing at least 80%, preferably at least 90%, yet more preferably at least 95%, such as at least 98% sequence identity therewith;
2) a gene encoding PRT2 of SEQ ID NO:44 or a functional homologue thereof sharing at least 80%, preferably at least 90%, yet more preferably at least 95%, such as at least 98% sequence identity therewith.

PRT2 is a transporter for di- and tripeptides, as well as other peptides into the yeast cell.

The yeast cell may for example have genotype II in embodiments of the invention, where the yeast cell has characteristics III, IV and/or V, such as in embodiment where the yeast cell has characteristics III and/or IV.

Genotype III

The yeast cell according to the invention may have the genotype III, wherein the genotype III is the presence of a gene encoding UBR1. In particular, it is preferred that the yeast cell according to the invention comprises a gene encoding UBR1 comprising SEQ ID NO:10, or UBR1 of SEQ ID NO:11 or a functional homologue of any of the aforementioned sharing at least 80%, preferably at least 90%, yet more preferably at least 95%, such as at least 98% sequence identity therewith. Preferably, the genotype III is the presence of at least two genes encoding UBR1 comprising SEQ ID NO:10, or UBR1 of SEQ ID NO:11 or a functional homologue of any of the aforementioned sharing at least 80%, preferably at least 90%, yet more preferably at least 95%, such as at least 98% sequence identity therewith.

For example the genotype III may be the presence of the following 2 genes:
1) a gene encoding UBR1 comprising SEQ ID NO:10 or SEQ ID NO:45 or a functional homologues of any of the aforementioned sharing at least 80%, preferably at least 90%, yet more preferably at least 95%, such as at least 98% sequence identity therewith; and
2) a gene encoding UBR1 of SEQ ID NO:11 or a functional homologue thereof sharing at least 80%, preferably at least 90%, yet more preferably at least 95%, such as at least 98% sequence identity therewith.

In particular, the genotype III may be the presence of the following 2 genes:
1) a gene encoding UBR1 of comprising SEQ ID NO:10; and
2) a gene encoding UBR1 of SEQ ID NO:11.

The yeast cell may for example have genotype III in embodiments of the invention, where the yeast cell has characteristics III and/or IV.

In one embodiment of the invention genotype III is that the yeast cell comprises at least one allelic genes encoding UBR1 selected from the group consisting of UBR1 comprising SEQ ID NO:10, UBR1 of SEQ ID NO:11, UBR1 comprising SEQ ID NO:41, UBR1 of SEQ ID NO:42, UBR1 comprising SEQ IDN NO:45 and functional homologues of any of the aforementioned sharing at least 80%, preferably at least 90%, yet more preferably at least 95%, such as at least 98% sequence identity therewith.

In one embodiment of the invention genotype III is that the yeast cell comprises at least two allelic genes encoding UBR1 individually selected from the group consisting of UBR1 comprising SEQ ID NO:10, UBR1 of SEQ ID NO:11, UBR1 comprising SEQ ID NO:41, UBR1 of SEQ ID NO:42 and functional homologues of any of the aforementioned sharing at least 80%, preferably at least 90%, yet more preferably at least 95%, such as at least 98% sequence identity therewith.

For example the genotype III may be the presence of the following 2 genes:
1) a gene encoding UBR1 comprising SEQ ID NO:41 or a functional homologues thereof sharing at least 80%, preferably at least 90%, yet more preferably at least 95%, such as at least 98% sequence identity therewith; and
2) a gene encoding UBR1 of SEQ ID NO:42 or a functional homologue thereof sharing at least 80%, preferably at least 90%, yet more preferably at least 95%, such as at least 98% sequence identity therewith.

The yeast cell may for example have genotype III in embodiments of the invention, where the yeast cell has characteristics III, IV and/or V, such as in embodiment where the yeast cell has characteristics III and/or IV.

Genotype IV

The yeast cell according to the invention may have the genotype IV, wherein the genotype IV is the presence of at least 3 allelic genes, preferably at least 4 allelic genes encoding IMA1p. In particular, it is preferred that the yeast cell according to the invention comprises at least 4 allelic genes encoding IMA1p selected from the group consisting of IMA1p of SEQ ID NO:12, IMA1p of SEQ ID NO:13, IMA1p of SEQ ID NO:14, IMA1p of SEQ ID NO:15 and functional homologues of any of the aforementioned sharing at least 80%, preferably at least 90%, yet more preferably at least 95%, such as at least 98% sequence identity therewith.

IMA1p may be encoded by different alleles, for example by the short allele of IMA1, or by the long allele of IMA1. One yeast cell may comprise both long and short alleles of IMA1. In one embodiment, it may be preferred that the yeast cell according to the invention comprises at least 3 long alleles encoding IMA1p.

For example the genotype IV may be the presence of at least 2 short alleles of IMA1. Said two short alleles of IMA1 may be genes encoding IMA1p selected from the group consisting of IMA1p SEQ ID NO:12, IMA1p of SEQ ID NO:13 and functional homologues of any of the aforementioned sharing at least 80%, preferably at least 90%, yet more preferably at least 95%, such as at least 98% sequence identity therewith.

In a preferred embodiment, the genotype IV may be the presence of at least 3 short alleles of IMA1. Said 3 short alleles of IMA1 may be allelic genes encoding IMA1p selected from the group consisting of IMA1p of SEQ ID NO:12, IMA1p of SEQ ID NO:13, IMA1p of SEQ ID NO:1, IMA1p of SEQ ID NO:2, IMA1p of SEQ ID NO:3, IMA1p of SEQ ID NO: 4, IMA1p of SEQ ID NO: 5, IMA1p of SEQ ID NO:33 and functional homologues of any of the aforementioned sharing at least 80%, preferably at least 90%, yet more preferably at least 95%, such as at least 98% sequence identity therewith.

For example the genotype IV may be the presence of at least 2 long alleles of IMA1. Said two long alleles of IMA1 may be genes encoding IMA1p selected from the group consisting of IMA1p of SEQ ID NO:14, IMA1p of SEQ ID NO:15 and functional homologues of any of the aforementioned sharing at least 80%, preferably at least 90%, yet more preferably at least 95%, such as at least 98% sequence identity therewith.

In one embodiment the genotype IV may be the presence of at least 3 long alleles of IMA1. Said 3 long alleles of IMA1 may be genes encoding IMA1p selected from the group consisting of IMA1p of SEQ ID NO:21, IMA1p of SEQ ID NO:22, IMA1p of SEQ ID NO:3, IMA1p of SEQ ID NO:24, IMA1p of SEQ ID NO:25 and functional homologues of any of the aforementioned sharing at least 80%, preferably at least 90%, yet more preferably at least 95%, such as at least 98% sequence identity therewith.

In a preferred embodiment, the genotype IV may be the presence of at least 3 short alleles of IMA1 and at least 2 long alleles of IMA1, wherein
a) said 3 short alleles of IMA1 individually are genes encoding IMA1p selected from the group consisting of of IMA1p of SEQ ID NO:12, IMA1p of SEQ ID NO:13, IMA1p of SEQ ID NO:1, IMA1p of SEQ ID NO:2, IMA1p of SEQ ID NO:3, IMA1p of SEQ ID NO: 4, IMA1p of SEQ ID NO: 5, IMA1p of SEQ ID NO:33 and functional homologues of any of the aforementioned sharing at least 80%, preferably at least 90%, yet more preferably at least 95%, such as at least 98% sequence identity therewith; and
b) said 2 long alleles of IMA1 individually are genes encoding IMA1p selected from the group consisting of IMA1p of SEQ ID NO:14, IMA1p of SEQ ID NO:15, IMA1p of SEQ ID NO:21, IMA1p of SEQ ID NO:22, IMA1p of SEQ ID NO:23, IMA1p of SEQ ID NO:24, IMA1p of SEQ ID NO:25 and functional homologues of any of the aforementioned sharing at least 80%, preferably at least 90%, yet more preferably at least 95%, such as at least 98% sequence identity therewith.

In one embodiment, the genotype IV may be that the yeast cell comprises at least 5 allelic genes encoding IMA1p, wherein said allelic genes individually are selected from the group consisting of genes encoding IMA1p of SEQ ID NO:1, IMA1p of SEQ ID NO:2, IMA1p of SEQ ID NO:3, IMA1p of SEQ ID NO:4, IMA1p of SEQ ID NO:5, IMA1p of SEQ ID NO:12, IMA1p of SEQ ID NO:13, IMA1p of SEQ ID NO:14, IMA1p of SEQ ID NO:15, IMA1p of SEQ ID NO:21, IMA1p of SEQ ID NO:22, IMA1p of SEQ ID NO:23, IMA1p of SEQ ID NO:24, IMA1p of SEQ ID NO:25 and IMA1p of SEQ ID NO:33.

In one embodiment, the genotype IV may be that the yeast cell comprises the following 4 allelic genes:
1) a gene encoding IMA1p of SEQ ID NO:12 or a functional homologue thereof sharing at least 80%, preferably at least 90%, yet more preferably at least 95%, such as at least 98% sequence identity therewith; and
2) a gene encoding IMA1p of SEQ ID NO:13 or a functional homologue thereof sharing at least 80%, preferably at least 90%, yet more preferably at least 95%, such as at least 98% sequence identity therewith; and
3) a gene encoding IMA1p of SEQ ID NO:14 or a functional homologue thereof sharing at least 80%, preferably at least 90%, yet more preferably at least 95%, such as at least 98% sequence identity therewith; and
4) a gene encoding IMA1p of SEQ ID NO:15 or a functional homologue thereof sharing at least 80%, preferably at least 90%, yet more preferably at least 95%, such as at least 98% sequence identity therewith.

In one embodiment, the genotype IV may be the presence of the following 4 allelic genes:
1) a gene encoding IMA1p of SEQ ID NO:12; and
2) a gene encoding IMA1p of SEQ ID NO:13; and
3) a gene encoding IMA1p of SEQ ID NO:14; and
4) a gene encoding IMA1p of SEQ ID NO:15.

In one embodiment, the genotype IV may be the presence of the following 3 allelic genes:
1) two genes both encoding IMA1p of SEQ ID NO:21 or a functional homologue thereof sharing at least 80%, preferably at least 90%, yet more preferably at least 95%, such as at least 98% sequence identity therewith; and
2) a gene encoding IMA1p of SEQ ID NO:22 or a functional homologue thereof sharing at least 80%, preferably at least 90%, yet more preferably at least 95%, such as at least 98% sequence identity therewith.

In one embodiment, the genotype IV may be the presence of the following 3 allelic genes:
1) a gene encoding IMA1p of SEQ ID NO:23 or a functional homologue thereof sharing at least 80%, preferably at least 90%, yet more preferably at least 95%, such as at least 98% sequence identity therewith; and
2) a gene encoding IMA1p of SEQ ID NO:24 or a functional homologue thereof sharing at least 80%, preferably at least 90%, yet more preferably at least 95%, such as at least 98% sequence identity therewith; and
3) a gene encoding IMA1p of SEQ ID NO:25 or a functional homologue thereof sharing at least 80%, preferably at least 90%, yet more preferably at least 95%, such as at least 98% sequence identity therewith.

In one embodiment, the genotype IV may be the presence of the following 5 allelic genes:

3) a gene encoding IMA1p of SEQ ID NO:12 or a functional homologue thereof sharing at least 80%, preferably at least 90%, yet more preferably at least 95%, such as at least 98% sequence identity therewith; and
4) a gene encoding IMA1p of SEQ ID NO:13 or a functional homologue thereof sharing at least 80%, preferably at least 90%, yet more preferably at least 95%, such as at least 98% sequence identity therewith; and
5) a gene encoding IMA1p of SEQ ID NO:1 or a functional homologue thereof sharing at least 80%, preferably at least 90%, yet more preferably at least 95%, such as at least 98% sequence identity therewith; and
6) a gene encoding IMA1p of SEQ ID NO:14 or a functional homologue thereof sharing at least 80%, preferably at least 90%, yet more preferably at least 95%, such as at least 98% sequence identity therewith; and
7) a gene encoding IMA1p of SEQ ID NO:15 or a functional homologue thereof sharing at least 80%, preferably at least 90%, yet more preferably at least 95%, such as at least 98% sequence identity therewith.

In one embodiment, the genotype IV may be the presence of the following 6 allelic genes:
1) a gene encoding IMA1p of SEQ ID NO:2 or a functional homologue thereof sharing at least 80%, preferably at least 90%, yet more preferably at least 95%, such as at least 98% sequence identity therewith; and
2) at least two genes encoding IMA1p of SEQ ID NO:3 or a functional homologue thereof sharing at least 80%, preferably at least 90%, yet more preferably at least 95%, such as at least 98% sequence identity therewith; and
3) at least two genes encoding IMA1p of SEQ ID NO:21 or a functional homologue thereof sharing at least 80%, preferably at least 90%, yet more preferably at least 95%, such as at least 98% sequence identity therewith; and
4) a gene encoding IMA1p of SEQ ID NO:22 or a functional homologue thereof sharing at least 80%, preferably at least 90%, yet more preferably at least 95%, such as at least 98% sequence identity therewith.

In one embodiment, the genotype IV may be the presence of the following 6 allelic genes:
1) a gene encoding IMA1p of SEQ ID NO:5 or a functional homologue thereof sharing at least 80%, preferably at least 90%, yet more preferably at least 95%, such as at least 98% sequence identity therewith; and
2) at least two genes encoding IMA1p of SEQ ID NO:33 or a functional homologue thereof sharing at least 80%, preferably at least 90%, yet more preferably at least 95%, such as at least 98% sequence identity therewith; and
3) at least two genes encoding IMA1p of SEQ ID NO:4 or a functional homologue thereof sharing at least 80%, preferably at least 90%, yet more preferably at least 95%, such as at least 98% sequence identity therewith; and
4) a gene encoding IMA1p of SEQ ID NO:24 or a functional homologue thereof sharing at least 80%, preferably at least 90%, yet more preferably at least 95%, such as at least 98% sequence identity therewith; and
5) at least two genes encoding IMA1p of SEQ ID NO:23 or a functional homologue thereof sharing at least 80%, preferably at least 90%, yet more preferably at least 95%, such as at least 98% sequence identity therewith; and
6) a gene encoding IMA1p of SEQ ID NO:25 or a functional homologue thereof sharing at least 80%, preferably at least 90%, yet more preferably at least 95%, such as at least 98% sequence identity therewith.

The yeast cell may for example have genotype IV in embodiments of the invention, where the yeast cell has characteristics I, II, IX and/or XI.

Genotype V

The yeast cell according to the invention may have the genotype V, wherein the genotype V is the presence of a gene encoding IMA5p. The genotype V may also be the presence of at least two allelic genes encoding IMA5p. In particular, it is preferred that the yeast cell according to the invention comprises at least one allelic gene encoding IMA5p selected from the group consisting of IMA5p of SEQ ID NO:16, IMA5p of SEQ ID NO:17 and functional homologues of any of the aforementioned sharing at least 80%, preferably at least 90%, yet more preferably at least 95%, such as at least 98% sequence identity therewith. Preferably, the genotype V is the presence of at least two genes encoding IMA5p of SEQ ID NO:16, or IMA5p of SEQ ID NO:17 or a functional homologue of any of the aforementioned sharing at least 80%, preferably at least 90%, yet more preferably at least 95%, such as at least 98% sequence identity therewith.

In one embodiment the yeast cell comprises at least two allelic genes encoding IMA5p individually selected from allelic genes encoding IMA5p of SEQ ID NO:16, IMA5p of SEQ ID NO:17, IMA5p of SEQ ID NO:34, IMA5p of SEQ ID NO:35, IMA5p of SEQ ID NO:36 and functional homologues of any of the aforementioned sharing at least 80%, preferably at least 90%, yet more preferably at least 95%, such as at least 98% sequence identity therewith.

In particular, the genotype V may be that the yeast cell comprises the following 2 allelic genes:
1) a gene encoding IMA5p of SEQ ID NO:16 or a functional homologue thereof sharing at least 80%, preferably at least 90%, yet more preferably at least 95%, such as at least 98% sequence identity therewith; and
2) a gene encoding IMA5p of SEQ ID NO:17 or a functional homologue thereof sharing at least 80%, preferably at least 90%, yet more preferably at least 95%, such as at least 98% sequence identity therewith.

In one embodiment, the genotype V may be that the yeast cell comprises the following 3 allelic genes:
1) a gene encoding IMA5p of SEQ ID NO:16 or a functional homologue thereof sharing at least 80%, preferably at least 90%, yet more preferably at least 95%, such as at least 98% sequence identity therewith; and
2) a gene encoding IMA5p of SEQ ID NO:17 or a functional homologue thereof sharing at least 80%, preferably at least 90%, yet more preferably at least 95%, such as at least 98% sequence identity therewith; and
3) a gene encoding IMA5p of SEQ ID NO:34 or a functional homologue thereof sharing at least 80%, preferably at least 90%, yet more preferably at least 95%, such as at least 98% sequence identity therewith.

In one embodiment, the genotype V may be that the yeast cell comprises the following 2 allelic genes:

1) a gene encoding IMA5p of SEQ ID NO:35 or a functional homologue thereof sharing at least 80%, preferably at least 90%, yet more preferably at least 95%, such as at least 98% sequence identity therewith; and
2) a gene encoding IMA5p of SEQ ID NO:36 or a functional homologue thereof sharing at least 80%, preferably at least 90%, yet more preferably at least 95%, such as at least 98% sequence identity therewith.

In particular, the genotype V may be the presence of the following 2 genes:
1) a gene encoding IMA5p of SEQ ID NO:16; and
2) a gene encoding IMA5p of SEQ ID NO:17.

The yeast cell may for example have genotype V in embodiments of the invention, where the yeast cell has characteristics I, II, IX and/or XI.

Genotype VI

The yeast cell according to the invention may have the genotype VI, wherein the genotype VI is the presence of at least 3 allelic genes encoding AGT1. In particular, it is preferred that the yeast cell according to the invention comprises at least 3 allelic genes encoding AGT1 selected from the group consisting of AGT1 of SEQ ID NO:18, AGT1 of SEQ ID NO:19, AGT1 of SEQ ID NO:20, AGT1 of SEQ ID NO:26, AGT1 of SEQ ID NO:27, AGT1 of SEQ ID NO:28, AGT1 of SEQ ID NO:29, AGT1 of SEQ ID NO:30, AGT1 of SEQ ID NO:31, AGT1 of SEQ ID NO:32 and functional homologues of any of the aforementioned sharing at least 80%, preferably at least 90%, yet more preferably at least 95%, such as at least 98% sequence identity therewith.

In one embodiment the yeast cell may have the genotype VI, wherein the genotype VI is the presence of at least 2 allelic genes encoding full length AGT1. In particular, it is preferred that the yeast cell according to the invention comprises at least 2 allelic genes encoding AGT1 selected from the group consisting of AGT1 of SEQ ID NO:18, AGT1 of SEQ ID NO:19, AGT1 of SEQ ID NO:20, AGT1 of SEQ ID NO:27, AGT1 of SEQ ID NO:28, AGT1 of SEQ ID NO:30, AGT1 of SEQ ID NO:31, AGT1 of SEQ ID NO:32 and functional homologues of any of the aforementioned sharing at least 80%, preferably at least 90%, yet more preferably at least 95%, such as at least 98% sequence identity therewith.

In one embodiment, the genotype VI may be that the yeast cell comprises the following 3 allelic genes:
1) a gene encoding AGT1 of SEQ ID NO:18 or a functional homologue thereof sharing at least 80%, preferably at least 90%, yet more preferably at least 95%, such as at least 98% sequence identity therewith; and
2) a gene encoding AGT1 of SEQ ID NO:19 or a functional homologue thereof sharing at least 80%, preferably at least 90%, yet more preferably at least 95%, such as at least 98% sequence identity therewith; and
3) a gene encoding AGT1 of SEQ ID NO:20 or a functional homologue thereof sharing at least 80%, preferably at least 90%, yet more preferably at least 95%, such as at least 98% sequence identity therewith.

In particular, the genotype VI may be the presence of the following 3 allelic genes:
1) a gene encoding AGT1 of SEQ ID NO:18; and
2) a gene encoding AGT1 of SEQ ID NO:19; and
3) a gene encoding AGT1 of SEQ ID NO:20.

In one embodiment, the genotype VI may be that the yeast cell comprises at the following two genes encoding AGT1:
1) a gene encoding AGT1 of SEQ ID NO:27 or a functional homologue thereof sharing at least 80%, preferably at least 90%, yet more preferably at least 95%, such as at least 98% sequence identity therewith; and
2) a gene encoding AGT1 of SEQ ID NO:28 or a functional homologue thereof sharing at least 80%, preferably at least 90%, yet more preferably at least 95%, such as at least 98% sequence identity therewith.

In one embodiment, the genotype VI may be that the yeast cell comprises the following 3 allelic genes encoding AGT1:
1) a gene encoding AGT1 of SEQ ID NO:30 or a functional homologue thereof sharing at least 80%, preferably at least 90%, yet more preferably at least 95%, such as at least 98% sequence identity therewith; and
2) gene encoding AGT1 of SEQ ID NO:31 or a functional homologue thereof sharing at least 80%, preferably at least 90%, yet more preferably at least 95%, such as at least 98% sequence identity therewith; and
3) a gene encoding AGT1 of SEQ ID NO:32 or a functional homologue thereof sharing at least 80%, preferably at least 90%, yet more preferably at least 95%, such as at least 98% sequence identity therewith.

The yeast cell may for example have genotype VI in embodiments of the invention, where the yeast cell has characteristics I, II, IX and/or XI.

Functional Homologue

The term "functional homologue" as used herein denotes a polypeptide sharing at least one biological function with a reference polypeptide. In general said functional homologue also shares a significant sequence identity with the reference polypeptide. Preferably a functional homologue of a reference polypeptide is a polypeptide, which has the same biological function as the reference protein and which shares a high level of sequence identity with the reference polypeptide.

A high level of sequence identity indicates likelihood that the first sequence is derived from the second sequence. Amino acid sequence identity requires identical amino acid sequences between two aligned sequences. Thus, a candidate sequence sharing 80% amino acid identity with a reference sequence, requires that, following alignment, 80% of the amino acids in the candidate sequence are identical to the corresponding amino acids in the reference sequence. Identity according to the present invention is determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available from as a ClustalW WWW Service at the European Bioinformatics Institute www.ebi.ac.uk/clustalw. Using this program with its default settings, the mature (bioactive) part of a query and a reference polypeptide are aligned. The number of fully conserved residues are counted and divided by the length of the reference polypeptide. Thus, sequence identity is determined over the entire length of the reference polypeptide.

It may be preferred that conserved amino acids are retained in the functional homologue. Conserved amino acids may be identified by preparing an alignment of similar polypeptide, and using said alignment identifying amino acids residues conserved between the polypeptides. Examples of useful alignments are shown herein in FIGS. 5-12.

Method for Producing a Beverage

It is an aspect of the invention to provide methods for producing a beverage, said method comprising the steps of
VIII. Providing a starting liquid
IX. Providing a yeast cell according to the invention, e.g. a yeast cell having one or more of characteristics I to X described above,
X. Fermenting said starting liquid with said yeast cell, thereby producing a beverage.

The starting liquid may in particular be a cereal extract, such as wort. Said starting liquid may for example be prepared by preparing an extract of malt by mashing and optionally sparging as described herein in this section.

Malt is barley kernels that have been malted. By the term "malting" is to be understood germination of steeped barley kernels in a process taking place under controlled environmental conditions, followed by a drying step. Said drying step may preferably be kiln drying of the germinated kernels at elevated temperatures.

This aforementioned sequence of malting events is important for the synthesis of numerous enzymes that cause grain modification, processes that principally depolymerize cell walls of the dead endosperm to mobilize the grain nutrients and activate other depolymerases. In the subsequent drying process, flavour and colour are generated due to chemical browning reactions.

Steeping may be performed by any conventional method known to the skilled person. One non-limiting example involves steeping at a temperature in the range of 10 to 25° C. with alternating dry and wet conditions. Germination may be performed by any conventional method known to the skilled person. One non-limiting example involves germination at a temperature in the range of 10 to 25° C., optionally with changing temperature in the range of 1 to 4 h.

The kiln drying may be performed at conventional temperatures, such as at least 75° C., for example in the range of 80 to 90° C., such as in the range of 80 to 85° C. Thus, the malt may, for example be produced by any of the methods described by Briggs et al. (1981) and by Hough et al. (1982). However, any other suitable method for producing malt may also be used with the present invention, such as methods for production of specialty malts, including, but not limited to, methods of roasting the malt.

Malt may be further processed, for example by milling. Preferably milling is performed in a dry state, i.e. the malt is milled while dry.

The malt, e.g. the milled malt may be mashed to prepare an aqueous extract of said malt. The starting liquid for preparing the beverage may be an aqueous extract of malt, e.g. an aqueous extract of malt prepared by mashing.

Thus, the method for preparing a beverage according to the invention may comprise a step of producing wort by mashing malt and optionally additional adjuncts. Said mashing step may also optionally comprise sparging, and accordingly said mashing step may be a mashing step including a sparging step or a mashing step excluding a sparging step.

In general, wort production is initiated by the milling of malt and/or barley. If additional adjuncts are added, these may also be milled depending on their nature. If the adjunct is a cereal, it may for example be milled, whereas syrups, sugars and the like will generally not be milled. Milling will facilitate water access to grain particles in the mashing phase. During mashing enzymatic depolymerization of substrates initiated during malting may be continued.

In general, wort is prepared by combining and incubating milled malt and water, i.e. in a mashing process. During mashing, the malt/liquid composition may be supplemented with additional carbohydrate-rich adjunct compositions, for example milled barley, maize, or rice adjuncts. Unmalted cereal adjuncts usually contain little or no active enzymes, making it important to supplement with malt or exogenous enzymes to provide enzymes necessary for polysaccharide depolymerization etc.

During mashing, milled malt and/or milled barley—and optionally additional adjuncts are incubated with a liquid fraction, such as water. The incubation temperature is in general either kept constant (isothermal mashing), or gradually increased, for example increased in a sequential manner. In either case, soluble substances in the malt/barley/adjuncts are liberated into said liquid fraction. A subsequent filtration confers separation of wort and residual solid particles, the latter also denoted "spent grain". The wort thus obtained may also be denoted "first wort". Additional liquid, such as water may be added to the spent grains during a process also denoted sparging. After sparging and filtration, a "second wort" may be obtained. Further worts may be prepared by repeating the procedure. Non-limiting examples of suitable procedures for preparation of wort is described by Briggs et al. (supra) and Hough et al. (supra).

As mentioned above, the wort composition may be prepared by mashing unmalted barley kernels. Unmalted barley kernels lack or contain only a limited amount of enzymes beneficial for wort production, such as enzymes capable of degrading cell walls or enzymes capable of depolymerising starch into sugars. Thus, in embodiments of the invention where unmalted barley is used for mashing, it is preferred that one or more suitable, external brewing enzymes are added to the mash. Suitable enzymes may be lipases, starch degrading enzymes (e.g. amylases), glucanases [preferably (1-4)- and/or (1-3,1-4)-β-glucanase], and/or xylanases (such as arabinoxylanase), and/or proteases, or enzyme mixtures comprising one or more of the aforementioned enzymes, e.g. Cereflo, Ultraflo, or Ondea Pro (Novozymes).

The wort composition may also be prepared by using a mixture of malted and unmalted barley kernels, in which case one or more suitable enzymes may be added during preparation. More specifically, barley of the invention can be used together with malt in any combination for mashing—with or without external brewing enzymes—such as, but not limited to, the proportions of barley: malt=approximately 100:0, or approximately 75:25, or approximately 50:50, or approximately 25:75.

In other embodiments of the invention, it is preferred that no external enzymes, in particular that no external protease, and/or no external celluluase and/or no external α-amylase and/or no external β-amylase and/or no external maltogenic α-amylase is added before or during mashing.

The wort obtained after mashing may also be referred to as "sweet wort". In conventional methods, the sweet wort is boiled with or without hops where after it may be referred to as boiled wort.

The term "approximately" as used herein means±10%, preferably ±5%, yet more preferably ±2%.

The wort may be heated or boiled before it is subjected to fermentation with the yeast of the invention. First, second and further worts may be combined, and thereafter subjected to heating or boiling. The wort may be heated or boiled for any suitable amount of time, e.g. in the range of 60 min to 120 min.

Thus, the starting liquid may be wort e.g. prepared as described above. The beverage may in be prepared by fermentation of the starting liquid, e.g. by fermentation of wort.

The beverage may in one preferred embodiment be malt beverages, even more preferred fermented beverages, such as fermented malt beverages, preferably alcoholic beverages, such as beer The beverage may be a non-alcoholic beverage, such as non-alcoholic beer or other kinds of non-alcoholic beverages, such as non-alcoholic malt beverages, such as maltina.

In one preferred embodiment the beverage is beer, for example the beer may be a lager beer or an ale. Thus, the beer may for example be selected from the group consisting of altbier, Amber ale, Barley wine, Berliner weisse, Bière de Garde, Bitter, Blonde Ale, Bock, Brown ale, California Common, Cream Ale, Dortmunder Export, Doppelbock, Dunkel, Dunkelweizen, Eisbock, Fruit Iambic, Golden Ale, Gose, Gueuze, Hefeweizen, Helles, India pale ale, Kölsch, Lambic, Light ale, Maibock, Malt liquor, Mild, Marzenbier, Old ale, Oud bruin, Pale ale, Pilsener, Porter, Red ale, Roggenbier, Saison, Scotch ale, Steam beer, Stout, Schwarzbier, lager, Witbier, Weissbier and Weizenbock.

Thus, the invention also relates to methods of producing a beverage comprising the steps of:
(i) providing a malt composition;
(ii) processing said malt composition into a beverage.

In general terms, alcoholic beverages—such as beer—may be manufactured from malted and/or unmalted barley grains. Malt, in addition to hops and yeast, contributes to flavour and colour of the beer. Furthermore, malt functions as a source of fermentable sugar and enzymes. Non-limited descriptions of examples of suitable methods for malting and brewing can be found, for example, in publications by Briggs et al. (1981) and Hough et al. (1982). Numerous, regularly updated methods for analyses of barley, malt and beer products are available, for example, but not limited to, American Association of Cereal Chemists (1995), American Society of Brewing Chemists (1992), European Brewery Convention (1998), and Institute of Brewing (1997). It is recognized that many specific procedures are employed for a given brewery, with the most significant variations relating to local consumer preferences. Any such method of producing beer may be used with the present invention.

The first step of producing beer from wort preferably involves heating said wort as described herein above, followed by a subsequent phase of wort cooling and optionally whirlpool rest. After being cooled, the wort may be transferred to fermentation tanks containing yeast according to the invention, i.e. yeast having one or more of characteristics I to X described above. The wort will be fermented for any suitable time period, in general in the range of 1 to 100 days. The fermentation is performed at any useful temperature e.g. at a temperature in the range of 1020° C.

During the several-day-long fermentation process, sugar is converted to alcohol and $CO_2$ concomitantly with the development of some flavour substances.

Subsequently, the beer may be further processed, for example chilled. It may also be filtered and/or lagered—a process that develops a pleasant aroma and a less yeasty flavour. Also additives may be added. Furthermore, $CO_2$ may be added. Finally, the beer may be pasteurized and/or filtered, before it is packaged (e.g. bottled or canned).

The beer produced by fermentation with the yeast according to the invention in general has a superior pleasant taste. Taste may be analyzed, for example, by a specialist beer taste panel. Preferably, said panel is trained in tasting and describing beer flavours, with special focus on aldehydes, papery taste, old taste, esters, higher alcohols, fatty acids and sulphury components.

In general, the taste panel will consist of in the range of 3 to 30 members, for example in the range of 5 to 15 members, preferably in the range of 8 to 12 members. The taste panel may evaluate the presence of various flavours, such as papery, oxidized, aged, and bready off-flavours as well as flavours of esters, higher alcohols, sulfur components and body of beer.

```
                        Sequence listing

SEQ ID NO: 1    Amino acid sequence of IMA1p short encoded by a unique
                allele from Hybrid yeast 1.

SEQ ID NO: 2    Amino acid sequence of_IMA1p short_from Hybrid yeast 4

SEQ ID NO: 3    Amino acid sequence of IMA1p short_from Hybrid yeast_4

SEQ ID NO: 4    Amino acid sequence of IMA1p short from Hybrid yeast 7

SEQ ID NO: 5    Amino acid sequence of IMA1p short from Hybrid yeast 7

SEQ ID NO: 6    Amino acid sequence of DAL5 encoded by Sc allele from
                Hybrid yeast 1

SEQ ID NO: 7    Amino acid sequence of PTR2 encoded by Sc allele from Ale
                yeast 1

SEQ ID NO: 8    Amino acid sequence of PTR2 encoded by Sc allele from
                Lager yeast 1

SEQ ID NO: 9    Amino acid sequence of PTR2 encoded by non-Sc allele from
                Hybrid yeast 1.

SEQ ID NO: 10   Partial amino acid sequence of UBR1 encoded by Sc allele
                from Hybrid yeast 1

SEQ ID NO: 11   Amino acid sequence of UBR1 encoded by non-Sc allele from
                Hybrid yeast 1
```

-continued

| Sequence listing | |
|---|---|
| SEQ ID NO: 12 | Amino acid sequence of IMA1p encoded by short Sc allele from Hybrid yeast 1 |
| SEQ ID NO: 13 | Amino acid sequence of IMA1p encoded by short Sc allele from Hybrid yeast 1 |
| SEQ ID NO: 14 | Amino acid sequence of IMA1p encoded by the long Sc allele from Hybrid yeast 1 |
| SEQ ID NO: 15 | Amino acid sequence of IMA1p encoded by a long Sc allele from Hybrid yeast 1 |
| SEQ ID NO: 16 | Amino acid sequence of IMA5p from Hybrid yeast 1 encoded by non-Sc IMA5 like |
| SEQ ID NO: 17 | Amino acid sequence of IMA5p from Hybrid yeast 1 encoded by Sc-IMA5 like |
| SEQ ID NO: 18 | Amino acid sequence of AGT1 from Hybrid yeast 1 encoded by non-Sc allele |
| SEQ ID NO: 19 | Amino acid sequence of AGT1 from Hybrid yeast 1 encoded by an Sc allele |
| SEQ ID NO: 20 | Amino acid sequence of AGT1 from Hybrid yeast 1 encoded by an Sc allele |
| SEQ ID NO: 21 | Amino acid sequence of IMA1p from Hybrid yeast 4 encoded by long IMA1 allele |
| SEQ ID NO: 22 | Amino acid sequence of IMA1p from Hybrid yeast 4 encoded by a long IMA1 allele |
| SEQ ID NO: 23 | Amino acid sequence of IMA1p from Hybrid yeast 7 encoded by a long IMA1 allele |
| SEQ ID NO: 24 | Amino acid sequence of IMA1p from Hybrid yeast 7 encoded by a long IMA1 allele |
| SEQ ID NO: 25 | Amino acid sequence of IMA1p from Hybrid yeast 7 encoded by a long IMA1 allele |
| SEQ ID NO: 26 | Amino acid sequence of truncated AGT1 from Hybrid yeast 4 encoded by an Sc allele |
| SEQ ID NO: 27 | Amino acid sequence of AGT1 from Hybrid yeast 4 encoded by a non-Sc allele |
| SEQ ID NO: 28 | Amino acid sequence of AGT1 from Hybrid yeast 4 encoded by a non-Sc allele |
| SEQ ID NO: 29 | Amino acid sequence of truncated AGT1 from Hybrid yeast 7 encoded by an Sc allele |
| SEQ ID NO: 30 | Amino acid sequence of AGT1 from Hybrid yeast 7 encoded by an Sc allele |
| SEQ ID NO: 31 | Amino acid sequence of AGT1 from Hybrid yeast 7 encoded by a non-Sc allele |
| SEQ ID NO: 32 | Amino acid sequence of AGT1 from Hybrid yeast 7 encoded by a non-Sc allele |
| SEQ ID NO: 33 | Amino acid sequence of IMA1p short from Hybrid yeast 7 |
| SEQ ID NO: 34 | Amino acid sequence of IMA5 from Hybrid yeast 1 |
| SEQ ID NO: 35 | Amino acid sequence of IMA5 from Hybrid yeast 7 |
| SEQ ID NO: 36 | Amino acid sequence of IMA5 from Hybrid yeast 7 |
| SEQ ID NO: 37 | Partial amino acid sequence of PTR2 from Hybrid yeast 7 |
| SEQ ID NO: 38 | Amino acid sequence of PTR2 of Hybrid yeast 7 |
| SEQ ID NO: 39 | Amino acid sequence of DAL 5 of Hybrid yeast 7 |

| Sequence listing |
| --- |

SEQ ID NO: 40    Amino acid sequence of DAL5 of Hybrid yeast 7

SEQ ID NO: 41    Partial amino acid sequence of UBR1 of Hybrid yeast 7

SEQ ID NO: 42    Amino acid sequence of UBR1 of Hybrid yeast 7

SEQ ID NO: 43    Amino acid sequence of PTR2 of Hybrid yeast 1

SEQ ID NO: 44    Amino acid sequence of PTR2 of Hybrid yeast 1

SEQ ID NO: 45    Partial amino acid sequence of UBR1 of Hybrid yeast 1

SEQ ID NO: 1
Amino acid sequence of SHORT_IMA1_from Hybrid yeast_1
MGYDIANYEKVWPTYGTNEDCFALIEKTHKLGMKFITDLVINHCSSEHEWFKESRSSKTNPKRD
WFFWRPPKGYDAEGKPIPPNNWKSYFGGSAWIFDEKTQEFYLRLFCSTQPDLNWENEDCRKAIY
ESAVGYWLDHGVDGFRIDVGSLYSKVVGLPDAPVVDKNSTWQSSDPYTLNGPRIHEFHQEMNQF
IRNRVKDGREIMTVGEMQHASDETKRLYTSASRHELSELFNFSHTDVGTSPLFRYNLVPFELKD
WKIALAELFRYINGTDCWSTIYLENHDQPRSITRFGDDSPKNRVISGKLLSVLLSALTGTLYVY
QGQELGQINFKNWPVEKYEDVEIRNNYNAIKEEHGENSEEMKKFLEGIALVSRDHARTPMPWTP
NEPNAGFSGPNTKPWFYLNESFRQGINVEEEQKNSDSVLAFWKKALEFRKNHKDIAVYGEDFKF
IDLDNKKLFSFTKRYNNKTLFAALNFSSDATDFKIPNDGSSFKLEFGNYPKNEVDASSRTLKPW
EGRIHINE.

SEQ ID NO: 2
Amino acid sequence of SHORT_IMA1_from Hybrid yeast 4
MGYDIANYEKVWPTYGTNEDCFALIEKTHKLGMKFITDLVINHCSSEHEWFKESRSSKTNPKRD
WFFWRPPKGYDAEGKPIPPNNWKSYFGGSAWIFDEKTQEFYLRLFCSTQPDLNWENEDCRKAIY
ESAVGYWLDHGVDGFRIDVGSLYSKVVGLPDAPVVDKNSTWQSSDPYTLNGPRIHEFHQEMNQF
IRNRVKDGREIMTVGEMQHASDETKRLYTSASRHELSELFNFSHTDVGTSPLFRYNLVPFELKD
WKIALAELFRYINGTDCWSTIYLENHDQPRSITRFGDDSPKNRVISGKLLSVLLSALTGTLYVY
QGQELGQINFKNWPVEKYEDVEIRNNYNAIKEEHGENSEEMKKFLEGIALVSRDHARTPMPWTP
NEPNAGFSGPNTKPWFYLNESFRQGINVEEEQKNSDSVLAFWKKALEFRKNHKDIAVYGEDFKF
IDLDNKKLFSFTKRYNNKTLFAALNFSSDATDFKIPNDGSSFKLEFGNYPKNEVDASSRTLKPW
EGRIYINE SEQ ID NO: 3
Amino acid sequence of SHORT_IMA1_from Hybrid yeast_4_
MGYDIANYEKVWPTYGTNEDCFALIEKTHKLGMKFITDLVINHCSSEHEWFKESRSSKTNPKRD
WFFWRPPKGYDAEGKPIPPNNWKSYFGGSAWIFDEKTQEFYLRLFCSTQPDLNWENEDCRKAIY
ESAVGYWLDHGVDGFRIDVGSLYSKVVGLPDAPVVDKNSTWQSSDPYTLNGPRIHEFHQEMNQF
IRNRVKDGREIMTVGEMQHASDETKRLYTSASRHELSELFNFSHTDVGTSPLFRYNLVPFELKD
WKIALAELFRFINGTDCWSTIYLENHDQPRSITRFGDDSPKNRVISGKLLSVLLSALTGTLYVY
QGQELGQINFKNWSVEKYEDVEIRNNYRLIKEECGENSEEMKKFLEGIALVSRDHARTPMPWTP
NEPNAGFSGPNTKPWFYLNESFRQGINVEEEQKNSDSVLAFWKKALEFRKNHKDIAVYGFDFKF
IDLDNKKLFSFTKRYNNKTLFAALNFSSDATDFKIPNDGSSFKLEFGNYPKNEVDASSRTLKPW
EGRIHINE.

SEQ ID NO: 4
Amino acid sequence of SHORT_IMA1_from Hybrid yeast_7_
MGYDIANYEKVWPTYGTNEDCFALIEKTHKLGMKFITDLVINHCSSEHEWFKESRSSKTNPKRD
WFFWRPPKGYDAEGKPIPPNNWKSYFGGSAWIFDEKTQEFYLRLFCSTQPDLNWENEDCRKAIY
ESAVGYWLDHGVDGFRIDVGSLYSKVVGLPDAPVVDKNSTWQSSDPYTLNGPRIHEFHQEMNQF
IRNRVKDGREIMTVGEMQHASDETKRLYTSASRHELSELFNFSHTDVGTSPLFRYNLVPFELKD
WKIALAELFRYINGTDCWSTIYLENHDQPRSITRFGDDSPKNRVISGKLLSVLLSALTGTLYVY
QGQELGQINFKNWPVEKYEDVEIRNNYNAIKEEHGENSEEMKKFLEGIALVSRDHARTPMPWTP
NEPNAGFSGPNTKPWFYLNESFRQGINVEEEQKNSDSVLAFWKKALEFRKNHKDIAVYGEDFKF
IDLDNKKLFSFTKRYNNKTLFAALNFSSDATDFKIPNDGSSFKLEFGNYPKNEVDVSSRTLKPW
EGRIYINE.

SEQ ID NO: 5
Amino acid sequence of SHORT_IMA1_from Hybrid_7_
MGYDIANYEKVWPTYGINEDCFALIEKTHKLGMKFITDLVINHCSSEHEWFKESRSSKINPKRD
WFFWRPPKGYDAEGKPIPPNNWKSYFGGSAWIFDEKTQEFYLRLFCSTQPDLNWENEDCRKAIY
ESAVGYWLDHGVDGFRIDVGSLYSKVVGLPDAPVVDKNSTWQSSDPYILNGPRIHEFHQEMNQF
IRNRVKDGREIMTVGEMQHASDETKRLYISASRHELSELFNFSHTDVGISPLFRYNLVPFELKD
WKIALAELFRYINGTDCWSTIYLENHDQPRSITRFGDDSPKNRVISGKLLSVLLSALIGTLYVY
QGQELGQINFKNWPVEKYEDVEIRNNYNAIKEEHGENSEEMKKFLEGIALVSRDHARIPMPWIP
NEPNAGFSGPNTKPWFYLNESFRQGINVEEEQKNSDSVLAFWKKALEFRKNHKDIAVYGFDFKF
IDLDNKKLFSFIKRYNNKTLFAALNFSSDATDFKIPNDGSSFKLEFGNYPKNEVDASSRILKPW
EGRIYINE.

Sequence listing

SEQ ID NO: 6
Amino acid sequence of DAL5 encoded by Sc allele from Hybrid
yeast 1
MSADASINSNASLDEKNLNITSEAEIKNEDVTAEPVLSTVLSPNGKIVYISDKVDEAMKLAEEA
KEIEVIPEEDRKLRWKIDYCMFPLMCILYAVQFMDKISTSSAAVMGLRIDLKMHGDQYSWVISA
FYFGYLFMNLGPVQFIFQRTSHMSKMLAVFIVIWGMLLALHAAPTVKYPSFIVLRVLLGCAESV
VTPCFTIITAQYWKTEEQFTRVSIWFGMNGLGSILINAIAYGVYIHQDSYAIKGWRILFVITGV
ITIFIGILIFLWIPDDPSKARFLSKREKLMVVQRIRSNQQGFGNHEIKKYQIIEALKDVRTWLY
FLFTVSSNIPNGGISSFMSILLNSDFGYSSKEILLMGLPTGAVELVGCPLFGILAVYAANKKIP
FWKYKLSWAIFAAVLALIASCMLGFAINSKKARLAGAYLWYISPVSFICVLSNISANSSGYSKK
WIVSSINLVAYAAANLAGPQTFIAKQAPKYHGAKVAMVVCYAVMIVLLSILLIVNLRENKRRDK
IAAERGFPEETENLEFSDLTDFENPNFRYTL.

SEQ ID NO: 7
Amino acid sequence of PIR2 of encoded by Sc allele from Ale
yeast 1
MLNHPSQGSDDAQDEKQGDFPVIEEEKTQAVMLKDSYVSDDVANSTERYNLSPSPEDEDFEAPT
EEEMQTLRHVGGKIPMRCWLIAIVELSERFSYYGLSAPFQNYMEYGPNDSPKGVLSLNSQGATG
LSYFFQFWCYVTPVFGGYVADTFWGKYNTICCGTAIYIAGIFILFITSIPSVGNRDSAIGGFIA
AIILIGIATGMIKANLSVLIADQLPKRKPSIKVLKSGERVIVDSNITLQNVFMFFYFMINVGSL
SLMATTELEYHKGFWAAYLLPPCFFWIAVVILIFGKKQYIQRPIGDKVIAKSFKVCWILTKNKF
DFNAAKPSVHPEKNYPWNDKFVDEIKRALAACKVFIFYPIYWTQYGTMISSFITQASMMELHGI
PNDFLQAFDSIALIIFIPIFEKFVYPPIRRYTPLKPITKIFXGFMFGSFAMTWAAVLQSFVYKA
GPWYNEPLGHNIPNHVHVCWQIPAYVLISFSEIFASITGLEYAYSKAPASMKSFIMSIFLLTNA
FGSAIGCALSPVTVDPKFTWLFTGLAVACFISGCLFWLCFRKYNDTEEEMNAMDYEEENEFDLN
PISAPKANDIEILEPMDSLRSTAKY.

SEQ ID NO: 8
Amino acid sequence of PIR2 encoded by Sc allele from Lager
yeast 1
MLNHPSQGSDDAQDEKQGDFPVIEEEKTQAVILKDSYVSDDVANSTERYNLSPSPEDEDFEAPT
EEEMQTLRHVGGKIPMRCWLIAIVELSERFSYYGLSAPFQNYMEYGPNDSPKGVLSLNSQGATG
LSYFFQFWCYVTPVFGGYVADTFWGKYNTICCGTAIYIAGIFILFITSIPSVGNRDSAIGGFIA
AIILIGIATGMIKANLSVLIADQLPKRKPSIKVLKSGERVIVDSNITLQNVFMFFYFMINVGSL
SLMATTELEYHKGFWAAYLLPFCFFWIAVVILIFGKKQYIQRPVGDKVIAKSFKVCWILTKNKF
DFNAAKPSVHPEKNYPWNDKFVDEIKRALAACKVFIFYPIYWTQYGTMISSFITQASMMELHGI
PNDFLQAFDSIALIIFIPIFEKFVYPPIRRYTPLKPITKIFFGFMFGSFAMTWAAVLQSFVYKA
GPWYNEPLGHNIPNHVHVCWQIPAYVLISFSEIFASITGLEYAYSKAPASMKSFIMSIFLLTNA
FGSAIGCALSPVTVDPKFTWLFTGLAVACFISGCLFWLCFRKYNDTEEEMNAMDYEEEDEFDLN
PISAPKANDIEILEPMESLRSTTKY SEQ ID NO: 9
Amino acid sequence of PIR2 encoded by non-Sc allele from Hybrid
yeast 1
MLNHLSQGSDDIQDEKQGDFPVIEEEKNQTVILKDSYVSDDAANSTEHYNLSPSLEEDEFEAPT
DEELRSLRHVGGKIPMRCWLIAIVELSERFSYYGLSAPFQNYMEYGPKDTPKGVLSLNSQGATG
LSYFFQFWCYVTPVFGGYVADTFWGKYNTICCGTAIYIAGIFILLITSIPSVGNRDSALGGFIA
SIILIGIATGMIKANLSVLIADQLPKRKPSIKVLKSGERVIVDSNITLQNVFMFFYFMINVGSL
SLMATTELEYHKGFWAAYLLPFCFFWAVVILVFGKKQYIQRPIGDKVIAKSFRVCWILTKNKF
DFNAAKPSVHPEKEYPWNDKFVDEIKRALAACKVFVFYPIYWTQYGTMISSFITQAGMMELHGI
PNDFLQAFDSIALIIFIPIFEKFIYPPIRRYTPFKPITKIFFGFMFGSLAMTWAAVLQSFVYKA
GPWYSAPLGHNIPNHVHVCWQIPAYVLISFSEIFASITGLEYAYSKAPASMKSFIMSIELLTNA
FGSAIGCALSPVTVDPKFTWLFTGLAVACFISGCLFWFCFRKYNDTEEEMNAMDYEEEDEFDLN
PISQPKGNDIEILEPMGSLKSTIKY SEQ ID NO: 10
Incomplete amino acid sequence of UBR1 encoded by Sc allele of
Hybrid yeast 1
FKEFCKVEGGVLIWQRVQKSNLIKSYSISFKQGLYTVEILLSKVHDPNIPLRPKEIISLLTLCK
LENGAWKIKRKEGEHVLHEDQNFISYLEYTTSIYSIIQTAEKVSEKSKDSIDSKLFLNAIRIIS
SFLGNRSLTYKLIYDSHEVIKFSVSHERVAFMNPLQTMLSFLIEKVSLKDAYEALEDCSDFLKI
SDFSLRSVVLCSQIDVGFWVRNGMSVLHQASYYKNNPELGSYSRDIHLNQLAILWERDDIPRII
YNILDRWELLDWFTGEVDYQHTVYEDKISFIIQQFIAFIYQILTERQYFKIFSSLKDRRMDQIK
NSIIYNLYMKPLSYSKLLRSVPDYLTEDTTEFDEALEEVSVFVEPKGLADNGVFKLKASLYAKV
DPLKLLNLENEFESS SEQ ID NO: 11
Amino acid sequence of UBR1 encoded by non-Sc allele of Hybrid
yeast 1
MSFIDNGLGSLKAHIRRILRSIHNLPYFRFTRGPTERADMSRALKEFIYRYLYFIISNDGENLS
TLFTAHPKQKSSNQELAVFPESLEDALDVDKITSQGTFPFYKIDESKIGDVHKHIGRNCGRKFK
IGEPLYRCHECGCDDICVLCIHCFNPKDHVNHHVCIDICSEFTSGICDCGDEEAWNSSLHCKAE
EQGNDISEDPSNFDSTKQKDVWNDPECIALVELVLSEVFDYIDVFNQNIEPLPTIQKDITIKL
REMTQQGKMYERAQFLNDLKYENDYMEDGITTAKTSPSNSPEASPSLAKIDPENYTVIIYNDEY
HNYSQATTALRQGVPDNVHIDLLTSRIDGEGRAMLKCSQDLSSVLGGFFAVQINGLSAILTSWS
EYLHQEACKYIILWITHCLNIPNPSFQITFRNMMGKSLCSEYLNATESRDMTPVVEKYFSTKFD

```
                            Sequence listing
KDDPYRYIDLSVLAEGNQIPLGHHKVLPESSTHSLSTLINDVENLISKEYSNTRLQHILYFDNR
YWKRLRKDIQNVIIPTLASSTLYKPIFCQQVVEIFNHITRSVAYMDREPQLTAIRECVVQLFIC
PINTRNIFENQSFLDILWSIIDIFKEFCKVEAGVLIWQRVQKSNLIKSYSLSFKQGLYTVEILL
SKVNDPNITIRPKVFISLLTLGKLENGAWKIKRKEGEHVLHEDQNFISYLEYTTSIYSIIQTAE
KVLEKSHDSLDLNLVLNAIRIVSSFLGNRSLTYKLIYDSHEIIKFSVSHERVAFMNPIQTMLSF
LIEKVSLKDAYESLENCPDFLKIADFSLRSVVLCSQIDVGFWVRNGMSVLHQASYYKNNPELGS
YSRDIHLNQLAIIWERDDLPRVIYNILDRWELLDWFMGEAEYQHTVYEDKISFMIQQFIAFIYQ
ILTERQYFKIFSLLRDRRMDMIKNSIMYNLYMKPLSYSKLLKSVPDYLTDDITEFDEALEEVSV
FVEPKGLADNGVFKLKAALYAKIDPLKLLNLENEFESSATIIKTHLAKNKDEVSKVVLIPQVST
KLLDKGAMNLGEFTRNIVFAKVIYKLLQVCLDMEDSTFLNELLHLVHGIFKDDELINGKDSIPE
AYLAKPICNLLLSIANAKSDIFSESIVRKADYLLEKMIMKKPDEIFESLIASEGNQYIDNYKDK
KLSQGVNLQETEKERKRRMAKKHQARLLAKENNQQSKFMKEHESEFDEQDNDVDMDGEKVYESE
DFICALCQDSSSIDFFVIPAYHDHIPIFRPGNIFNPREFMAKWDGFYNDDDKQAYIDDEVLESL
KENGTRGSRKVEVSCNHHIHHNCFKRYVQKKRESSNAFICPLCQTESNCTLPICPTSRANTGLS
LDMFLKSELSLDILSRLFKPFTEDNYRTINSIFSLMVSQCQGDKVVRKHVNFTHKDVSLVLSV
HWANTISMLEVASRLEKPHNISFFRSREQKYKILKNILICIMLFTFVIGKPSMEFEPYPVESDI
ICNQNQLFQYIVRKSLFSPASLRETITEALTVFCKQFLDDFVQGLSDAEQVDKLYTEAKKLGDV
YNVDESILITLMSITVVKTEGLESRSIYDLAYISLLKSLLPTIRRCLVMVKVLHELVKDSENET
MVIDGEDVEEELEFEGLPGFVDKALKLITDKESFVDLEKTKQAIVPSHPYLERIPYEYCGIVKL
IDLSKFLNTYVTQSKEIKLREERSQHMKNADNRLDFKICLICGVKVHLRADRHEMTKHLNKNCF
KSFGAFLMPNSSEVCLHLTQFPSNIFVSAPYLNSHGEVGRNAMRRGDLTTLNLKRYEHLNRLWI
NNEIPGYISRVMGDEFRVTILSNGFLFAFNREPRPRRVPPIDEDDEDMEEGEEGFFTEENDDMD
VDDETGQAANLFGVGAEGIGDGGVRNFFQFFENFRNTLQPQGNDDEDAPQNPPPILQFLGPQFD
GATIIRNTNQRNLDEDDSSENDDSDEREIW SEQ ID NO: 12
Amino acid sequence of IMA1p encoded by short Sc allele from
Hybrid yeast 1
MGYDIANYEKVWPTYGINEDCFALIEKTHKLGMKFITDLVINHCSSEHEWFKESRSSKINPKRD
WFFWRPPKGYDAEGKPIPPNNWKSYFGGSAWIFDEKTQEFYLRLFCSTQPDLNWENEDCRKAIY
ESAVGYWLDHGVDGFRIDVGSLYSKVVGLPDAPVVDKNSTWQSSDPYILNGPRIHEFHQEMNQF
IRNRVKDGREIMTVGEMQHASDETKRLYISASRHELSELFNFSHTDVGISPLFRYNLVPFELKD
WKIALAELFRFINGTDCWSTIYLENHDQPRSITRFGDDSPKNRVISGKLLSVLLSALIGTLYVY
QGQELGQINFKNWSVEKYEDVEIRNNYRLIKEECGENSEEMKKFLEGIALVSRDHARIPMPWIP
NEPNAGFSGPNTKPWFYLNESFRQGINVEEEQKNSDSVLAFWKKALEFRKNHKDIAVYGEDFKF
IDLDNKKLFSFIKRYNNKTLFAALNFSSDATDFKIPNDGSSFKLEFGNYPKNEVDASSRILKPW
EGRIHINE SEQ ID NO: 13
Amino acid sequence of IMA1p encoded by short Sc allele from
Hybrid yeast 1
MGYDIANYEKVWPTYGINEDCFALIEKTHKLGMKFITDLVINHCSSEHEWFKESRSSKINPKRD
WFFWRPPKGYDAEGKPIPPNNWKSYFGGSAWIFDEKTQEFYLRLFCSTQPDLNWENEDCRKAIY
ESAVGYWLDHGVDGFRIDVGSLYSKVVGLPDAPVVDKNSTWQSSDPYILNGPRIHEFHQEMNQF
IRNRVKGGREIMTVGEMQHASDETKRLYISASRHELSELFNFSHTDVGISPLFRYNLVPFELKD
WKIALAELFRFINGTDCWSTIYLENHDQPRSITRFGDDSPKNRVISGKLLSVLLSALIGTLYVY
QGQELGQINFKNWSVEKYEDVEIRNNYRLIKEECGENSEEMKKFLEGIALVSRDHARIPMPWIP
NEPNAGFSGPNTKPWFYLNESFRQGINVEEEQKNSDSVLAFWKKALEFRKNHKDIAVYGEDFKF
IDLDNKKLFSFIKRYNNKTLFAALNFSSDATDFKIPNDGSSFKLEFGNYPKNEVDASSRILKPW
EGRIHINE SEQ ID NO: 14
Amino acid sequence of IMA1p encoded by long Sc allele from
Hybrid yeast 1
MTISSAHPETEPKWWKEATFYQIYPASFKDSNDDGWGDMKGISSKLEYIKELGVDAIWISPLYD
SPQDDMGYDIANYEKVWPTYGINEDCFALIEKTHKLGMKFITDLVINHCSSEHEWFKESRSSKT
NPKRDWSFWRPPKGYDAEGKPIPPNNWKSYFGGSAWIFDEKTQEFYLRLFCSTQPDLNWENEDC
RKAIYESAVGYWLDHGVDGFRIDVGSLYSKVVGLPDAPVVDKNSTWQSSDPYILNGPRIHEFHQ
EMNQFIRNRVKDGREIMTVGEMQHASDETKRLYISASRHELSELFNFSHTDVGISPLFRYNLVP
FELKDWKIALAELFRYINGTDCWSTIYLENHDQPRSITRFGDDSPKNRVISGKLLSVLLSALTG
TLYVYQGQELGQINFKNWPVEKYEDVEIRNNYNAIKEEHGENSEEMKKFLEGIALVSRDHARTP
MPWIPNEPNAGFSGPSAKPWFYLNDSFREGINVEDEIKDPNSVLNEWEALKFRKAHKDITVYG
YDFEFIDLDNKKLFSFIKKYNNKTLFAALNFSSDATDFKIPNDDSSFKLEFGNYPKKEVDASSR
TLKPWEGRIYISE SEQ ID NO: 15
Amino acid sequence of IMA1p encoded by long Sc allele from
Hybrid yeast 1
MTISSAHPEAEPKWWKEATFYQIYPASFKDSNDDGWGDMKGISSKLEYIKELGADAIWISPFYD
SPQDDMGYDIANYEKVWPTYGINEDCFALIEKTHKLGMKFITDLVINHCSSEHEWLKESRSSKT
NPKRDWFFWRPPKGYDAEGKPIPPNNWKSYFGGSAWIFDEKTQEFYLRLFCSTQPFDLNWENEDC
RKAIYESAVGYWLDHGVDGFRIDVGSLYSKVVGLPDAPVVDKNSTWQSSDPYILNGPRIHEFHQ
EMNQFIRNRVKDGREIMTVGEMQHASDETKKLYISASRHELSELFNFSHTDVGISPLFRYNLVP
FELKDWKIALAELFRFINGTDCWSTIYLENHDQPRSITRFGDDSPKNRVISGKLLSVLLSALTG
TLYVYQGQELGQINFKNWPVEKYEDVEIRNNYNAIKEEHGENSEEMKKFLEAIALISRDHARTP
```

```
MQWSREEPNAGFSGPSAKPWFYLNDSFREGINVEDEIKDPNSVLNEWKEALKFRKAHKDITVYG
YDFEFIDLDNKKLFSFIKKYNNKTLFAALNFSSDATDFKIPNDDSSFKLEFGNYPKKEVDASSR
TLKPWEGRIYISE

SEQ ID NO: 16
Amino acid sequence of IMA5p from Hybrid yeast 1 encoded by non-
Sc IMA5 like allele
MTIIHNPKWWKEATIYQIYPASFKDSNNDGWGDLAGITSKLDYIKELGVDAIWVCPFYDSPQED
MGYDIANYEKVWPRYGTSEDCFQMIEESHKRGIKVIVDLVINHCSEEHEWFKESRSSKTNAKRD
WFFWKPPKGYEIDGIPIPPNNWRSFFGGSAWKYDENTEEFFLHVFAPGQPDFNWENKECRQAIY
DSSVGFWLRHNVDGFRIDVGSMYSKVEGLPDASITDPIVPYQDGIDFFVNGPRIHEYHKEMRQY
MYTQIPEGKEIMTVGEVGIGNEKDFKDYISSKEEEFNMMENPKHTSVGESPEFKYELIPFTLKD
FKLALAESFLFIEGTDCWSTIYLENHDQPRSVSRFGSDSPEWREISSKMLATLIISLIGTVFIY
QGQELGMPNFKNRKIEQIKCVEGIGTYGAIKRDYGEDSEKMKKEYEALALISRDHGRIPFPWSG
EKPYAGESKNAKPWIDINESFVEGINAEAELNDENSVFFEWKRALQVRKEHKNMLVYGDNFQFY
DLDNEKLEMETKDSGDKKMFAVENFCSDSTEFSVPDNKASYDMFFGNYANSDGKSYTLKPWEGR
LYYSN SEQ ID NO: 17
Amino acid sequence of IMA5p from Hybrid yeast lencoded by Sc-
IMA5 like
MTIIHNPKWWKEATVYQIYPASNKDSNNDGWGDLAGITSKLDYVKELGVDAIWVCLFYDSPQED
MGYDIANYEKVWPRYGINEDCFQMIEEAHKRGIKVIVDLVINHCSEEHEWFKESKSSKINPKRD
WFFWRPPKGEDEKGNPIPPNNWRSFEGGSAWRYDEKTGEFFLHVFAPGQPDFNWENEECRKAIY
DSSVGYWLRHNVDGFRIDVGSMYSKVEGLPDAPITDPIVPYQKGTEFFINGSRIHEYHKEMRKY
MLSQIPEGKEIMTVGEVGVGNEEDFRDYISAKEGELNMMENFKHTSVGESPECKYELIPFTLKD
FKLALAESELFIENTDCWSTIYLENHDQPRSVSREGSDSPKWRAISSKMLATLIISLIGTVFIY
QGQELGMSNFKNRRIEQIKCVEGIGTYAAIKRDYGEDSEKMKKFFEALALISRDHGRIPFPWSA
DEPSAGFSKDAKPRIDMNESFRDGINAEAELKDKNSVFFFWKKALQVRKEHKDILVYGHNFQFI
DLDNDKLEMETKDIDNKKMFAVFNESSDDIDFSVPDNEASYTMFFGNYANSNGDSRTLQPWEGR
LYLLK SEQ ID NO: 18
Amino acid sequence of AGT1 from Hybrid yeast 1 encoded by non-
Sc allele
MKNILSLVGRKENTPEDVTANLADISSTIVMQAKDLVIEDFEERKKNDAFELNHLELTTNATQL
SDSDEDKENVIRVAEATDDANEANNEEKSMILRQALRKYPKAALWSILVSTILVMEGYDTALLS
ALYALPVFQRKFGTMNAEGSYEITSQWQIGLNMCVLCGEMIGLQIITYMVEFMGNRYTMITALS
LLTAYIFILYYCKSLAMIAVGQILSAMPWGCFQSLAVIYASEVCPLALRYYMTSYSNICWLFGQ
IFASGIMKNSQENLGNSDLGYKLPFALQWIWPAPLIIGIFFAPESPWWLVRKNKIVEAKKSLNR
ILSGTVIEKEIQVDITLKQIEMTIEKERLRASKSGSFFSCFKGVDGRRTRLACLIWVAQNSSGA
VLLGYSTYFFERAGMATDKAFTESLIQYCLGLAGILGSWVISGRVGRWTILTYGLSFQMVCLFI
IGGMGFASGSSASNAAGGLLLALSFFYNAGIGAVVYCIVAEIPSAELRIKTIVLARICYNLMAV
FNAILTPYMLNVSDWNWGAKTGLYWGGFTALTLAWVIIDLPETTGRIFSEINELFSQGVPARKF
ASTVVDPFGKRGLQNRPQVDNIIDRFSSASQQAL SEQ ID NO: 19
Amino acid sequence of AGT1 from Hybrid yeast 1 encoded by an Sc
allele
MKNIISLVSKKKAASKNEDKNISESSRDIVNQQEVENTENFEEGRKDSAFELDHLEFTINSAQL
GDSDEDNENVINETNITDDANEANSEEKSMILKQALLIYPKAALWSILVSTILVMEGYDTALLN
ALYALPVFQRKFGTLNGEGSYEITSQWQIGLNMCVQCGEIIGLQIIPYMVEFMGNRYTMITALG
LLTAYVFILYYCKSLAMIAVGQVLSAMPWGCFQGLIVIYASEVCPLALRYYMTSYSNICWLFGQ
IFASGIMKNSQENLGNSDLGYKLPFALQWIWPAPLMIGIFFAPESPWWLVRKDRVAEARKSLSR
ILSGKGAEKDIQIDLILKQIELTIEKERLLASKSGSFLDCFKGVNGRRIRLACLIWVAQNTSGA
CLLGYSTYFFERAGMATDKAFTESVIQYCLGLAGTLCSWVISGRVGRWTILTYGLAFQMVCLFI
IGGMGFGSGSGASNGAGGLLLALSFFYNAGIGAVVYCIVTEIPSAELRIKTIVLARICYNIMAV
INAILTPYMLNVSDWNWGAKTGLYWGGFTAVTLAWVIIDLPETSGRIFSEINELFNQGVPARKF
ASTVVDPFGKGKTQHDSLDDESISQSSSIKQRELNAADKC SEQ ID NO: 20
Amino acid sequence of AGT1 from Hybrid yeast lencoded by an Sc
allele
MKNIISLVSKKKAASKNEDKNISESSRDIVNQQEVENTENFEEGRKDSAFELDHLEFTINSAQL
GDSDEDNENVINETNITDDANEANSEEKSMILKQALLIYPKAALWSILVSTILVMEGYDTALLN
ALYALPVFQRKFGTLNGEGSYEITSQWQIGLNMCVQCGEIIGLQIIPYMVEFMGNRYTMITALG
LLTAYVFILYYCKSLAMIAVGQVLSAMPWGCFQGLIVIYASEVCPLALRYYMTSYSNICWLFGQ
IFASGIMKNSQENLGNSDLGYKLPFALQWIWPAPLMIGIFFAPESPWWLVRKDRVAEARKSLSR
ILSGKGAEKDIQIDLILKQIELTIEKERLLASKSGSFFDCFKGVNGRRIRLACLIWVAQNTSGA
CLLGYSAYFFERAGMATDKAFTESVIQYCLGLAGTLCSWVISGRVGRWTILTYGLAFQMVCLFI
IGGMGFGSGSGASNGAGGLLLALSFFYNAGIGAVVYCIVTEIPSAELRIKTIVLARICYNIMAV
INAILTPYMLNVSDWNWGAKTGLYWGGFTAVTLAWVIIDLPETSGRIFSEINELFNQGVPARKF
ASTVVDPFGKGKTQHDSLDDESISQSSSIKQRELNAADKC
```

Sequence listing

SEQ ID NO: 21
Amino acid sequence of IMA1p encoded by long IMA1 allele from Hybrid yeast 4
MTISSAHPETEPKWWKEATFYQIYPASFKDSNDDGWGDMKGISSKLEYIKELGVDAIWISPFYD
SPQDDMGYDIANYEKVWPTYGINEDCFALIEKTHKLGMKFITDLVINHCSSEHEWFKESRSSKT
NPKRDWFFWRPPKGYDAEGKPIPPNNWKSYFGGSAWIFDEKTQEFYLRLFCSTQFDLNWENEDC
RKAIYESAVGYWLDHGVDGFRIDVGSLYSKVVGLPDAPVVDKNSTWQSSDPYILNGPRIHEFHQ
EMNQFIRNRVKDGREIMTVGEMQHASDETKRLYISASRHELSELFNFSHTDVGISPLFRYNLVP
FELKDWKIALAELFRFINGTDCWSTIYLENHDQPRSITRFGDDSPKNRVISGKLLSVLLSALTG
TLYVYQGQELGQINFKNWPVEKYEDVEIRNNYNAIKEEHGENSEEMKKFLEAIALISRDHARTP
MQWSREEPNAGFSGPSAKPWFYLNDSFREGINVEDEIKDPNSVLNEWKEALKFRKAHKDITVYG
YDFEFIDLDNKKLFSFIKKYNNKTLFAALNFSSDATDFKIPNDDSSFKLEFGNYPKKEVDASSR
TLKPWEGRIYISE.

SEQ ID NO: 22
Amino acid sequence of IMA1p encoded by long IMA1 allele from Hybrid yeast 4
MTISSAHPETEPKWWKEATFYQIYPASFKDSNDDGWGDMKGISSKLEYIKELGVDAIWISPFYD
SPQDDMGYDIANYEKVWPTYGINEDCFALIEKTHKLGMKFITDLVINHCSSEHEWFKESRSSKT
NPKRDWFFWRPPKGYDAEGKPIPPNNWKSYFGGSAWIFDEKTQEFYLRLFCSTQFDLNWENEDC
RKAIYESAVGYWLDHGVDGFRIDVGSLYSKVVGLPDAPVVDKNSTWQSSDPYILNGPRIHEFHQ
EMNQFIRNRVKDGREIMTVGEMQHASDETKRLYISASRHELSELFNFSHTDVGISPLFRYNLVP
FELKDWKIALAELFRYINGTDCWSTIYLENHDQPRSITRFGDDSPKNRVISGKLLSVLLSALTG
TLYVYQGQELGQINFKNWPVEKYEDVEIRNNYNAIKEEHGENSEEMKKFLEAIALISRDHARTP
MQWSREEPNAGFSGPSAKPWFYLNDSFREGINVEDEIKDPNSVLNEWKEALKFRKAHKDITVYG
YDFEFIDLDNKKLFSFIKKYNNKTLFAALNFSSDATDFKIPNDDSSFKLEFGNYPKKEVDASSR
TLKPWEGRIYISE.

SEQ ID NO: 23
Amino acid sequence of IMA1p encoded by long IMA1 allele from Hybrid yeast 7
MTISSAHPETEPKWWKEATFYQIYPASFKDSNDDGWGDMKGISSKLEYIKELGVDAIWISPFYD
SPQDDMGYDIANYEKVWPTYGINEDCFALIEKTHKLGMKFITDLVINHCSSEHEWFKESRSSKT
NPKRDWFFWRPPKGYDAEGKPIPPNNWKSYFGGSAWIFDEKTQEFYLRLFCSTQFDLNWENEDC
RKAIYESAVGYWLDHGVDGFRIDVGSLYSKVVGLPDAPVVDKNSTWQSSDPYILNGPRIHEFHQ
EMNQFIRNRVKDGREIMTVGEMQHASDETKKLYISASRHELSELFNFSHTDVGISPLFRYNLVP
FELKDWKIALAELFRFINGTDCWSTIYLENHDQPRSITRFGDDSPKNRVISGKLLSVLLSALTG
TLYVYQGQELGQINFKNWPVEKYEDVEIRNNYNAIKEEHGENSEEMKKFLEAIALISRDHARTP
MQWSREEPNAGFSGPSAKPWFYLNDSFREGINVEDEIKDPNSVLNEWKEALKFRKAHKDITVYG
YDFEFIDLDNKKLFSFIKKYNNKTLFAALNFSSDATDFKIPNDDSSFKLEFGNYPKKEVDASSR
TLKPWEGRIYISE.

SEQ ID NO: 24
Amino acid sequence of IMA1p encoded by long IMA1 allele from Hybrid yeast 7
MTISSAHPETEPKWWKEATFYQIYPASFKDSNDDGWGDMKGISSKLEYIKELGVDAIWISPFYD
SPQDDMGYDIANYEKVWPTYGINEDCFALIEKTHKLGMKFITDLVINHCSSEHEWFKESRSSKT
NPKRDWFFWRPPKGYDAEGKPIPPNNWKSYFGGSAWIFDEKTQEFYLRLFCSTQPDLNWENEDC
RKAIYESAVGYWLDHGVDGFRIDVGSLYSKVVGLPDAPVVDKNSTWQSSDPYILNGPRIHEFHQ
EMNQFIRNRVKDGREIMTVGEMQHASDETKRLYISASRHELSELFNFSHTDVGISPLFRYNLVP
FELKDWKIALAELFRYINGTDCWSTIYLENHDQPRSITRFGDDSPKNRVISGKLLSVLLSALTG
TLYVYQGQELGQINFKNWPVEKYEDVEIRNNYNAIKEEHGENSEEMKKFLEAIALISRDHARTP
MQWSREEPNAGFSGPSAKPWFYLNDSFREGINVEDEIKDPNSVLNEWKEALKFRKAHKDITVYG
YDFEFIDLDNKKLFSFIKKYNNKTLFAALNFSSDATDFKIPNDDSSFKLEFGNYPKKEVDASSR
TLKPWEGRIYISE.

SEQ ID NO: 25
Amino acid sequence of IMA1p encoded by long IMA1 allele from Hybrid yeast 7
MTISSAHPETEPKWWKEATFYQIYPASFKDSNDDGWGDMKGISSKLEYIKELGVDAIWISPFYD
SPQDDMGYDIANYEKVWPTYGINEDCFALIEKTHKLGMKFITDLVINHCSSEHEWFKESRSSKT
NPKRDWFFWRPPKGYDAEGKPIPPNNWKSYFGGSAWIFDEKTQEFYLRLFCSTQFDLNWENEDC
RKAIYESAVGYWLDHGVDGFRIDVGSLYSKVVGLPDAPVVDKNSTWQSSDPYILNGPRIHEFHQ
EMNQFIRNRVKDGREIMTVGEMQHASDETKRLYISASRHELSELFNFSHTDVGISPLFRYNLVP
FELKDWKIALAELFRYINGTDCWSTIYLENHDQPRSITRFGDDSPKNRVISGKLLSVLLSALTG
TLYVYQGQELGQINFKNWPVEKYEDVEIRNNYNAIKEEHGENSEEMKKFLEAIALISRDHARTP
MQWSREEPNAGFSGPSAKPWFYLNDSFREGINVEDEIKDPNSVLNEWKEALKFRKAHKDITVYG
YDFEFIDLDNKKLFSFIKKYNNKTLFAALNFSSDATDFKIPNDDSSFKLEFGNYPKKEVDASSR
TLKPWEGRIYISE.

SEQ ID NO: 26
Amino acid sequence of truncated AGT1 encoded by Sc allele from Hybrid yeast 4
MKNIISLVSKKKAASKNEDKNISESSRDIVNQQEVENTENFEEGKKDSAFELDHLEFTINSAQL
GDSDEDNENMINEMNATDEANEANSEEKSMILKQALLKYPKAALWSILVSTILVMEGYDTALLN
ALYALPVFQRKFGTLNGEGSYEITSQWQIGLNMCVQCGEMIGLQIITYMVEFMGNRYTMITALG

```
LLTAYIFILYYCKSLAMIAVGQVLSAMPWGCFQGLIVIYASEVCPLALRYYMTSYSNICWLFGQ
IFASGIMKNSQENLGNSDLDYKLPFALQWIWPAPLMIGIFFAPESPWWLVRKDRVAEARKSLSR
ILSGKGAEKDIQVDLILKQIELTIEKERLLASKSGSFFDCFKGVNGRRIRLACLAWVAQNTSGA
CLLGYSTYFF.

SEQ ID NO: 27
Amino acid sequence of AGT1 encoded by non-Sc allele from Hybrid
yeast 4
MKNILSLVGRKENTPEDVTANLADISSTIVMQAKDLVIEDFEERKKNDAFELNHLELTTNATQL
SDSDEDKENVIRVAEATDDANEANNEEKSMILRQALRKYPKAALWSILVSTILVMEGYDTALLS
ALYALPVFQRKFGTMNAEGSYEITSQWQIGLNMCVLCGEMIGLQIITYMVEFMGNRYTMITALS
LLTAYIFILYYCKSLAMIAVGQILSAMPWGCFQSLAVIYASEVCPLALRYYMTSYSNICWLFGQ
IFASGIMKNSQENLGNSDLGYKLPFALQWIWPAPLIIGIFFAPESPWWLVRKNKIVEAKKSLNR
ILSGTVIEKEIQVDITLKQIEMTIEKERLRASKSGSFFSCFKGVDGRRTRLACLIWVAQNSSGA
VLLGYSTYFFERAGMATDKAFTFSLIQYCLGLAGILGSWVISGRVGRWTILTYGLSFQMVCLFI
IGGMGFASGSSASNAAGGLLLALSFFYNAGIGAVVYCIVAEIPSAELRIKTIVLARICYNLMAV
FNAILTPYMLNVSDWNWGAKTGLYWGDFTALTLAWVIIDLPETTGRIFSEINELFSQGVPARKF
ASTVVDPFGKRGLQNRPQVDNIIDRFSSASQQAL.

SEQ ID NO: 28
Amino acid sequence of AGT1 encoded by non-Sc allele from Hybrid
yeast 4
MKNILSLVGRKENTPEDVTANLADISSTIVMQAKDLVIEDFEERKKNDAFELNHLELTTNATQL
SDSDEDKENVIRVAEATDDANEANNEEKSMILRQALRKYPKAALWSILVSTILVMEGYDTALLS
ALYALPVFQRKFGTMNAEGSYEITSQWQIGLNMCVLCGEMIGLQIITYMVEFMGNRYTMITALS
LLTAYIFILYYCKSLAMIAVGQILSAMPWGCFQSLAVIYASEVCPLALRYYMTSYSNICWLFGQ
IFASGIMKNSQENLGNSDLGYKLPFALQWIWPAPLIIGIFFAPESPWWLVRKNKIVEAKKSLNR
ILSGTVIEKEIQVDITLKQIEMTIEKERLRASKSGSFFSCFKGVDGRRTRLACLIWVAQNSSGA
VLLGYSTYFFERAGMATDKAFTFSLIQYCLGLAGILGSWVISGRVGRWTILTYGLSFQMVCLFI
IGGMGFASGSSASNAAGGLLLALSFFYNAGIGAVVYCIVAEIPSAELRIKTIVLARICYNLMAV
FNAILTPYMLNVSDWNWGAKTGLYWGGFTALTLAWVIIDLPETTGRIFSEINELFSQGVPARKF
ASTVVDPFGKRGLQNRPQVDNIIDRFSSASQQAL.

SEQ ID NO: 29
Amino acid sequence of truncated AGT1 encoded by Sc-allele from
Hybrid yeast 7
MKNIISLVSKKKAASKNEDKNISESSRDIVNQQEVENTENFEEGKKDSAFELDHLEFTINSAQL
GDSDEDNENMINEMNATDEANEANSEEKSMILKQALLKYPKAALWSILVSTILVMEGYDTALLN
ALYALPVFQRKFGTLNGEGSYEITSQWQIGLNMCVQCGEMIGLQIITYMVEFMGNRYTMITALG
LLTAYIFILYYCKSLAMIAVGQVLSAMPWGCFQGLIVIYASEVCPLALRYYMTSYSNICWLFGQ
IFASGIMKNSQENLGNSDLDYKLPFALQWIWPAPLMIGIFFAPESPWWLVRKDRVAEARKSLSR
ILSGKGAEKDIQVDLILKQIELTIEKERLLASKSGSFFDCFKGVNGRRIRLACLAWVAQNTSGA
CLLGYSTYFF.

SEQ ID NO: 30
Amino acid sequence of AGT1 encoded by Sc allele from Hybrid
yeast 7
MKNIISLVSKKKAASKNEDKNISESSRDIVNQQEVENTENFEEGRKDSAFELDHLEFTINSAQL
GDSDEDNENVINETNITDDANEANSEEKSMILKQALLIYPKAALWSILVSTILVMEGYDTALLN
ALYALPVFQRKFGTLNGEGSYEITSQWQIGLNMCVQCGEIIGLQIIPYMVEFMGNRYTMITALG
LLTAYVFILYYCKSLAMIAVGQVLSAMPWGCFQGLIVIYASEVCPLALRYYMTSYSNICWLFGQ
IFASGIMKNSQENLGNSDLGYKLPFALQWIWPAPLMIGIFFAPESPWWLVRKDRVAEARKSLSR
ILSGKGAEKDIQIDLILKQIELTIEKERLLASKSGSFFDCFKGVNGRRIRLACLIWVAQNSSGA
CLLGYSTYFFERAGMATDKAFTFSVIQYCLGAGTLCSWVISGRVGRWTILTYGLAFQMVCLFI
IGGMGFGSGSGASNGAGGLLLALSFFYNAGIGAVVYCIVTEIPSAELRIKTIVLARICYNIMAV
INAILTPYMLNVSDWNWGAKTGLYWGGFTAVTLAWVIIDLPETSGRIFSEINELFNQGVPARKF
ASTVVDPFGKGKTQHDSLDDESISQSSSIKQRELNAADKC.

SEQ ID NO: 31
Amino acid sequence of AGT1 encoded by non-Sc allele from Hybrid
yeast 7
MKNILSLVGRKENTPEDVTANLADISSTIVMQAKDLVIEDFEERKKNDAFELNHLELTTNATQL
SDSDEDKENVIRVAEATDDANEANNEEKSMILRQALRKYPKAALWSILVSTILVMEGYDTALLS
ALYALPVFQRKFGTMNAEGSYEITSQWQIGLNMCVLCGEMIGLQIITYMVEFMGNRYTMITALS
LLTAYIFILYYCKSLAMIAVGQILSAMPWGCFQSLAVIYASEVCPLALRYYMTSYSNICWLFGQ
IFASGIMKNSQENLGNSDLGYKLPFALQWIWPAPLIIGIFFAPESPWWLVRKNKIVEAKKSLNR
ILSGTVIEKEIQVDITLKQIEMTIEKERLRASKSGSFFSCFKGVDGRRTRLACLIWVAQNSSGA
VLLGYSTYFFERAGMATDKAFTFSLIQYCLGLAGILGSWVISGRVGRWTILTYGLSFQMVCLFI
IGGMGFASGSSASNAAGGLLLALSFFYNAGIGAVVYCIVAEIPSAELRIKTIVLARICYNLMAV
FNAILTPYMLNVSDWNWGAKTGLYWGGFTALTLAWVIIDLPETTGRIFSEINELFSQGVPARKF
ASTVVDPFGKRGLQNRPQVDNIIDRFSSASQQAL.

SEQ ID NO: 32
Amino acid sequence of AGT1 encoded by non-Sc allele from Hybrid
yeast 7
MKNILSLVGRKENTPEDVTANLADISSTIVMQAKDLVIEDFEERKKNDAFELNHLELTTNATQL
SDSDEDKENVIRVAEATDDANEANNEEKSMILRQALRKYPKAALWSILVSTILVMEGYDTALLS
```

```
ALYALPVFQRKFGTMNAEGSYEITSQWQIGLNMCVLCGEMIGLQIITYMVEFMGNRYTMITALS
LLTAYIFILYYCKSLAMIAVGQILSAMPWGCFQSLAVIYASEVCPLALRYYMTSYSNICWLFGQ
IFASGIMKNSQENLGNSDLGYKLPFALQWIWPAPLIIGIFFAPESPWWLVRKNKIVEAKKSLNR
ILSGTVIEKEIQVDITLKQIEMTIEKERLRASKSGSFFSCFKGVDGRRTRLACLIWVAQNSSGA
VLLGYSTYFFERAGMATDKAFTFSLIQYCLGLAGILGSWVISGRVGRWTILTYGLSFQMVCLFI
IGGMGFASGSSASNAAGGLLLALSFFYNAGIGAVVYCIVAEIPSAELRIKTIVLARICYNLMAV
FNAILTPYMLNVSDWNWGAKTGLYWGGFTALTLAWVIIDLPETTGRIFGEINELFSQGVPARKF
ASTVVDPFGKRGLQNRPQVDNIIDRFSSASQQAL.

SEQ ID NO: 33
Amino acid sequence of SHORT IMA1 from Hybrid yeast_7_
MGYDIANYEKVWPTYGINEDCFALIEKTHKLGMKFITDLVINHCSSEHEWFKESRSSKINPKRD
WFFWRPPKGYDAEGKPIPPNNWKSYFGGSAWIFDEKTQEFYLRLFCSTQPDLNWENEDCRKAIY
ESAVGYWLDHGVDGFRIDVGSLYSKVVGLPDAPVVDKNSTWQSSDPYILNGPRIHEFHQEMNQF
IRNRVKDGREIMTVGEMQHASDETKRLYISASRHELSELFNFSHTDVGISPLFRYNLVPFELKD
WKIALAELFRFINGTDCWSTIYLENHDQPRSITRFGDDSPKNRVISGKLLSVLLSALIGTLYVY
QGQELGQINFKNWSVEKYEDVEIRNNYRLIKEECGENSEEMKKFLEGIALVSRDHARIPMPWIP
NEPNAGFSGPNTKPWFYLNESFRQGINVEEEQKNSDSVLAFWKKALEFRKNHKDIAVYGFDFKF
IDLDNKKLFSFIKRYNNKTLFAALNFSSDATDFKIPNDGSSFKLEFGNYPKNEVDASSRILKPW
EGRIHINE.

SEQ ID NO: 34
Amino acid sequence of IMA5 from_Hybrid yeast_1_
MTIIHNPKWWKEATVYQIYPASNKDSNNDGWGDLAGITSKLDYVKELGVDAIWVCLFYDSPQED
MGYDIANYEKVWPRYGINEDCFQMIEEAHKRGIKVIVDLVINHCSEEHEWFKESKSSKINPKRD
WFFWRPPKGFDEKGNPIPPNNWRSFFGGSAWRYDEKTGEFFLHVFAPGQPDFNWENEECRKAIY
DSSVGYWLRHNVDGFRIDVGSMYSKVEGLPDAPITDPIVPYQKGTEFFINGPRIHEYHKEMRKY
MLSQIPEGKEIMTVGEVGVGNEEDFRDYISAKEGELNMMENFKHTSVGESPECKYELIPFTLKD
FKLALAESELFIENTDCWSTIYLENHDQPRSVSREGSDSPKWRAISSKMLATLIISLIGTVFIY
QGQELGMSNFKNRRIEQIKCVEGIGTYAAIKRDYGEDSEKMKKFFEALALISRDHGRIPFPWSA
DEPSAGFSKDAKPWIDMNESFRDGINAEAELKDKNSVFFFWKKALQVRKEHKDILVYGHNFQFI
DLDNDKLEMETKDIDNKKMFAVFNESSDNIDFSVPDNEASYTMFFGNYANSNGDSRTLQPWEGR
LYLLK SEQ ID NO: 35
Amino acid sequence of the Hybrid Sc_IMA5_Hybrid_7 allele
MTIIHNPKWWKEATVYQIYPASNKDSNNDGWGDLAGITSKLDYVKELGVDAIWVCLFYDSPQED
MGYDIANYEKVWPRYGINEDCFQMIEEAHKRGIKVIVDLVINHCSEEHEWFKESKSSKINPKRD
WFFWRPPKGEDEKGNPIPPNNWRSFEGGSAWRYDEKTGEFFLHVFAPGQPDFNWENEKCRKAIY
DSSVGYWLRHNVDGFRIDVGSMYSKVEGLPDAPITDPIVPYQKGTEFFINGPRIHEYHKEMRKY
MLSQIPEGKEIMTVGEVGVGNEEDFRDYISAKEGELNMMENFKHTSVGESPECKYELIPFTLKD
FKLALAESELFIENTDCWSTIYLENHDQPRSVSREGSDSPKWRAISSKMLATLIISLIGTVFIY
QGQELGMSNFKNRRIEQIKCVEGIGTYAAIKRDYGEDSEKMKKFFEALALISRDHGRIPFPWSA
DEPSAGFSKDAKPWIDMNESFRDGINAEAELKDKNSVFFFWKKALQVRKEHKDILVYGHNFQFI
DLDNDKLEMETKDIDNKKMFAVFNESSDNIDFSVPDNEASYTMFFGNYANSNGDSRTLQPWEGR
LYLLK.

SEQ ID NO: 36
Amino acid sequence of the nonSc_IMA5_Hybrid_7 allele; first 6
amino acids are missing from the genomic sequence;
PKWWKEATIYQIYPASPKDSNNDGWGDLAGITSKLDYIKELGVDAIWVCPFYDSPQEDMGYDIA
NYEKVWPRYGTSEDCFQMIEESHKRGIKVIVDLVINHCSEEHEWFKESRSSKTNAKRDWFFWKP
PKGYEIDGIPIPPNNWRSFFGGSAWKYDENTEEFFLHVFAPGQPDFNWENKECRQAIYDSSVGF
WLRHNVDGFRIDVGSMYSKVEGLPDASITDPIVPYQDGIDFFVNGPRIHEYHKEMRQYMYTQIP
EGKEIMTVGEVGIGNEKDFKDYISSKEEEFNMMENFKHTSVGESPEFKYELIPFTLKDFKLALA
ESFLFIEGTDCWSTIYLENHDQPRSVSRFGSDSPEWREISSKMLATLIISLIGTVFIYQGQELG
MPNFKNRKIEQIKCVEGIGTYGAIKRDYGEDSEKMKKEYEALALISRDHGRIPFPWSGEKPYAG
FSKNAKPWIDINESFVEGINAEAELNDENSVFFEWKRALQVRKEHKNMLVYGDNFQFYDLDNEK
LEMETKDSGDKKMFAVENFCSDSTEFSVPDNKASYDMFFGNYANSDGKSYTLKPWEGRLYYSN.

SEQ ID NO: 37
Amino acid sequence of PIR2 encoded by Sc allele of_Hybrid_yeast
7 (incomplete sequence)
NSTERYNLSPSPEDEDFEAPTEEEMQTLRHVGGKIPMRCWLIAIVELSERFSYYGLSAPFQNYM
EYGPNDSPKGVLSLNSQGATGLSYFFQFWCYVTPVFGGYVADTFWGKYNTICCGTAIYIAGIFI
LFITSIPSVGNRDSAIGGFIAAIILIGIATGMIKANLSVLIADQLPKRKPSIKVLKSGERVIVD
SNITLQNVFMFFYFMINVGSLSLMATTELEYHKGFWAAYLLPFCFFWIAVVILIFGKKQYIQRP
IGDKVIAKSFKVCWILTKNKFDFNAAKPSVHPEKNYPWNDKFVDEIKRALAACKVFIFYPIYWT
QYGTMISSFITQASMMELHGIPNDFLQAFDSIALIIFIPIFEKFVYPFIRRYTPLKPITKIFFG
FMFGSFAMTWAAVLQSFVYKAGPWYNEPLGHNIPNHVHVCWQIPAYVLISFSEIFASITGLEYA
YSKAPASMKSFIMSIFLLTNAFGSAIGCLSPVTVDPKFTWLFTGLAVACFISGCLFWLCFRKY
NDTEEEMNAMDYEEEDEFDLNPISAPKANDIEILEPMESLRSTTKY.
```

SEQ ID NO: 38
Protein sequence of PIR2 encoded by nonSc allele of Hybrid yeast_7
MLNHLSQGSDDIQDEKQGDFPVIEEEKNQTVILKDSYVSDDAANSTEHYNLSPSLEEDEFEAPT
DEELRSLRHVGGKIPMRCWLIAIVELSERFSYYGLSAPFQNYMEYGPKDTPKGVLSLNSQGATG
LSYFFQFWCYVTPVFGGYVADTFWGKYNTICCGTAIYIAGIFILLITSIPSVGNRDSALGGFIA
SIILIGIATGMIKANLSVLIADQLPKRKPSIKVLKSGERVIVDSNITLQNVFMFFYFMINVGSL
SLMATTELEYHKGFWAAYLLPFCFFWVAVVILVFGKKQYIQRPIGDKVIAKSFRVCWILTKNKF
DFNAAKPSVHPEKEYPWNDKFVDEIKRALAACKVFVFYPIYWTQYGTMISSFITQAGMMELHGI
PNDFLQAFDSIALIIFIPIFEKFIYPFIRRYTPFKPITKIFFGFMFGSLAMTWAAVLQSFVYKA
GPWYSAPLGHNIPNHVHVCWQIPAYVLISFSEIFASITGLEYAYSKAPASMKSFIMSIFLLTNA
FGSAIGCALSPVTVDPKFTWLFTGLAVACFISGCLFWFCFRKYNDTEEEMNAMDYEEEDEFDLN
PISQPKGNDIEILEPMGSLKSTIKY.

SEQ ID NO: 39
Amino acid sequence of DAL5 encoded by Sc allele of Hybrid yeast_7
MSADASINSNASLDEKNLNITSEAEIKNEDVTAEPVLSTVLSPNGKIVYISDKVDEAMKLAEEA
KEIEVIPEEDRKLRWKIDYCMFPLMCILYAVQFMDKISTSSAAVMGLRIDLKMHGDQYSWVISA
FYFGYLFMNLGPVQFIFQRTSHMSKMLAVFIVIWGMLLALHAAPTVKYPSFIVLRVLLGCAESV
VTPCFTIITAQYWKTEEQFTRVSIWFGMNGLGSILINAIAYGVYIHQDSYAIKGWRILFVITGV
ITIFIGILIFLWIPDDPSKARFLSKREKLMVVQRIRSNQQGFGNHEIKKYQIIEALKDVRTWLY
FLFTVSSNIPNGGISSFMSILLNSDFGYSSKEILLMGLPTGAVELVGCPLFGILAVYAANKKIP
FWKYKLSWAIFAAVLALIASCMLGFAINSKKARLAGAYLWYISPVSFICVLSNISANSSGYSKK
WIVSSINLVAYAAANLAGPQTFIAKQAPKYHGAKVAMVVCYAVMIVLLSILLIVNLRENKRRDK
IAAERGFPEETENLEFSDLTDFENPNFRYTL.

SEQ ID NO: 40
Amino acid sequence of DAL5 encoded by nonSC allele of_Hybrid yeast_7
MSGGASINSNASIDEKNLNITSEAEIKNEDVYAEPVLSTVLSPNGKVVYISDKVDEAMKLADEA
KEIEVIPEEDRKLRWKIDYCMFPLMCILYAVQFMDKISTSSAAVMGLRIDLKMHGDQYSWVISA
FYFGYLFMNLGPVQLIFQKSKHMSKMLAIFIIVWGLLLALHAVPSVKYSSFIALRVLLGCAESV
VTPCFTIITAQYWKTEEQFTRISIWFGMNGLGSILINAIAYGVYIHQESYAIKGWRALFVITGV
ITIFVGALIFLWIPDDPSKARFLSKREKLMVVQRIRSNQQGFGNHEIKKYQIVEALKDVRTWLY
FLFTVSSNIPNGGISSFMSILLNSDFGYLSKDILLMGLPTGAVELVGCPLFGILAVYAANKKIP
FWKYKLAWAIFAAVLALIASCMLGFATSSKKARLAGAYLWYISPVSFICVLSNISANSSGYSKK
WIVSSINLAAYAAANLAGPQTFIAKQAPKYHGAKVAMVVCYAVMIVLLSALLLINMRENKRRDK
IAAERGYPEETANLEFSDLTDFENPNFRYTL.

SEQ ID NO: 41
Amino acid sequence of UBR1 encoded by Sc allele of Hybrid_yeast 7 (incomplete sequence)
MSVADDDLGSLQGHIRRILRSIHNLPYFRYTRGPTERADMSRALKEFIYRYLYFVISNSGENLP
TLFNAHPKQKLSNPELTVFPDSLEDAVDIDKITSQQTIPFYKIDESRIGDVHKHIGRNCGRKFK
IGEPLYRCHECGCDDICVLCIHCFNPKDHVNHHVCIDICTEFTSGICDCGDEEAWNSPLHCKAE
EQENDISEDPATNADIKEEDVWNDSVNIALVELVLAEVFDYFIDVFNQNIEPLPTIQKDITIKL
REMTQQGKMYERAQFLNDLKYENDYMFDGITTAKTSPSNSPEASPSLAKIDPENYTVIIYNDEY
HNYSQATTALRQGVPDNVHIDLLTSRIDGEGRAMLKCSQDSSSVLGGFFAVQINGLSAILTSWS
EYLHQEICKYIILWITHCLNIPNSSFQTTFRNMMGKILCSEYLNATECRDMTPVVEKYFSNKFD
KNDPYRYIDLSILADGNQIPLGHHKILPESSTHSLSPLINDVETPTSRTYSNTRLQHILYFDNR
YWKRLRKDIQNVIIPTLASSNLYKPIFCQQVVEIFNHITRSVAYMDREPQLTAIRECVVQLFIC
PINAKNIFENQSFLDIVWSIIDIFKEFCKVEGGVLIWQRVQKSNLIKSYSISFKQGLYTVEILL
SKVHDPNIPLRPKEIISLLTLCKLFNGAWKIKRKEGEHVLHEDQNFISYLEYTTSIYSIIQTAE
KVSEKSKDSIDSKLFLNAIRIISSFLGNRSLTYKLIYDSHEVIKFSVSHERVAFMNPLQTMLSF
LIEKVSLKDAYEALEDCSDFLKISDFSLRSVVLCSQIDVGFWVRNGMSVLHQASYYKNNP SEQ ID NO: 42
Amino acid sequence of UBR1 encoded by nonSc allele of_Hybrid yeast_7
MSFIDNGLGSLKAHIRRILRSIHNLPYFRFTRGPTERADMSRALKEFIYRYLYFIISNDGENLS
TLFTAHPKQKSSNQELAVFPESLEDALDVDKITSQGTFPPFYKIDESKIGDVHKHIGRNCGRKFK
IGEPLYRCHECGCDDICVLCIHCFNPKDHINHHVCIDICSEFTSGICDCGDEEAWNSSLHCKAE
EQGNDISEDPSNFDSTKQKDVWNDPECIALVELVLSEVFDYFIDVFNQNIEPLPTIQKDITIKL
REMTQQGKMYERAQFLNDLKYENDYMEDGITTAKTSPSNSPEASPSLAKIDPENYTVIIYNDEY
HNYSQATTALRQGVPDNVHIDLLTSRIDGEGRAMLKCSQDLSSVLGGFFAVQINGLSAILTSWS
EYLHQEACKYIILWITHCLNIPNPSFQITFRNMMGKSLCSEYLNATESRDMTPVVEKYFSTKFD
KDDPYRYIDLSVLAEGNQIPLGHHKVLPESSTHSLSTLINDVENLISKEYSNTRLQHILYFDNR
YWKRLRKDIQNVIIPTLASSTLYKPIFCQQVVEIFNHITRSVAYMDREPQLTAIRECVVQLFIC
PINTRNIFENQSFLDILWSIIDIFKEFCKVEAGVLIWQRVQKSNLIKSYSLSFKQGLYTVEILL
SKVNDPNITIRPKVFISLLTLGKLENGAWKIKRKEGEHVLHEDQNFISYLEYTTSIYSIIQTAE
KVLEKSHDSLDLNLVLNAIRIVSSFLGNRSLTYKLIYDSHEIIKFSVSHERVAFMNPIQTMLSF
LIEKVSLKDAYESLENCPDFLKIADFSLRSVVLCSQIDVGFWVRNGMSVLHQASYYKNNPELGS
YSRDIHLNQLAIIWERDDLPRVIYNILDRWELLDWFMGEAEYQHTVYEDKISFMIQQFIAFIYQ
ILTERQYFKIFSLLRDRRMDMIKNSIMYNLYMKPLSYSKLLKSVPDYLTDDITEFDEALEEVSV
FVEPKGLADNGVFKLKAALYAKIDPLKLLNLENEFESSATIIKTHLAKNKDEVSKVVLIPQVST

```
Sequence listing

KLLDKGAMNLGEFTRNIVFAKVIYKLLQVCLDMEDSTFLNELLHLVHGIFKDDELINGKDSIPE
AYLAKPICNLLLSIANAKSDIFSESIVRKADYLLEKMIMKKPDEIFESLIASEGNQYIDNYKDK
KLSQGVNLQETEKERKRRMAKKHQARLLAKFNNQQSKFMKEHESEFDEQDNDVDMDGEKVYESE
DFICALCQDSSSIDFFVIPAYHDHIPIFRPGNIFNPREFMAKWDGFYNDDDKQAYIDDEVLESL
KENGTRGSRKVEVSCNHHIHHNCFKRYVQKKRESSNAFICPLCQTESNCTLPICPTSRANTGLS
LDMFLKSELSLDILSRLFKPFTEDNYRTINSIFSLMVSQCQGFDKVVRKHVNFTHKDVSLVLSV
HWANTISMLEVASRLEKPHNISFFRSREQKYKILKNILICIMLFTFVIGKPSMEFEPYPVESDI
ICNQNQLFQYIVRKSLFSPASLRETITEALTVFCKQFLDDFVQGLSDAEQVDKLYTEAKKLGDV
YNVDESILITLMSITVVKTEGLESRSIYDLAYISLLKSLLPTIRRCLVMVKVLHELVKDSENET
MVIDGEDVEEELEFEGLPGFVDKALKLITDKESFVDLEKTKQAIVPSHPYLERIPYEYCGIVKL
IDLSKFLNTYVTQSKEIKLREERSQHMKNADNRLDFKICLICGVKVHLRADRHEMTKHLNKNCF
KSFGAFLMPNSSEVCLHLTQFPSSNIFVSAPYLNSHGEVGRNAMRRGDLTTLNLKRYEHLNRLWI
NNEIPGYISRVMGDEFRVTILSNGFLFAFNREPRPRRVPPIDEDDEDMEEGEEGFFTEENDDMD
VDDETGQAANLFGVGAEGIGDGGVRNFFQFFENFRNTLQPQGNDDEDAPQNPPPILQFLGPQFD
GATIIRNTNQRNLDEDDSSENDDSDEREIW.

SEQ ID NO: 43
Amino acid sequence of PIR2 encoded by Sc allele of Hybrid yeast
1
MLNHPSQGSDDAQDEKQGDFPVIEEEKTQAVMLKDSYVSDDVANSTERYNLSPSPEDEDFEAPT
EEEMQTLRHVGGKIPMRCWLIAIVELSERFSYYGLSAPFQNYMEYGPNDSPKGVLSLNSQGATG
LSYFFQFWCYVTPVFGGYVADTFWGKYNTICCGTAIYIAGIFILFITSIPSVGNRDSAIGGFIA
AIILIGIATGMIKANLSVLIADQLPKRKPSIKVLKSGERVIVDSNITLQNVFMFFYFMINVGSL
SLMATTELEYHKGFWAAYLLPFCFFWIAVVILIFGKKQYIQRPIGDKVIAKSFKVCWILTKNKF
DFNAAKPSVHPEKNYPWNDKFVDEIKRALAACKVFIFYPIYWTQYGTMISSFITQASMMELHGI
PNDFLQAFDSIALIIFIPIFEKFVYPPIRRYTPLKPITKIFVGFMFGSFAMTWAAVLQSFVYKA
GPWYNEPLGHNIPNHVHVCWQIPAYVLISFSEIFASITGLEYAYSKAPASMKSFIMSIELLTNA
FGSAIGCALSPVTVDPKFTWLFTGLAVACFISGCLFWLCFRKYNDTEEEMNAMDYEEENEFDLN
PISAPKANDIEILEPMDSLRSTTKY.

SEQ ID NO: 44
Amino acid sequence of PIR2 encoded by nonSc allele of Hybrid
yeast 1
MLNHLSQGSDDIQDEKQGDFPVIEEEKNQTVILKDSYVSDDAANSTEHYNLSPSLEEDEFEAPT
DEELRSLRHVGGKIPMRCWLIAIVELSERFSYYGLSAPFQNYMEYGPKDTPKGVLSLNSQGATG
LSYFFQFWCYVTPVFGGYVADTFWGKYNTICCGTAIYIAGIFILLITSIPSVGNRDSALGGFIA
SIILIGIATGMIKANLSVLIADQLPKRKPSIKVLKSGERVIVDSNITLQNVFMFFYFMINVGSL
SLMATTELEYHKGFWAAYLLPFCFFWVAVVILVFGKKQYIQRPIGDKVIAKSFRVCWILTKNKF
DFNAAKPSVHPEKEYPWNDKFVDEIKRALAACKVFVFYPIYWTQYGTMISSFITQAGMMELHGI
PNDFLQAFDSIALIIFIPIFEKFIYPPIRRYTPFKPITKIFFGFMFGSLAMTWAAVLQSFVYKA
GPWYSAPLGHNIPNHVHVCWQIPAYVLISFSEIFASITGLEYAYSKAPASMKSFIMSIFLLTNA
FGSAIGCALSPVTVDPKFTWLFTGLAVACFISGCLFWFCFRKYNDTEEEMNAMDYEEEDEFDLN
PISQPKGNDIEILEPMGSLKSTIKY.

SEQ ID NO: 45
Partial amino acid sequence of UBR1 encoded by Sc allele of
Hybrid yeast 1
MSVADDDLGSLQGHIRRILRSIHNLPYFRYTRGPTERADMSRALKEFIYRYLYFVISNSGENLP
TLFNAHPKQKLSNPELTVFPDSLEDAVDIDKITSQQTIPFYKIDESRIGDVHKHIGRNCGRKFK
IGEPLYRCHECGCDDICVLCIHCFNPKDHVNHHVCIDICTEFTSGICDCGDEEAWNSPLHCKAE
EQENDISEDPATNADIKEEDVWNDSVNIALVELVLAEVFDYFIDVFNQNIEPLPTIQKDITIKL
REMTQQGKMYERAQFLNDLKYENDYMFDGITTAKTSPSNSPEASPSLAKIDPENYTVIIYNDEY
HNYSQATTALRQGVPDNVHIDLLTSRIDGEGRAMLKCSQDL.
```

Items

The invention may furthermore be defined by the following items:

1. A yeast cell having at least one of the following characteristics:
   II. capable of utilizing panose as sole carbon source;
   III. capable of utilizing one or more dipeptides as sole nitrogen source.
2. The yeast cell according to item 1 having both of characteristics II. and III.
3. The yeast cell according to any one of the preceding items, wherein the yeast cell furthermore has characteristic:
   I. Capable of utilizing isomaltose as sole carbon source.
4. The yeast cell according to any one of the preceding items, wherein said yeast cell is capable of utilizing isomaltose as sole carbon source when said isomaltose is present at a concentration of in the range of 1 to 5 g/L, such as on the range of 1 to 3 g/L, for example 2 g/L.
5. The yeast cell according to any one of the preceding items, wherein said yeast cell is capable of utilizing panose as sole carbon source when said panose is present at a concentration of in the range of 1 to 5 g/L, such as on the range of 1 to 3 g/L, for example 2 g/L.
6. The yeast cell according to any one of the preceding items, wherein said yeast cell is capable of removing at least 45% of the panose present in wort.
7. The yeast cell according to any one of the preceding items, wherein said yeast cell is capable of removing at least 50% of the panose present in wort after incubation for 5 days at 16° C.
8. The yeast cell according to any one of the preceding items, wherein the yeast cell further has the characteristic:

III. capable of utilizing one or more dipeptides as sole nitrogen source.
9. The yeast cell according to any one of the preceding items, wherein one or more of said dipeptides are selected from the group consisting of Met-Tyr, Leu-Tyr, Val-Met, Phe-Tyr, Ile-Leu and Ile-Asn.
10. The yeast cell according to any one of items 1 to 8, wherein one or more of said dipeptides are dipeptides of the formula Ala-Xaa, wherein Xaa denotes any amino acid.
11. The yeast cell according to item 10, wherein Xaa is an amino acid selected from the group consisting of Glu, Gly, His and Thr.
12. The yeast cell according to any one of items 1 to 8, wherein one or more of said dipeptides are selected from the group consisting of Gly-Arg, Ile-Asn, Lys-Tyr, Met-Lys, Val-Ala, Val-Asn, Val-Gly, Val-Gln, Val-Met and Val-Ser.
13. The yeast cell according to any one of items 1 to 8, wherein one or more of said dipeptides are dipeptides of the formula Val-Xaa, wherein Xaa denotes any amino acid.
14. The yeast cell according to any one of the preceding items, wherein the yeast cell furthermore is capable of utilizing allantoine as sole nitrogen source.
15. The yeast cell according to any one of the preceding items, wherein the yeast cell further has the characteristic:
    IV. capable of utilizing one or more tri-peptides as sole nitrogen source.
16. The yeast cell according to item 15, wherein one of said tri-peptides is Gly-Gly-Gly.
17. The yeast cell according to any one of the preceding items, wherein the yeast cell further has the characteristic:
    V. capable of reducing the level of one or more amino acids to no more than 10% of the starting concentration after incubation for 5 days under conditions allowing growth of said yeast cells.
18. The yeast cell according to any one of the preceding items, wherein the yeast cell is capable of reducing the level of at least 12, such as at least 13, for example of at least 14 different amino acids to less than 10% of the starting concentration after incubation for 5 days under conditions allowing growth of said yeast cells.
19. The yeast cell according to any one of the preceding items, wherein the yeast cell is capable of reducing the total level of amino acids to less than 30%, such as less than 25% of the starting concentration after incubation for 5 days under conditions allowing growth of said yeast cells.
20. The yeast cell according to any one of the preceding items, wherein the yeast cell is capable of reducing the level of all of the amino acids Met, Val, Ile, Leu and Phe to less than 10%, preferably less than 5%, even more preferably to at the most 2% of the starting concentration after incubation for 5 days under conditions allowing growth of said yeast cells.
21. The yeast cell according to any one of the preceding items, wherein the yeast cell is capable of reducing the total level of the amino acids Met, Val, Ile, Leu and/or Phe to at the most 400 mg/L, such as at the most 100 mg/L, such as at the most 50 mg/L, for example to at the most 10 mg/L after incubation for 6 days under conditions allowing growth of said yeast cell.
22. The yeast cell according to any one of the preceding items, wherein the yeast cell further has the characteristic:
    VI. capable of generating at least 4.7 promille ethanol per ° Plato, when said yeast cell is added to a wort composition having a sugar content of at least 10° Plato and incubated until level of diacetyl is in spec.
23. The yeast cell according to any one of the preceding items, wherein the yeast cell further has the characteristic:
    VII. capable of fermenting sugar with a real degree of fermentation of at least 68, such as at least 70, when said yeast cell is added to a wort composition having a sugar content of at least 10° Plato and incubated until level of diacetyl is in spec.
24. The yeast cell according to any one of the preceding items, wherein the yeast cell has characteristic VII, wherein characteristic VII is that the yeast cell is capable for fermenting sugar with an RDF, which is at least 1 higher than the RDF of one of its parental strains.
25. The yeast cell according to any one of the preceding items, wherein the yeast cell further has the characteristic:
    VIII. capable of utilizing melibiose as the sole carbon source.
26. The yeast cell according to any one of the preceding items, wherein the yeast cell further has the characteristic:
    X. capable of sedimentation so that at the most 12 million, such as at the most 10 million cells/ml are in suspension when said yeast cell is added to a wort composition having a sugar content of at least 10° Plato and incubated for 4 days.
27. The yeast cell according to item 26, wherein the number of cells in suspension per ml is at the most 80%, such as at the most 70%, for example at the most 60%, such as at the most 50%, for example at the most 40% of the starting number of cells per ml after 5 days incubation under conditions allowing growth of said cells.
28. The yeast cell according to any one of the preceding items, wherein the yeast cell further has characteristic:
    IX. capable of utilizing one or more disaccharides and/or trisaccharides in addition to isomaltose, panose, and/or melibiose.
29. The yeast cell according to item 28, wherein the disaccharide is selected from the group consisting of kojibiose, nigerose, sucrose, turanose, leucrose, and palatinose.
30. The yeast cell according to item 28, wherein the disaccharide is kojibiose.
31. The yeast cell according to any one of the preceding items, wherein said yeast cell is capable of utilizing kojibiose as sole carbon source when said kojibiose is present at a concentration of in the range of 1 to 5 g/L, such as on the range of 1 to 3 g/L, for example 2 g/L.
32. The yeast cell according to item 28, wherein the disaccharide is maltulose.
33. The yeast cell according to any one of the preceding items, wherein said yeast cell is capable of utilizing maltulose as sole carbon source when said maltulose is present at a concentration of in the range of 1 to 5 g/L, such as on the range of 1 to 3 g/L, for example 2 g/L.
34. The yeast cell according to item 28, wherein the trisaccharide is selected from the group consisting of maltotriose and isomaltotriose.

35. The yeast cell according to any one of the preceding items, wherein the yeast cell is capable or utilizing maltotriose as the sole carbon source, when said maltotriose is present at a concentration of in the range of 1 to 5 g/L, such as on the range of 1 to 3 g/L, for example 2 g/L.

36. The yeast cell according to any one of the preceding items, wherein the yeast cell furthermore has characteristic
   XI: capable of fermenting wort with a time of primary fermentation of at the most 4 days, for example at the most 3 days.

37. The yeast cells according to item 36, wherein said time of primary fermentation is determined after pitching wort with a sugar content of in the range of 10° Plato to 20° Plato with in the range of 10 to 20 million viable cells/ml.

38. The yeast cell according to any one of the preceding items, wherein the yeast cell has genotype:
   I. comprising a gene encoding DAL5.

39. A yeast cell having genotype:
   I. comprising a gene encoding DAL5.

40. The yeast cell according to any one of items 38 to 39, wherein the genotype I is that said yeast cell comprises at least one allelic gene encoding DAL5, wherein the allelic gene encoding DAL5 encodes DAL5 selected from the group consisting of DAL5 of SEQ ID NO:6, DAL5 of SEQ ID NO:39, DAL5 of SEQ ID NO:40 and functional homologues thereof sharing at least 80%, preferably at least 90%, yet more preferably at least 95%, such as at least 98% sequence identity with any of the aforementioned.

41. The yeast cell according to any one of items 38 to 40, wherein the genotype I is that said yeast cell comprises at least one allelic gene encoding DAL5 of SEQ ID NO:6 or a functional homologue thereof sharing at least 80%, preferably at least 90%, yet more preferably at least 95%, such as at least 98% sequence identity therewith.

42. The yeast cell according to any one of items 38 to 41, wherein the yeast cell, furthermore has characteristic III, for example characteristic III as defined in any one of items 8 to 14.

43. The yeast cell according to any one of items 38 to 42, wherein the yeast cell, furthermore has characteristics IV, for example characteristic IV as defined in any one of items 15 to 16.

44. The yeast cell according to any one of items 38 to 43, wherein the yeast cell, furthermore has characteristics V, for example characteristic V as defined in any one of items 17 to 21.

45. The yeast cell according to any one of the preceding items, wherein the yeast cell has genotype:
   II. comprising at least 2 allelic genes encoding PTR2.

46. A yeast cell having genotype:
   II. comprising at least 2 allelic genes encoding PTR2.

47. The yeast cell according to any one of items 45 to 46, wherein said PTR2 may be selected from the group consisting of PTR2 of SEQ ID NO:7, PTR2 of SEQ ID:8, PRT2 of SEQ ID NO:9 and functional homologues of each of the aforementioned sharing at least 80%, preferably at least 90%, yet more preferably at least 95%, such as at least 98% sequence identity therewith.

48. The yeast cell according to any one of items 45 to 47, wherein genotype II is said yeast cell comprising at least two allelic genes encoding PTR2 individually selected from the group consisting of genes encoding PTR2 of SEQ ID NO:7, PTR2 of SEQ ID:8, PRT2 of SEQ ID NO:9, PRT2 comprising SEQ ID NO:37, PRT2 of SEQ ID NO:38, PRT2 of SEQ ID NO:43, PRT2 of SEQ ID NO:44 and functional homologues of each of the aforementioned sharing at least 80%, preferably at least 90%, yet more preferably at least 95%, such as at least 98% sequence identity therewith.

49. The yeast cell according to any one of items 45 to 48, wherein genotype II is that the yeast cell comprises the following 3 genes:
   1) a gene encoding PRT2 of SEQ ID NO:7 or a functional homologue thereof sharing at least 80%, preferably at least 90%, yet more preferably at least 95%, such as at least 98% sequence identity therewith;
   2) a gene encoding PRT2 of SEQ ID NO:8 or a functional homologue thereof sharing at least 80%, preferably at least 90%, yet more preferably at least 95%, such as at least 98% sequence identity therewith; and
   3) a gene encoding PRT2 of SEQ ID NO:9 or a functional homologue thereof sharing at least 80%, preferably at least 90%, yet more preferably at least 95%, such as at least 98% sequence identity therewith.

50. The yeast cell according to any one of items 45 to 49, wherein the yeast cell furthermore has genotype I, such as genotype I as defined in any one of items 39 to 41.

51. The yeast cell according to any one of items 45 to 50, wherein the yeast cell furthermore has characteristic III, for example characteristic III as defined in any one of items 8 to 14.

52. The yeast cell according to any one of items 45 to 51, wherein the yeast cell furthermore has characteristic IV, for example characteristic IV as defined in any one of items 15 to 16.

53. The yeast cell according to any one of items 45 to 52, wherein the yeast cell furthermore has characteristic V, for example characteristic V as defined in any one of items 17 to 21.

54. The yeast cell according to any one of the preceding items, wherein the yeast cell has the genotype:
   III. comprising a gene encoding UBR1.

55. A yeast cell having the genotype:
   III. comprising a gene encoding UBR1.

56. The yeast cell according to any one of items 54 to 55, wherein genotype III is said yeast cell comprising at least two allelic genes encoding UBR1 individually selected from the group consisting of UBR1 comprising SEQ ID NO:10, UBR1 of SEQ ID NO:11, UBR1 comprising SEQ ID NO:41, UBR1 of SEQ ID NO:42, UBR1 comprising SEQ ID NO:45 and functional homologues of any of the aforementioned sharing at least 80%, preferably at least 90%, yet more preferably at least 95%, such as at least 98% sequence identity therewith.

57. The yeast cell according to any one of items 54 to 56, wherein genotype III is that said yeast cell comprises a gene encoding UBR1 selected from the group consisting of UBR1 comprising SEQ ID NO:10, UBR1 of SEQ ID NO:11 and functional homologues of any of the aforementioned sharing at least 80%, preferably at least 90%, yet more preferably at least 95%, such as at least 98% sequence identity therewith.

58. The yeast cell according to any one of items 54 to 57, wherein genotype III is that the yeast cell comprises the following 2 genes:
   1) a gene encoding UBR1 comprising SEQ ID NO:10 or a functional homologue thereof sharing at least 80%, preferably at least 90%, yet more preferably at least 95%, such as at least 98% sequence identity therewith;
   2) a gene encoding UBR2 of SEQ ID NO:11 or a functional homologue thereof sharing at least 80%, preferably at least 90%, yet more preferably at least 95%, such as at least 98% sequence identity therewith.
59. The yeast cell according to any one of items 54 to 58, wherein the yeast cell furthermore has the genotype I, for example genotype I as defined in any one of items 39 to 41.
60. The yeast cell according to any one of items 55 to 59, wherein the yeast cell furthermore has genotype II, such as genotype II as defined in any one of items 46 and 49.
61. The yeast cell according to any one of items 55 to 60, wherein the yeast cell furthermore has characteristic III, for example characteristic III as defined in any one of items 8 to 14.
62. The yeast cell according to any one of items 55 to 61, wherein the yeast cell furthermore has characteristic IV, for example characteristic IV as defined in any one of items 15 to 16.
63. The yeast cell according to any one of items 55 to 62, wherein the yeast cell furthermore has characteristic V, for example characteristic V as defined in any one of items 17 to 21.
64. The yeast cell according to any one of the preceding items, wherein the yeast cell has the genotype:
   IV. comprising at least 3 genes, such as at least 4 genes encoding IMA1p.
65. A yeast cell having the genotype:
   IV. comprising at least 3 genes, such as at least 4 genes encoding IMA1p.
66. The yeast cell according to any one of items 64 and 65, wherein IMA1p is selected from the group consisting of IMA1p of SEQ ID NO:12, IMA1p of SEQ ID NO:13, IMA1p of SEQ ID NO:14, IMA1p of SEQ ID NO:15, IMA1p of SEQ ID NO:21, IMA1p of SEQ ID NO:22, IMA1p of SEQ ID NO:23, IMA1p of SEQ ID NO:24, IMA1p of SEQ ID NO:25 and functional homologues of any of the aforementioned sharing at least 80%, preferably at least 90%, yet more preferably at least 95%, such as at least 98% sequence identity therewith.
67. The yeast cell according to any one of items 64 to 66, wherein the genotype IV is that the yeast cell comprises at least 2 short alleles of IMA1, said two short alleles of IMA1 encoding IMA1p selected from the group consisting of IMA1p SEQ ID NO:12, IMA1p of SEQ ID NO:13 and functional homologues of any of the aforementioned sharing at least 80%, preferably at least 90%, yet more preferably at least 95%, such as at least 98% sequence identity therewith.
68. The yeast cell according to any one of items 64 to 67, wherein the genotype IV that said yeast cell comprises at least 3 short alleles of IMA1, which individually are genes encoding IMA1p selected from the group consisting of IMA1p of SEQ ID NO:12, IMA1p of SEQ ID NO:13, IMA1p of SEQ ID NO:1, IMA1p of SEQ ID NO:2, IMA1p of SEQ ID NO:3, IMA1p of SEQ ID NO: 4, IMA1p of SEQ ID NO: 5, IMA1p of SEQ ID NO:33 and functional homologues of any of the aforementioned sharing at least 80%, preferably at least 90%, yet more preferably at least 95%, such as at least 98% sequence identity therewith.
69. The yeast cell according to any one of items 64 to 68, wherein the genotype IV is that the yeast cell comprises at least 2 long alleles of IMA1, said two long alleles of IMA1 encoding IMA1p selected from the group consisting of IMA1p SEQ ID NO:14, IMA1p of SEQ ID NO:15 and functional homologues of any of the aforementioned sharing at least 80%, preferably at least 90%, yet more preferably at least 95%, such as at least 98% sequence identity therewith.
70. The yeast cell according to any one of items 64 to 69, wherein the genotype IV is that said yeast cell comprises at least 3 short alleles of IMA1 and at least 2 long alleles of IMA1, wherein
   a) said 3 short alleles of IMA1 individually are genes encoding IMA1p selected from the group consisting of of IMA1p of SEQ ID NO:12, IMA1p of SEQ ID NO:13, IMA1p of SEQ ID NO:1, IMA1p of SEQ ID NO:2, IMA1p of SEQ ID NO:3, IMA1p of SEQ ID NO: 4, IMA1p of SEQ ID NO: 5, IMA1p of SEQ ID NO:33 and functional homologues of any of the aforementioned sharing at least 80%, preferably at least 90%, yet more preferably at least 95%, such as at least 98% sequence identity therewith; and
   b) said 2 long alleles of IMA1 individually are genes encoding IMA1p selected from the group consisting of IMA1p of SEQ ID NO:14, IMA1p of SEQ ID NO:15, IMA1p of SEQ ID NO:21, IMA1p of SEQ ID NO:22, IMA1p of SEQ ID NO:23, IMA1p of SEQ ID NO:24, IMA1p of SEQ ID NO:25 and functional homologues of any of the aforementioned sharing at least 80%, preferably at least 90%, yet more preferably at least 95%, such as at least 98% sequence identity therewith.
71. The yeast cell according to any one of items 64 to 70, wherein the genotype IV is that the yeast cell comprises at least 5 genes encoding IMA1p, wherein said genes individually are selected from the group consisting of genes encoding IMA1p of SEQ ID NO:1, IMA1p of SEQ ID NO:2, IMA1p of SEQ ID NO:3, IMA1p of SEQ ID NO:4, IMA1p of SEQ ID NO:5, IMA1p of SEQ ID NO:12, IMA1p of SEQ ID NO:13, IMA1p of SEQ ID NO:14, IMA1p of SEQ ID NO:15, IMA1p of SEQ ID NO:21, IMA1p of SEQ ID NO:22, IMA1p of SEQ ID NO:23, IMA1p of SEQ ID NO:24, IMA1p of SEQ ID NO:25 and IMA1p of SEQ ID NO:33.
72. The yeast cell according to any one of items 64 to 71, wherein the genotype IV is that the yeast cell comprises the following 4 genes:
   1) a gene encoding IMA1p of SEQ ID NO:12 or a functional homologue thereof sharing at least 80%, preferably at least 90%, yet more preferably at least 95%, such as at least 98% sequence identity therewith; and
   2) a gene encoding IMA1p of SEQ ID NO:13 or a functional homologue thereof sharing at least 80%, preferably at least 90%, yet more preferably at least 95%, such as at least 98% sequence identity therewith; and
   3) a gene encoding IMA1p of SEQ ID NO:14 or a functional homologue thereof sharing at least 80%, preferably at least 90%, yet more preferably at least 95%, such as at least 98% sequence identity therewith; and
   4) a gene encoding IMA1p of SEQ ID NO:15 or a functional homologue thereof sharing at least 80%, preferably at least 90%, yet more preferably at least 95%, such as at least 98% sequence identity therewith.

73. The yeast cell according to any one of items 64 to 72, wherein the genotype IV is the presence of at least 3 long alleles of IMA1 encoding IMA1p selected from the group consisting of IMA1p of SEQ ID NO:21, IMA1p of SEQ ID NO:22, IMA1p of SEQ ID NO:3, IMA1p of SEQ ID NO:24, IMA1p of SEQ ID NO:25 and functional homologues of any of the aforementioned sharing at least 80%, preferably at least 90%, yet more preferably at least 95%, such as at least 98% sequence identity therewith.

74. The yeast cell according to any one of items 64 to 73, wherein the genotype IV is that the yeast cell comprises the following 3 genes:
   1) two genes both encoding IMA1p of SEQ ID NO:21 or a functional homologue thereof sharing at least 80%, preferably at least 90%, yet more preferably at least 95%, such as at least 98% sequence identity therewith; and
   2) a gene encoding IMA1p of SEQ ID NO:22 or a functional homologue thereof sharing at least 80%, preferably at least 90%, yet more preferably at least 95%, such as at least 98% sequence identity therewith.

75. The yeast cell according to any one of items 64 to 74, wherein the genotype IV is that the yeast cell comprises the following 3 genes:
   1) a gene encoding IMA1p of SEQ ID NO:23 or a functional homologue thereof sharing at least 80%, preferably at least 90%, yet more preferably at least 95%, such as at least 98% sequence identity therewith; and
   2) a gene encoding IMA1p of SEQ ID NO:24 or a functional homologue thereof sharing at least 80%, preferably at least 90%, yet more preferably at least 95%, such as at least 98% sequence identity therewith; and
   3) a gene encoding IMA1p of SEQ ID NO:25 or a functional homologue thereof sharing at least 80%, preferably at least 90%, yet more preferably at least 95%, such as at least 98% sequence identity therewith.

76. The yeast cell according to any one of items 64 to 75, wherein the yeast cell furthermore has the genotype I, for example genotype I as defined in any one of items 39 to 41.

77. The yeast cell according to any one of items 64 to 76, wherein the yeast cell furthermore has genotype II, such as genotype II as defined in any one of items 46 and 49.

78. The yeast cell according to any one of items 64 to 77, wherein the yeast cell furthermore has genotype III, such as genotype III as defined in any one of items 55 and 58.

79. The yeast cell according to any one of items 64 to 78, wherein the yeast cell furthermore has characteristic I, for example characteristic I as defined in any one of items 3 to 4.

80. The yeast cell according to any one of items 64 to 79, wherein the yeast cell furthermore has characteristic II, for example characteristic II as defined in any one of items 1 and 5 to 7.

81. The yeast cell according to any one of items 64 to 80, wherein the yeast cell furthermore has characteristic IX, for example characteristic IX as defined in any one of items 28 to 35.

82. The yeast cell according to any one of the preceding items, wherein the yeast cell has the genotype
   V. Comprising a gene encoding IMA5p.

83. A yeast cell having the genotype
   V. Comprising a gene encoding IMA5p.

84. The yeast cell according to any one of items 82 and 83, wherein IMA5p is selected from the group consisting of IMA5p of SEQ ID NO:16, IMA5p of SEQ ID NO:17 and functional homologues of any of the aforementioned sharing at least 80%, preferably at least 90%, yet more preferably at least 95%, such as at least 98% sequence identity therewith.

85. The yeast cell according to any one of items 82 and 83, wherein IMA5p is selected from the group consisting of IMA5p of SEQ ID NO:34, IMA5p of SEQ ID NO:35, IMA5p of SEQ ID NO:36 and functional homologues of any of the aforementioned sharing at least 80%, preferably at least 90%, yet more preferably at least 95%, such as at least 98% sequence identity therewith.

86. The yeast cell according to any one of items 82 to 85, wherein the genotype V is that the yeast cell comprise at least two genes encoding IMA5p of SEQ ID NO:16, or IMA5p of SEQ ID NO:17 or a functional homologue of any of the aforementioned sharing at least 80%, preferably at least 90%, yet more preferably at least 95%, such as at least 98% sequence identity therewith.

87. The yeast cell according to any one of items 82 to 86, wherein the genotype V is that the yeast cell comprises at least two allelic genes encoding IMA5p individually selected from allelic genes encoding IMA5p of SEQ ID NO:16, IMA5p of SEQ ID NO:17, IMA5p of SEQ ID NO:34, IMA5p of SEQ ID NO:35, IMA5p of SEQ ID NO:36 and functional homologues of any of the aforementioned sharing at least 80%, preferably at least 90%, yet more preferably at least 95%, such as at least 98% sequence identity therewith.

88. The yeast cell according to any one of items 82 to 87, wherein the genotype V is that the yeast cell comprises the following 2 genes:
   1) a gene encoding IMA5p of SEQ ID NO:16 or a functional homologue thereof sharing at least 80%, preferably at least 90%, yet more preferably at least 95%, such as at least 98% sequence identity therewith; and
   2) a gene encoding IMA5p of SEQ ID NO:17 or a functional homologue thereof sharing at least 80%, preferably at least 90%, yet more preferably at least 95%, such as at least 98% sequence identity therewith.

89. The yeast cell according to any one of items 82 to 88, wherein the yeast cell furthermore has the genotype I, for example genotype I as defined in any one of items 39 to 41.

90. The yeast cell according to any one of items 82 to 89, wherein the yeast cell furthermore has genotype II, such as genotype II as defined in any one of items 46 and 49.

91. The yeast cell according to any one of items 82 to 90, wherein the yeast cell furthermore has genotype III, such as genotype III as defined in any one of items 55 and 58.
92. The yeast cell according to any one of items 82 to 91, wherein the yeast cell furthermore has genotype IV, such as genotype IV as defined in any one of items 64 to 75.
93. The yeast cell according to any one of items 82 to 92, wherein the yeast cell furthermore has characteristic I, for example characteristic I as defined in any one of items 3 to 4.
94. The yeast cell according to any one of items 82 to 93, wherein the yeast cell furthermore has characteristic II, for example characteristic II as defined in any one of items 1 and 5 to 7.
95. The yeast cell according to any one of items 82 to 94, wherein the yeast cell furthermore has characteristic IX, for example characteristic IX as defined in any one of items 28 to 35.
96. The yeast cell according to any one of the preceding items, wherein the yeast cell has the genotype;
    VI. comprising at least 3 genes encoding AGT1 selected from the group consisting of AGT1 of SEQ ID NO:18, AGT1 of SEQ ID NO:19, AGT1 of SEQ ID NO:20, AGT1 of SEQ ID NO:26, AGT1 of SEQ ID NO:27, AGT1 of SEQ ID NO:28, AGT1 of SEQ ID NO:29, AGT1 of SEQ ID NO:30, AGT1 of SEQ ID NO:31, AGT1 of SEQ ID NO:32 and functional homologues of any of the aforementioned sharing at least 80%, preferably at least 90%, yet more preferably at least 95%, such as at least 98% sequence identity therewith.
97. A yeast cell having the genotype;
    VI. comprising at least 3 genes encoding AGT1 selected from the group consisting of AGT1 of SEQ ID NO:18, AGT1 of SEQ ID NO:19, AGT1 of SEQ ID NO:20, AGT1 of SEQ ID NO:26, AGT1 of SEQ ID NO:27, AGT1 of SEQ ID NO:28, AGT1 of SEQ ID NO:29, AGT1 of SEQ ID NO:30, AGT1 of SEQ ID NO:31, AGT1 of SEQ ID NO:32 and functional homologues of any of the aforementioned sharing at least 80%, preferably at least 90%, yet more preferably at least 95%, such as at least 98% sequence identity therewith.
98. The yeast cell according to any one of items 96 to 97, wherein the yeast cell comprises at least two genes encoding full length AGT1 selected from the group consisting of AGT1 of SEQ ID NO:18, AGT1 of SEQ ID NO:19, AGT1 of SEQ ID NO:20, AGT1 of SEQ ID NO:27, AGT1 of SEQ ID NO:28, AGT1 of SEQ ID NO:30, AGT1 of SEQ ID NO:31, AGT1 of SEQ ID NO:32 and functional homologues of any of the aforementioned sharing at least 80%, preferably at least 90%, yet more preferably at least 95%, such as at least 98% sequence identity therewith.
99. The yeast cell according to any one of items 96 to 98, wherein the genotype VI is that the yeast cell comprises the following 3 genes:
    1) a gene encoding AGT1 of SEQ ID NO:18 or a functional homologue thereof sharing at least 80%, preferably at least 90%, yet more preferably at least 95%, such as at least 98% sequence identity therewith; and
    2) a gene encoding AGT1 of SEQ ID NO:19 or a functional homologue thereof sharing at least 80%, preferably at least 90%, yet more preferably at least 95%, such as at least 98% sequence identity therewith; and
    3) a gene encoding AGT1 of SEQ ID NO:20 or a functional homologue thereof sharing at least 80%, preferably at least 90%, yet more preferably at least 95%, such as at least 98% sequence identity therewith.
100. The yeast cell according to any one of items 96 to 99, wherein the genotype VI is that the yeast cell comprises the following 2 genes:
    1) a gene encoding AGT1 of SEQ ID NO:27 or a functional homologue thereof sharing at least 80%, preferably at least 90%, yet more preferably at least 95%, such as at least 98% sequence identity therewith; and
    2) a gene encoding AGT1 of SEQ ID NO:28 or a functional homologue thereof sharing at least 80%, preferably at least 90%, yet more preferably at least 95%, such as at least 98% sequence identity therewith.
101. The yeast cell according to any one of items 96 to 100, wherein the genotype VI is that the yeast cell comprises the following 3 genes:
    1) a gene encoding AGT1 of SEQ ID NO:30 or a functional homologue thereof sharing at least 80%, preferably at least 90%, yet more preferably at least 95%, such as at least 98% sequence identity therewith; and
    2) gene encoding AGT1 of SEQ ID NO:31 or a functional homologue thereof sharing at least 80%, preferably at least 90%, yet more preferably at least 95%, such as at least 98% sequence identity therewith; and
    3) a gene encoding AGT1 of SEQ ID NO:32 or a functional homologue thereof sharing at least 80%, preferably at least 90%, yet more preferably at least 95%, such as at least 98% sequence identity therewith.
102. The yeast cell according to any one of items 96 to 101, wherein the yeast cell furthermore has the genotype I, for example genotype I as defined in any one of items 39 to 41.
103. The yeast cell according to any one of items 96 to 102, wherein the yeast cell furthermore has genotype II, such as genotype II as defined in any one of items 46 and 49.
104. The yeast cell according to any one of items 96 to 103, wherein the yeast cell furthermore has genotype III, such as genotype III as defined in any one of items 55 and 58.
105. The yeast cell according to any one of items 96 to 104, wherein the yeast cell furthermore has genotype IV, such as genotype IV as defined in any one of items 64 to 75.
106. The yeast cell according to any one of items 96 to 105, wherein the yeast cell furthermore has genotype V, such as genotype V as defined in any one of items 82 to 88.
107. The yeast cell according to any one of items 96 to 106, wherein the yeast cell furthermore has characteristic I, for example characteristic I as defined in any one of items 3 to 4.
108. The yeast cell according to any one of items 96 to 107, wherein the yeast cell furthermore has characteristic II, for example characteristic II as defined in any one of items 1 and 5 to 7.

109. The yeast cell according to any one of items 96 to 108, wherein the yeast cell furthermore has characteristic IX, for example characteristic IX as defined in any one of items 28 to 35.
110. A method for producing a beverage, said method comprising the steps of
    a. Providing a starting liquid
    b. Providing a yeast cell according to any one of items 1 to 109
    c. Fermenting said starting liquid with said yeast cell, thereby producing a beverage.
111. The method according to item 110, wherein the starting liquid comprises an aqueous extract of barley.
112. The method according to any one of items 110 to 111, wherein the starting liquid comprises an aqueous extract of malt,
113. The method according any one of items 110 to 112, wherein the starting liquid is wort.
114. The method according to any one of items 110 to 113, wherein the fermentation is performed at a temperature in the range of 10 to 20° C.

EXAMPLES

The invention is further illustrated by the following examples, which should however not be construed as limiting for the invention.

In the examples the following yeast strains are used:

| Name of yeast strain | Species/Description |
|---|---|
| Lager yeast 1 | S. pastorianus |
| Lager yeast 2 | S. pastorianus |
| Ale yeast 1 | S. cerevisiae |
| S. diastaticus 1 | S. diastaticus |
| Hybrid yeast 1 | Hybrid between Ale yeast 1 and Lager yeast 1 |
| Hybrid yeast 2 | Hybrid between Lager yeast 2 and Ale yeast 1 |
| Hybrid yeast 3 | Hybrid between Lager yeast 2 and Ale yeast 1 |
| Hybrid yeast 4 | Hybrid between Lager yeast 2 and Ale yeast 1 |
| Hybrid yeast 5 | Hybrid between Lager yeast 2 and Ale yeast 1 |
| Hybrid yeast 6 | Hybrid between Lager yeast 2 and Ale yeast 1 |
| Hybrid yeast 7 | Hybrid between Lager yeast 2 and Ale yeast 1 |
| Hybrid yeast 8 | Hybrid between S. diastaticus 1 and Ale yeast 1 |

The genomic sequence of Hybrid yeast 1 is provided as SEQ ID NO:1 in priority founding Danish patent application PA 2014 70825. SEQ ID NO:1 of PA 2014 70825 shows the sequence of assembled scaffolds from the genomic sequence of Hybrid 1. The sequences are provided in fasta format. The term "scaffold" as used in this connection refers to a portion of the genome sequence reconstructed from overlapped contigs. The term "contig" refers to a contiguous overlapping sequence originating from reassembly of short DNA fragments.

SEQ ID NO:1 of PA 2014 70825 provides the sequence of a total of 1629 scaffolds, numbered from number 0 to 1628. In SEQ ID NO:1 of PA 2014 70825 the sequences of each scaffold is provided separated by the term ">Scaffold_X", wherein X indicates the number of the scaffold having the following sequence.

Thus, the genome of Hybrid yeast 1 preferably comprises all of the Scaffolds 0 to 1628 distributed over a plurality of chromosomes.

The genomic sequence of Hybrid yeast 1 is also available under the DDBJ/EMBL/Gen Bank accession number LOQJ00000000. Thus, the Whole Genome Shotgun project regarding Hybrid yeast 1 has been deposited at DDBJ/EMBL/GenBank under the accession LOQJ00000000. The version described in this patent is version LOQJ01000000.

The data of the submission were as follows:

| SUBID | BioProject | BioSample | Accession |
|---|---|---|---|
| SUB1207553 | PRJNA304272 | SAMN04297180 | LOQJ00000000 |

The Whole Genome Shotgun project shows the sequence of assembled scaffolds from the genomic sequence of Hybrid yeast 1. The term "scaffold" as used in this connection refers to a portion of the genome sequence reconstructed from overlapped contigs. The term "contig" refers to a contiguous overlapping sequence originating from reassembly of short DNA fragments. The DDBJ/EMBL/Gen Bank the accession LOQJ00000000, version LOQJ01000000 provides the sequence of a total of 8919 scaffolds. Thus, the genome of Hybrid yeast 1 preferably comprises all of the Scaffolds 0 to 8919 distributed over a plurality of chromosomes. Accordingly, a yeast cell according to the invention also may comprise all of the Scaffolds 0 to 8919 distributed over a plurality of chromosomes.

The genomic sequence of Hybrid yeast 7 is available under the DDBJ/EMBL/Gen Bank accession number LOQK00000000.

Thus, the Whole Genome Shotgun project regarding Hybrid yeast 7 has been deposited at DBJ/EMBL/GenBank under the accession LOQK00000000. The version described in this patent is version LOQK01000000.

The data of the submission were as follows:

| SUBID | BioProject | BioSample | Accession |
|---|---|---|---|
| SUB1208131 | PRJNA304273 | SAMN04297181 | LOQK00000000 |

The Whole Genome Shotgun project shows the sequence of assembled scaffolds from the genomic sequence of Hybrid yeast 7. The term "scaffold" as used in this connection refers to a portion of the genome sequence reconstructed from overlapped contigs. The term "contig" refers to a contiguous overlapping sequence originating from reassembly of short DNA fragments. The DDBJ/EMBL/GenBank the accession LOQK00000000, version LOQK01000000 provides the sequence of a total of 9492 scaffolds. Thus, the genome of Hybrid yeast 7 preferably comprises all of the Scaffolds 0 to 9492 distributed over a plurality of chromosomes. Accordingly, a yeast cell according to the invention also may comprise all of the Scaffolds 0 to 9492 distributed over a plurality of chromosomes.

Example 1

10 hl beer was prepared by inoculating 10 million of viable cells/ml of yeast to a commercial malt based wort (16° Plato) supplied by Soufflet followed by fermentation at 17° C. until diacetyl was below a predefined threshold, which is set at a level below the threshold considered off-flavor in lager beer. In the present example the diacetyl threshold was set to 30 ppb.

In lager beers, vicinal diketones such as diacetyl and 2,3-pentanedione give undesirable off-flavour if they are present over a threshold concentration. Both, diacetyl and 2,3-pentanedione have a butterscotch aroma, but the threshold for diacetyl is 10 times lower. Part of the fermentation management is to ensure that the finished beer contains vicinal diketones, especially diacetyl, below their thresholds.

The yeast cells were propagated in one tank (9 hL scale) that was used to get the cell inoculum of generation 1 of the beer that was then followed by generation 2 of the beer (10 hL scale each). The purpose of the propagation is to produce a healthy pure culture of yeast in sufficient amounts to inoculate yeast for the real beer fermentation. Beer fermentation is done in successive fermentations and yeast is typically replaced after 5 to 10 successive fermentations; however the frequency of introducing newly propagated yeast into the brewery is an individual decision. The successive fermentations serve as cell inoculum for the following beer fermentation and often only the propagation tank provides yeast cell inoculum for the first beer fermentation so-called generation 1 of the beer. The beer fermentation made after generation 1 is called generation 2 and so on and so forth. Most beer fermentations are conducted with yeast drawn from previous beer fermentation and not from the propagation tank. The cell inoculum for the beer fermentation is typically $10^7$ yeast cells/ml.

3 different yeast strains were used in this example. The same wort and fermentation conditions were employed.

Ale yeast 1

Lager yeast 1

Hybrid yeast 1

Ale yeast 1 is a yeast of the species *S. cerevisiae*. Lager yeast 1 is a yeast of the species *S. pastorianus*. Ale yeast 1 and Lager yeast 1 were hybridized and one of the hybrid strains was selected named Hybrid yeast 1.

Table 1 shows the final values of Plato, Table 2 shows % ethanol (% v/v) and Table 3 shows the final beer RDF, days to have diacetyl under the predefined threshold and days for the primary fermentation from beer of generation 1 and 2 in beer prepared using the 3 yeast strains at the end of the propagation tank (9 hL) and/or in generations 1 and 2 of beer.

Hybrid strain 1 has the ability to grow at 37° C. (data not shown) and also ferment well at lower temperatures such as 16° C. (see Tables 1 to 3).

TABLE 1

| Plato values | | | |
|---|---|---|---|
| Final °PLATO | Lager yeast 1 | Hybrid yeast 1 | Ale yeast 1 |
| At the end of Propagation (9 hL), 16° C. | 2.54 | 1.97 | 2.03 |
| End Generation 1, 16° C. | 2.55 | 2.35 | 2.48 |
| End Generation 2, 18° C. | 2.86 | 2.37 | 3.36 |
| AVERAGE Generation 1 + 2 | 2.7 | 2.36 | 2.92 |

TABLE 2

| % ethanol (% v/v) | | | |
|---|---|---|---|
| % ETHANOL (% v/v) | Lager yeast 1 | Hybrid yeast 1 | Ale yeast 1 |
| Generation 1, 16° C. | 7.51 | 7.64 | 7.58 |
| Generation 2, 18° C. | 7.33 | 7.61 | 7.19 |
| AVERAGE Generation 1 + 2 | 7.42 | 7.625 | 7.38 |

TABLE 3

| 10 hl Scale - Average of generation 1 and 2 (beer 02 and 03) | | | |
|---|---|---|---|
| name (yeast) | Lager yeast 1 | Hybrid yeast 1 | Ale yeast 1 |
| Plato wort | 15.85 | 15.85 | 15.85 |
| Ferm. temp. | 16° C. and 18° C. | 16° C. and 18° C. | 16° C. and 18° C. |
| Pitching rate | 10 | 10 | 10 |
| beer RDF (%) | 69.3 | 71.0 | 68.9 |
| days to DA in spec. | 6.5 | 9 | 13 |
| days to primary ferm. | 5.5 | 6 | 9.5 |

Pitching rate is the amount of viable yeast/mL added as cell inoculum to start the fermentation. The hybrid yeast 1 had improved the RDF with 2% as compared to the two parental strains (Lager yeast 1 and Ale yeast 1)(See Table 3). Hybrid yeast 1 had also lower levels of final Plato.

The hybrid yeast 1 has improved ethanol yield by 0.2% ethanol or more as compared to the two parental strains. Hybrid yeast 1 has improved fermentation performance at both 16° C. and 18° C. of temperature. Hybrid 1 had improved in terms of having a shorter time to have diacetyl levels below threshold (Days to DA in spec.) as compared to Ale yeast 1

The hybrid yeast 1 is almost fermenting at the same rate as Lager yeast 1 (See days to primary ferment in Table 3) but it had a bit longer time to have diacetyl under threshold (See days to DA in spec.).

Example 2

Yeast cells from frozen stocks were streaked on YPD plates. They were used to inoculate 20 ml of pasteurized conventional malt wort in 50 ml bottles and grown at 22° C. of temperature. Cell cultures from the 20 ml culture were used to repitch cells into 200 ml volume of wort into 500 ml bottles and grown at 22° C. From the 200 ml volume of wort, a propagation tank of 1.8 L was inoculated aiming at inoculating 14-15 million of viable cells/ml and growing at 16 or 18° C. temperature (same as the fermentation temperature). The malt used to prepare the wort was purchased from DMG in Denmark.

The number of total and viable cells was measured with NucleoCounter. From the propagation tank, the number of viable cells was also measured. 14-15 million of viable cells were used to inoculate 2 L wort with a sugar content of 15° Plato, which was allowed to ferment for 6 days at either 16° C. (Hybrid yeast 2, 3 and 4 and its respective controls) or 18° C. (Hybrid yeast 1 and its respective controls) to obtain the so-called generation 1 of beer. At the end of the generation 1, 14-15 million of viable cells were used to inoculate the generation 2 of beer. At day 4 of incubation the number of cells in suspension was determined. The resulting cell numbers from the beer from generation 2 are shown in Table 4. The number of cells in suspension does not reflect the overall growth of cells, but rather the flocculation and/or sedimentation. The number of cells min suspension is generally preferred to be as low as possible at the later stages of fermentation, which indicates increased flocculation and/or sedimentation. If the flocculation is increased too early in the process time, this can lead to premature flocculation resulting in sluggish fermentation at the end of the process.

TABLE 4a

Generation 2 of beer made in 2 L scale. The results shown are from biological duplicates of the same experiment.

| 18° C. Fermentations Yeast | pitching rate mill/ml | cells in suspension (day 4) mill/ml |
|---|---|---|
| Lager yeast 1 | 15 | 17 |
| Lager yeast 1 | 15 | 19 |
| Ale yeast 1 | 15 | 12 |
| Ale yeast 1 | 15 | 22.6 |
| Hybrid yeast 1 | 15 | 3.58 |
| Hybrid yeast 1 | 15 | 3.75 |

Hybrid yeast 1 produced more biomass (measured by grams of harvested yeast) than lager yeast 1 but still hybrid 1 had less cells in suspension.

TABLE 4b

| 16° C. Fermentations Yeast | pitching rate mill/ml | cells in susp. (day 6) mill/ml |
|---|---|---|
| Lager yeast 1 | 14 | 20 |
| Lager yeast 1 | 14 | 23 |
| Ale yeast 1 | 14 | 14 |
| Ale yeast 1 | 14 | 13 |
| Hybrid yeast 2 | 14 | 2.3 |
| Hybrid yeast 2 | 14 | 3.2 |
| Hybrid yeast 3 | 14 | 4.4 |
| Hybrid yeast 3 | 14 | 3.3 |
| Hybrid yeast 4 | 14 | 5.8 |
| Hybrid yeast 4 | 14 | 5 |
| Lager yeast 2 | 14 | 12 |
| Lager yeast 2 | 14 | 23 |

As shown above hybrid yeast 2, 3 and 4 have less cells in suspension than the lager yeasts, even though they produced a bit more biomass (in grams of harvested cells at the end of fermentation).

In a different trial, it was found that the hybrid yeast 2 had 7 mill/ml cells in suspension after 6 days of fermentation, whereas the ale yeast 1 had only 4 mill/ml cells in suspension and the Lager yeast 2 has 39 mill/ml cells in suspension after 6 days of fermentation. Thus, also in this trial the hybrid yeast had a much lower level of cells in suspension compared to the Lager yeast.

The hybrids made from Ale yeast 1 and Lager yeast 1 (Hybrid yeast 1) or Lager yeast 2 (Hybrids yeast 2, 3, 4 and 7) had less cells in suspension than the two parental strains: Ale yeast 1 and either of the lager strains (Lager yeast 1 or 2). So the hybrids had improved cell sedimentation. That is of interest in brewing to avoid downstream processing of the yeast cell paste that should be collected and used for the cell re-pitching of the next generations of the beer process.

Results from yet another trial is shown in Table 4c. The experimental settings were as described herein above except that the indicated yeast cells were tested.

TABLE 4c

| 18° C. Generation 2 yeast | Pitching rate mill/ml | Yeast cells in suspension (Day 7) mill/ml |
|---|---|---|
| Lager yeast 2 | 15.0 | 26 |
| Lager yeast 2 | 15.0 | 28 |
| Hybrid yeast 7 | 15.0 | 4 |
| Hybrid yeast 7 | 15.0 | 8.3 |
| Hybrid yeast 8 | 15.0 | 7.2 |
| Hybrid yeast 8 | 15.0 | 7.5 |
| S. diastaticus | 15.0 | 40 |
| S. diastaticus | 15.0 | 39 |

Example 3

50 L beer was prepared by inoculating conventional malt based wort (18° Plato) with 10 million of viable cells/ml of yeast followed by fermentation at 18° C. The malt used to prepare the wort was purchased from DMG in Denmark.

2 different yeast strains were used. The same wort and fermentation conditions were employed.

Lager yeast 1
Hybrid yeast 1

Table 5a shows the final values of beer AE for the 2 strains compared in the 50 L scale tank from beer made with generation 1 and 2.

AE as used herein is the "apparent extract" which is a measure of the density of beer wort in terms of the percentage of extract by weight and that is expressed in the Plato scale.

TABLE 5a

Lager 1 versus Hybrid 1 - test in 50 L

| Strain name | Lager yeast 1 | Hybrid 1 |
|---|---|---|
| Generation 1 beer | | |
| Generation | 1 | 1 |
| Plato wort (Starting value) | 17.76 | 17.76 |
| Fermentation temperature | 18 | 18 |
| Pitching rate | 10 | 10 |
| beer AE | 3.21 | 2.71 |
| Generation 2 of beer | | |
| Generation | 2 | 2 |
| Plato wort (Starting value) | 17.91 | 17.91 |
| Fermentation temperature | 18 | 18 |
| Pitching rate | 10 | 10 |
| beer AE | 3.46 | 2.86 |

The hybrid yeast 1 had improved 0.5% AE by 0.5% as compared to the lager yeast 1.

A similar test was performed with Lager yeast 2, Hybrid yeast 4, Hybrid yeast 7, Hybrid yeast 8 and S. diastaticus. AE and RDF at day 7 after pitching are shown in Table 5b. The experimental settings were as described herein in Experiment 2 above with the indicated yeast cells tested.

TABLE 5b

| 18° C. Generation 2 Yeast | Pitching rate, mill/ml | AE after 7 days, % Plato | RDF, Day 7 |
|---|---|---|---|
| Lager yeast 2 | 15.0 | 3.01 | 64.4 |
| Lager yeast 2 | 15.0 | 2.93 | 66.3 |
| Hybrid yeast 4 | 15.0 | 2.49 | 69.0 |
| Hybrid yeast 4 | 15.0 | 2.53 | 68.8 |
| Hybrid yeast 7 | 15.0 | 2.35 | 69.0 |

TABLE 5b-continued

| | | | |
|---|---|---|---|
| Hybrid yeast 7 | 15.0 | 2.39 | 69.6 |
| Hybrid yeast 8 | 12.4 | 1.1 | 75.9 |
| Hybrid yeast 8 | 12.4 | 1.12 | 75.1 |
| S. diastaticus | 14.7 | 1.67 | 73.1 |
| S. diastaticus | 15.0 | 1.66 | 73.0 |

| | Lager yeast 2 | Hybrid yeast 4 | Hybrid yeast 7 |
|---|---|---|---|
| Av. AE, 7 days | 2.97 | 2.51 | 2.37 |
| Extra AE increase vs Lager yeast 2 | | 0.46 | 0.6 |
| Av. RDF, 7 days | 65.35 | 68.9 | 69.3 |
| Extra RDF vs Lager yeast 2 | | 3.55 | 3.95 |

RDF is provided in %.

Figure 16:
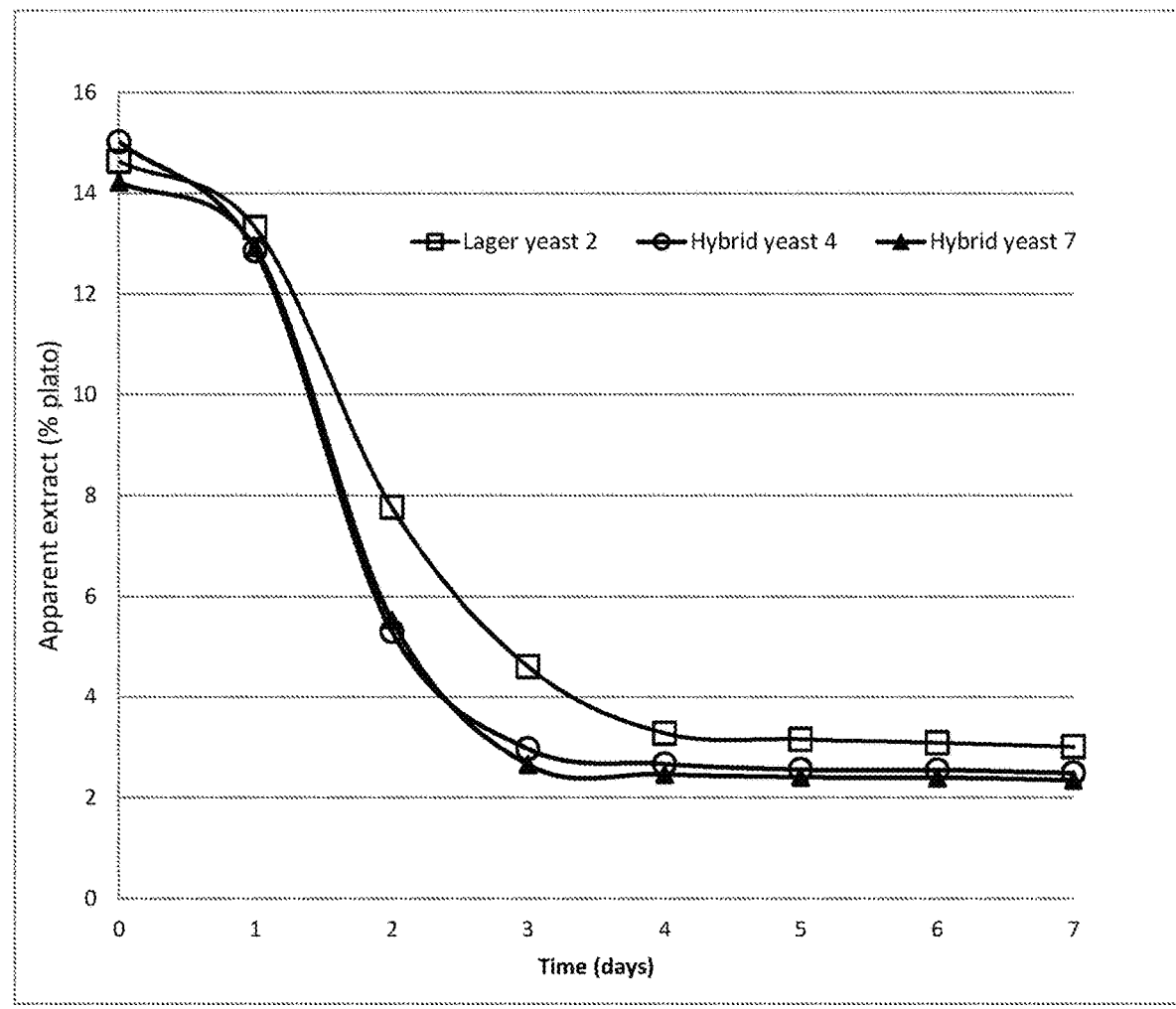
FIG. 16 shows the apparent extract as a function of time during fermentation of wort with Lager yeast 2, Hybrid yeast 4 and Hybrid yeast 7.

The rate of fermentation was also determined for Lager yeast 2, Hybrid yeast 4 and 7. The experimental settings were as described herein in Experiment 2 except that the apparent extract was determined at several time points during the course of fermentation and incubation was at 18° C. FIG. 16 shows the apparent extract in ° Plato over time after pitching wort. The wort used had a starting sugar content of 15° Plato. As shown then the time of primary fermentation for Hybrid yeast 4 and 7 is about 3 days, whereas the time of primary fermentation for Lager yeast 2 is about 4 days.

Example 4

The amino acid content of starting wort and beer produced as described in Example 1 was determined by HPLC with fluorescence detector.

Table 6a shows the amino acid concentration in the final beer.

TABLE 6a

| | | Lager yeast 1 | Ale yeast 1 | Hybrid yeast 1 | % amino acid reduction in final beer brew with Hybrid yeast 1 as compared to Lager yeast 1 |
|---|---|---|---|---|---|
| Aspartic acid W | mg/l | 32 | 51 | 3 | 90% |
| Glutamic acid W | mg/l | 44 | 47 | 14 | 68% |
| Serine W | mg/l | 11 | 23 | 8 | 27% |
| Histidine W | mg/l | 42 | 46 | 25 | 40% |
| Glycine W | mg/l | 49 | 57 | 35 | 28% |
| Threonine W | mg/l | 12 | 16 | 5 | 58% |
| Arginine W | mg/l | 152 | 136 | 86 | 43% |
| Alanine W | mg/l | 147 | 145 | 80 | 45% |
| Tyrosine W | mg/l | 129 | 140 | 118 | 8% |
| Methionine W | mg/l | 26 | 28 | 10 | 61% |
| Valine W | mg/l | 136 | 159 | 121 | 11% |
| Phenylalanine W | mg/l | 134 | 166 | 117 | 12% |
| Isoleucine W | mg/l | 59 | 71 | 33 | 44% |
| Leucine W | mg/l | 113 | 173 | 78 | 31% |
| Lysine W | mg/l | 29 | 25 | 1 | 97% |

Hybrid yeast 1 has much less leftover amino acids in the final beer which is beneficial in terms of beer aging and beer stability. Beer fermented with hybrid 1 will generate lower amounts of strecker aldehydes, which are being formed from those amino acids.

Strecker aldehydes are important constituents of the "aged" flavor in beer that partly originate from the amino acids of the bottled beer itself. Amino acids that have been shown to be involved in formation of Strecker aldehydes with a low sensory threshold include valine, isoleucine, leucine, methionine and phenylalanine (Table 2). Strecker aldehyde formation plays a crucial role because an increase in their concentration, gives an increasing sensory perception of "aged flavours". Beer fermented with hybrid yeast 1 will have then less aging flavours due to the higher consumption of amino acids.

TABLE 2

Amino acids that act as precursors in the formation of off-flavour strecker aldehydes.

| Amino acid | Strecker aldehyde |
|---|---|
| Methionine | Methional |
| Leucine | 3-methylbutanal |
| Valine | 2-methylpropanal |
| Isoleucine | 2-methylbutanal |
| Phenylalanine | Phenylacetaldehyde, benzaldehyde |

Another fermentation with Lager yeast 2, Hybrid yeast 4 or Hybrid yeast 7 was prepared and the amino acid concentration in the "green beer" on the Day 7 of fermentation was determined. The result is shown in Table 6b. Experimental settings were as described in Example 2 and amino acid analysis was done as described in Example 9. Hybrids, especially Hybrid yeast 7, has less amino acids left in the "green beer" than Lager yeast 2; it means that there are less precursors for the formation of the aging compounds in the beer;

TABLE 6b

| Amino acid | | Lager yeast 2 | Hybrid yeast 4 | % amino acid reduction in Hybrid yeast 4 in comparison with Lager yeast 2 | Hybrid yeast 7 | % amino acid reduction in Hybrid yeast 7 in comparison with Lager yeast 2 |
|---|---|---|---|---|---|---|
| His | mg/L | 40 | 25.5 | 36.25% | 11.5 | 71.25% |
| Asn | -"- | 8.5 | 5.5 | 35.3% | 3 | 64.7% |
| Ser | -"- | 3 | 3.5 | na | 0 | 100% |
| Gln | -"- | 32 | 3 | 90.6% | 0 | 100% |
| Arg | -"- | 52 | 24 | 53.85% | 6.5 | 87.5% |
| Gly | -"- | 50.5 | 49.5 | 2.0% | 26.5 | 47.5% |
| Asp | -"- | 17.5 | 6.5 | 62.9% | 2 | 88.6% |
| Glu | -"- | 75.5 | 20 | 73.5% | 8.5 | 88.7% |
| Thr | -"- | 0 | 2 | na | 0 | Na |
| Ala | -"- | 175.5 | 131 | 25.3% | 36 | 79.5 |
| Pro | -"- | 606.5 | 656.5 | na | 599.5 | 1.15% |
| Cys | -"- | 0 | 0 | na | 0 | Na |
| Lys | -"- | 2 | 1 | na | 1 | Na |
| Tyr | -"- | 110 | 117 | na | 91 | 17.3% |
| Met | -"- | 7.5 | 5.5 | 26.7% | 2 | 73.3% |
| Val | -"- | 113.5 | 117 | na | 66.5 | 43.2% |
| Ile | -"- | 44 | 31.5 | 28.4% | 6 | 86.4% |
| Leu | -"- | 74.5 | 62 | 16.8% | 18.5 | 75.2% |
| Phe | -"- | 97 | 99 | na | 58 | 40.2% |
| Trp | -"- | 51.5 | 51 | 1% | 40.5 | 21.3% |

(na)—not applicable;

REFERENCES

Baert, J. J., J. De Clippeleer, P. S. Hughes, L. De Cooman and G. Aerts (2012). "On the Origin of Free and Bound Staling Aldehydes in Beer." *Journal of Agricultural and Food Chemistry* 60(46): 11449-11472.

Clapperton, J. F. and I. C. MacWilliam (1971). "Fermentation of minor wort carbohydrates by brewing yeasts." *Journal of the Institute of Brewing* 77(6): 519-522.

Deng, X., M. Petitjean, M. A. Teste, W. Kooli, S. Tranier, J. M. Francois and J. L. Parrou (2014). "Similarities and differences in the biochemical and enzymological properties of the four isomaltases from *Saccharomyces cerevisiae*." *FEBS Open Bio* 4: 200-212.

Teste, M. A., J. M. Francois and J. L. Parrou (2010). "Characterization of a new multigene family encoding isomaltases in the yeast *Saccharomyces cerevisiae*, the IMA family." *J Biol Chem* 285(35): 26815-26824.

Example 5

50 L beer was prepared as specified in Example 3 by inoculating conventional malt based wort (16° Plato) prepared from two different kinds of malt.

Conventional malt based wort was inoculated with 10 million of viable cells/ml of yeast followed by fermentation at 16° C. until diacetyl was under the threshold in beer specified in Example 1.

Another malt was inoculated with 15 million of viable cells/ml of yeast followed by fermentation at 16° C. for Lager yeast 1 and 18° C. for Hybrid yeast 1, until diacetyl was under the threshold in beer specified in Example 1.

2 different yeast strains and two different worts made of 2 different malts were used. The same wort and fermentation conditions were employed to compare the 2 strains in parallel.
  Lager yeast 1
  Hybrid yeast 1

The level of isomaltose and panose in the beer was determined by HPLC. The results are shown in Table 7.

TABLE 7

| Yeast | Malt | Isomaltose (mg/L) | Panose (mg/L) |
|---|---|---|---|
| Lager yeast 1 | Malt 1 | 390 | 300 |
| Hybrid yeast 1 | Malt 1 | 15 | 160 |
| Lager yeast 1 | Malt 2 | 240 | 240 |
| Hybrid yeast 1 | Malt 2 | 15 | 60 |

The starting concentration of panose and isomaltose is wort-dependent but it has been published that it is in the range of 0.5 to 1 g/L of isomaltose and 0.4 to 0.8 g/L of panose (Clapperton et al. 1971). Thus, it is believed that Hybrid yeast 1 utilizes in the range of 60% to 93% of the panose.

Quantitative data of panose and isomaltose utilization was obtained by measuring the growth of the different yeasts in defined medium with 2 g/L panose or 2 g/L isomaltose as sole carbon sources:

Yeast cells from frozen stocks were streaked on YPD plates (1% Yeast extract, 2% peptone, 2% glucose and 2% agar-agar) and growing cells were inoculated into liquid YPD (1% Yeast extract, 2% peptone, 2% glucose).

3 µL of the overnight liquid YPD culture was inoculated into 100 µL culture of YNB (6.7 g/L) without amino acids but with ammonium sulfate and buffered with potassium hydrogen phthalate to pH 5.5 (Hahn-Hägerdal B. et al. 2005) and with 2 g/L panose or 2 g/L isomaltose as sole carbon sources. Cell growth was followed by measuring the optical density at 600 nm with continuous agitation and incubating at 20° C. of temperature using Bioscreen C MBR (Oy Growth Curves Ab Ltd, Finland).

The selected hybrid yeast strains of lager and ale with improved fermentation performance had acquired the ability to utilize panose (FIG. 1A) and isomaltose (FIG. 2). This sugar utilization improvement is exemplified with two hybrids in FIGS. 1A and 2A.

Similar experiments were performed with Ale yeast 1, Lager yeast 2 and Hybrid yeast 7, as well as with *S. diastaticus* and Hybrid yeast 8 using defined medium with 2 g/L panose as sole carbon source. The results are shown in FIGS. 1B and 1C, respectively and are representative of biological replicates. As can be seen neither Lager yeast 1, nor Lager yeast 2, nor *S. diastaticus* is capable of utilizing panose as sole carbon source.

Similar experiments were also performed with Ale yeast 1, Lager yeast 2 and Hybrid yeast 7 using defined medium with 2 g/L isommaltose as sole carbon source. The results are shown in FIG. 2B and are representative of biological replicates. As can be seen neither Lager yeast 1, nor Lager yeast 2, nor *S. diastaticus* is capable of utilizing isomaltose as sole carbon source.

REFERENCES

Clapperton J F, MacWilliam I C (1971) Fermentation of minor wort carbohydrates by brewing yeasts. Journal of the Institute of Brewing 77, 6: 519-522.

Hahn-Hägerdal B, Karhumaa K, Larsson C U, Gorwa-Grauslund M, Görgens J, van Zyl W H. (2005). Role of cultivation media in the development of yeast strains for large scale industrial use. Microbial Cell Factories 10: 4-31.

Example 6

Yeast cells from frozen stocks were streaked on YPD plates. They were used to inoculate 3 ml of liquid YPD and grown overnight under agitation at 22° C. in 15 ml tubes. The 3 ml grown culture was centrifuged, the supernatant was discarded and the cells were dissolved in water. The tubes were centrifuged again, the supernatant was discarded and dissolved in 3 ml of water.

Optical density (OD620 nm) was measured and adjusted to start at OD=0.2 for all the strains and solutions of the wells of the 96 well plates commercially provided by the Biolog Inc. technology (Hayward Calif., USA). All the solutions of the Biolog plates were specified for procedures for *S. cerevisiae* and other yeasts. The 96 well plates were incubated for 4.5 days at 22° C.

The Biolog system makes possible to assay quantitatively the level of thousands of cellular phenotypes in a single experiment. Each well of the assay is designed to test one individual phenotype. Biolog uses redox chemistry as a general reporter system to analyze cell respiration. It has a tetrazolium dye that is reduced, developing colour, when the cell can respire the compound present in the well or in the presence of the compound in that specific well.

Three yeast strains were compared, the 2 parental strains (Lager yeast 1 and ale yeast 1) and the resultant hybrid (Hybrid yeast 1). Details on the yeast strains are provided in Example 1. In some of the conditions the 3 strains were showing differences in the phenotype. The hybrid strain 1 was able to gain new phenotypic characteristics for example the ability to utilize several dipeptides and some tripeptides (See Table 8a).

TABLE 8a

| Peptides | Lager yeast 1 | Ale yeast 1 | Hybrid yeast 1 |
|---|---|---|---|
| MET-TYR | − | − | + |
| LEU-TYR | − | − | + |
| VAL-MET | − | − | + |
| PHE-TYR | − | − | + |
| ILE-LEU | − | − | + |
| ILE-ASN | − | − | + |
| GLY-GLY-GLY | − | − | + |

\+ Indicates growth on medium containing the indicated peptides as only nitrogen source
− Indicates no growth on medium containing the indicated peptides as only nitrogen source.

In a similar experiment 6 yeast strains were compared, namely, the yeast strains Lager yeast 1, Lager yeast 2, Ale yeast 1, Hybrid yeast 1, Hybrid yeast 4 and Hybrid yeast 7. The results are shown herein below in Table 8b. As is seen Hybrids have new properties that is not observed in the parents. Lager yeast 1 showed minor growth on Ile-Asn in this experiment, even-though no growth was observed in the former experiment. However, the growth of Lager yeast 1 was still significantly less than the growth of Hybrid yeast 1.

TABLE 8b

| Peptides | Lager yeast 1 | Lager yeast 2 | Ale yeast 1 | Hybrid yeast 1 | Hybrid yeast 4 | Hybrid yeast 7 |
|---|---|---|---|---|---|---|
| Gly-Arg | − | − | − | −/+ | + | + |
| Ile-Asn | −/+ | − | − | + | + | + |
| Lys-Tyr | −/+ | − | − | −/+ | + | + |
| Met-Lys | −/+ | − | − | −/+ | + | + |
| Val-Ala | −/+ | − | − | + | + | + |
| Val-Asn | − | − | − | −/+ | + | + |
| Val-Gly | − | − | − | −/+ | + | + |
| Val-Gln | − | − | − | + | + | + |
| Val-Met | − | − | − | + | + | −/+ |
| Val-Ser | −/+ | − | − | + | + | + |

Hybrid yeast 4 and 7 did not show any significant growth on Met-Tyr, Leu-Tyr, Phe-Tyr, Ile-Leu or GLy-Gly-Gly as sole nitrogen source.

The Hybrid yeast 1 also has acquired several phenotypes not found in Lager yeast 1, for example the ability to grow on several di-peptides having the formula Ala-Xaa, wherein Xaa may be any amino acid. This ability is often linked to the ability to utilize allantoin, which the Hybrid yeast also is capable of utilizing (see Table 9a).

TABLE 9a

| Peptides | Lager yeast 1 | Ale yeast 1 | Hybrid yeast 1 |
|---|---|---|---|
| Ala-Glu | − | + | + |
| Ala-Gly | − | + | + |
| Ala-His | −/+ | + | + |
| Ala-Thr | −/+ | + | + |
| Allantoin | − | + | + |

\+ Indicates growth on medium containing the indicated peptides as only nitrogen source
− Indicates no growth on medium containing the indicated peptides as only nitrogen source.
−/+ meaning delayed growth or growth with a lag-phase Also Hybrid yeast 4 and 7 are capable of utilizing Ala-Xaa dipeptides as sole nitrogen source as shown in Table 9b.

TABLE 9b

| Peptides | Lager yeast 2 | Hybrid yeast 4 | Hybrid yeast 7 |
|---|---|---|---|
| Ala-Glu | − | −/+ | + |
| Ala-Gly | − | −/+ | + |
| Ala-Thr | −/+ | + | + |

Dipeptides and tripeptides are part of FAN. FAN is free amino nitrogen, and it is a measure for nitrogen content of wort or beer. FAN is made of amino acids, ammonium ions and small peptides that are in the wort and they ensure desirable fermentation performance for the yeast (Lekkas C, et al. 2009). Many different dipeptide combinations may be found in wort.

Hybrid yeast 1 can utilize several different tested dipeptides/tripeptides that could be present in wort and has therefore a higher range of substrates from FAN that could be precursors for cell biomass, carbon source or precursors for flavours.

REFERENCES

Lekkas C, Hill A E, Taidi B, Hodgson J, Stewart G G (2009). The role of small wort peptides in brewing fermentations. J. Inst. Brew. 115 (2), 134-139.

Example 7

Qualitative data of melibiose utilization was done by replica-plating YPD liquid cultures of yeasts grown in 96 well plate into YPGalactose plates (1% Yeast extract, 2% peptone, 2% galactose and 2% agar-agar) with 50 μg/ml of x-alpha-gal (Clontech, Mountain View, US) and incubating the plates for 5 days at 22° C. X-alpha gal is a chromogenic analog of melibiose and if the yeast is able to utilize melibiose the yeast colony will become blue and if the yeast is unable to utilize melibiose then the yeast colony will be white.

The results show (Table 9 that all the lager yeasts tested were positive for melibiose utilization (blue colony color), all the ale yeasts tested were negative for melibiose utilization (white colony color) and the hybrids were positive or negative for melibiose utilization (blue or white colony color) depending of what they have inherited.

TABLE 9

| Yeast | Colour of yeast colony |
|---|---|
| Lager yeast 1, 2, 3 and 4 | Blue |
| Ale yeast 1, 2, 3, 4 and 5 | White |
| Hybrid yeast 1 | White |
| Hybrid yeast 4 | Blue |
| Hybrid yeast 5 | Blue |
| Hybrid yeast 6 | Blue |

Quantitative data of melibiose was done by measuring the growth of yeast in defined medium with 2 g/L melibiose as sole carbon source:

Yeast cells from frozen stocks were streaked on YPD plates and growing cells were inoculated into liquid YPD.

3 μL of the overnight liquid YPD culture was inoculated into 100 μL culture of YNB (6.7 g/L) without aminoacids but with ammonium sulfate buffered with potassium hydrogen phfalate to pH 5.5 (Hahn-Hägerdal B. et al. 2005) and with 2 g/L melibiose as carbon source. Cell growth was followed by measuring the optical density at 600 nm with continuous agitation and incubating at 20° C. of temperature using Bioscreen C MBR (Oy Growth Curves Ab Ltd, Finland). Hybrids of lager and ale had acquired the ability to utilize melibiose but not all the hybrids (this is exemplified with three hybrids in FIG. 3)

REFERENCES

Hahn-Hägerdal B, Karhumaa K, Larsson C U, Gorwa-Grauslund M, Görgens J, van Zyl W H. (2005). Role of cultivation media in the development of yeast strains for large scale industrial use. Microbial Cell Factories 10: 4-31.

Example 8

Improved Disaccharide and Trisaccharide Utilization

50 L beer was prepared as specified in Example 3 by inoculating malt based wort with 15 mill viable cells/ml followed by fermentation until diacetyl was under 30 ppb. The malt was prepared from conventional malting barley, or from null-LOX barley.

2 different yeast strains were used: lager yeast 1 and Hybrid yeast 1. The same wort and fermentation conditions were employed to compare the 2 strains in parallel except that fermentation with Lager yeast 1 was carried out at 18° C. whereas the fermentation with Hybrid yeast 1 was carried out at 16° C. There were three independent brews prepared with the same strains and the level of different sugars was determined by NMR, Representative results are shown in FIG. 4 for the levels of specific sugars that were different in the final bottled beer.

The NMR results show that the hybrid yeast 1 had improved utilization of isomaltose, panose, nigerose, kojibiose and other unidentified carbohydrates (FIG. 4). However lager yeast 1 is not able to utilize those sugars.

The disaccharide isomaltose, maltulose and the trisaccharides panose and maltotriulose are minor sugars in the wort media used for brewing beer (Clapperton and MacWilliam 1971). Our results show that there is also other disasaccharides like nigerose, kojibiose and trehalose that were present in the beer brewed with lager yeast 1 (FIG. 4). Improvement of the sugar utilization of those sugars present in low amounts can account for better total sugar utilization and an improvement of ethanol yield production by Hybrid yeast 1.

Example 9

50 L of beer from generation 1 was prepared by inoculating conventional malt based wort (13.6° Plato) prepared from all malt with 15 million of viable yeast cells/ml as inoculum followed by fermentation at 18° C. for 5 days and at 14° C. for 2 days. The cell inoculum was obtained from a previous propagation tank. The malt used to prepare the wort was purchased from DMG in Denmark. At day 6, samples of fermented wort, corresponding to the samples of "green beer", were taken and centrifuged and the supernatant was frozen down at −20° C. until it was analyzed (Table 10). The concentration of free amino acids were determined by UPLC with Photo Diode Array detection using the AccQ-Tag Ultra derivatization kit from Waters, essentially as described by the supplier. Separations were performed on a Waters AccQ-Tag Ultra Amino acid Analysis Column using premixed eluent A and B according to manufacturer's instructions (Waters). A sample of the original wort used to ferment was also compared with the samples that have been fermented. Amino acid concentration was compared between all the green beer samples versus a sample of the original wort (Table 10).

The level of residual amino acids in green beer fermented with hybrid yeasts are much lower compared to green beer fermented with Lager yeast 1, which is beneficial in terms of beer aging and beer stability. It is believed that in beer made with hybrid yeasts fewer strecker aldehydes will be formed from those amino acids during storage. Strecker aldehydes are important constituents of the "aged" flavor in beer that partly originate from the amino acids of the bottled beer itself. Amino acids that have shown to form strecker aldehydes with a low sensory threshold are valine, isoleucine, leucine, methionine and phenylalanine (Baert, De Clippeleer et al. 2012). Strecker aldehyde formation plays a crucial role because an increase in their concentration, gives an increasing sensory perception of "aged flavours". Beer brewed with hybrid yeast 1 and 4 will have less aging flavours due to the higher consumption in amino acids and this effect will be more pronounced in high gravity fermentations or wort malts with higher concentrations of FAN sources.

The amino acid proline was also utilized by the hybrid yeasts 1 and 4 but not by the lager yeast in the green beer. The amino acid proline is the major amino acid constituent in wort although it is the most difficult to be assimilated so hybrid yeasts with improved proline utilization will have this extra ability of utilizing this nitrogen source that lager yeast cannot utilize.

TABLE 10

| | Aminoacid analysis (mg/L) of green beer from day | | | | | | |
|---|---|---|---|---|---|---|---|
| | His | Asn | Ser | Gln | Arg | Gly | Asp |
| ORIGINAL WORT | 44 | 78 | 65 | 21 | 93 | 27 | 56 |
| GREEN BEER Hybrid Yeast 1 Total level (% of level in wort) | 4 (9%) | 2 (3%) | 0 (0%) | 15 (71%) | 0 (0%) | 6 (22%) | 0 (0%) |
| GREEN BEER Lager Yeast 1 Total level (% of level in wort) | 18 (41%) | 3 (4%) | 2 (3%) | 20 (95%) | 11 (12%) | 20 (74%) | 3 (5%) |
| GREEN BEER Hybrid Yeast 4 Total level (% of level in wort) | 10 (23%) | 2 (3%) | 0 (0%) | 17 (81%) | 3 (3%) | 11 (41%) | 0 (0%) |

TABLE 10-continued

| Aminoacid analysis (mg/L) of green beer from day | | | | | | | |
|---|---|---|---|---|---|---|---|
| | Glu | Thr | Ala | Pro | Cys | Lys | Tyr |
| ORIGINAL WORT | 84 | 50 | 92 | 270 | 0 | 74 | 78 |
| GREEN BEER Hybrid Yeast 1 Total level (% of level in wort) | 0 (0%) | 0 (0%) | 4 (4%) | 227 (84%) | 0 (0%) | 2 (3%) | 0 (0%) |
| GREEN BEER Lager Yeast 1 Total level (% of level in wort) | 21 (25%) | 0 (0%) | 68 (74%) | 270 (100%) | 0 (0%) | 4 (5%) | 22 (28%) |
| GREEN BEER Hybrid Yeast 4 Total level (% of level in wort) | 2 (2%) | 0 (0%) | 14 (15%) | 250 (93%) | 13 — | 2 (3%) | 0 (0%) |

| | Met | Val | Ile | Leu | Phe | Trp | Total Sum |
|---|---|---|---|---|---|---|---|
| ORIGINAL WORT | 24 | 88 | 47 | 112 | 98 | 48 | 1448 |
| GREEN BEER Hybrid Yeast 1 Total level (% of level in wort) | 0 (0%) | 0 (0%) | 0 (0%) | 0 (0%) | 0 (0%) | 3 (6%) | 263 (18%) |
| GREEN BEER Lager Yeast 1 Total level (% of level in wort) | 0 (0%) | 15 (17%) | 2 (4%) | 2 (2%) | 10 (10%) | 28 (58%) | 518 (36%) |
| GREEN BEER Hybrid Yeast 4 Total level (% of level in wort) | 0 (0%) | 2 (2%) | 0 (0%) | 2 (2%) | 0 (0%) | 18 (38%) | 346 (24%) |

Baert, J. J., J. De Clippeleer, P. S. Hughes, L. De Cooman and G. Aerts (2012). "On the Origin of Free and Bound Staling Aldehydes in Beer." *Journal of Agricultural and Food Chemistry* 60(46): 11449-11472.

Example 10

The genomic sequence of the Hybrid yeast 1 described in Example 1 was determined as follows.

Genomic DNA extraction and whole genome sequencing and assembly of the genome was done by LGC Genomics GmbH (Berlin, Germany). For extra individual sequencing of genes, genomic DNA extraction of the strains was performed by MasterPure TM Yeast DNA Purification Kit (Epicentre, Ilumina Denmark ApS, Copenhagen, Denmark). PCR amplification from genomic DNA was performed with High Fidelity PCR enzyme mix or Dream Taq polymerase with a low number of PCR cycles both of them from Thermo Fisher Scientific Baltics UAB (Vilnius, Lithuania). PCR products were purified by NucleoSpin PCR Clean-up (Macherey-Nagel, Duren, Germany). Cloning of the PCR products was carried out with the TOPO®TA Cloning® Kit for Sequencing and selected on LB ampicillin plates supplemented with beta-X-Galactose. Plasmids were purified with the GeneJET Plasmid Miniprep kit from Thermo Fisher Scientific Baltics UAB (Vilnius, Lithuania). Plasmid sequencing was performed at Eurofins Genomics (Ebersberg, Germany).

Hybrid yeast 1, Lager yeast 1 and Ale yeast 1 were analysed for various selected genes using either the assembled genome sequence and/or the sequence of PCR products. The protein sequence was deduced from the gene sequence or from the sequence of the PCR products using the genetic code.

Hybrid yeast 4, Hybrid yeast 7 and Lager yeast 2 were analysed for various selected genes using the sequence of PCR products. Sequences were obtained by PCR amplification with High Fidelity PCR enzyme, followed by cloning and sequencing of the individual PCR clones when applicable. The allelic genes of Hybrid yeast 4 and Hybrid yeast 7 were identified by PCR, cloning and sequencing. The allelic genes of Lager yeast 2 were identified by PCR and sequencing (IMA1) or was assembled from the genomic sequence (AGT1). The protein sequence was deduced from the sequence of the PCR products using the genetic code.

The LONG-IMA1 alleles presented here are defined by a 3 amino acids combination: I (Isoleucine) or T (Threonine) at the position 165, R (Arginine) or K (Lysine) at the position 287, and Y (Tyrosine) or F (Phenylalanine) at the position 336. The amino acid signature motif for Ale 1 LONG_IMA1 alleles being I-R-F and I-K-F. Lager yeast 1 and Lager yeast 2 have T-R-Y motif. Hybrid yeast 1 contains an I-K-F allele and a T-R-Y allele. Hybrid yeast 4 contains an I-R-F motif. Hybrid yeast 4 also contains a new hybrid allele with signature motif of I-R-Y. Hybrid yeast 7 contains an I-K-F allele, and an T-R-Yallele. Hybrid yeast 7 also contains a new hybrid allele with I-R-Y motif that is identical to the protein encoded for by Hybrid yeast_4.

Table 11a summarizes the status of various gene involved in dipeptide utilization in Lager Yeast 1, Ale yeast 1 and Hybrid yeast 1.

TABLE 11a

| Gene | Function | Lager yeast 1 | Ale yeast 1 | Hybrid yeast 1 |
|---|---|---|---|---|
| DAL5* | Transport of dipeptides with Ala at N-terminus | nonSc | Sc | Sc allele encoding SEQ ID NO: 6 |
| PTR2** | Peptide transporter (di-/tripeptides) | Sc; nonSc | Sc | 2 Sc alleles encoding SEQ ID NO: 7 and SEQ ID NO: 8 nonSc allele encoding SEQ ID: 9 |
| UBR1*** | E3 ubiquitin ligase (N-recognin): peptide degradation pathway | Sc; nonSc | Sc (early stop codon - truncated protein) | Sc allele encoding UBR1 comprising SEQ ID NO: 10; nonSc allele encoding SEQ ID NO: 11 |

Figure 7:
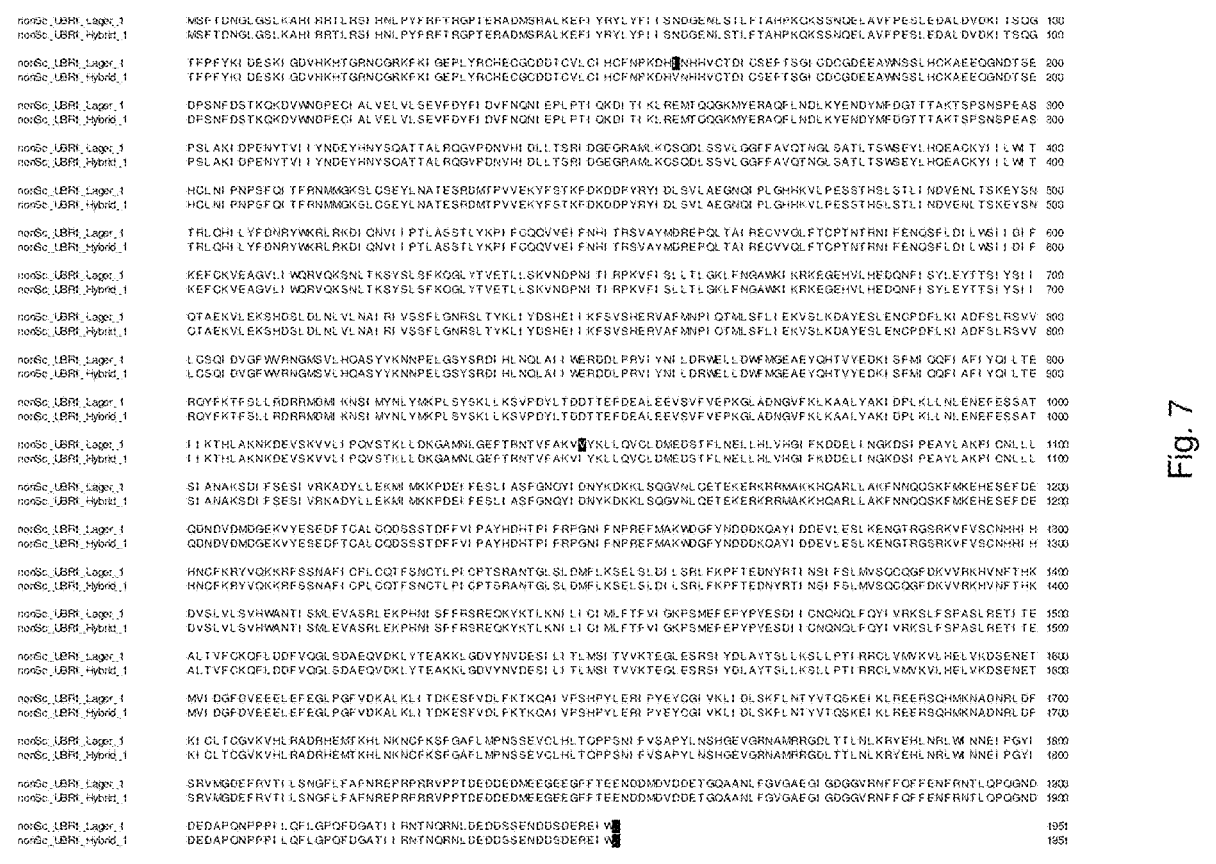

*DAL5 is an example of a gene inherited by Hybrid yeast 1 from parent Ale yeast 1. The term Sc in relation to DAL5 refers to the *S. cerevisiae* DAL5 protein of SEQ ID NO: 6. An alignment of DAL5 protein sequences is shown in FIG. 5.
**PTR2 is an example, where Hybrid yeast 1 has an increase copy number. Thus, Hybrid yeast 1 has inherited a nonSc allele from Lager yeast 1 and at least 2 Sc alleles from both its parents. Only fragments of the PTR2 alleles of Hybrid yeast 1 were investigated.
***UBR1 is an example of a gene with activity complementation in Hybrid yeast 1. Ale yeast 1 encodes a truncated protein (900 aa instead of 1951 aa) that leads to the absence of the domain responsible for Cup9p degradation activation and correspondingly to repression of PTR2 expression; Hybrid yeast 1 has inherited both Sc and nonSc alleles from Lager yeast 1 thus complementing the Ubr1p activity toward Cup9p degradation, and correspondingly ability of PTR2 expression to be activated further. An alignment of the Sc alleles of PTR2 from Ale yeast 1, Hybrid yeast 1 and Lager yeast 1 is shown in FIG. 6, and an alignment of the non Sc alleles of Lager yeast 1 and Hybrid yeast 1 is shown in FIG. 7.

The genomic sequences of Hybrid yeast 1 and Hybrid yeast 7 were further studied and the results summarized in Table 11b. These analyses are based on the genomic sequences available under DDBJ/EMBL/GenBank accession number LOQJ00000000, version LOQJ01000000 and DDBJ/EMBL/GenBank the accession LOQK00000000, version LOQK01000000TPTR2, respectively.

PTR2 analysis of the allelic variation was done based on the genomic sequences (see accession numbers above). Hybrid yeast 1 and Hybrid yeast 7 both retained non-Sc_PTR2 copy. In Table 11a a fragmented Sc_copy of Hybrid yeast 1 is presented. Table 11 b shows the intact copy of Sc_PTR2 in Hybrid yeast 1 in the genomic sequence. It is possible that Hybrid yeast 1 contains 3 alleles encoding PTR2 as indicated in Table 11a. Hybrid yeast 7 has Sc_PTR2 as well. In both Hybrids Sc_PTR2 protein sequence shows hybridization between Sc_PTR2 Ale yeast 1 and Sc_PTR2 Lager yeast 1 and 2 copies.

DAL5 analysis of the alleleic variation was done based on the genomic sequences (see accession numbers above). Hybrid yeast 1 and Hybrid yeast 7 has retained Sc_DAL5 from Ale yeast 1. Hybrid yeast 7 has retained nonSc_DAL5 as well.

UBR1 analysis of the alleleic variation was done based on the the genomic sequences (see accession numbers above). Both Lager parental yeast has Sc_copy that is truncated differently. Previously, Lager 1 genomic data search yielded only fragmented sequence that did not allowed to determine early stop codon. Both Hybrid yeasts retained nonSc_UBR1 from Lager parent. Sc_copy detected in both Hybrids was inherited from Ale 1 parent.

TABLE 11b

|  | Lager yeast 2 (Lager 2) | Ale yeast 1 (Ale 1) | Hybrid yeast 1 (Hybrid 1) | Hybrid yeast 7 (Hybrid 7) |
|---|---|---|---|---|
| PTR2 | Sc_copy nonSc_copy | Sc_copy with 6 amino acids difference from Lagers Sc-copy | One Sc_like hybrid allele encoding SEQ ID NO: 43; One nonSc allele encoding SEQ ID NO: 44 | One Sc_like hybrid allele encoding a protein comprising SEQ ID NO. 37; One nonSc allele encoding SEQ ID NO: 38 |
| DAL5 | nonSc_copy | Sc_copy | One Sc_copy (see Table 11a) | One Sc allele encoding SEQ ID NO: 39; One nonSc allele encoding SEQ ID NO: 40 |
| UBR1 | Sc_copy truncated, 1544; nonSc_copy | Sc_copy truncated, 900 amino acids; | One Sc allele encoding protein comprising SEQ ID NO: 45 One nonSc allele (see Table 11a) | One Sc_allele - same as in Ale 1 encoding a protein comprising SEQ ID NO: 41; One nonSc_allele encoding SEQ ID NO: 42 |

Table 12a summarizes the status of various genes involved in sugar utilization in Lager Yeast 1, Ale yeast 1 and Hybrid yeast 1.

|                      | Lager 1 | Ale 1 | Hybrid 1 |
|---|---|---|---|
| IMA1_Sc_allele_short | Not found | 1 allele | 2 alleles encoding SEQ ID NO: 12 and SEQ ID NO: 13, respectively. |
| IMA1_Sc_allele_long  | 1 allele encoding protein with 99% amino acid sequence identity with *Saccharomyces cerevisiae* AWRI1631 and Kyokai no. 7 | 2 alleles | 1 allele similar to Lager 1 encoding SEQ ID NO: 14 1 allele with similar Ale 1 allele encoding SEQ ID NO: 15 |
| IMA5 | 2 alleles: Allele 1: Sc-IMA5 like copy, Allele 2: non-sc-IMA5 | 1 allele: Sc-IMA5 like copy | 2 alleles: Non-Sc-IMA5 like copy encoding SEQ ID NO: 16 Sc-IMA5-like similar to Ale 1 allele encoding SEQ ID NO: 17 |
| AGT1 | 2 alleles but only one functional: Allele 1: Sc copy has STOP codon (extra T in poly-T) → Truncated CDS. Allele 2: Non-Sc copy encoding protein with 87% sequence identity to S288C | 1 allele: Sc COPY | 3 alleles: Non-sc copy 100% identical to non-sc copy of AGT1 found in Lager 1. The non-sc copy of AGT1 encodes SEQ ID NO: 18. 2 Sc alleles very similar to the Sc copy found in Ale 1 encoding SEQ ID NO: 19 and SEQ ID NO: 20, respectively. |

|       | Lager yeast 2 | Hybrid yeast 4 | Hybrid yeast 7 |
|---|---|---|---|
| LONG_IMA1 | 1 allele: | 3 alleles: Two alleles encoding SEQ ID NO: 21 and one allele encoding SEQ ID NO: 22. All alleles have hybrid nature based on nucleotide sequence. | 3 alleles: One allele is identical to Lager 2 allele and encodes SEQ ID NO: 24; one allele is identical to one of the ale 1 alleles and encodes SEQ ID NO: 23; and one allele has hybrid nature and encodes SEQ ID NO: 25. |
| AGT1 | 2 alleles: Allele 1: Sc allele contains a premature STOP codon, and encodes a truncated protein Allele 2: Non-Sc allele | 3 alleles: Allele 1: Sc allele containing a STOP codon encoding a truncated protein, SEQ ID NO: 26. 2 nonSc alleles: one identical to Lager 2 nonSc copy encoding SEQ ID NO: 28, and one encoding SEQ ID NO: 27 having 1 amino acid change | 4 alleles: 2 non-Sc alleles: one identical to Lager 2 non-Sc copy encoding SEQ ID NO: 31, and one encoding SEQ ID NO: 32 having 1 amino acid change 2 Sc alleles: one identical to Ale 1 Sc allele encoding SEQ ID NO: 30, and another identical to Lager 2 Sc allele encoding a truncated protein SEQ ID NO: 29. |

Several genes may be involved in utilization of isomaltose. This includes Agt1p that is a sugar transporter that can transport isomaltose. Furthermore, there are 5 different isomaltase enzymes which are alpha-1,6-glucosidases but which also have other glucosidase activities.

Based on genomic sequence information no IMA1 gene with a full coding sequence was identified in lager yeast 1 and other *S. pastorianus* strains found in the NCBI database also did not have a copy of the *S. cerevisiae* IMA1 gene. Interestingly, Hybrid yeast 1 contains 4 different alleles of the IMA1 gene of two different lengths.

IMA5-like sequence is present in the genome of lager yeast 1. In Hybrid yeast 1 there were 2 alleles, one Non-*S. cerevisiae* copy identical to the lager yeast 1 and one *S. cerevisiae* copy very similar to the sequence found in Ale 1 yeast but with 3 amino acid changes.

The transport of maltotriose and isomaltose has been shown to be facilitated by the high-affinity alpha-glucoside transporter encoded by the gene AGT1. This transporter has a broad substrate specificity.

We found in the lager yeast 1 only one full copy of the AGT1 transporter of Non-*S. cerevisiae* origin, the *S. cerevisiae* copy was truncated. Hybrid yeast 1 in contrast had 3 full copies of AGT1 gene, one identical to the Non-*S. cerevisiae* copy found in lager yeast 1, and two *S. cerevisiae* alleles very similar to the AGT1 genes found in Ale yeast 1 but with one amino acid change.

In Hybrid yeast 4, 2 full length copies of Non-*S. cerevisiae* AGT1 were identified with one copy carrying 1 amino acid change. In Hybrid yeast 7, 3 full length copies were identified: one fully identical to Ale yeast 1 AGT1, and 2 alleles of non-*S. cerevisiae* AGT1 with one copy carrying 1 amino acid change.

In addition to study of the genomic sequence as described above, additional information was obtained on IMA1 short in Lager yeast 1 and Lager yeast 2, as well as in Hybrid yeast 1, Hybrid yeast 4 and Hybrid yeast 7 by cloning and sequencing using specific primers for IMA1_short locus of Ale yeast 1 as described above. Based on genomic sequence information, no IMA1_short gene was found in Lager 1 and Lager 2 yeasts genomic sequences. However, cloning and sequencing of the IMA1-short from both Lager yeasts parents showed that one gene is present, but it encodes a protein with 6 amino acid difference from the corresponding Ale yeast 1 IMA1 short protein. The data is summarized in Table 12c below.

In Hybrid yeast 1 cloning and sequencing identified 3 IMA1 short alleles—the two alleles described herein above and an additional allele with hybrid nature based on nucleotide sequence and also on the protein level (protein sequence provided as SEQ ID NO:1). Hybrid yeasts 4 and 7 retained IMA1_short from both parents, but cloning also identified additional alleles with unique amino acids change in both Hybrids. Thus, all three hybrid strains contained 3 IMA1 short alleles.

IMA5 analysis of the allelic variation was done based on the sequences available in the genomic sequences. In addition to the alleles described above in Table 12a, Hybrid yeast 1 contained one additional allele. Thus Hybrid yeast 1 and Hybrid yeast 7 both retained Sc_IMA5 and nonSc_IMA5 copies. Hybrid yeast 7 has unique hybrid Sc_IMA5 allele resulted from recombination between Ale yeast 1 and Lager yeast 2 at Sc_IMA5 locus. Hybridization is evident from nucleotide sequences, and visible on the protein sequence.

TABLE 12c

|  | Lager yeast 1 (Lager 1) | Lager yeast 2 (Lager 2) | Ale yeast 1 (Ale 1) |
|---|---|---|---|
| IMA1_short | 1 allele cloned by PCR with 6 amino acids difference from Ale 1 | 1 allele cloned by PCR and identical to Lager 1 (SEQ ID NO: 2) | 1 allele (confirmed by cloning) |
| IMA5 | 2 alleles: Sc_IMA5 copy (3 amino acids difference with Ale 1) nonSc_IMA5 | 2 alleles: Sc_IMA5 I copy (identical to Lager 1) nonSc_IMA5 (has 2 SNPs with respect to lager 1 in coding region) | 1 allele: Sc-IMA5 copy |

|  | Hybrid yeast 1 (Hybrid 1) | Hybrid yeast 4 (Hybrid 4) | Hybrid yeast 7 (Hybrid 7) |
|---|---|---|---|
| IMA1_short | 3 alleles found through cloning: One Allele (vA) is identical to allele of Ale 1 and one allele (vB) is as Ale1 with one amino acid change. These two alleles encodes SEQ ID NO: 12 and SEQ ID NO: 13. One allele is unique in the Hybrid 1 and enclodes SEQ ID NO: 1 | 3 alleles found through cloning: One allele identical to allele of Lager 2 and encodes SEQ ID NO: 2; One allele is identical to allele of Ale 1 encoding SEQ ID NO: 3, and another allele has a nucleotide change, but also encodes SEQ ID NO: 3. | 3 alleles found through cloning: One allele is identical to allele from Lager 2 and encodies SEQ ID NO: 5 One allele is identical to allel from Ale 1 and encodes SEQ ID NO: 33; One allele is similar to allele from Lager 2 with nucleotide change and unique amino acid change (SEQ ID NO: 4) |
| IMA5 | 3 alleles: One Sc IMA5 allele similar to allele of Ale 1 encoding SEQ ID NO: 17; One unique allele identified by cloning encoding IMA5 with unique 3 amino acid changes (SEQ ID NO: 34) | ND | 2 alleles: One Sc_IMA5 allele, which is a unique_hybrid copy encoding SEQ ID NO: 35 One nonSc_IMA5 allele identical to allele of lager 2 encoding SEQ ID NO; 36 |

TABLE 12c-continued

One NonSc_IMA5 allele
like allele of lager 1
encoding SEQ ID NO; 16

Example 11

Data of maltulose, maltotriose and kojibiose utilization was obtained by measuring the growth of the different yeasts in defined medium with 2 g/L maltulose or 2 g/L maltotriose or 2 g/L kojibiose as sole carbon sources:

Yeast cells from frozen stocks were streaked on YPD plates (1% Yeast extract, 2% peptone, 2% glucose and 2% agar-agar) and growing cells were inoculated into liquid YPD (1% Yeast extract, 2% peptone, 2% glucose).

3 µL of the overnight liquid YPD culture was inoculated into 100 µL culture of YNB (6.7 g/L) without amino acids but with ammonium sulfate and buffered with potassium hydrogen phthalate to pH 5.5 (Hahn-Hägerdal B. et al. 2005) and with 2 g/L maltulose or 2 g/L maltotriose or 2 g/L kojibiose as sole carbon sources.

Cell growth was followed by measuring the optical density at 600 nm with continuous agitation and incubating at 20° C. of temperature using Bioscreen C MBR (Oy Growth Curves Ab Ltd, Finland).

Figure 13:
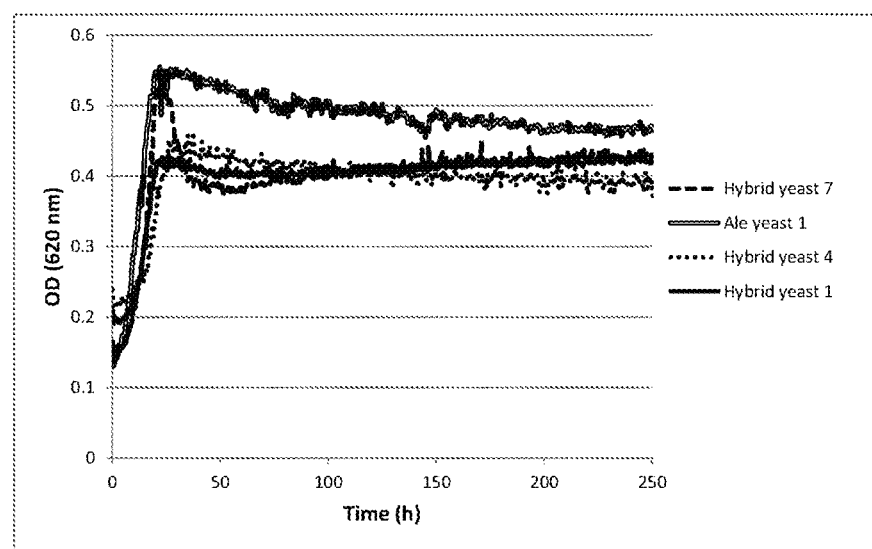
FIG. 13 shows growth of yeast in defined medium with 2 g/L maltotriose as sole carbon source. The data shown is representative of biological replicates.

It was tested whether Ale yeast 1, Hybrid yeast 1, Hybrid yeast 4 and Hybrid yeast 7 are capable of utilizing maltotriose as sole carbon source. The results are shown in FIG. 13.

It was also tested whether Ale yeast 1, Hybrid yeast 1, Hybrid yeast 4, Hybrid yeast 7, *S. diastaticus* and Hybrid yeast 8 are capable of utilizing maltulose as sole carbon source. The results are shown in FIG. 14.

It was also tested whether Ale yeast 1, Lager yeast 1, Lager yeast 2, *S. diastaticus*, Hybrid yeast 1, Hybrid yeast 4, Hybrid yeast 7 and Hybrid yeast 8 are capable of utilizing kojibiose as sole carbon source. The results are shown in FIG. 15. As can be seen neither Lager yeast 1 nor Lager yeast 2 can utilize kojibiose as sole carbon source, whereas *S. diastaticus* only can utilize kojibiose sole carbon source very poorly.

Example 12

To further investigate the real degree of fermentation obtained when fermenting using the Hybrid yeast 7, large scale trials were performed. Wort prepared in large scale from different mixtures were fermented in different locations with either Lager yeast 2 or with Hybrid yeast 7 until diacetyl was in spec. The real degree of fermentation (RDF) was determined. Table 13 shows the absolute increase in % RDF obtained after fermentation with Hybrid yeast 7 compared with the RDF obtained after fermentation with Lager yeast 2.

Wort was prepared by mashing different ratios of malt, barley (i.e. unmalted barley kernels) and rice. In addition varying amounts of glucose syrup was added. The ration of malt:barley:glucose syrup:rie used for preparing the different wort are also indicated in table 13.

TABLE 13

| Country | Poland | India | Finland | Russia |
|---|---|---|---|---|
| Recipe (malt:barley:glucose syrup:rice) | 51:20:29:0 | 35:0:0:65 | 68:22:10:0 | 73.20:7.0 |
| RDF increase | 2% | 1% | 3% | 2.3% |

ABBREVIATIONS

RDF—real degree of fermentation

YPD—(1% Yeast extract, 2% peptone, 2% glucose)

YPD plates (1% Yeast extract, 2% peptone, 2% glucose and 2% agar-agar)

YNB (Yeast Nitrogen Base)

OD: Optical Density

HPLC: High Performance Liquid Chromatography

YPGalactose plates (1% Yeast extract, 2% peptone, 2% galactose and 2% agar-agar)

The invention claimed is:

1. A yeast cell having each of the following characteristics:
    characteristic II: capable of utilizing panose as sole carbon source; and
    characteristic VIII: capable of utilizing melibiose as sole carbon source;
    wherein the yeast cell comprises nucleotide sequences of at least 3 genes each individually encoding an IMA1p, wherein the IMA1p is selected from the group consisting of: an IMA1p comprising the amino acid sequence of SEQ ID NO: 12, an IMA1p comprising the amino acid sequence of SEQ ID NO: 13, an IMA1p of SEQ ID NO: 14, an IMA1p comprising the amino acid sequence of SEQ ID NO: 15, an IMA1p comprising the amino acid sequence of SEQ ID NO:21, an IMA1p comprising the amino acid sequence of SEQ ID NO:22, an IMA1p comprising the amino acid sequence of SEQ ID NO:23, an IMA1p comprising the amino acid sequence of SEQ ID NO:24, an IMA1p comprising the amino acid sequence of SEQ ID NO:25, an IMA1p comprising an amino acid sequence having at least 95% sequence identity to SEQ ID NO: 12, an IMA1p comprising an amino acid sequence having at least 95% sequence identity to SEQ ID NO: 13, an IMA1p comprising an amino acid sequence having at least 95% sequence identity to SEQ ID NO: 14, an IMA1p comprising an amino acid sequence having at least 95% sequence identity to SEQ ID NO: 15, an IMA1p comprising an amino acid sequence having at least 95% sequence identity to SEQ ID NO: 21, an IMA1p comprising an amino acid sequence having at least 95% sequence identity to SEQ ID NO: 22, an IMA1p comprising an amino acid sequence having at least 95% sequence identity to SEQ ID NO: 23, an IMA1p comprising an amino acid sequence having at least 95% sequence identity to SEQ ID NO: 24, and an IMA1p comprising an amino acid sequence having at least 95% sequence identity to SEQ ID NO: 25; and wherein the yeast cell comprises nucleotide sequences of at least 2 genes each individually encoding an AGT1, wherein the AGT1 is selected from the group consisting of: an AGT1 comprising the amino acid sequence of SEQ ID NO: 18, an AGT1 comprising the amino acid sequence of SEQ ID NO: 19, an AGT1 comprising the amino acid sequence of SEQ ID NO:20, an AGT1 comprising the amino acid sequence of SEQ ID NO:27, an AGT1 comprising the amino acid sequence of SEQ ID NO:28, an AGT1 comprising the amino acid sequence of SEQ ID NO:30, an AGT1 comprising the amino acid sequence of SEQ ID NO:31, an AGT1 comprising the amino acid sequence of SEQ ID NO:32, an AGT1 comprising an amino acid sequence having at least 95% sequence identity to SEQ ID NO: 18, an AGT1 comprising an amino acid sequence having at least 95% sequence identity to SEQ ID NO: 19, an AGT1 comprising an amino acid sequence having at least 95% sequence identity to SEQ ID NO: 20, an AGT1 comprising an amino acid sequence having at least 95% sequence identity to SEQ ID NO: 27, an AGT1 comprising an amino acid sequence having at least 95% sequence identity to SEQ ID NO: 28, an AGT1 comprising an amino acid sequence having at least 95% sequence identity to SEQ ID NO: 30, an AGT1 comprising an amino acid sequence having at least 95% sequence identity to SEQ ID NO: 31, and an AGT1 comprising an amino acid sequence having at least 95% sequence identity to SEQ ID NO: 32.

2. The yeast cell according to claim 1, wherein the yeast cell furthermore has characteristic (I) capable of utilizing isomaltose as sole carbon source.

3. The yeast cell according to claim 1, wherein the yeast cell furthermore has characteristic (III) capable of utilizing one or more dipeptides as sole nitrogen source.

4. The yeast cell according to claim 1, wherein the yeast cell further has characteristic (IV) capable of utilizing one or more tri-peptides as sole nitrogen source.

5. The yeast cell according to claim 1, wherein the yeast cell further have characteristics:
(VI) capable of generating at least 4.7 promille ethanol per °Plato, when said yeast cell is added to a wort composition having a sugar content of at least 10° Plato and incubated until level of diacetyl is in spec, and/or
(VII) capable of fermenting sugar with a real degree of fermentation (RDF) of at least 68 when said yeast cell is added to a wort composition having a sugar content of at least 10° Plato and incubated until level of diacetyl is 30 ppb or below.

6. The yeast cell according to claim 1, wherein the yeast cell is furthermore capable of fermenting sugar with an RDF at least 1 unit higher than the RDF of one of its parental strains.

7. The yeast cell according to claim 1, wherein the yeast cell further has characteristic (X) capable of sedimentation so that at the most 12 million cells/ml are in suspension when said yeast cell is added to a wort composition having a sugar content of at least 10° Plato and incubated for 4 days.

8. The yeast cell according to claim 1, wherein the yeast cell further has characteristic (IX) capable of utilizing one or more disaccharides and/or trisaccharides in addition to isomaltose, panose, and/or melibiose as sole carbon source.

9. The yeast cell according to claim 8, wherein the one or more disaccharides are selected from the group consisting of maltulose, kojibiose, nigerose, sucrose, turanose, leucrose, and palatinose.

10. The yeast cell according to claim 1, wherein the yeast cell furthermore has characteristic (XI) capable of fermenting wort with a time of primary fermentation of at the most 4 days.

11. The yeast cell according to claim 1, wherein the yeast cell furthermore comprises a nucleotide sequence encoding DAL5, wherein DAL5 comprises the amino acid sequence of SEQ ID NO: 6, SEQ ID NO: 39, or SEQ ID NO: 40, or an amino acid sequence having at least 95% sequence identity to SEQ ID NO: 6, at least 95% sequence identity to SEQ ID NO: 39, or at least 95% sequence identity to SEQ ID NO: 40.

12. The yeast cell according to claim 1, wherein the yeast cell furthermore comprises at least 2 nucleotide sequences encoding peptide transporter 2 (PTR2), wherein PTR2 comprises the amino acid sequence of SEQ ID NO: 7, SEQ ID NO: 8, SEQ ID NO: 9, SEQ ID NO: 37, SEQ ID NO: 38, SEQ ID NO: 43, or SEQ ID NO: 44, or an amino acid sequence having at least 95% sequence identity to SEQ ID NO: 7, at least 95% sequence identity to SEQ ID NO:8, at least 95% sequence identity to SEQ ID NO: 9, at least 95% sequence identity to SEQ ID NO: 37, at least 95% sequence identity to SEQ ID NO: 38, at least 95% sequence identity to SEQ ID NO: 43, or at least 95% sequence identity to SEQ ID NO: 44.

13. The yeast cell according to claim 1, wherein the yeast cell furthermore comprises a nucleotide sequence encoding ubiquitin ligase E3 component N-recognin 1 (UBR1), wherein UBR1 comprises the amino acid sequence of SEQ ID NO: 10, SEQ ID NO: 11, SEQ ID NO:41, SEQ ID NO:42, or SEQ ID NO:45, or an amino acid sequence having at least 95% sequence identity to SEQ ID NO: 10, at least 95% sequence identity to SEQ ID NO: 11, at least 95% sequence identity to SEQ ID NO: 41, at least 95% sequence identity to SEQ ID NO: 42, or at least 95% sequence identity to SEQ ID NO: 45.

14. The yeast cell according to claim 1, wherein the yeast cell comprises nucleotide sequences of at least 5 genes, each individually encoding IMA1p, wherein the IMA1p is selected from the group consisting of: an IMA1p comprising the amino acid sequence of SEQ ID NO:1, an IMA1p comprising the amino acid sequence of SEQ ID NO:2, an IMA1p comprising the amino acid sequence of SEQ ED NO:3, an IMA1p comprising the amino acid sequence of SEQ ID NO:4, an IMA1p comprising the amino acid sequence of SEQ ID NO:5, an IMA1p comprising the amino acid sequence of SEQ ID NO: 12, an IMA1p comprising the amino acid sequence of SEQ ID NO: 13, an IMA1p comprising the amino acid sequence of SEQ ID NO: 14, an IMA1p comprising the amino acid sequence of SEQ ID NO:15, an IMA1p comprising the amino acid sequence of SEQ ID NO:21, an IMA1p comprising the amino acid sequence of SEQ ID NO:22, an IMA1p comprising the amino acid sequence of SEQ ID NO:23, an IMA1p comprising the amino acid sequence of SEQ ID NO:24, an IMA1p comprising the amino acid sequence of SEQ ID NO:25, an IMA1p comprising the amino acid sequence of SEQ ID NO:33, an IMA1p comprising an amino acid sequence having at least 95% sequence identity to SEQ ID NO: 2, at least 95% sequence identity to SEQ ID NO: 3, an IMA1p comprising an amino acid sequence having at least 95% sequence identity to SEQ ID NO: 4, an IMA1p comprising an amino acid sequence having at least 95% sequence identity identical to SEQ ID NO: 5, an IMA1p comprising an amino acid sequence having at least 95% sequence identity to SEQ ID NO: 12, an IMA1p comprising an amino acid sequence having at least 95% sequence identity to SEQ ED NO: 13, an IMA1p comprising an amino acid sequence having at least 95% sequence identity to SEQ ED NO: 14, an IMA1p comprising an amino acid sequence having at least 95% sequence identity to SEQ ID NO: 15, an IMA1p comprising an amino acid sequence having at least 95% sequence identity to SEQ ID NO: 21, an IMA1p comprising an amino acid sequence having at least 95% sequence identity to SEQ ID NO: 22, an IMA1p comprising an amino acid sequence having at least 95% sequence identity to SEQ ID NO: 23, an IMA1p comprising an amino acid sequence having at least 95% sequence identity to SEQ ID NO: 24, an IMA1p comprising an amino acid sequence having at least 95% sequence identity to SEQ ED NO: 25, and an IMA1p comprising an amino acid sequence having at least 95% sequence identity to SEQ ED NO: 33.

15. The yeast cell according to claim 1, wherein the nucleotide sequences of at least 3 genes each individually encode an IMA1p wherein said at least 3 genes comprise at least 3 short alleles of IMA 1 and at least 2 long alleles of IMA1, wherein
  a) said 3 short alleles of IMA1 individually are genes encoding an IMA1p, wherein the IMA1p is selected from the group consisting of: SEQ ID NO:12, SEQ ID NO:13, SEQ ID NO:1, SEQ ID NO:2, SEQ ID NO:3, SEQ ID NO: 4, SEQ ID NO:5, SEQ ID NO:33, a sequence having at least 95% sequence identity to SEQ ID NO: 12, a sequence having at least 95% sequence identity to SEQ ID NO: 13, a sequence having at least 95% sequence identity to SEQ ID NO: 1, a sequence having at least 95% sequence identity to SEQ ID NO: 2, a sequence having at least 95% sequence identity to SEQ ID NO: 3, a sequence having at least 95% sequence identity to SEQ ID NO: 4, a sequence having at least 95% sequence identity to SEQ ID NO: 5, and a sequence having at least 95% sequence identity to SEQ ID NO: 33; and
  b) said 2 long alleles of IMA1 individually are genes encoding an IMA1p, wherein the IMA1p is selected from the group consisting of: SEQ ID NO: 14, SEQ ID NO: 15, SEQ ID NO:21, SEQ ID NO:22, SEQ ID NO:23, SEQ ID NO:24, SEQ ID NO:25, a sequence having at least 95% sequence identity to SEQ ID NO: 14, a sequence having at least 95% sequence identity to SEQ ID NO: 15, a sequence having at least 95% sequence identity to SEQ ID NO: 21, a sequence having at least 95% sequence identity to SEQ ID NO: 22, a sequence having at least 95% sequence identity to SEQ ID NO: 23, a sequence having at least 95% sequence identity to SEQ ID NO: 24, and a sequence having at least 95% sequence identity to SEQ ID NO: 25.

16. The yeast cell according to claim 1, wherein the yeast cell furthermore comprises a nucleotide sequence encoding IMA5p, wherein IMA5p comprises the amino acid sequence of SEQ ID NO:16, SEQ ID NO:17, SEQ ID NO:34, SEQ ID NO:35, or SEQ ID NO:36, or an amino acid sequence having at least 95% sequence identity to SEQ ID NO: 16, an amino acid sequence having at least 95% sequence identity to SEQ ID NO: 17, an amino acid sequence having at least 95% sequence identity to SEQ ID NO: 34, an amino acid sequence having at least 95% sequence identity to SEQ ID NO: 35, or an amino acid sequence having at least 95% sequence identity to SEQ ID NO: 36.

17. The yeast cell according to claim 1, wherein the yeast cell comprises the nucleotide sequences of at least 3 genes each individually encoding an AGT1 comprising the amino acid sequence of SEQ ID NO: 18, SEQ ID NO: 19, SEQ ID NO:20, SEQ ID NO:26, SEQ ID NO:27, SEQ ID NO:28, SEQ ID NO:29, SEQ ID NO:30, SEQ ID NO:31, or SEQ ID NO:32, or comprising an amino acid sequence having at least 95% sequence identity to SEQ ID NO: 18, an amino acid sequence having at least 95% sequence identity to SEQ ID NO: 19, an amino acid sequence having at least 95% sequence identity to SEQ ID NO: 20, an amino acid sequence having at least 95% sequence identity to SEQ ID NO: 26, an amino acid sequence having at least 95% sequence identity to SEQ ID NO: 27, an amino acid sequence having at least 95% sequence identity to SEQ ID NO: 28, an amino acid sequence having at least 95% sequence identity to SEQ ID NO: 29, an amino acid sequence having at least 95% sequence identity to SEQ ID NO: 30, an amino acid sequence having at least 95% sequence identity to SEQ ID NO: 31, or an amino acid sequence having at least 95% sequence identity to SEQ ID NO: 32.

\* \* \* \* \*

SEQUENCE LISTING

```
<160> NUMBER OF SEQ ID NOS: 69

<210> SEQ ID NO 1
<211> LENGTH: 520
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 1

Met Gly Tyr Asp Ile Ala Asn Tyr Glu Lys Val Trp Pro Thr Tyr Gly
1               5                  10                  15

Thr Asn Glu Asp Cys Phe Ala Leu Ile Glu Lys Thr His Lys Leu Gly
            20                  25                  30

Met Lys Phe Ile Thr Asp Leu Val Ile Asn His Cys Ser Ser Glu His
        35                  40                  45
```

-continued

Glu Trp Phe Lys Glu Ser Arg Ser Lys Thr Asn Pro Lys Arg Asp
50                  55                  60

Trp Phe Phe Trp Arg Pro Lys Gly Tyr Asp Ala Glu Gly Lys Pro
65                  70                  75                  80

Ile Pro Pro Asn Asn Trp Lys Ser Tyr Phe Gly Gly Ser Ala Trp Thr
                85                  90                  95

Phe Asp Glu Lys Thr Gln Glu Phe Tyr Leu Arg Leu Phe Cys Ser Thr
            100                 105                 110

Gln Pro Asp Leu Asn Trp Glu Asn Glu Asp Cys Arg Lys Ala Ile Tyr
            115                 120                 125

Glu Ser Ala Val Gly Tyr Trp Leu Asp His Gly Val Asp Gly Phe Arg
130                 135                 140

Ile Asp Val Gly Ser Leu Tyr Ser Lys Val Val Gly Leu Pro Asp Ala
145                 150                 155                 160

Pro Val Val Asp Lys Asn Ser Thr Trp Gln Ser Ser Asp Pro Tyr Thr
                165                 170                 175

Leu Asn Gly Pro Arg Ile His Glu Phe His Gln Glu Met Asn Gln Phe
            180                 185                 190

Ile Arg Asn Arg Val Lys Asp Gly Arg Glu Ile Met Thr Val Gly Glu
            195                 200                 205

Met Gln His Ala Ser Asp Glu Thr Lys Arg Leu Tyr Thr Ser Ala Ser
210                 215                 220

Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
                245                 250                 255

Trp Lys Ile Ala Leu Ala Glu Leu Phe Arg Tyr Ile Asn Gly Thr Asp
            260                 265                 270

Cys Trp Ser Thr Ile Tyr Leu Glu Asn His Asp Gln Pro Arg Ser Ile
            275                 280                 285

Thr Arg Phe Gly Asp Asp Ser Pro Lys Asn Arg Val Ile Ser Gly Lys
290                 295                 300

Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Pro Val Glu
                325                 330                 335

Lys Tyr Glu Asp Val Glu Ile Arg Asn Asn Tyr Asn Ala Ile Lys Glu
            340                 345                 350

Glu His Gly Glu Asn Ser Glu Met Lys Lys Phe Leu Glu Gly Ile
            355                 360                 365

Ala Leu Val Ser Arg Asp His Ala Arg Thr Pro Met Pro Trp Thr Pro
370                 375                 380

Asn Glu Pro Asn Ala Gly Phe Ser Gly Pro Asn Thr Lys Pro Trp Phe
385                 390                 395                 400

Tyr Leu Asn Glu Ser Phe Arg Gln Gly Ile Asn Val Glu Glu Gln
                405                 410                 415

Lys Asn Ser Asp Ser Val Leu Ala Phe Trp Lys Lys Ala Leu Glu Phe
            420                 425                 430

Arg Lys Asn His Lys Asp Ile Ala Val Tyr Gly Phe Asp Phe Lys Phe
            435                 440                 445

Ile Asp Leu Asp Asn Lys Lys Leu Phe Ser Phe Thr Lys Arg Tyr Asn
450                 455                 460

```
Asn Lys Thr Leu Phe Ala Ala Leu Asn Phe Ser Ser Asp Ala Thr Asp
465                 470                 475                 480

Phe Lys Ile Pro Asn Asp Gly Ser Ser Phe Lys Leu Glu Phe Gly Asn
            485                 490                 495

Tyr Pro Lys Asn Glu Val Asp Ala Ser Ser Arg Thr Leu Lys Pro Trp
        500                 505                 510

Glu Gly Arg Ile His Ile Asn Glu
        515                 520
```

<210> SEQ ID NO 2
<211> LENGTH: 520
<212> TYPE: PRT
<213> ORGANISM: Unknown
<220> FEATURE:
<223> OTHER INFORMATION: Hybrid between S. cerevisiae and S. pastorianus
      (Hybrid yeast 4)

<400> SEQUENCE: 2

```
Met Gly Tyr Asp Ile Ala Asn Tyr Glu Lys Val Trp Pro Thr Tyr Gly
1               5                   10                  15

Thr Asn Glu Asp Cys Phe Ala Leu Ile Glu Lys Thr His Lys Leu Gly
            20                  25                  30

Met Lys Phe Ile Thr Asp Leu Val Ile Asn His Cys Ser Ser Glu His
        35                  40                  45

Glu Trp Phe Lys Glu Ser Arg Ser Ser Lys Thr Asn Pro Lys Arg Asp
50                  55                  60

Trp Phe Phe Trp Arg Pro Pro Lys Gly Tyr Asp Ala Glu Gly Lys Pro
65                  70                  75                  80

Ile Pro Pro Asn Asn Trp Lys Ser Tyr Phe Gly Gly Ser Ala Trp Thr
                85                  90                  95

Phe Asp Glu Lys Thr Gln Glu Phe Tyr Leu Arg Leu Phe Cys Ser Thr
            100                 105                 110

Gln Pro Asp Leu Asn Trp Glu Asn Glu Asp Cys Arg Lys Ala Ile Tyr
        115                 120                 125

Glu Ser Ala Val Gly Tyr Trp Leu Asp His Gly Val Asp Gly Phe Arg
130                 135                 140

Ile Asp Val Gly Ser Leu Tyr Ser Lys Val Val Gly Leu Pro Asp Ala
145                 150                 155                 160

Pro Val Val Asp Lys Asn Ser Thr Trp Gln Ser Ser Asp Pro Tyr Thr
                165                 170                 175

Leu Asn Gly Pro Arg Ile His Glu Phe His Gln Glu Met Asn Gln Phe
            180                 185                 190

Ile Arg Asn Arg Val Lys Asp Gly Arg Glu Ile Met Thr Val Gly Glu
        195                 200                 205

Met Gln His Ala Ser Asp Glu Thr Lys Arg Leu Tyr Thr Ser Ala Ser
210                 215                 220

Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
                245                 250                 255

Trp Lys Ile Ala Leu Ala Glu Leu Phe Arg Tyr Ile Asn Gly Thr Asp
            260                 265                 270

Cys Trp Ser Thr Ile Tyr Leu Glu Asn His Asp Gln Pro Arg Ser Ile
        275                 280                 285

Thr Arg Phe Gly Asp Asp Ser Pro Lys Asn Arg Val Ile Ser Gly Lys
290                 295                 300
```

```
Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Pro Val Glu
            325                 330                 335

Lys Tyr Glu Asp Val Glu Ile Arg Asn Tyr Asn Ala Ile Lys Glu
            340                 345                 350

Glu His Gly Glu Asn Ser Glu Glu Met Lys Lys Phe Leu Glu Gly Ile
            355                 360                 365

Ala Leu Val Ser Arg Asp His Ala Arg Thr Pro Met Pro Trp Thr Pro
370                 375                 380

Asn Glu Pro Asn Ala Gly Phe Ser Gly Pro Asn Thr Lys Pro Trp Phe
385                 390                 395                 400

Tyr Leu Asn Glu Ser Phe Arg Gln Gly Ile Asn Val Glu Glu Glu Gln
                405                 410                 415

Lys Asn Ser Asp Ser Val Leu Ala Phe Trp Lys Lys Ala Leu Glu Phe
            420                 425                 430

Arg Lys Asn His Lys Asp Ile Ala Val Tyr Gly Phe Asp Phe Lys Phe
            435                 440                 445

Ile Asp Leu Asp Asn Lys Lys Leu Phe Ser Phe Thr Lys Arg Tyr Asn
450                 455                 460

Asn Lys Thr Leu Phe Ala Ala Leu Asn Phe Ser Ser Asp Ala Thr Asp
465                 470                 475                 480

Phe Lys Ile Pro Asn Asp Gly Ser Ser Phe Lys Leu Glu Phe Gly Asn
                485                 490                 495

Tyr Pro Lys Asn Glu Val Asp Ala Ser Ser Arg Thr Leu Lys Pro Trp
            500                 505                 510

Glu Gly Arg Ile Tyr Ile Asn Glu
            515                 520

<210> SEQ ID NO 3
<211> LENGTH: 520
<212> TYPE: PRT
<213> ORGANISM: Unknown
<220> FEATURE:
<223> OTHER INFORMATION: Hybrid between S. cerevisiae and S. pastorianus
      (Hybrid yeast 4)

<400> SEQUENCE: 3

Met Gly Tyr Asp Ile Ala Asn Tyr Glu Lys Val Trp Pro Thr Tyr Gly
1               5                   10                  15

Thr Asn Glu Asp Cys Phe Ala Leu Ile Glu Lys Thr His Lys Leu Gly
            20                  25                  30

Met Lys Phe Ile Thr Asp Leu Val Ile Asn His Cys Ser Ser Glu His
            35                  40                  45

Glu Trp Phe Lys Glu Ser Arg Ser Ser Lys Thr Asn Pro Lys Arg Asp
50                  55                  60

Trp Phe Phe Trp Arg Pro Pro Lys Gly Tyr Asp Ala Glu Gly Lys Pro
65                  70                  75                  80

Ile Pro Pro Asn Asn Trp Lys Ser Tyr Phe Gly Gly Ser Ala Trp Thr
                85                  90                  95

Phe Asp Glu Lys Thr Gln Glu Phe Tyr Leu Arg Leu Phe Cys Ser Thr
            100                 105                 110

Gln Pro Asp Leu Asn Trp Glu Asn Glu Asp Cys Arg Lys Ala Ile Tyr
            115                 120                 125

Glu Ser Ala Val Gly Tyr Trp Leu Asp His Gly Val Asp Gly Phe Arg
```

```
            130                 135                 140
Ile Asp Val Gly Ser Leu Tyr Ser Lys Val Val Gly Leu Pro Asp Ala
145                 150                 155                 160

Pro Val Val Asp Lys Asn Ser Thr Trp Gln Ser Ser Asp Pro Tyr Thr
                165                 170                 175

Leu Asn Gly Pro Arg Ile His Glu Phe His Gln Glu Met Asn Gln Phe
            180                 185                 190

Ile Arg Asn Arg Val Lys Asp Gly Arg Glu Ile Met Thr Val Gly Glu
                195                 200                 205

Met Gln His Ala Ser Asp Glu Thr Lys Arg Leu Tyr Thr Ser Ala Ser
        210                 215                 220

Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
                245                 250                 255

Trp Lys Ile Ala Leu Ala Glu Leu Phe Arg Phe Ile Asn Gly Thr Asp
                260                 265                 270

Cys Trp Ser Thr Ile Tyr Leu Glu Asn His Asp Gln Pro Arg Ser Ile
            275                 280                 285

Thr Arg Phe Gly Asp Asp Ser Pro Lys Asn Arg Val Ile Ser Gly Lys
        290                 295                 300

Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Ser Val Glu
                325                 330                 335

Lys Tyr Glu Asp Val Glu Ile Arg Asn Asn Tyr Arg Leu Ile Lys Glu
                340                 345                 350

Glu Cys Gly Glu Asn Ser Glu Glu Met Lys Lys Phe Leu Glu Gly Ile
            355                 360                 365

Ala Leu Val Ser Arg Asp His Ala Arg Thr Pro Met Pro Trp Thr Pro
        370                 375                 380

Asn Glu Pro Asn Ala Gly Phe Ser Gly Pro Asn Thr Lys Pro Trp Phe
385                 390                 395                 400

Tyr Leu Asn Glu Ser Phe Arg Gln Gly Ile Asn Val Glu Glu Glu Gln
                405                 410                 415

Lys Asn Ser Asp Ser Val Leu Ala Phe Trp Lys Lys Ala Leu Glu Phe
                420                 425                 430

Arg Lys Asn His Lys Asp Ile Ala Val Tyr Gly Phe Asp Phe Lys Phe
            435                 440                 445

Ile Asp Leu Asp Asn Lys Lys Leu Phe Ser Phe Thr Lys Arg Tyr Asn
        450                 455                 460

Asn Lys Thr Leu Phe Ala Ala Leu Asn Phe Ser Ser Asp Ala Thr Asp
465                 470                 475                 480

Phe Lys Ile Pro Asn Asp Gly Ser Ser Phe Lys Leu Glu Phe Gly Asn
                485                 490                 495

Tyr Pro Lys Asn Glu Val Asp Ala Ser Ser Arg Thr Leu Lys Pro Trp
                500                 505                 510

Glu Gly Arg Ile His Ile Asn Glu
                515                 520

<210> SEQ ID NO 4
<211> LENGTH: 520
<212> TYPE: PRT
<213> ORGANISM: Unknown
```

```
<220> FEATURE:
<223> OTHER INFORMATION: Hybrid between S. cerevisiae and S. pastorianus
      (Hybrid yeast 7)

<400> SEQUENCE: 4

Met Gly Tyr Asp Ile Ala Asn Tyr Glu Lys Val Trp Pro Thr Tyr Gly
1               5                   10                  15

Thr Asn Glu Asp Cys Phe Ala Leu Ile Glu Lys Thr His Lys Leu Gly
            20                  25                  30

Met Lys Phe Ile Thr Asp Leu Val Ile Asn His Cys Ser Ser Glu His
        35                  40                  45

Glu Trp Phe Lys Glu Ser Arg Ser Ser Lys Thr Asn Pro Lys Arg Asp
    50                  55                  60

Trp Phe Phe Trp Arg Pro Lys Gly Tyr Asp Ala Glu Gly Lys Pro
65                  70                  75                  80

Ile Pro Pro Asn Asn Trp Lys Ser Tyr Phe Gly Gly Ser Ala Trp Thr
                85                  90                  95

Phe Asp Glu Lys Thr Gln Glu Phe Tyr Leu Arg Leu Phe Cys Ser Thr
            100                 105                 110

Gln Pro Asp Leu Asn Trp Glu Asn Glu Asp Cys Arg Lys Ala Ile Tyr
        115                 120                 125

Glu Ser Ala Val Gly Tyr Trp Leu Asp His Gly Val Asp Gly Phe Arg
    130                 135                 140

Ile Asp Val Gly Ser Leu Tyr Ser Lys Val Val Gly Leu Pro Asp Ala
145                 150                 155                 160

Pro Val Val Asp Lys Asn Ser Thr Trp Gln Ser Ser Asp Pro Tyr Thr
                165                 170                 175

Leu Asn Gly Pro Arg Ile His Glu Phe His Gln Glu Met Asn Gln Phe
            180                 185                 190

Ile Arg Asn Arg Val Lys Asp Gly Arg Glu Ile Met Thr Val Gly Glu
        195                 200                 205

Met Gln His Ala Ser Asp Glu Thr Lys Arg Leu Tyr Thr Ser Ala Ser
    210                 215                 220

Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
                245                 250                 255

Trp Lys Ile Ala Leu Ala Glu Leu Phe Arg Tyr Ile Asn Gly Thr Asp
            260                 265                 270

Cys Trp Ser Thr Ile Tyr Leu Glu Asn His Asp Gln Pro Arg Ser Ile
        275                 280                 285

Thr Arg Phe Gly Asp Asp Ser Pro Lys Asn Arg Val Ile Ser Gly Lys
    290                 295                 300

Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Pro Val Glu
                325                 330                 335

Lys Tyr Glu Asp Val Glu Ile Arg Asn Asn Tyr Asn Ala Ile Lys Glu
            340                 345                 350

Glu His Gly Glu Asn Ser Glu Met Lys Lys Phe Leu Glu Gly Ile
        355                 360                 365

Ala Leu Val Ser Arg Asp His Ala Arg Thr Pro Met Pro Trp Thr Pro
370                 375                 380

Asn Glu Pro Asn Ala Gly Phe Ser Gly Pro Asn Thr Lys Pro Trp Phe
```

```
                385                 390                 395                 400
Tyr Leu Asn Glu Ser Phe Arg Gln Gly Ile Asn Val Glu Glu Glu Gln
                    405                 410                 415
Lys Asn Ser Asp Ser Val Leu Ala Phe Trp Lys Lys Ala Leu Glu Phe
                420                 425                 430
Arg Lys Asn His Lys Asp Ile Ala Val Tyr Gly Phe Asp Phe Lys Phe
            435                 440                 445
Ile Asp Leu Asp Asn Lys Lys Leu Phe Ser Phe Thr Lys Arg Tyr Asn
450                 455                 460
Asn Lys Thr Leu Phe Ala Ala Leu Asn Phe Ser Ser Asp Ala Thr Asp
465                 470                 475                 480
Phe Lys Ile Pro Asn Asp Gly Ser Ser Phe Lys Leu Glu Phe Gly Asn
                485                 490                 495
Tyr Pro Lys Asn Glu Val Asp Val Ser Ser Arg Thr Leu Lys Pro Trp
            500                 505                 510
Glu Gly Arg Ile Tyr Ile Asn Glu
        515                 520

<210> SEQ ID NO 5
<211> LENGTH: 520
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 5

Met Gly Tyr Asp Ile Ala Asn Tyr Glu Lys Val Trp Pro Thr Tyr Gly
1               5                   10                  15
Thr Asn Glu Asp Cys Phe Ala Leu Ile Glu Lys Thr His Lys Leu Gly
                20                  25                  30
Met Lys Phe Ile Thr Asp Leu Val Ile Asn His Cys Ser Ser Glu His
            35                  40                  45
Glu Trp Phe Lys Glu Ser Arg Ser Ser Lys Thr Asn Pro Lys Arg Asp
    50                  55                  60
Trp Phe Phe Trp Arg Pro Pro Lys Gly Tyr Asp Ala Glu Gly Lys Pro
65                  70                  75                  80
Ile Pro Pro Asn Asn Trp Lys Ser Tyr Phe Gly Gly Ser Ala Trp Thr
                85                  90                  95
Phe Asp Glu Lys Thr Gln Glu Phe Tyr Leu Arg Leu Phe Cys Ser Thr
                100                 105                 110
Gln Pro Asp Leu Asn Trp Glu Asn Glu Asp Cys Arg Lys Ala Ile Tyr
            115                 120                 125
Glu Ser Ala Val Gly Tyr Trp Leu Asp His Gly Val Asp Gly Phe Arg
    130                 135                 140
Ile Asp Val Gly Ser Leu Tyr Ser Lys Val Val Gly Leu Pro Asp Ala
145                 150                 155                 160
Pro Val Val Asp Lys Asn Ser Thr Trp Gln Ser Ser Asp Pro Tyr Thr
                165                 170                 175
Leu Asn Gly Pro Arg Ile His Glu Phe His Gln Glu Met Asn Gln Phe
            180                 185                 190
Ile Arg Asn Arg Val Lys Asp Gly Arg Glu Ile Met Thr Val Gly Glu
        195                 200                 205
Met Gln His Ala Ser Asp Glu Thr Lys Arg Leu Tyr Thr Ser Ala Ser
    210                 215                 220
```

-continued

```
Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
            245                 250                 255

Trp Lys Ile Ala Leu Ala Glu Leu Phe Arg Tyr Ile Asn Gly Thr Asp
        260                 265                 270

Cys Trp Ser Thr Ile Tyr Leu Glu Asn His Asp Gln Pro Arg Ser Ile
    275                 280                 285

Thr Arg Phe Gly Asp Asp Ser Pro Lys Asn Arg Val Ile Ser Gly Lys
290                 295                 300

Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Pro Val Glu
            325                 330                 335

Lys Tyr Glu Asp Val Glu Ile Arg Asn Asn Tyr Asn Ala Ile Lys Glu
        340                 345                 350

Glu His Gly Glu Asn Ser Glu Glu Met Lys Lys Phe Leu Glu Gly Ile
    355                 360                 365

Ala Leu Val Ser Arg Asp His Ala Arg Thr Pro Met Pro Trp Thr Pro
370                 375                 380

Asn Glu Pro Asn Ala Gly Phe Ser Gly Pro Asn Thr Lys Pro Trp Phe
385                 390                 395                 400

Tyr Leu Asn Glu Ser Phe Arg Gln Gly Ile Asn Val Glu Glu Gln
            405                 410                 415

Lys Asn Ser Asp Ser Val Leu Ala Phe Trp Lys Lys Ala Leu Glu Phe
        420                 425                 430

Arg Lys Asn His Lys Asp Ile Ala Val Tyr Gly Phe Asp Phe Lys Phe
    435                 440                 445

Ile Asp Leu Asp Asn Lys Lys Leu Phe Ser Phe Thr Lys Arg Tyr Asn
450                 455                 460

Asn Lys Thr Leu Phe Ala Ala Leu Asn Phe Ser Ser Asp Ala Thr Asp
465                 470                 475                 480

Phe Lys Ile Pro Asn Asp Gly Ser Ser Phe Lys Leu Glu Phe Gly Asn
            485                 490                 495

Tyr Pro Lys Asn Glu Val Asp Ala Ser Ser Arg Thr Leu Lys Pro Trp
        500                 505                 510

Glu Gly Arg Ile Tyr Ile Asn Glu
    515                 520

<210> SEQ ID NO 6
<211> LENGTH: 543
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 6

Met Ser Ala Asp Ala Ser Thr Asn Ser Asn Ala Ser Leu Asp Glu Lys
1               5                   10                  15

Asn Leu Asn Ile Thr Ser Glu Ala Glu Ile Lys Asn Glu Asp Val Thr
            20                  25                  30

Ala Glu Pro Val Leu Ser Thr Val Leu Ser Pro Asn Gly Lys Ile Val
        35                  40                  45

Tyr Ile Ser Asp Lys Val Asp Glu Ala Met Lys Leu Ala Glu Glu Ala
    50                  55                  60
```

```
Lys Glu Ile Glu Val Thr Pro Glu Glu Asp Arg Lys Leu Arg Trp Lys
 65                  70                  75                  80

Ile Asp Tyr Cys Met Phe Pro Leu Met Cys Ile Leu Tyr Ala Val Gln
                 85                  90                  95

Phe Met Asp Lys Ile Ser Thr Ser Ser Ala Ala Val Met Gly Leu Arg
            100                 105                 110

Thr Asp Leu Lys Met His Gly Asp Gln Tyr Ser Trp Val Thr Ser Ala
            115                 120                 125

Phe Tyr Phe Gly Tyr Leu Phe Met Asn Leu Gly Pro Val Gln Phe Ile
        130                 135                 140

Phe Gln Arg Thr Ser His Met Ser Lys Met Leu Ala Val Phe Ile Val
145                 150                 155                 160

Ile Trp Gly Met Leu Leu Ala Leu His Ala Ala Pro Thr Val Lys Tyr
                165                 170                 175

Pro Ser Phe Ile Val Leu Arg Val Leu Leu Gly Cys Ala Glu Ser Val
            180                 185                 190

Val Thr Pro Cys Phe Thr Ile Ile Thr Ala Gln Tyr Trp Lys Thr Glu
        195                 200                 205

Glu Gln Phe Thr Arg Val Ser Ile Trp Phe Gly Met Asn Gly Leu Gly
210                 215                 220

Ser Ile Leu Ile Asn Ala Ile Ala Tyr Gly Val Tyr Ile His Gln Asp
225                 230                 235                 240

Ser Tyr Ala Ile Lys Gly Trp Arg Thr Leu Phe Val Ile Thr Gly Val
                245                 250                 255

Ile Thr Ile Phe Ile Gly Ile Leu Phe Leu Trp Ile Pro Asp Asp
            260                 265                 270

Pro Ser Lys Ala Arg Phe Leu Ser Lys Arg Glu Lys Leu Met Val Val
        275                 280                 285

Gln Arg Ile Arg Ser Asn Gln Gln Gly Phe Gly Asn His Glu Ile Lys
290                 295                 300

Lys Tyr Gln Ile Ile Glu Ala Leu Lys Asp Val Arg Thr Trp Leu Tyr
305                 310                 315                 320

Phe Leu Phe Thr Val Ser Ser Asn Ile Pro Asn Gly Gly Ile Ser Ser
                325                 330                 335

Phe Met Ser Ile Leu Leu Asn Ser Asp Phe Gly Tyr Ser Ser Lys Glu
            340                 345                 350

Thr Leu Leu Met Gly Leu Pro Thr Gly Ala Val Glu Leu Val Gly Cys
        355                 360                 365

Pro Leu Phe Gly Ile Leu Ala Val Tyr Ala Ala Asn Lys Lys Ile Pro
        370                 375                 380

Phe Trp Lys Tyr Lys Leu Ser Trp Ala Ile Phe Ala Ala Val Leu Ala
385                 390                 395                 400

Leu Ile Ala Ser Cys Met Leu Gly Phe Ala Thr Asn Ser Lys Lys Ala
                405                 410                 415

Arg Leu Ala Gly Ala Tyr Leu Trp Tyr Ile Ser Pro Val Ser Phe Ile
            420                 425                 430

Cys Val Leu Ser Asn Ile Ser Ala Asn Ser Ser Gly Tyr Ser Lys Lys
            435                 440                 445

Trp Thr Val Ser Ser Ile Asn Leu Val Ala Tyr Ala Ala Asn Leu
        450                 455                 460

Ala Gly Pro Gln Thr Phe Ile Ala Lys Gln Ala Pro Lys Tyr His Gly
465                 470                 475                 480
```

```
Ala Lys Val Ala Met Val Cys Tyr Ala Val Met Ile Val Leu Leu
                485                 490                 495

Ser Ile Leu Leu Ile Val Asn Leu Arg Glu Asn Lys Arg Asp Lys
            500                 505                 510

Ile Ala Ala Glu Arg Gly Phe Pro Glu Glu Thr Glu Asn Leu Glu Phe
            515                 520                 525

Ser Asp Leu Thr Asp Phe Glu Asn Pro Asn Phe Arg Tyr Thr Leu
            530                 535                 540

<210> SEQ ID NO 7
<211> LENGTH: 601
<212> TYPE: PRT
<213> ORGANISM: S. cerevisiae
<220> FEATURE:
<221> NAME/KEY: misc_feature
<222> LOCATION: (426)..(426)
<223> OTHER INFORMATION: Xaa can be any naturally occurring amino acid

<400> SEQUENCE: 7

Met Leu Asn His Pro Ser Gln Gly Ser Asp Asp Ala Gln Asp Glu Lys
 1               5                  10                  15

Gln Gly Asp Phe Pro Val Ile Glu Glu Lys Thr Gln Ala Val Met
                20                  25                  30

Leu Lys Asp Ser Tyr Val Ser Asp Val Ala Asn Ser Thr Glu Arg
            35                  40                  45

Tyr Asn Leu Ser Pro Ser Pro Glu Asp Glu Asp Phe Glu Ala Pro Thr
        50                  55                  60

Glu Glu Glu Met Gln Thr Leu Arg His Val Gly Gly Lys Ile Pro Met
 65                 70                  75                  80

Arg Cys Trp Leu Ile Ala Ile Val Glu Leu Ser Glu Arg Phe Ser Tyr
                85                  90                  95

Tyr Gly Leu Ser Ala Pro Phe Gln Asn Tyr Met Glu Tyr Gly Pro Asn
                100                 105                 110

Asp Ser Pro Lys Gly Val Leu Ser Leu Asn Ser Gln Gly Ala Thr Gly
            115                 120                 125

Leu Ser Tyr Phe Phe Gln Phe Trp Cys Tyr Val Thr Pro Val Phe Gly
        130                 135                 140

Gly Tyr Val Ala Asp Thr Phe Trp Gly Lys Tyr Asn Thr Ile Cys Cys
145                 150                 155                 160

Gly Thr Ala Ile Tyr Ile Ala Gly Ile Phe Ile Leu Phe Ile Thr Ser
                165                 170                 175

Ile Pro Ser Val Gly Asn Arg Asp Ser Ala Ile Gly Gly Phe Ile Ala
            180                 185                 190

Ala Ile Ile Leu Ile Gly Ile Ala Thr Gly Met Ile Lys Ala Asn Leu
        195                 200                 205

Ser Val Leu Ile Ala Asp Gln Leu Pro Lys Arg Lys Pro Ser Ile Lys
    210                 215                 220

Val Leu Lys Ser Gly Glu Arg Val Ile Val Asp Ser Asn Ile Thr Leu
225                 230                 235                 240

Gln Asn Val Phe Met Phe Phe Tyr Phe Met Ile Asn Val Gly Ser Leu
                245                 250                 255

Ser Leu Met Ala Thr Thr Glu Leu Glu Tyr His Lys Gly Phe Trp Ala
            260                 265                 270

Ala Tyr Leu Leu Pro Phe Cys Phe Phe Trp Ile Ala Val Val Thr Leu
        275                 280                 285

Ile Phe Gly Lys Lys Gln Tyr Ile Gln Arg Pro Ile Gly Asp Lys Val
```

```
                290                 295                 300

Ile Ala Lys Ser Phe Lys Val Cys Trp Ile Leu Thr Lys Asn Lys Phe
305                 310                 315                 320

Asp Phe Asn Ala Ala Lys Pro Ser Val His Pro Glu Lys Asn Tyr Pro
                325                 330                 335

Trp Asn Asp Lys Phe Val Asp Glu Ile Lys Arg Ala Leu Ala Ala Cys
                340                 345                 350

Lys Val Phe Ile Phe Tyr Pro Ile Tyr Trp Thr Gln Tyr Gly Thr Met
                355                 360                 365

Ile Ser Ser Phe Ile Thr Gln Ala Ser Met Met Glu Leu His Gly Ile
                370                 375                 380

Pro Asn Asp Phe Leu Gln Ala Phe Asp Ser Ile Ala Leu Ile Ile Phe
385                 390                 395                 400

Ile Pro Ile Phe Glu Lys Phe Val Tyr Pro Phe Ile Arg Arg Tyr Thr
                405                 410                 415

Pro Leu Lys Pro Ile Thr Lys Ile Phe Xaa Gly Phe Met Phe Gly Ser
                420                 425                 430

Phe Ala Met Thr Trp Ala Ala Val Leu Gln Ser Phe Val Tyr Lys Ala
                435                 440                 445

Gly Pro Trp Tyr Asn Glu Pro Leu Gly His Asn Thr Pro Asn His Val
                450                 455                 460

His Val Cys Trp Gln Ile Pro Ala Tyr Val Leu Ile Ser Phe Ser Glu
465                 470                 475                 480

Ile Phe Ala Ser Ile Thr Gly Leu Glu Tyr Ala Tyr Ser Lys Ala Pro
                485                 490                 495

Ala Ser Met Lys Ser Phe Ile Met Ser Ile Phe Leu Leu Thr Asn Ala
                500                 505                 510

Phe Gly Ser Ala Ile Gly Cys Ala Leu Ser Pro Val Thr Val Asp Pro
                515                 520                 525

Lys Phe Thr Trp Leu Phe Thr Gly Leu Ala Val Ala Cys Phe Ile Ser
                530                 535                 540

Gly Cys Leu Phe Trp Leu Cys Phe Arg Lys Tyr Asn Asp Thr Glu Glu
545                 550                 555                 560

Glu Met Asn Ala Met Asp Tyr Glu Glu Glu Asn Glu Phe Asp Leu Asn
                565                 570                 575

Pro Ile Ser Ala Pro Lys Ala Asn Asp Ile Glu Ile Leu Glu Pro Met
                580                 585                 590

Asp Ser Leu Arg Ser Thr Ala Lys Tyr
                595                 600

<210> SEQ ID NO 8
<211> LENGTH: 601
<212> TYPE: PRT
<213> ORGANISM: S. pastorianus

<400> SEQUENCE: 8

Met Leu Asn His Pro Ser Gln Gly Ser Asp Asp Ala Gln Asp Glu Lys
1               5                   10                  15

Gln Gly Asp Phe Pro Val Ile Glu Glu Glu Lys Thr Gln Ala Val Thr
                20                  25                  30

Leu Lys Asp Ser Tyr Val Ser Asp Val Ala Asn Ser Thr Glu Arg
                35                  40                  45

Tyr Asn Leu Ser Pro Ser Pro Glu Asp Glu Asp Phe Glu Ala Pro Thr
                50                  55                  60
```

Glu Glu Glu Met Gln Thr Leu Arg His Val Gly Gly Lys Ile Pro Met
65                  70                  75                  80

Arg Cys Trp Leu Ile Ala Ile Val Glu Leu Ser Glu Arg Phe Ser Tyr
            85                  90                  95

Tyr Gly Leu Ser Ala Pro Phe Gln Asn Tyr Met Glu Tyr Gly Pro Asn
            100                 105                 110

Asp Ser Pro Lys Gly Val Leu Ser Leu Asn Ser Gln Gly Ala Thr Gly
            115                 120                 125

Leu Ser Tyr Phe Phe Gln Phe Trp Cys Tyr Val Thr Pro Val Phe Gly
    130                 135                 140

Gly Tyr Val Ala Asp Thr Phe Trp Gly Lys Tyr Asn Thr Ile Cys Cys
145                 150                 155                 160

Gly Thr Ala Ile Tyr Ile Ala Gly Ile Phe Ile Leu Phe Ile Thr Ser
                165                 170                 175

Ile Pro Ser Val Gly Asn Arg Asp Ser Ala Ile Gly Gly Phe Ile Ala
                180                 185                 190

Ala Ile Ile Leu Ile Gly Ile Ala Thr Gly Met Ile Lys Ala Asn Leu
        195                 200                 205

Ser Val Leu Ile Ala Asp Gln Leu Pro Lys Arg Lys Pro Ser Ile Lys
    210                 215                 220

Val Leu Lys Ser Gly Glu Arg Val Ile Val Asp Ser Asn Ile Thr Leu
225                 230                 235                 240

Gln Asn Val Phe Met Phe Phe Tyr Phe Met Ile Asn Val Gly Ser Leu
                245                 250                 255

Ser Leu Met Ala Thr Thr Glu Leu Glu Tyr His Lys Gly Phe Trp Ala
            260                 265                 270

Ala Tyr Leu Leu Pro Phe Cys Phe Phe Trp Ile Ala Val Val Thr Leu
        275                 280                 285

Ile Phe Gly Lys Lys Gln Tyr Ile Gln Arg Pro Val Gly Asp Lys Val
        290                 295                 300

Ile Ala Lys Ser Phe Lys Val Cys Trp Ile Leu Thr Lys Asn Lys Phe
305                 310                 315                 320

Asp Phe Asn Ala Ala Lys Pro Ser Val His Pro Glu Lys Asn Tyr Pro
                325                 330                 335

Trp Asn Asp Lys Phe Val Asp Glu Ile Lys Arg Ala Leu Ala Ala Cys
            340                 345                 350

Lys Val Phe Ile Phe Tyr Pro Ile Tyr Trp Thr Gln Tyr Gly Thr Met
        355                 360                 365

Ile Ser Ser Phe Ile Thr Gln Ala Ser Met Met Glu Leu His Gly Ile
    370                 375                 380

Pro Asn Asp Phe Leu Gln Ala Phe Asp Ser Ile Ala Leu Ile Ile Phe
385                 390                 395                 400

Ile Pro Ile Phe Glu Lys Phe Val Tyr Pro Phe Ile Arg Arg Tyr Thr
                405                 410                 415

Pro Leu Lys Pro Ile Thr Lys Ile Phe Phe Gly Phe Met Phe Gly Ser
            420                 425                 430

Phe Ala Met Thr Trp Ala Ala Val Leu Gln Ser Phe Val Tyr Lys Ala
        435                 440                 445

Gly Pro Trp Tyr Asn Glu Pro Leu Gly His Asn Thr Pro Asn His Val
            450                 455                 460

His Val Cys Trp Gln Ile Pro Ala Tyr Val Leu Ile Ser Phe Ser Glu
465                 470                 475                 480

Ile Phe Ala Ser Ile Thr Gly Leu Glu Tyr Ala Tyr Ser Lys Ala Pro

```
                        485                 490                 495
Ala Ser Met Lys Ser Phe Ile Met Ser Ile Phe Leu Leu Thr Asn Ala
            500                 505                 510

Phe Gly Ser Ala Ile Gly Cys Ala Leu Ser Pro Val Thr Val Asp Pro
            515                 520                 525

Lys Phe Thr Trp Leu Phe Thr Gly Leu Ala Val Ala Cys Phe Ile Ser
            530                 535                 540

Gly Cys Leu Phe Trp Leu Cys Phe Arg Lys Tyr Asn Asp Thr Glu Glu
545                 550                 555                 560

Glu Met Asn Ala Met Asp Tyr Glu Glu Asp Glu Phe Asp Leu Asn
                565                 570                 575

Pro Ile Ser Ala Pro Lys Ala Asn Asp Ile Glu Ile Leu Glu Pro Met
            580                 585                 590

Glu Ser Leu Arg Ser Thr Thr Lys Tyr
            595                 600

<210> SEQ ID NO 9
<211> LENGTH: 601
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 9

Met Leu Asn His Leu Ser Gln Gly Ser Asp Asp Ile Gln Asp Glu Lys
1               5                   10                  15

Gln Gly Asp Phe Pro Val Ile Glu Glu Lys Asn Gln Thr Val Thr
            20                  25                  30

Leu Lys Asp Ser Tyr Val Ser Asp Asp Ala Ala Asn Ser Thr Glu His
            35                  40                  45

Tyr Asn Leu Ser Pro Ser Leu Glu Glu Asp Glu Phe Glu Ala Pro Thr
    50                  55                  60

Asp Glu Glu Leu Arg Ser Leu Arg His Val Gly Gly Lys Ile Pro Met
65                  70                  75                  80

Arg Cys Trp Leu Ile Ala Ile Val Glu Leu Ser Glu Arg Phe Ser Tyr
                85                  90                  95

Tyr Gly Leu Ser Ala Pro Phe Gln Asn Tyr Met Glu Tyr Gly Pro Lys
            100                 105                 110

Asp Thr Pro Lys Gly Val Leu Ser Leu Asn Ser Gln Gly Ala Thr Gly
            115                 120                 125

Leu Ser Tyr Phe Phe Gln Phe Trp Cys Tyr Val Thr Pro Val Phe Gly
            130                 135                 140

Gly Tyr Val Ala Asp Thr Phe Trp Gly Lys Tyr Asn Thr Ile Cys Cys
145                 150                 155                 160

Gly Thr Ala Ile Tyr Ile Ala Gly Ile Phe Ile Leu Leu Ile Thr Ser
                165                 170                 175

Ile Pro Ser Val Gly Asn Arg Asp Ser Ala Leu Gly Gly Phe Ile Ala
            180                 185                 190

Ser Ile Ile Leu Ile Gly Ile Ala Thr Gly Met Ile Lys Ala Asn Leu
            195                 200                 205

Ser Val Leu Ile Ala Asp Gln Leu Pro Lys Arg Lys Pro Ser Ile Lys
            210                 215                 220

Val Leu Lys Ser Gly Glu Arg Val Ile Val Asp Ser Asn Ile Thr Leu
225                 230                 235                 240
```

```
Gln Asn Val Phe Met Phe Phe Tyr Phe Met Ile Asn Val Gly Ser Leu
                245                 250                 255

Ser Leu Met Ala Thr Thr Glu Leu Glu Tyr His Lys Gly Phe Trp Ala
            260                 265                 270

Ala Tyr Leu Leu Pro Phe Cys Phe Phe Trp Val Ala Val Val Thr Leu
        275                 280                 285

Val Phe Gly Lys Lys Gln Tyr Ile Gln Arg Pro Ile Gly Asp Lys Val
    290                 295                 300

Ile Ala Lys Ser Phe Arg Val Cys Trp Ile Leu Thr Lys Asn Lys Phe
305                 310                 315                 320

Asp Phe Asn Ala Ala Lys Pro Ser Val His Pro Glu Lys Glu Tyr Pro
                325                 330                 335

Trp Asn Asp Lys Phe Val Asp Glu Ile Lys Arg Ala Leu Ala Ala Cys
            340                 345                 350

Lys Val Phe Val Phe Tyr Pro Ile Tyr Trp Thr Gln Tyr Gly Thr Met
        355                 360                 365

Ile Ser Ser Phe Ile Thr Gln Ala Gly Met Met Glu Leu His Gly Ile
    370                 375                 380

Pro Asn Asp Phe Leu Gln Ala Phe Asp Ser Ile Ala Leu Ile Ile Phe
385                 390                 395                 400

Ile Pro Ile Phe Glu Lys Phe Ile Tyr Pro Phe Ile Arg Arg Tyr Thr
                405                 410                 415

Pro Phe Lys Pro Ile Thr Lys Ile Phe Phe Gly Phe Met Phe Gly Ser
            420                 425                 430

Leu Ala Met Thr Trp Ala Ala Val Leu Gln Ser Phe Val Tyr Lys Ala
        435                 440                 445

Gly Pro Trp Tyr Ser Ala Pro Leu Gly His Asn Thr Pro Asn His Val
    450                 455                 460

His Val Cys Trp Gln Ile Pro Ala Tyr Val Leu Ile Ser Phe Ser Glu
465                 470                 475                 480

Ile Phe Ala Ser Ile Thr Gly Leu Glu Tyr Ala Tyr Ser Lys Ala Pro
                485                 490                 495

Ala Ser Met Lys Ser Phe Ile Met Ser Ile Phe Leu Leu Thr Asn Ala
            500                 505                 510

Phe Gly Ser Ala Ile Gly Cys Ala Leu Ser Pro Val Thr Val Asp Pro
        515                 520                 525

Lys Phe Thr Trp Leu Phe Thr Gly Leu Ala Val Ala Cys Phe Ile Ser
    530                 535                 540

Gly Cys Leu Phe Trp Phe Cys Phe Arg Lys Tyr Asn Asp Thr Glu Glu
545                 550                 555                 560

Glu Met Asn Ala Met Asp Tyr Glu Glu Glu Asp Glu Phe Asp Leu Asn
                565                 570                 575

Pro Ile Ser Gln Pro Lys Gly Asn Asp Ile Glu Ile Leu Glu Pro Met
            580                 585                 590

Gly Ser Leu Lys Ser Thr Thr Lys Tyr
        595                 600

<210> SEQ ID NO 10
<211> LENGTH: 399
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 10
```

```
Phe Lys Glu Phe Cys Lys Val Glu Gly Gly Val Leu Ile Trp Gln Arg
1               5                   10                  15

Val Gln Lys Ser Asn Leu Thr Lys Ser Tyr Ser Ile Ser Phe Lys Gln
            20                  25                  30

Gly Leu Tyr Thr Val Glu Thr Leu Leu Ser Lys Val His Asp Pro Asn
        35                  40                  45

Ile Pro Leu Arg Pro Lys Glu Ile Ile Ser Leu Leu Thr Leu Cys Lys
50                  55                  60

Leu Phe Asn Gly Ala Trp Lys Ile Lys Arg Lys Gly Glu His Val
65                  70                  75                  80

Leu His Glu Asp Gln Asn Phe Ile Ser Tyr Leu Glu Tyr Thr Thr Ser
                85                  90                  95

Ile Tyr Ser Ile Ile Gln Thr Ala Glu Lys Val Ser Glu Lys Ser Lys
                100                 105                 110

Asp Ser Ile Asp Ser Lys Leu Phe Leu Asn Ala Ile Arg Ile Ile Ser
            115                 120                 125

Ser Phe Leu Gly Asn Arg Ser Leu Thr Tyr Lys Leu Ile Tyr Asp Ser
    130                 135                 140

His Glu Val Ile Lys Phe Ser Val Ser His Glu Arg Val Ala Phe Met
145                 150                 155                 160

Asn Pro Leu Gln Thr Met Leu Ser Phe Leu Ile Glu Lys Val Ser Leu
                165                 170                 175

Lys Asp Ala Tyr Glu Ala Leu Glu Asp Cys Ser Asp Phe Leu Lys Ile
            180                 185                 190

Ser Asp Phe Ser Leu Arg Ser Val Leu Cys Ser Gln Ile Asp Val
    195                 200                 205

Gly Phe Trp Val Arg Asn Gly Met Ser Val Leu His Gln Ala Ser Tyr
210                 215                 220

Tyr Lys Asn Asn Pro Glu Leu Gly Ser Tyr Ser Arg Asp Ile His Leu
225                 230                 235                 240

Asn Gln Leu Ala Ile Leu Trp Glu Arg Asp Ile Pro Arg Ile Ile
            245                 250                 255

Tyr Asn Ile Leu Asp Arg Trp Glu Leu Leu Asp Trp Phe Thr Gly Glu
            260                 265                 270

Val Asp Tyr Gln His Thr Val Tyr Glu Asp Lys Ile Ser Phe Ile Ile
        275                 280                 285

Gln Gln Phe Ile Ala Phe Ile Tyr Gln Ile Leu Thr Glu Arg Gln Tyr
    290                 295                 300

Phe Lys Thr Phe Ser Ser Leu Lys Asp Arg Arg Met Asp Gln Ile Lys
305                 310                 315                 320

Asn Ser Ile Ile Tyr Asn Leu Tyr Met Lys Pro Leu Ser Tyr Ser Lys
            325                 330                 335

Leu Leu Arg Ser Val Pro Asp Tyr Leu Thr Glu Asp Thr Thr Glu Phe
        340                 345                 350

Asp Glu Ala Leu Glu Glu Val Ser Val Phe Val Glu Pro Lys Gly Leu
            355                 360                 365

Ala Asp Asn Gly Val Phe Lys Leu Lys Ala Ser Leu Tyr Ala Lys Val
370                 375                 380

Asp Pro Leu Lys Leu Leu Asn Leu Glu Asn Glu Phe Glu Ser Ser
385                 390                 395

<210> SEQ ID NO 11
<211> LENGTH: 1950
```

```
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 11
```

| | | | | | | | | | | | | | | |
|---|---|---|---|---|---|---|---|---|---|---|---|---|---|---|
|Met|Ser|Phe|Thr|Asp|Asn|Gly|Leu|Gly|Ser|Leu|Lys|Ala|His|Ile|Arg|
|1| | | |5| | | | |10| | | | |15|
|Arg|Thr|Leu|Arg|Ser|Ile|His|Asn|Leu|Pro|Tyr|Phe|Arg|Phe|Thr|Arg|
| | | |20| | | | |25| | | | |30| | |
|Gly|Pro|Thr|Glu|Arg|Ala|Asp|Met|Ser|Arg|Ala|Leu|Lys|Glu|Phe|Ile|
| | | |35| | | | |40| | | | |45| | |
|Tyr|Arg|Tyr|Leu|Tyr|Phe|Ile|Ile|Ser|Asn|Asp|Gly|Glu|Asn|Leu|Ser|
| |50| | | | |55| | | | |60| | | | |
|Thr|Leu|Phe|Thr|Ala|His|Pro|Lys|Gln|Lys|Ser|Ser|Asn|Gln|Glu|Leu|
|65| | | | |70| | | | |75| | | | |80|
|Ala|Val|Phe|Pro|Glu|Ser|Leu|Glu|Asp|Ala|Leu|Asp|Val|Asp|Lys|Ile|
| | | | |85| | | | |90| | | | |95| |
|Thr|Ser|Gln|Gly|Thr|Phe|Pro|Phe|Tyr|Lys|Ile|Asp|Glu|Ser|Lys|Ile|
| | | |100| | | | |105| | | | |110| | |
|Gly|Asp|Val|His|Lys|His|Thr|Gly|Arg|Asn|Cys|Gly|Arg|Lys|Phe|Lys|
| | | |115| | | | |120| | | | |125| | |
|Ile|Gly|Glu|Pro|Leu|Tyr|Arg|Cys|His|Glu|Cys|Gly|Cys|Asp|Asp|Thr|
|130| | | | |135| | | | |140| | | | | |
|Cys|Val|Leu|Cys|Ile|His|Cys|Phe|Asn|Pro|Lys|Asp|His|Val|Asn|His|
|145| | | | |150| | | | |155| | | | |160|
|His|Val|Cys|Thr|Asp|Ile|Cys|Ser|Glu|Phe|Thr|Ser|Gly|Ile|Cys|Asp|
| | | | |165| | | | |170| | | | |175| |
|Cys|Gly|Asp|Glu|Glu|Ala|Trp|Asn|Ser|Ser|Leu|His|Cys|Lys|Ala|Glu|
| | | |180| | | | |185| | | | |190| | |
|Glu|Gln|Gly|Asn|Asp|Thr|Ser|Glu|Asp|Pro|Ser|Asn|Phe|Asp|Ser|Thr|
| | | |195| | | | |200| | | | |205| | |
|Lys|Gln|Lys|Asp|Val|Trp|Asn|Asp|Pro|Glu|Cys|Ile|Ala|Leu|Val|Glu|
| |210| | | | |215| | | | |220| | | | |
|Leu|Val|Leu|Ser|Glu|Val|Phe|Asp|Tyr|Phe|Ile|Asp|Val|Phe|Asn|Gln|
|225| | | | |230| | | | |235| | | | |240|
|Asn|Ile|Glu|Pro|Leu|Pro|Thr|Ile|Gln|Lys|Asp|Ile|Thr|Ile|Lys|Leu|
| | | | |245| | | | |250| | | | |255| |
|Arg|Glu|Met|Thr|Gln|Gln|Gly|Lys|Met|Tyr|Glu|Arg|Ala|Gln|Phe|Leu|
| | | |260| | | | |265| | | | |270| | |
|Asn|Asp|Leu|Lys|Tyr|Glu|Asn|Asp|Tyr|Met|Phe|Asp|Gly|Thr|Thr|Thr|
| | |275| | | | |280| | | | |285| | | |
|Ala|Lys|Thr|Ser|Pro|Ser|Asn|Ser|Pro|Glu|Ala|Ser|Pro|Ser|Leu|Ala|
| | |290| | | | |295| | | | |300| | | |
|Lys|Ile|Asp|Pro|Glu|Asn|Tyr|Thr|Val|Ile|Ile|Tyr|Asn|Asp|Glu|Tyr|
|305| | | | |310| | | | |315| | | | |320|
|His|Asn|Tyr|Ser|Gln|Ala|Thr|Thr|Ala|Leu|Arg|Gln|Gly|Val|Pro|Asp|
| | | | |325| | | | |330| | | | |335| |
|Asn|Val|His|Ile|Asp|Leu|Leu|Ser|Arg|Ile|Asp|Gly|Glu|Gly|Arg|
| | | |340| | | | |345| | | | |350| | |
|Ala|Met|Leu|Lys|Cys|Ser|Gln|Asp|Leu|Ser|Ser|Val|Leu|Gly|Gly|Phe|
| | | |355| | | | |360| | | | |365| | |
|Phe|Ala|Val|Gln|Thr|Asn|Gly|Leu|Ser|Ala|Thr|Leu|Ser|Trp|Ser|
| |370| | | | |375| | | | |380| | | | |

-continued

Glu Tyr Leu His Gln Glu Ala Cys Lys Tyr Ile Ile Leu Trp Ile Thr
385                 390                 395                 400

His Cys Leu Asn Ile Pro Asn Pro Ser Phe Gln Ile Thr Phe Arg Asn
            405                 410                 415

Met Met Gly Lys Ser Leu Cys Ser Glu Tyr Leu Asn Ala Thr Glu Ser
        420                 425                 430

Arg Asp Met Thr Pro Val Val Glu Lys Tyr Phe Ser Thr Lys Phe Asp
            435                 440                 445

Lys Asp Asp Pro Tyr Arg Tyr Ile Asp Leu Ser Val Leu Ala Glu Gly
450                 455                 460

Asn Gln Ile Pro Leu Gly His His Lys Val Leu Pro Glu Ser Ser Thr
465                 470                 475                 480

His Ser Leu Ser Thr Leu Ile Asn Asp Val Glu Asn Leu Thr Ser Lys
            485                 490                 495

Glu Tyr Ser Asn Thr Arg Leu Gln His Ile Leu Tyr Phe Asp Asn Arg
            500                 505                 510

Tyr Trp Lys Arg Leu Arg Lys Asp Ile Gln Asn Val Ile Ile Pro Thr
            515                 520                 525

Leu Ala Ser Ser Thr Leu Tyr Lys Pro Ile Phe Cys Gln Gln Val Val
530                 535                 540

Glu Ile Phe Asn His Ile Thr Arg Ser Val Ala Tyr Met Asp Arg Glu
545                 550                 555                 560

Pro Gln Leu Thr Ala Ile Arg Glu Cys Val Val Gln Leu Phe Thr Cys
            565                 570                 575

Pro Thr Asn Thr Arg Asn Ile Phe Glu Asn Gln Ser Phe Leu Asp Ile
            580                 585                 590

Leu Trp Ser Ile Ile Asp Ile Phe Lys Glu Phe Cys Lys Val Glu Ala
            595                 600                 605

Gly Val Leu Ile Trp Gln Arg Val Gln Lys Ser Asn Leu Thr Lys Ser
            610                 615                 620

Tyr Ser Leu Ser Phe Lys Gln Gly Leu Tyr Thr Val Glu Thr Leu Leu
625                 630                 635                 640

Ser Lys Val Asn Asp Pro Asn Ile Thr Ile Arg Pro Lys Val Phe Ile
            645                 650                 655

Ser Leu Leu Thr Leu Gly Lys Leu Phe Asn Gly Ala Trp Lys Ile Lys
            660                 665                 670

Arg Lys Glu Gly Glu His Val Leu His Glu Asp Gln Asn Phe Ile Ser
            675                 680                 685

Tyr Leu Glu Tyr Thr Thr Ser Ile Tyr Ser Ile Ile Gln Thr Ala Glu
            690                 695                 700

Lys Val Leu Glu Lys Ser His Asp Ser Leu Asp Leu Asn Leu Val Leu
705                 710                 715                 720

Asn Ala Ile Arg Ile Val Ser Ser Phe Leu Gly Asn Arg Ser Leu Thr
            725                 730                 735

Tyr Lys Leu Ile Tyr Asp Ser His Glu Ile Ile Lys Phe Ser Val Ser
            740                 745                 750

His Glu Arg Val Ala Phe Met Asn Pro Ile Gln Thr Met Leu Ser Phe
            755                 760                 765

Leu Ile Glu Lys Val Ser Leu Lys Asp Ala Tyr Glu Ser Leu Glu Asn
            770                 775                 780

Cys Pro Asp Phe Leu Lys Ile Ala Asp Phe Ser Leu Arg Ser Val Val
785                 790                 795                 800

```
Leu Cys Ser Gln Ile Asp Val Gly Phe Trp Val Arg Asn Gly Met Ser
                805                 810                 815

Val Leu His Gln Ala Ser Tyr Tyr Lys Asn Asn Pro Glu Leu Gly Ser
        820                 825                 830

Tyr Ser Arg Asp Ile His Leu Asn Gln Leu Ala Ile Ile Trp Glu Arg
            835                 840                 845

Asp Asp Leu Pro Arg Val Ile Tyr Asn Ile Leu Asp Arg Trp Glu Leu
850                 855                 860

Leu Asp Trp Phe Met Gly Glu Ala Glu Tyr Gln His Thr Val Tyr Glu
865                 870                 875                 880

Asp Lys Ile Ser Phe Met Ile Gln Gln Phe Ile Ala Phe Ile Tyr Gln
                885                 890                 895

Ile Leu Thr Glu Arg Gln Tyr Phe Lys Thr Phe Ser Leu Leu Arg Asp
            900                 905                 910

Arg Arg Met Asp Met Ile Lys Asn Ser Ile Met Tyr Asn Leu Tyr Met
                915                 920                 925

Lys Pro Leu Ser Tyr Ser Lys Leu Leu Lys Ser Val Pro Asp Tyr Leu
            930                 935                 940

Thr Asp Asp Thr Thr Glu Phe Asp Glu Ala Leu Glu Glu Val Ser Val
945                 950                 955                 960

Phe Val Glu Pro Lys Gly Leu Ala Asp Asn Gly Val Phe Lys Leu Lys
                965                 970                 975

Ala Ala Leu Tyr Ala Lys Ile Asp Pro Leu Lys Leu Asn Leu Glu
            980                 985                 990

Asn Glu Phe Glu Ser Ser Ala Thr Ile Ile Lys Thr His Leu Ala Lys
        995                 1000                1005

Asn Lys Asp Glu Val Ser Lys Val Val Leu Ile Pro Gln Val Ser
    1010                1015                1020

Thr Lys Leu Leu Asp Lys Gly Ala Met Asn Leu Gly Glu Phe Thr
    1025                1030                1035

Arg Asn Thr Val Phe Ala Lys Val Ile Tyr Lys Leu Leu Gln Val
    1040                1045                1050

Cys Leu Asp Met Glu Asp Ser Thr Phe Leu Asn Glu Leu Leu His
    1055                1060                1065

Leu Val His Gly Ile Phe Lys Asp Asp Glu Leu Ile Asn Gly Lys
    1070                1075                1080

Asp Ser Ile Pro Glu Ala Tyr Leu Ala Lys Pro Ile Cys Asn Leu
    1085                1090                1095

Leu Leu Ser Ile Ala Asn Ala Lys Ser Asp Ile Phe Ser Glu Ser
    1100                1105                1110

Ile Val Arg Lys Ala Asp Tyr Leu Leu Glu Lys Met Ile Met Lys
    1115                1120                1125

Lys Pro Asp Glu Ile Phe Glu Ser Leu Ile Ala Ser Phe Gly Asn
    1130                1135                1140

Gln Tyr Ile Asp Asn Tyr Lys Asp Lys Lys Leu Ser Gln Gly Val
    1145                1150                1155

Asn Leu Gln Glu Thr Glu Lys Glu Arg Lys Arg Arg Met Ala Lys
    1160                1165                1170

Lys His Gln Ala Arg Leu Leu Ala Lys Phe Asn Asn Gln Gln Ser
    1175                1180                1185

Lys Phe Met Lys Glu His Glu Ser Glu Phe Asp Glu Gln Asp Asn
    1190                1195                1200

Asp Val Asp Met Asp Gly Glu Lys Val Tyr Glu Ser Glu Asp Phe
```

-continued

```
            1205                1210                1215
Thr Cys Ala Leu Cys Gln Asp Ser Ser Thr Asp Phe Phe Val
        1220                1225                1230

Ile Pro Ala Tyr His Asp His Thr Pro Ile Phe Arg Pro Gly Asn
        1235                1240                1245

Ile Phe Asn Pro Arg Glu Phe Met Ala Lys Trp Asp Gly Phe Tyr
        1250                1255                1260

Asn Asp Asp Asp Lys Gln Ala Tyr Ile Asp Asp Glu Val Leu Glu
        1265                1270                1275

Ser Leu Lys Glu Asn Gly Thr Arg Gly Ser Arg Lys Val Phe Val
        1280                1285                1290

Ser Cys Asn His His Ile His His Asn Cys Phe Lys Arg Tyr Val
        1295                1300                1305

Gln Lys Lys Arg Phe Ser Ser Asn Ala Phe Ile Cys Pro Leu Cys
        1310                1315                1320

Gln Thr Phe Ser Asn Cys Thr Leu Pro Ile Cys Pro Thr Ser Arg
        1325                1330                1335

Ala Asn Thr Gly Leu Ser Leu Asp Met Phe Leu Lys Ser Glu Leu
        1340                1345                1350

Ser Leu Asp Ile Leu Ser Arg Leu Phe Lys Pro Phe Thr Glu Asp
        1355                1360                1365

Asn Tyr Arg Thr Ile Asn Ser Ile Phe Ser Leu Met Val Ser Gln
        1370                1375                1380

Cys Gln Gly Phe Asp Lys Val Val Arg Lys His Val Asn Phe Thr
        1385                1390                1395

His Lys Asp Val Ser Leu Val Leu Ser Val His Trp Ala Asn Thr
        1400                1405                1410

Ile Ser Met Leu Glu Val Ala Ser Arg Leu Glu Lys Pro His Asn
        1415                1420                1425

Ile Ser Phe Phe Arg Ser Arg Glu Gln Lys Tyr Lys Thr Leu Lys
        1430                1435                1440

Asn Ile Leu Ile Cys Ile Met Leu Phe Thr Phe Val Ile Gly Lys
        1445                1450                1455

Pro Ser Met Glu Phe Glu Pro Tyr Pro Val Glu Ser Asp Ile Ile
        1460                1465                1470

Cys Asn Gln Asn Gln Leu Phe Gln Tyr Ile Val Arg Lys Ser Leu
        1475                1480                1485

Phe Ser Pro Ala Ser Leu Arg Glu Thr Ile Thr Glu Ala Leu Thr
        1490                1495                1500

Val Phe Cys Lys Gln Phe Leu Asp Asp Phe Val Gln Gly Leu Ser
        1505                1510                1515

Asp Ala Glu Gln Val Asp Lys Leu Tyr Thr Glu Ala Lys Lys Leu
        1520                1525                1530

Gly Asp Val Tyr Asn Val Asp Glu Ser Ile Leu Ile Thr Leu Met
        1535                1540                1545

Ser Ile Thr Val Val Lys Thr Glu Gly Leu Glu Ser Arg Ser Ile
        1550                1555                1560

Tyr Asp Leu Ala Tyr Thr Ser Leu Leu Lys Ser Leu Leu Pro Thr
        1565                1570                1575

Ile Arg Arg Cys Leu Val Met Val Lys Val Leu His Glu Leu Val
        1580                1585                1590

Lys Asp Ser Glu Asn Glu Thr Met Val Ile Asp Gly Phe Asp Val
        1595                1600                1605
```

Glu Glu Glu Leu Glu Phe Glu Gly Leu Pro Gly Phe Val Asp Lys
1610             1615                 1620

Ala Leu Lys Leu Ile Thr Asp Lys Glu Ser Phe Val Asp Leu Phe
    1625                 1630                1635

Lys Thr Lys Gln Ala Ile Val Pro Ser His Pro Tyr Leu Glu Arg
    1640                 1645                1650

Ile Pro Tyr Glu Tyr Cys Gly Ile Val Lys Leu Ile Asp Leu Ser
1655                 1660                1665

Lys Phe Leu Asn Thr Tyr Val Thr Gln Ser Lys Glu Ile Lys Leu
    1670                1675                1680

Arg Glu Glu Arg Ser Gln His Met Lys Asn Ala Asp Asn Arg Leu
    1685                1690                1695

Asp Phe Lys Ile Cys Leu Thr Cys Gly Val Lys Val His Leu Arg
    1700                1705                1710

Ala Asp Arg His Glu Met Thr Lys His Leu Asn Lys Asn Cys Phe
    1715                1720                1725

Lys Ser Phe Gly Ala Phe Leu Met Pro Asn Ser Ser Glu Val Cys
    1730                1735                1740

Leu His Leu Thr Gln Pro Pro Ser Asn Ile Phe Val Ser Ala Pro
1745                 1750                1755

Tyr Leu Asn Ser His Gly Glu Val Gly Arg Asn Ala Met Arg Arg
    1760                1765                1770

Gly Asp Leu Thr Thr Leu Asn Leu Lys Arg Tyr Glu His Leu Asn
    1775                1780                1785

Arg Leu Trp Ile Asn Asn Glu Ile Pro Gly Tyr Ile Ser Arg Val
    1790                1795                1800

Met Gly Asp Glu Phe Arg Val Thr Ile Leu Ser Asn Gly Phe Leu
1805                 1810                1815

Phe Ala Phe Asn Arg Glu Pro Arg Pro Arg Val Pro Pro Thr
    1820                1825                1830

Asp Glu Asp Asp Glu Asp Met Glu Glu Gly Glu Glu Gly Phe Phe
    1835                1840                1845

Thr Glu Glu Asn Asp Asp Met Asp Val Asp Asp Glu Thr Gly Gln
    1850                1855                1860

Ala Ala Asn Leu Phe Gly Val Gly Ala Glu Gly Ile Gly Asp Gly
    1865                1870                1875

Gly Val Arg Asn Phe Phe Gln Phe Phe Glu Asn Phe Arg Asn Thr
    1880                1885                1890

Leu Gln Pro Gln Gly Asn Asp Asp Glu Asp Ala Pro Gln Asn Pro
    1895                1900                1905

Pro Pro Ile Leu Gln Phe Leu Gly Pro Gln Phe Asp Gly Ala Thr
1910                 1915                1920

Ile Ile Arg Asn Thr Asn Gln Arg Asn Leu Asp Glu Asp Asp Ser
    1925                1930                1935

Ser Glu Asn Asp Asp Ser Asp Glu Arg Glu Ile Trp
    1940                1945                1950

<210> SEQ ID NO 12
<211> LENGTH: 520
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 12

```
Met Gly Tyr Asp Ile Ala Asn Tyr Glu Lys Val Trp Pro Thr Tyr Gly
1               5                   10                  15

Thr Asn Glu Asp Cys Phe Ala Leu Ile Glu Lys Thr His Lys Leu Gly
            20                  25                  30

Met Lys Phe Ile Thr Asp Leu Val Ile Asn His Cys Ser Ser Glu His
        35                  40                  45

Glu Trp Phe Lys Glu Ser Arg Ser Ser Lys Thr Asn Pro Lys Arg Asp
    50                  55                  60

Trp Phe Phe Trp Arg Pro Pro Lys Gly Tyr Asp Ala Glu Gly Lys Pro
65                  70                  75                  80

Ile Pro Pro Asn Asn Trp Lys Ser Tyr Phe Gly Gly Ser Ala Trp Thr
                85                  90                  95

Phe Asp Glu Lys Thr Gln Glu Phe Tyr Leu Arg Leu Phe Cys Ser Thr
            100                 105                 110

Gln Pro Asp Leu Asn Trp Glu Asn Glu Asp Cys Arg Lys Ala Ile Tyr
        115                 120                 125

Glu Ser Ala Val Gly Tyr Trp Leu Asp His Gly Val Asp Gly Phe Arg
    130                 135                 140

Ile Asp Val Gly Ser Leu Tyr Ser Lys Val Val Gly Leu Pro Asp Ala
145                 150                 155                 160

Pro Val Val Asp Lys Asn Ser Thr Trp Gln Ser Ser Asp Pro Tyr Thr
                165                 170                 175

Leu Asn Gly Pro Arg Ile His Glu Phe His Gln Glu Met Asn Gln Phe
            180                 185                 190

Ile Arg Asn Arg Val Lys Asp Gly Arg Glu Ile Met Thr Val Gly Glu
        195                 200                 205

Met Gln His Ala Ser Asp Glu Thr Lys Arg Leu Tyr Thr Ser Ala Ser
    210                 215                 220

Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
                245                 250                 255

Trp Lys Ile Ala Leu Ala Glu Leu Phe Arg Phe Ile Asn Gly Thr Asp
            260                 265                 270

Cys Trp Ser Thr Ile Tyr Leu Glu Asn His Asp Gln Pro Arg Ser Ile
        275                 280                 285

Thr Arg Phe Gly Asp Asp Ser Pro Lys Asn Arg Val Ile Ser Gly Lys
    290                 295                 300

Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Ser Val Glu
                325                 330                 335

Lys Tyr Glu Asp Val Glu Ile Arg Asn Asn Tyr Arg Leu Ile Lys Glu
            340                 345                 350

Glu Cys Gly Glu Asn Ser Glu Glu Met Lys Lys Phe Leu Glu Gly Ile
        355                 360                 365

Ala Leu Val Ser Arg Asp His Ala Arg Thr Pro Met Pro Trp Thr Pro
    370                 375                 380

Asn Glu Pro Asn Ala Gly Phe Ser Gly Pro Asn Thr Lys Pro Trp Phe
385                 390                 395                 400

Tyr Leu Asn Glu Ser Phe Arg Gln Gly Ile Asn Val Glu Glu Glu Gln
                405                 410                 415
```

```
Lys Asn Ser Asp Ser Val Leu Ala Phe Trp Lys Lys Ala Leu Glu Phe
                420                 425                 430

Arg Lys Asn His Lys Asp Ile Ala Val Tyr Gly Phe Asp Phe Lys Phe
            435                 440                 445

Ile Asp Leu Asp Asn Lys Lys Leu Phe Ser Phe Thr Lys Arg Tyr Asn
450                 455                 460

Asn Lys Thr Leu Phe Ala Ala Leu Asn Phe Ser Ser Asp Ala Thr Asp
465                 470                 475                 480

Phe Lys Ile Pro Asn Asp Gly Ser Ser Phe Lys Leu Glu Phe Gly Asn
                485                 490                 495

Tyr Pro Lys Asn Glu Val Asp Ala Ser Ser Arg Thr Leu Lys Pro Trp
                500                 505                 510

Glu Gly Arg Ile His Ile Asn Glu
            515                 520

<210> SEQ ID NO 13
<211> LENGTH: 520
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 13

Met Gly Tyr Asp Ile Ala Asn Tyr Glu Lys Val Trp Pro Thr Tyr Gly
1               5                   10                  15

Thr Asn Glu Asp Cys Phe Ala Leu Ile Glu Lys Thr His Lys Leu Gly
            20                  25                  30

Met Lys Phe Ile Thr Asp Leu Val Ile Asn His Cys Ser Ser Glu His
            35                  40                  45

Glu Trp Phe Lys Glu Ser Arg Ser Ser Lys Thr Asn Pro Lys Arg Asp
        50                  55                  60

Trp Phe Phe Trp Arg Pro Pro Lys Gly Tyr Asp Ala Glu Gly Lys Pro
65              70                  75                  80

Ile Pro Pro Asn Asn Trp Lys Ser Tyr Phe Gly Gly Ser Ala Trp Thr
                85                  90                  95

Phe Asp Glu Lys Thr Gln Glu Phe Tyr Leu Arg Leu Phe Cys Ser Thr
            100                 105                 110

Gln Pro Asp Leu Asn Trp Glu Asn Glu Asp Cys Arg Lys Ala Ile Tyr
        115                 120                 125

Glu Ser Ala Val Gly Tyr Trp Leu Asp His Gly Val Asp Gly Phe Arg
    130                 135                 140

Ile Asp Val Gly Ser Leu Tyr Ser Lys Val Val Gly Leu Pro Asp Ala
145                 150                 155                 160

Pro Val Val Asp Lys Asn Ser Thr Trp Gln Ser Ser Asp Pro Tyr Thr
                165                 170                 175

Leu Asn Gly Pro Arg Ile His Glu Phe His Gln Glu Met Asn Gln Phe
            180                 185                 190

Ile Arg Asn Arg Val Lys Gly Gly Arg Glu Ile Met Thr Val Gly Glu
        195                 200                 205

Met Gln His Ala Ser Asp Glu Thr Lys Arg Leu Tyr Thr Ser Ala Ser
    210                 215                 220

Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
```

```
              245                 250                 255
Trp Lys Ile Ala Leu Ala Glu Leu Phe Arg Phe Ile Asn Gly Thr Asp
            260                 265                 270

Cys Trp Ser Thr Ile Tyr Leu Glu Asn His Asp Gln Pro Arg Ser Ile
        275                 280                 285

Thr Arg Phe Gly Asp Asp Ser Pro Lys Asn Arg Val Ile Ser Gly Lys
    290                 295                 300

Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Ser Val Glu
                325                 330                 335

Lys Tyr Glu Asp Val Glu Ile Arg Asn Asn Tyr Arg Leu Ile Lys Glu
            340                 345                 350

Glu Cys Gly Glu Asn Ser Glu Glu Met Lys Lys Phe Leu Glu Gly Ile
        355                 360                 365

Ala Leu Val Ser Arg Asp His Ala Arg Thr Pro Met Pro Trp Thr Pro
    370                 375                 380

Asn Glu Pro Asn Ala Gly Phe Ser Gly Pro Asn Thr Lys Pro Trp Phe
385                 390                 395                 400

Tyr Leu Asn Glu Ser Phe Arg Gln Gly Ile Asn Val Glu Glu Glu Gln
                405                 410                 415

Lys Asn Ser Asp Ser Val Leu Ala Phe Trp Lys Lys Ala Leu Glu Phe
            420                 425                 430

Arg Lys Asn His Lys Asp Ile Ala Val Tyr Gly Phe Asp Phe Lys Phe
        435                 440                 445

Ile Asp Leu Asp Asn Lys Lys Leu Phe Ser Phe Thr Lys Arg Tyr Asn
    450                 455                 460

Asn Lys Thr Leu Phe Ala Ala Leu Asn Phe Ser Ser Asp Ala Thr Asp
465                 470                 475                 480

Phe Lys Ile Pro Asn Asp Gly Ser Ser Phe Lys Leu Glu Phe Gly Asn
                485                 490                 495

Tyr Pro Lys Asn Glu Val Asp Ala Ser Ser Arg Thr Leu Lys Pro Trp
            500                 505                 510

Glu Gly Arg Ile His Ile Asn Glu
        515                 520

<210> SEQ ID NO 14
<211> LENGTH: 589
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 14

Met Thr Ile Ser Ser Ala His Pro Glu Thr Glu Pro Lys Trp Trp Lys
1               5                  10                  15

Glu Ala Thr Phe Tyr Gln Ile Tyr Pro Ala Ser Phe Lys Asp Ser Asn
                20                  25                  30

Asp Asp Gly Trp Gly Asp Met Lys Gly Ile Ser Ser Lys Leu Glu Tyr
            35                  40                  45

Ile Lys Glu Leu Gly Val Asp Ala Ile Trp Ile Ser Pro Leu Tyr Asp
        50                  55                  60

Ser Pro Gln Asp Asp Met Gly Tyr Asp Ile Ala Asn Tyr Glu Lys Val
65                  70                  75                  80
```

```
Trp Pro Thr Tyr Gly Thr Asn Glu Asp Cys Phe Ala Leu Ile Glu Lys
                85                  90                  95
Thr His Lys Leu Gly Met Lys Phe Ile Thr Asp Leu Val Ile Asn His
            100                 105                 110
Cys Ser Ser Glu His Glu Trp Phe Lys Glu Ser Arg Ser Ser Lys Thr
            115                 120                 125
Asn Pro Lys Arg Asp Trp Ser Phe Trp Arg Pro Pro Lys Gly Tyr Asp
            130                 135                 140
Ala Glu Gly Lys Pro Ile Pro Pro Asn Asn Trp Lys Ser Tyr Phe Gly
145                 150                 155                 160
Gly Ser Ala Trp Thr Phe Asp Glu Lys Thr Gln Glu Phe Tyr Leu Arg
                165                 170                 175
Leu Phe Cys Ser Thr Gln Pro Asp Leu Asn Trp Glu Asn Glu Asp Cys
            180                 185                 190
Arg Lys Ala Ile Tyr Glu Ser Ala Val Gly Tyr Trp Leu Asp His Gly
            195                 200                 205
Val Asp Gly Phe Arg Ile Asp Val Gly Ser Leu Tyr Ser Lys Val Val
    210                 215                 220
Gly Leu Pro Asp Ala Pro Val Val Asp Lys Asn Ser Thr Trp Gln Ser
225                 230                 235                 240
Ser Asp Pro Tyr Thr Leu Asn Gly Pro Arg Ile His Glu Phe His Gln
            245                 250                 255
Glu Met Asn Gln Phe Ile Arg Asn Arg Val Lys Asp Gly Arg Glu Ile
            260                 265                 270
Met Thr Val Gly Glu Met Gln His Ala Ser Asp Glu Thr Lys Arg Leu
            275                 280                 285
Tyr Thr Ser Ala Ser Arg His Glu Leu Ser Glu Leu Phe Asn Phe Ser
    290                 295                 300
His Thr Asp Val Gly Thr Ser Pro Leu Phe Arg Tyr Asn Leu Val Pro
305                 310                 315                 320
Phe Glu Leu Lys Asp Trp Lys Ile Ala Leu Ala Glu Leu Phe Arg Tyr
            325                 330                 335
Ile Asn Gly Thr Asp Cys Trp Ser Thr Ile Tyr Leu Glu Asn His Asp
            340                 345                 350
Gln Pro Arg Ser Ile Thr Arg Phe Gly Asp Asp Ser Pro Lys Asn Arg
            355                 360                 365
Val Ile Ser Gly Lys Leu Leu Ser Val Leu Leu Ser Ala Leu Thr Gly
    370                 375                 380
Thr Leu Tyr Val Tyr Gln Gly Gln Glu Leu Gly Gln Ile Asn Phe Lys
385                 390                 395                 400
Asn Trp Pro Val Glu Lys Tyr Glu Asp Val Glu Ile Arg Asn Asn Tyr
            405                 410                 415
Asn Ala Ile Lys Glu Glu His Gly Glu Asn Ser Glu Glu Met Lys Lys
            420                 425                 430
Phe Leu Glu Gly Ile Ala Leu Val Ser Arg Asp His Ala Arg Thr Pro
            435                 440                 445
Met Pro Trp Thr Pro Asn Glu Pro Asn Ala Gly Phe Ser Gly Pro Ser
    450                 455                 460
Ala Lys Pro Trp Phe Tyr Leu Asn Asp Ser Phe Arg Glu Gly Ile Asn
465                 470                 475                 480
Val Glu Asp Glu Ile Lys Asp Pro Asn Ser Val Leu Asn Phe Trp Lys
            485                 490                 495
Glu Ala Leu Lys Phe Arg Lys Ala His Lys Asp Ile Thr Val Tyr Gly
```

```
                500                 505                 510
Tyr Asp Phe Glu Phe Ile Asp Leu Asp Asn Lys Lys Leu Phe Ser Phe
            515                 520                 525

Thr Lys Lys Tyr Asn Asn Lys Thr Leu Phe Ala Ala Leu Asn Phe Ser
        530                 535                 540

Ser Asp Ala Thr Asp Phe Lys Ile Pro Asn Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585

<210> SEQ ID NO 15
<211> LENGTH: 589
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 15

Met Thr Ile Ser Ser Ala His Pro Glu Ala Glu Pro Lys Trp Trp Lys
1               5                   10                  15

Glu Ala Thr Phe Tyr Gln Ile Tyr Pro Ala Ser Phe Lys Asp Ser Asn
            20                  25                  30

Asp Asp Gly Trp Gly Asp Met Lys Gly Ile Ser Ser Lys Leu Glu Tyr
        35                  40                  45

Ile Lys Glu Leu Gly Ala Asp Ala Ile Trp Ile Ser Pro Phe Tyr Asp
    50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
            100                 105                 110

Cys Ser Ser Glu His Glu Trp Leu Lys Glu Ser Arg Ser Ser Lys Thr
        115                 120                 125

Asn Pro Lys Arg Asp Trp Phe Phe Trp Arg Pro Pro Lys Gly Tyr Asp
    130                 135                 140

Ala Glu Gly Lys Pro Ile Pro Pro Asn Asn Trp Lys Ser Tyr Phe Gly
145                 150                 155                 160

Gly Ser Ala Trp Ile Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Val
    210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
                245                 250                 255

Glu Met Asn Gln Phe Ile Arg Asn Arg Val Lys Asp Gly Arg Glu Ile
            260                 265                 270
```

Met Thr Val Gly Glu Met Gln His Ala Ser Asp Glu Thr Lys Lys Leu
            275                 280                 285

Tyr Thr Ser Ala Ser Arg His Glu Leu Ser Glu Leu Phe Asn Phe Ser
290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Phe
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Ala Ile Ala Leu Ile Ser Arg Asp His Ala Arg Thr Pro
        435                 440                 445

Met Gln Trp Ser Arg Glu Glu Pro Asn Ala Gly Phe Ser Gly Pro Ser
450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
530                 535                 540

Ser Asp Ala Thr Asp Phe Lys Ile Pro Asn Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585

<210> SEQ ID NO 16
<211> LENGTH: 581
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 16

Met Thr Ile Ile His Asn Pro Lys Trp Trp Lys Glu Ala Thr Ile Tyr
1               5                   10                  15

Gln Ile Tyr Pro Ala Ser Phe Lys Asp Ser Asn Asn Asp Gly Trp Gly
            20                  25                  30

Asp Leu Ala Gly Ile Thr Ser Lys Leu Asp Tyr Ile Lys Glu Leu Gly
        35                  40                  45

```
Val Asp Ala Ile Trp Val Cys Pro Phe Tyr Asp Ser Pro Gln Glu Asp
         50                  55                  60

Met Gly Tyr Asp Ile Ala Asn Tyr Glu Lys Val Trp Pro Arg Tyr Gly
65               70                  75                  80

Thr Ser Glu Asp Cys Phe Gln Met Ile Glu Glu Ser His Lys Arg Gly
                 85                  90                  95

Ile Lys Val Ile Val Asp Leu Val Ile Asn His Cys Ser Glu Glu His
             100                 105                 110

Glu Trp Phe Lys Glu Ser Arg Ser Ser Lys Thr Asn Ala Lys Arg Asp
             115                 120                 125

Trp Phe Phe Trp Lys Pro Pro Lys Gly Tyr Glu Ile Asp Gly Thr Pro
         130                 135                 140

Ile Pro Pro Asn Asn Trp Arg Ser Phe Gly Gly Ser Ala Trp Lys
145                 150                 155                 160

Tyr Asp Glu Asn Thr Glu Glu Phe Phe Leu His Val Phe Ala Pro Gly
                 165                 170                 175

Gln Pro Asp Phe Asn Trp Glu Asn Lys Glu Cys Arg Gln Ala Ile Tyr
             180                 185                 190

Asp Ser Ser Val Gly Phe Trp Leu Arg His Asn Val Asp Gly Phe Arg
         195                 200                 205

Ile Asp Val Gly Ser Met Tyr Ser Lys Val Glu Gly Leu Pro Asp Ala
         210                 215                 220

Ser Ile Thr Asp Pro Thr Val Pro Tyr Gln Asp Gly Thr Asp Phe Phe
225                 230                 235                 240

Val Asn Gly Pro Arg Ile His Glu Tyr His Lys Glu Met Arg Gln Tyr
                 245                 250                 255

Met Tyr Thr Gln Ile Pro Glu Gly Lys Glu Ile Met Thr Val Gly Glu
             260                 265                 270

Val Gly Ile Gly Asn Glu Lys Asp Phe Lys Asp Tyr Thr Ser Ser Lys
         275                 280                 285

Glu Glu Glu Phe Asn Met Met Phe Asn Phe Lys His Thr Ser Val Gly
         290                 295                 300

Glu Ser Pro Glu Phe Lys Tyr Glu Leu Ile Pro Phe Thr Leu Lys Asp
305                 310                 315                 320

Phe Lys Leu Ala Leu Ala Glu Ser Phe Leu Phe Ile Glu Gly Thr Asp
                 325                 330                 335

Cys Trp Ser Thr Ile Tyr Leu Glu Asn His Asp Gln Pro Arg Ser Val
             340                 345                 350

Ser Arg Phe Gly Ser Asp Ser Pro Glu Trp Arg Glu Ile Ser Ser Lys
         355                 360                 365

Met Leu Ala Thr Leu Ile Ile Ser Leu Thr Gly Thr Val Phe Ile Tyr
         370                 375                 380

Gln Gly Gln Glu Leu Gly Met Pro Asn Phe Lys Asn Arg Lys Ile Glu
385                 390                 395                 400

Gln Ile Lys Cys Val Glu Gly Thr Gly Thr Tyr Gly Ala Ile Lys Arg
                 405                 410                 415

Asp Tyr Gly Glu Asp Ser Glu Lys Met Lys Lys Phe Tyr Glu Ala Leu
             420                 425                 430

Ala Leu Ile Ser Arg Asp His Gly Arg Thr Pro Phe Pro Trp Ser Gly
             435                 440                 445

Glu Lys Pro Tyr Ala Gly Phe Ser Lys Asn Ala Lys Pro Trp Ile Asp
450                 455                 460
```

```
Ile Asn Glu Ser Phe Val Glu Gly Ile Asn Ala Glu Ala Glu Leu Asn
465                 470                 475                 480

Asp Glu Asn Ser Val Phe Phe Trp Lys Arg Ala Leu Gln Val Arg
            485                 490                 495

Lys Glu His Lys Asn Met Leu Val Tyr Gly Asp Asn Phe Gln Phe Tyr
            500                 505                 510

Asp Leu Asp Asn Glu Lys Leu Phe Met Phe Thr Lys Asp Ser Gly Asp
            515                 520                 525

Lys Lys Met Phe Ala Val Phe Asn Phe Cys Ser Asp Ser Thr Glu Phe
            530                 535                 540

Ser Val Pro Asp Asn Lys Ala Ser Tyr Asp Met Phe Phe Gly Asn Tyr
545                 550                 555                 560

Ala Asn Ser Asp Gly Lys Ser Tyr Thr Leu Lys Pro Trp Glu Gly Arg
            565                 570                 575

Leu Tyr Tyr Ser Asn
            580

<210> SEQ ID NO 17
<211> LENGTH: 581
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 17

Met Thr Ile Ile His Asn Pro Lys Trp Trp Lys Glu Ala Thr Val Tyr
1               5                   10                  15

Gln Ile Tyr Pro Ala Ser Asn Lys Asp Ser Asn Asn Asp Gly Trp Gly
            20                  25                  30

Asp Leu Ala Gly Ile Thr Ser Lys Leu Asp Tyr Val Lys Glu Leu Gly
            35                  40                  45

Val Asp Ala Ile Trp Val Cys Leu Phe Tyr Asp Ser Pro Gln Glu Asp
50                  55                  60

Met Gly Tyr Asp Ile Ala Asn Tyr Glu Lys Val Trp Pro Arg Tyr Gly
65                  70                  75                  80

Thr Asn Glu Asp Cys Phe Gln Met Ile Glu Glu Ala His Lys Arg Gly
            85                  90                  95

Ile Lys Val Ile Val Asp Leu Val Ile Asn His Cys Ser Glu Glu His
            100                 105                 110

Glu Trp Phe Lys Glu Ser Lys Ser Ser Lys Thr Asn Pro Lys Arg Asp
            115                 120                 125

Trp Phe Phe Trp Arg Pro Pro Lys Gly Phe Asp Glu Lys Gly Asn Pro
            130                 135                 140

Ile Pro Pro Asn Asn Trp Arg Ser Phe Phe Gly Gly Ser Ala Trp Arg
145                 150                 155                 160

Tyr Asp Glu Lys Thr Gly Glu Phe Phe Leu His Val Phe Ala Pro Gly
            165                 170                 175

Gln Pro Asp Phe Asn Trp Glu Asn Glu Glu Cys Arg Lys Ala Ile Tyr
            180                 185                 190

Asp Ser Ser Val Gly Tyr Trp Leu Arg His Asn Val Asp Gly Phe Arg
            195                 200                 205

Ile Asp Val Gly Ser Met Tyr Ser Lys Val Glu Gly Leu Pro Asp Ala
            210                 215                 220

Pro Ile Thr Asp Pro Thr Val Pro Tyr Gln Lys Gly Thr Glu Phe Phe
225                 230                 235                 240
```

```
Ile Asn Gly Ser Arg Ile His Glu Tyr His Lys Glu Met Arg Lys Tyr
            245                 250                 255
Met Leu Ser Gln Ile Pro Glu Gly Lys Glu Ile Met Thr Val Gly Glu
            260                 265                 270
Val Gly Val Gly Asn Glu Glu Asp Phe Arg Asp Tyr Thr Ser Ala Lys
            275                 280                 285
Glu Gly Glu Leu Asn Met Met Phe Asn Phe Lys His Thr Ser Val Gly
            290                 295                 300
Glu Ser Pro Glu Cys Lys Tyr Glu Leu Ile Pro Phe Thr Leu Lys Asp
305                 310                 315                 320
Phe Lys Leu Ala Leu Ala Glu Ser Phe Leu Phe Ile Glu Asn Thr Asp
                325                 330                 335
Cys Trp Ser Thr Ile Tyr Leu Glu Asn His Asp Gln Pro Arg Ser Val
                340                 345                 350
Ser Arg Phe Gly Ser Asp Ser Pro Lys Trp Arg Ala Ile Ser Ser Lys
                355                 360                 365
Met Leu Ala Thr Leu Ile Ile Ser Leu Thr Gly Thr Val Phe Ile Tyr
            370                 375                 380
Gln Gly Gln Glu Leu Gly Met Ser Asn Phe Lys Asn Arg Arg Ile Glu
385                 390                 395                 400
Gln Ile Lys Cys Val Glu Gly Thr Gly Thr Tyr Ala Ala Ile Lys Arg
                405                 410                 415
Asp Tyr Gly Glu Asp Ser Glu Lys Met Lys Lys Phe Phe Glu Ala Leu
                420                 425                 430
Ala Leu Ile Ser Arg Asp His Gly Arg Thr Pro Phe Pro Trp Ser Ala
            435                 440                 445
Asp Glu Pro Ser Ala Gly Phe Ser Lys Asp Ala Lys Pro Arg Ile Asp
450                 455                 460
Met Asn Glu Ser Phe Arg Asp Gly Ile Asn Ala Glu Ala Glu Leu Lys
465                 470                 475                 480
Asp Lys Asn Ser Val Phe Phe Phe Trp Lys Lys Ala Leu Gln Val Arg
                485                 490                 495
Lys Glu His Lys Asp Ile Leu Val Tyr Gly His Asn Phe Gln Phe Ile
            500                 505                 510
Asp Leu Asp Asn Asp Lys Leu Phe Met Phe Thr Lys Asp Thr Asp Asn
            515                 520                 525
Lys Lys Met Phe Ala Val Phe Asn Phe Ser Asp Asp Thr Asp Phe
            530                 535                 540
Ser Val Pro Asp Asn Glu Ala Ser Tyr Thr Met Phe Phe Gly Asn Tyr
545                 550                 555                 560
Ala Asn Ser Asn Gly Asp Ser Arg Thr Leu Gln Pro Trp Glu Gly Arg
                565                 570                 575
Leu Tyr Leu Leu Lys
            580

<210> SEQ ID NO 18
<211> LENGTH: 610
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 18

Met Lys Asn Ile Leu Ser Leu Val Gly Arg Lys Glu Asn Thr Pro Glu
```

```
1               5                   10                  15
Asp Val Thr Ala Asn Leu Ala Asp Thr Ser Ser Thr Thr Val Met Gln
                20                  25                  30

Ala Lys Asp Leu Val Ile Glu Asp Phe Glu Glu Arg Lys Lys Asn Asp
                35                  40                  45

Ala Phe Glu Leu Asn His Leu Glu Leu Thr Thr Asn Ala Thr Gln Leu
                50                  55                  60

Ser Asp Ser Asp Glu Asp Lys Glu Asn Val Ile Arg Val Ala Glu Ala
 65                 70                  75                  80

Thr Asp Asp Ala Asn Glu Ala Asn Asn Glu Glu Lys Ser Met Thr Leu
                    85                  90                  95

Arg Gln Ala Leu Arg Lys Tyr Pro Lys Ala Ala Leu Trp Ser Ile Leu
                100                 105                 110

Val Ser Thr Thr Leu Val Met Glu Gly Tyr Asp Thr Ala Leu Leu Ser
                115                 120                 125

Ala Leu Tyr Ala Leu Pro Val Phe Gln Arg Lys Phe Gly Thr Met Asn
                130                 135                 140

Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Ser
                180                 185                 190

Leu Leu Thr Ala Tyr Ile Phe Ile Leu Tyr Tyr Cys Lys Ser Leu Ala
                195                 200                 205

Met Ile Ala Val Gly Gln Ile Leu Ser Ala Met Pro Trp Gly Cys Phe
210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
                260                 265                 270

Ser Asp Leu Gly Tyr Lys Leu Pro Phe Ala Leu Gln Trp Ile Trp Pro
                275                 280                 285

Ala Pro Leu Ile Ile Gly Ile Phe Phe Ala Pro Glu Ser Pro Trp Trp
                290                 295                 300

Leu Val Arg Lys Asn Lys Ile Val Glu Ala Lys Lys Ser Leu Asn Arg
305                 310                 315                 320

Ile Leu Ser Gly Thr Val Thr Glu Lys Glu Ile Gln Val Asp Ile Thr
                325                 330                 335

Leu Lys Gln Ile Glu Met Thr Ile Glu Lys Glu Arg Leu Arg Ala Ser
                340                 345                 350

Lys Ser Gly Ser Phe Phe Ser Cys Phe Lys Gly Val Asp Gly Arg Arg
                355                 360                 365

Thr Arg Leu Ala Cys Leu Thr Trp Val Ala Gln Asn Ser Ser Gly Ala
                370                 375                 380

Val Leu Leu Gly Tyr Ser Thr Tyr Phe Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Gly Ser Trp Val Ile Ser Gly Arg Val Gly Arg Trp
                420                 425                 430
```

-continued

```
Thr Ile Leu Thr Tyr Gly Leu Ser Phe Gln Met Val Cys Leu Phe Ile
            435                 440                 445

Ile Gly Gly Met Gly Phe Ala Ser Gly Ser Ser Ala Ser Asn Ala Ala
450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
            485                 490                 495

Thr Lys Thr Ile Val Leu Ala Arg Ile Cys Tyr Asn Leu Met Ala Val
            500                 505                 510

Phe Asn Ala Ile Leu Thr Pro Tyr Met Leu Asn Val Ser Asp Trp Asn
            515                 520                 525

Trp Gly Ala Lys Thr Gly Leu Tyr Trp Gly Gly Phe Thr Ala Leu Thr
            530                 535                 540

Leu Ala Trp Val Ile Ile Asp Leu Pro Glu Thr Thr Gly Arg Thr Phe
545                 550                 555                 560

Ser Glu Ile Asn Glu Leu Phe Ser Gln Gly Val Pro Ala Arg Lys Phe
            565                 570                 575

Ala Ser Thr Val Val Asp Pro Phe Gly Lys Arg Gly Leu Gln Asn Arg
            580                 585                 590

Pro Gln Val Asp Asn Ile Ile Asp Arg Phe Ser Ser Ala Ser Gln Gln
            595                 600                 605

Ala Leu
    610

<210> SEQ ID NO 19
<211> LENGTH: 616
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 19

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asn Phe Glu Glu Gly Arg Lys Asp Ser
        35                  40                  45

Ala Phe Glu Leu Asp His Leu Glu Phe Thr Ile Asn Ser Ala Gln Leu
    50                  55                  60

Gly Asp Ser Asp Glu Asp Asn Glu Asn Val Ile Asn Glu Thr Asn Thr
65                  70                  75                  80

Thr Asp Asp Ala Asn Glu Ala Asn Ser Glu Glu Lys Ser Met Thr Leu
            85                  90                  95

Lys Gln Ala Leu Leu Ile Tyr Pro Lys Ala Ala Leu Trp Ser Ile Leu
            100                 105                 110

Val Ser Thr Thr Leu Val Met Glu Gly Tyr Asp Thr Ala Leu Leu Asn
            115                 120                 125

Ala Leu Tyr Ala Leu Pro Val Phe Gln Arg Lys Phe Gly Thr Leu Asn
        130                 135                 140

Gly Glu Gly Ser Tyr Glu Ile Thr Ser Gln Trp Gln Ile Gly Leu Asn
145                 150                 155                 160

Met Cys Val Gln Cys Gly Glu Ile Ile Gly Leu Gln Ile Thr Pro Tyr
```

```
                165                 170                 175
Met Val Glu Phe Met Gly Asn Arg Tyr Thr Met Ile Thr Ala Leu Gly
                180                 185                 190

Leu Leu Thr Ala Tyr Val Phe Ile Leu Tyr Tyr Cys Lys Ser Leu Ala
                195                 200                 205

Met Ile Ala Val Gly Gln Val Leu Ser Ala Met Pro Trp Gly Cys Phe
            210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
                260                 265                 270

Ser Asp Leu Gly Tyr Lys Leu Pro Phe Ala Leu Gln Trp Ile Trp Pro
            275                 280                 285

Ala Pro Leu Met Ile Gly Ile Phe Phe Ala Pro Glu Ser Pro Trp Trp
            290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Ile Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Leu Asp Cys Phe Lys Gly Val Asn Gly Arg Arg
            355                 360                 365

Thr Arg Leu Ala Cys Leu Thr Trp Val Ala Gln Asn Thr Ser Gly Ala
            370                 375                 380

Cys Leu Leu Gly Tyr Ser Thr Tyr Phe Glu Arg Ala Gly Met Ala
385                 390                 395                 400

Thr Asp Lys Ala Phe Thr Phe Ser Val Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
            435                 440                 445

Ile Gly Gly Met Gly Phe Gly Ser Gly Ser Gly Ala Ser Asn Gly Ala
            450                 455                 460

Gly Gly Leu Leu Leu Ala Leu Ser Phe Phe Tyr Asn Ala Gly Ile Gly
465                 470                 475                 480

Ala Val Val Tyr Cys Ile Val Thr Glu Ile Pro Ser Ala Glu Leu Arg
                485                 490                 495

Thr Lys Thr Ile Val Leu Ala Arg Ile Cys Tyr Asn Ile Met Ala Val
                500                 505                 510

Ile Asn Ala Ile Leu Thr Pro Tyr Met Leu Asn Val Ser Asp Trp Asn
            515                 520                 525

Trp Gly Ala Lys Thr Gly Leu Tyr Trp Gly Gly Phe Thr Ala Val Thr
            530                 535                 540

Leu Ala Trp Val Ile Asp Leu Pro Glu Thr Ser Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590
```

Ser Leu Asp Asp Glu Ser Ile Ser Gln Ser Ser Ser Ile Lys Gln Arg
      595                 600                 605

Glu Leu Asn Ala Ala Asp Lys Cys
    610                 615

<210> SEQ ID NO 20
<211> LENGTH: 616
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 20

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asn Phe Glu Glu Gly Arg Lys Asp Ser
        35                  40                  45

Ala Phe Glu Leu Asp His Leu Glu Phe Thr Ile Asn Ser Ala Gln Leu
    50                  55                  60

Gly Asp Ser Asp Glu Asp Asn Glu Asn Val Ile Asn Glu Thr Asn Thr
65                  70                  75                  80

Thr Asp Ala Asn Glu Ala Asn Ser Glu Glu Lys Ser Met Thr Leu
                85                  90                  95

Lys Gln Ala Leu Leu Ile Tyr Pro Lys Ala Ala Leu Trp Ser Ile Leu
            100                 105                 110

Val Ser Thr Thr Leu Val Met Glu Gly Tyr Asp Thr Ala Leu Leu Asn
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Gln Cys Gly Glu Ile Ile Gly Leu Gln Ile Thr Pro Tyr
                165                 170                 175

Met Val Glu Phe Met Gly Asn Arg Tyr Thr Met Ile Thr Ala Leu Gly
            180                 185                 190

Leu Leu Thr Ala Tyr Val Phe Ile Leu Tyr Tyr Cys Lys Ser Leu Ala
        195                 200                 205

Met Ile Ala Val Gly Gln Val Leu Ser Ala Met Pro Trp Gly Cys Phe
    210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Ile Asp Leu Thr

```
                    325                 330                 335

Leu Lys Gln Ile Glu Leu Thr Ile Glu Lys Glu Arg Leu Leu Ala Ser
            340                 345                 350

Lys Ser Gly Ser Phe Phe Asp Cys Phe Lys Gly Val Asn Gly Arg Arg
        355                 360                 365

Thr Arg Leu Ala Cys Leu Thr Trp Val Ala Gln Asn Thr Ser Gly Ala
    370                 375                 380

Cys Leu Leu Gly Tyr Ser Ala Tyr Phe Glu Arg Ala Gly Met Ala
385                 390                 395                 400

Thr Asp Lys Ala Phe Thr Phe Ser Val Ile Gln Tyr Cys Leu Gly Leu
                405                 410                 415

Ala Gly Thr Leu Cys Ser Trp Val Ile Ser Arg Val Gly Arg Trp
            420                 425                 430

Thr Ile Leu Thr Tyr Gly Leu Ala Phe Gln Met Val Cys Leu Phe Ile
        435                 440                 445

Ile Gly Gly Met Gly Phe Gly Ser Gly Ser Ala Ser Asn Gly Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Thr Glu Ile Pro Ser Ala Glu Leu Arg
                485                 490                 495

Thr Lys Thr Ile Val Leu Ala Arg Ile Cys Tyr Asn Ile Met Ala Val
            500                 505                 510

Ile Asn Ala Ile Leu Thr Pro Tyr Met Leu Asn Val Ser Asp Trp Asn
        515                 520                 525

Trp Gly Ala Lys Thr Gly Leu Tyr Trp Gly Gly Phe Thr Ala Val Thr
    530                 535                 540

Leu Ala Trp Val Ile Ile Asp Leu Pro Glu Thr Ser Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Asp Asp Glu Ser Ile Ser Gln Ser Ser Ile Lys Gln Arg
        595                 600                 605

Glu Leu Asn Ala Ala Asp Lys Cys
    610                 615

<210> SEQ ID NO 21
<211> LENGTH: 589
<212> TYPE: PRT
<213> ORGANISM: Unknown
<220> FEATURE:
<223> OTHER INFORMATION: Hybrid between S. cerevisiae and S. pastorianus
      (Hybrid yeast 4)

<400> SEQUENCE: 21

Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
            20                  25                  30

Asp Asp Gly Trp Gly Asp Met Lys Gly Ile Ser Ser Lys Leu Glu Tyr
        35                  40                  45

Ile Lys Glu Leu Gly Val Asp Ala Ile Trp Ile Ser Pro Phe Tyr Asp
    50                  55                  60
```

```
Ser Pro Gln Asp Asp Met Gly Tyr Asp Ile Ala Asn Tyr Glu Lys Val
 65                  70                  75                  80

Trp Pro Thr Tyr Gly Thr Asn Glu Asp Cys Phe Ala Leu Ile Glu Lys
                 85                  90                  95

Thr His Lys Leu Gly Met Lys Phe Ile Thr Asp Leu Val Ile Asn His
            100                 105                 110

Cys Ser Ser Glu His Glu Trp Phe Lys Glu Ser Arg Ser Ser Lys Thr
        115                 120                 125

Asn Pro Lys Arg Asp Trp Phe Trp Arg Pro Lys Gly Tyr Asp
    130                 135                 140

Ala Glu Gly Lys Pro Ile Pro Pro Asn Asn Trp Lys Ser Tyr Phe Gly
145                 150                 155                 160

Gly Ser Ala Trp Ile Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Val
    210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
                245                 250                 255

Glu Met Asn Gln Phe Ile Arg Asn Arg Val Lys Asp Gly Arg Glu Ile
            260                 265                 270

Met Thr Val Gly Glu Met Gln His Ala Ser Asp Glu Thr Lys Arg Leu
        275                 280                 285

Tyr Thr Ser Ala Ser Arg His Glu Leu Ser Glu Leu Phe Asn Phe Ser
    290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Phe
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
    370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Ala Ile Ala Leu Ile Ser Arg Asp His Ala Arg Thr Pro
        435                 440                 445

Met Gln Trp Ser Arg Glu Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
```

```
            485                 490                 495
Glu Ala Leu Lys Phe Arg Lys Ala His Lys Asp Ile Thr Val Tyr Gly
            500                 505                 510
Tyr Asp Phe Glu Phe Ile Asp Leu Asp Asn Lys Lys Leu Phe Ser Phe
            515                 520                 525
Thr Lys Lys Tyr Asn Asn Lys Thr Leu Phe Ala Ala Leu Asn Phe Ser
            530                 535                 540
Ser Asp Ala Thr Asp Phe Lys Ile Pro Asn Asp Asp Ser Ser Phe Lys
545                 550                 555                 560
Leu Glu Phe Gly Asn Tyr Pro Lys Lys Glu Val Asp Ala Ser Ser Arg
                565                 570                 575
Thr Leu Lys Pro Trp Glu Gly Arg Ile Tyr Ile Ser Glu
            580                 585

<210> SEQ ID NO 22
<211> LENGTH: 589
<212> TYPE: PRT
<213> ORGANISM: Unknown
<220> FEATURE:
<223> OTHER INFORMATION: Hybrid between S. cerevisiae and S. pastorianus
      (Hybrid yeast 4)

<400> SEQUENCE: 22

Met Thr Ile Ser Ser Ala His Pro Glu Thr Glu Pro Lys Trp Trp Lys
1               5                   10                  15
Glu Ala Thr Phe Tyr Gln Ile Tyr Pro Ala Ser Phe Lys Asp Ser Asn
            20                  25                  30
Asp Asp Gly Trp Gly Asp Met Lys Gly Ile Ser Ser Lys Leu Glu Tyr
        35                  40                  45
Ile Lys Glu Leu Gly Val Asp Ala Ile Trp Ile Ser Pro Phe Tyr Asp
    50                  55                  60
Ser Pro Gln Asp Asp Met Gly Tyr Asp Ile Ala Asn Tyr Glu Lys Val
65                  70                  75                  80
Trp Pro Thr Tyr Gly Thr Asn Glu Asp Cys Phe Ala Leu Ile Glu Lys
                85                  90                  95
Thr His Lys Leu Gly Met Lys Phe Ile Thr Asp Leu Val Ile Asn His
            100                 105                 110
Cys Ser Ser Glu His Glu Trp Phe Lys Glu Ser Arg Ser Ser Lys Thr
        115                 120                 125
Asn Pro Lys Arg Asp Trp Phe Phe Trp Arg Pro Pro Lys Gly Tyr Asp
    130                 135                 140
Ala Glu Gly Lys Pro Ile Pro Pro Asn Asn Trp Lys Ser Tyr Phe Gly
145                 150                 155                 160
Gly Ser Ala Trp Ile Phe Asp Glu Lys Thr Gln Glu Phe Tyr Leu Arg
                165                 170                 175
Leu Phe Cys Ser Thr Gln Pro Asp Leu Asn Trp Glu Asn Glu Asp Cys
            180                 185                 190
Arg Lys Ala Ile Tyr Glu Ser Ala Val Gly Tyr Trp Leu Asp His Gly
        195                 200                 205
Val Asp Gly Phe Arg Ile Asp Val Gly Ser Leu Tyr Ser Lys Val Val
    210                 215                 220
Gly Leu Pro Asp Ala Pro Val Val Asp Lys Asn Ser Thr Trp Gln Ser
225                 230                 235                 240
Ser Asp Pro Tyr Thr Leu Asn Gly Pro Arg Ile His Glu Phe His Gln
                245                 250                 255
```

```
Glu Met Asn Gln Phe Ile Arg Asn Arg Val Lys Asp Gly Arg Glu Ile
            260                 265                 270

Met Thr Val Gly Glu Met Gln His Ala Ser Asp Glu Thr Lys Arg Leu
        275                 280                 285

Tyr Thr Ser Ala Ser Arg His Glu Leu Ser Glu Leu Phe Asn Phe Ser
    290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Tyr
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
    370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Ala Ile Ala Leu Ile Ser Arg Asp His Ala Arg Thr Pro
        435                 440                 445

Met Gln Trp Ser Arg Glu Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
530                 535                 540

Ser Asp Ala Thr Asp Phe Lys Ile Pro Asn Asp Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585

<210> SEQ ID NO 23
<211> LENGTH: 589
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 23

Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
            20                  25                  30
```

```
Asp Asp Gly Trp Gly Asp Met Lys Gly Ile Ser Ser Lys Leu Glu Tyr
         35                  40                  45

Ile Lys Glu Leu Gly Val Asp Ala Ile Trp Ile Ser Pro Phe Tyr Asp
 50                  55                  60

Ser Pro Gln Asp Met Gly Tyr Asp Ile Ala Asn Tyr Glu Lys Val
 65              70                  75                  80

Trp Pro Thr Tyr Gly Thr Asn Glu Asp Cys Phe Ala Leu Ile Glu Lys
                 85                  90                  95

Thr His Lys Leu Gly Met Lys Phe Ile Thr Asp Leu Val Ile Asn His
                100                 105                 110

Cys Ser Ser Glu His Glu Trp Phe Lys Glu Ser Arg Ser Ser Lys Thr
            115                 120                 125

Asn Pro Lys Arg Asp Trp Phe Phe Trp Arg Pro Pro Lys Gly Tyr Asp
130                 135                 140

Ala Glu Gly Lys Pro Ile Pro Pro Asn Asn Trp Lys Ser Tyr Phe Gly
145                 150                 155                 160

Gly Ser Ala Trp Ile Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
            195                 200                 205

Val Asp Gly Phe Arg Ile Asp Val Gly Ser Leu Tyr Ser Lys Val Val
210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
                245                 250                 255

Glu Met Asn Gln Phe Ile Arg Asn Arg Val Lys Asp Gly Arg Glu Ile
            260                 265                 270

Met Thr Val Gly Glu Met Gln His Ala Ser Asp Glu Thr Lys Lys Leu
            275                 280                 285

Tyr Thr Ser Ala Ser Arg His Glu Leu Ser Glu Leu Phe Asn Phe Ser
            290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Phe
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
            355                 360                 365

Val Ile Ser Gly Lys Leu Leu Ser Val Leu Leu Ser Ala Leu Thr Gly
370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Ala Ile Ala Leu Ile Ser Arg Asp His Ala Arg Thr Pro
            435                 440                 445
```

```
Met Gln Trp Ser Arg Glu Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
530                 535                 540

Ser Asp Ala Thr Asp Phe Lys Ile Pro Asn Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585
```

<210> SEQ ID NO 24
<211> LENGTH: 589
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 24

```
Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
                20                  25                  30

Asp Asp Gly Trp Gly Asp Met Lys Gly Ile Ser Ser Lys Leu Glu Tyr
            35                  40                  45

Ile Lys Glu Leu Gly Val Asp Ala Ile Trp Ile Ser Pro Phe Tyr Asp
50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
            100                 105                 110

Cys Ser Ser Glu His Glu Trp Phe Lys Glu Ser Arg Ser Ser Lys Thr
        115                 120                 125

Asn Pro Lys Arg Asp Trp Phe Phe Trp Arg Pro Lys Gly Tyr Asp
130                 135                 140

Ala Glu Gly Lys Pro Ile Pro Pro Asn Asn Trp Lys Ser Tyr Phe Gly
145                 150                 155                 160

Gly Ser Ala Trp Thr Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Val
210                 215                 220
```

```
Gly Leu Pro Asp Ala Pro Val Asp Lys Asn Ser Thr Trp Gln Ser
225                 230                 235                 240

Ser Asp Pro Tyr Thr Leu Asn Gly Pro Arg Ile His Glu Phe His Gln
            245                 250                 255

Glu Met Asn Gln Phe Ile Arg Asn Arg Val Lys Asp Gly Arg Glu Ile
        260                 265                 270

Met Thr Val Gly Glu Met Gln His Ala Ser Asp Glu Thr Lys Arg Leu
    275                 280                 285

Tyr Thr Ser Ala Ser Arg His Glu Leu Ser Glu Leu Phe Asn Phe Ser
290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Tyr
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Met Lys Lys
            420                 425                 430

Phe Leu Glu Ala Ile Ala Leu Ile Ser Arg Asp His Ala Arg Thr Pro
                435                 440                 445

Met Gln Trp Ser Arg Glu Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
    530                 535                 540

Ser Asp Ala Thr Asp Phe Lys Ile Pro Asn Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585

<210> SEQ ID NO 25
<211> LENGTH: 589
<212> TYPE: PRT
<213> ORGANISM: Unknown
<220> FEATURE:
<223> OTHER INFORMATION: Hybrid between S. cerevisiae and S. pastorianus
      (Hybrid yeast 7)
```

```
<400> SEQUENCE: 25

Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
                20                  25                  30

Asp Asp Gly Trp Gly Asp Met Lys Gly Ile Ser Ser Lys Leu Glu Tyr
            35                  40                  45

Ile Lys Glu Leu Gly Val Asp Ala Ile Trp Ile Ser Pro Phe Tyr Asp
50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
                100                 105                 110

Cys Ser Ser Glu His Glu Trp Phe Lys Glu Ser Arg Ser Ser Lys Thr
            115                 120                 125

Asn Pro Lys Arg Asp Trp Phe Phe Trp Arg Pro Pro Lys Gly Tyr Asp
130                 135                 140

Ala Glu Gly Lys Pro Ile Pro Pro Asn Asn Trp Lys Ser Tyr Phe Gly
145                 150                 155                 160

Gly Ser Ala Trp Ile Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Val
210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
                245                 250                 255

Glu Met Asn Gln Phe Ile Arg Asn Arg Val Lys Asp Gly Arg Glu Ile
            260                 265                 270

Met Thr Val Gly Glu Met Gln His Ala Ser Asp Glu Thr Lys Arg Leu
        275                 280                 285

Tyr Thr Ser Ala Ser Arg His Glu Leu Ser Glu Leu Phe Asn Phe Ser
290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Tyr
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415
```

-continued

```
Asn Ala Ile Lys Glu Glu His Gly Glu Asn Ser Glu Met Lys Lys
            420                 425                 430

Phe Leu Glu Ala Ile Ala Leu Ile Ser Arg Asp His Ala Arg Thr Pro
            435                 440                 445

Met Gln Trp Ser Arg Glu Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
    530                 535                 540

Ser Asp Ala Thr Asp Phe Lys Ile Pro Asn Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585
```

<210> SEQ ID NO 26
<211> LENGTH: 394
<212> TYPE: PRT
<213> ORGANISM: Unknown
<220> FEATURE:
<223> OTHER INFORMATION: Hybrid between S. cerevisiae and S. pastorianus
      (Hybrid yeast 4)

<400> SEQUENCE: 26

```
Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asn Phe Glu Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Met Ile Asn Glu Met Asn Ala
65                  70                  75                  80

Thr Asp Glu Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Asn
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Gln Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
```

```
                180             185             190
Leu Leu Thr Ala Tyr Ile Phe Ile Leu Tyr Tyr Cys Lys Ser Leu Ala
            195                 200             205

Met Ile Ala Val Gly Gln Val Leu Ser Ala Met Pro Trp Gly Cys Phe
            210                 215                 220

Gln Gly Leu Thr Val Thr Tyr Ala Ser Glu Val Cys Pro Leu Ala Leu
225                     230                 235                 240

Arg Tyr Tyr Met Thr Ser Tyr Ser Asn Ile Cys Trp Leu Phe Gly Gln
                    245                 250                 255

Ile Phe Ala Ser Gly Ile Met Lys Asn Ser Gln Glu Asn Leu Gly Asn
                260                 265                 270

Ser Asp Leu Asp Tyr Lys Leu Pro Phe Ala Leu Gln Trp Ile Trp Pro
            275                 280                 285

Ala Pro Leu Met Ile Gly Ile Phe Phe Ala Pro Glu Ser Pro Trp Trp
            290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                    325                 330                 335

Leu Lys Gln Ile Glu Leu Thr Ile Glu Lys Glu Arg Leu Leu Ala Ser
                340                 345                 350

Lys Ser Gly Ser Phe Phe Asp Cys Phe Lys Gly Val Asn Gly Arg Arg
            355                 360                 365

Thr Arg Leu Ala Cys Leu Ala Trp Val Ala Gln Asn Thr Ser Gly Ala
            370                 375                 380

Cys Leu Leu Gly Tyr Ser Thr Tyr Phe Phe
385                     390

<210> SEQ ID NO 27
<211> LENGTH: 610
<212> TYPE: PRT
<213> ORGANISM: Unknown
<220> FEATURE:
<223> OTHER INFORMATION: Hybrid between S. cerevisiae and S. pastorianus
      (Hybrid yeast 4)

<400> SEQUENCE: 27

Met Lys Asn Ile Leu Ser Leu Val Gly Arg Lys Glu Asn Thr Pro Glu
1               5                   10                  15

Asp Val Thr Ala Asn Leu Ala Asp Thr Ser Ser Thr Val Met Gln
            20                  25                  30

Ala Lys Asp Leu Val Ile Glu Asp Phe Glu Glu Arg Lys Lys Asn Asp
            35                  40                  45

Ala Phe Glu Leu Asn His Leu Glu Leu Thr Thr Asn Ala Thr Gln Leu
        50                  55                  60

Ser Asp Ser Asp Glu Asp Lys Glu Asn Val Ile Arg Val Ala Glu Ala
65                  70                  75                  80

Thr Asp Asp Ala Asn Glu Ala Asn Asn Glu Glu Lys Ser Met Thr Leu
                85                  90                  95

Arg Gln Ala Leu Arg Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
            115                 120                 125

Ala Leu Tyr Ala Leu Pro Val Phe Gln Arg Lys Phe Gly Thr Met Asn
        130                 135                 140
```

```
Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Ser
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Met Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Ile Ile Gly Ile Phe Phe Ala Pro Glu Ser Pro Trp Trp
    290                 295                 300

Leu Val Arg Lys Asn Lys Ile Val Glu Ala Lys Lys Ser Leu Asn Arg
305                 310                 315                 320

Ile Leu Ser Gly Thr Val Thr Glu Lys Glu Ile Gln Val Asp Ile Thr
                325                 330                 335

Leu Lys Gln Ile Glu Met Thr Ile Glu Lys Glu Arg Leu Arg Ala Ser
            340                 345                 350

Lys Ser Gly Ser Phe Phe Ser Cys Phe Lys Gly Val Asp Gly Arg Arg
        355                 360                 365

Thr Arg Leu Ala Cys Leu Thr Trp Val Ala Gln Asn Ser Ser Gly Ala
    370                 375                 380

Val Leu Leu Gly Tyr Ser Thr Tyr Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Gly Ser Trp Val Ile Ser Gly Arg Val Gly Arg Trp
            420                 425                 430

Thr Ile Leu Thr Tyr Gly Leu Ser Phe Gln Met Val Cys Leu Phe Ile
        435                 440                 445

Ile Gly Gly Met Gly Phe Ala Ser Gly Ser Ala Ser Asn Ala Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Phe Asn Ala Ile Leu Thr Pro Tyr Met Leu Asn Val Ser Asp Trp Asn
        515                 520                 525

Trp Gly Ala Lys Thr Gly Leu Tyr Trp Gly Asp Phe Thr Ala Leu Thr
    530                 535                 540

Leu Ala Trp Val Ile Ile Asp Leu Pro Glu Thr Thr Gly Arg Thr Phe
545                 550                 555                 560

Ser Glu Ile Asn Glu Leu Phe Ser Gln Gly Val Pro Ala Arg Lys Phe
```

```
                  565                 570                 575
Ala Ser Thr Val Val Asp Pro Phe Gly Lys Arg Gly Leu Gln Asn Arg
            580                 585                 590

Pro Gln Val Asp Asn Ile Ile Asp Arg Phe Ser Ser Ala Ser Gln Gln
        595                 600                 605

Ala Leu
    610

<210> SEQ ID NO 28
<211> LENGTH: 610
<212> TYPE: PRT
<213> ORGANISM: Unknown
<220> FEATURE:
<223> OTHER INFORMATION: Hybrid between S. cerevisiae and S. pastorianus
      (Hybrid yeast 4)

<400> SEQUENCE: 28

Met Lys Asn Ile Leu Ser Leu Val Gly Arg Lys Glu Asn Thr Pro Glu
1               5                   10                  15

Asp Val Thr Ala Asn Leu Ala Asp Thr Ser Ser Thr Val Met Gln
            20                  25                  30

Ala Lys Asp Leu Val Ile Glu Asp Phe Glu Arg Lys Lys Asn Asp
        35                  40                  45

Ala Phe Glu Leu Asn His Leu Glu Leu Thr Thr Asn Ala Thr Gln Leu
    50                  55                  60

Ser Asp Ser Asp Glu Asp Lys Glu Asn Val Ile Arg Val Ala Glu Ala
65                  70                  75                  80

Thr Asp Asp Ala Asn Glu Ala Asn Asn Glu Glu Lys Ser Met Thr Leu
                85                  90                  95

Arg Gln Ala Leu Arg Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Met Asn
    130                 135                 140

Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Ser
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Met Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Ile Ile Gly Ile Phe Phe Ala Pro Glu Ser Pro Trp Trp
    290                 295                 300
```

```
Leu Val Arg Lys Asn Lys Ile Val Glu Ala Lys Ser Leu Asn Arg
305                 310                 315                 320

Ile Leu Ser Gly Thr Val Thr Glu Lys Glu Ile Gln Val Asp Ile Thr
            325                 330                 335

Leu Lys Gln Ile Glu Met Thr Ile Glu Lys Glu Arg Leu Arg Ala Ser
                340                 345                 350

Lys Ser Gly Ser Phe Phe Ser Cys Phe Lys Gly Val Asp Gly Arg Arg
            355                 360                 365

Thr Arg Leu Ala Cys Leu Thr Trp Val Ala Gln Asn Ser Ser Gly Ala
370                 375                 380

Val Leu Gly Tyr Ser Thr Tyr Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Gly Ser Trp Val Ile Ser Gly Arg Val Gly Arg Trp
            420                 425                 430

Thr Ile Leu Thr Tyr Gly Leu Ser Phe Gln Met Val Cys Leu Phe Ile
                435                 440                 445

Ile Gly Gly Met Gly Phe Ala Ser Gly Ser Ser Ala Ser Asn Ala Ala
450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Phe Asn Ala Ile Leu Thr Pro Tyr Met Leu Asn Val Ser Asp Trp Asn
                515                 520                 525

Trp Gly Ala Lys Thr Gly Leu Tyr Trp Gly Gly Phe Thr Ala Leu Thr
530                 535                 540

Leu Ala Trp Val Ile Ile Asp Leu Pro Glu Thr Thr Gly Arg Thr Phe
545                 550                 555                 560

Ser Glu Ile Asn Glu Leu Phe Ser Gln Gly Val Pro Ala Arg Lys Phe
                565                 570                 575

Ala Ser Thr Val Val Asp Pro Phe Gly Lys Arg Gly Leu Gln Asn Arg
            580                 585                 590

Pro Gln Val Asp Asn Ile Ile Asp Arg Phe Ser Ser Ala Ser Gln Gln
                595                 600                 605

Ala Leu
    610

<210> SEQ ID NO 29
<211> LENGTH: 394
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 29

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
                20                  25                  30

Gln Glu Val Phe Asn Thr Glu Asn Phe Glu Glu Gly Lys Lys Asp Ser
            35                  40                  45
```

```
Ala Phe Glu Leu Asp His Leu Glu Phe Thr Thr Asn Ser Ala Gln Leu
        50                  55                  60

Gly Asp Ser Asp Glu Asp Asn Glu Asn Met Ile Asn Glu Met Asn Ala
 65                  70                  75                  80

Thr Asp Glu Ala Asn Glu Ala Asn Ser Glu Glu Lys Ser Met Thr Leu
                     85                  90                  95

Lys Gln Ala Leu Leu Lys Tyr Pro Lys Ala Ala Leu Trp Ser Ile Leu
                100                 105                 110

Val Ser Thr Thr Leu Val Met Glu Gly Tyr Asp Thr Ala Leu Leu Asn
            115                 120                 125

Ala Leu Tyr Ala Leu Pro Val Phe Gln Arg Lys Phe Gly Thr Leu Asn
130                 135                 140

Gly Glu Gly Ser Tyr Glu Ile Thr Ser Gln Trp Gln Ile Gly Leu Asn
145                 150                 155                 160

Met Cys Val Gln Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
                180                 185                 190

Leu Leu Thr Ala Tyr Ile Phe Ile Leu Tyr Tyr Cys Lys Ser Leu Ala
            195                 200                 205

Met Ile Ala Val Gly Gln Val Leu Ser Ala Met Pro Trp Gly Cys Phe
210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
                260                 265                 270

Ser Asp Leu Asp Tyr Lys Leu Pro Phe Ala Leu Gln Trp Ile Trp Pro
            275                 280                 285

Ala Pro Leu Met Ile Gly Ile Phe Phe Ala Pro Glu Ser Pro Trp Trp
290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
                340                 345                 350

Lys Ser Gly Ser Phe Phe Asp Cys Phe Lys Gly Val Asn Gly Arg Arg
            355                 360                 365

Thr Arg Leu Ala Cys Leu Ala Trp Val Ala Gln Asn Thr Ser Gly Ala
370                 375                 380

Cys Leu Leu Gly Tyr Ser Thr Tyr Phe Phe
385                 390
```

<210> SEQ ID NO 30
<211> LENGTH: 616
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 30

Met Lys Asn Ile Ile Ser Leu Val Ser Lys Lys Lys Ala Ala Ser Lys

-continued

```
1               5                   10                  15
Asn Glu Asp Lys Asn Ile Ser Glu Ser Ser Arg Asp Ile Val Asn Gln
                20                  25                  30
Gln Glu Val Phe Asn Thr Glu Asn Phe Glu Glu Gly Arg Lys Asp Ser
                35                  40                  45
Ala Phe Glu Leu Asp His Leu Glu Phe Thr Ile Asn Ser Ala Gln Leu
                50                  55                  60
Gly Asp Ser Asp Glu Asp Asn Glu Asn Val Ile Asn Glu Thr Asn Thr
65                  70                  75                  80
Thr Asp Asp Ala Asn Glu Ala Asn Ser Glu Glu Lys Ser Met Thr Leu
                85                  90                  95
Lys Gln Ala Leu Leu Ile Tyr Pro Lys Ala Ala Leu Trp Ser Ile Leu
                100                 105                 110
Val Ser Thr Thr Leu Val Met Glu Gly Tyr Asp Thr Ala Leu Leu Asn
                115                 120                 125
Ala Leu Tyr Ala Leu Pro Val Phe Gln Arg Lys Phe Gly Thr Leu Asn
                130                 135                 140
Gly Glu Gly Ser Tyr Glu Ile Thr Ser Gln Trp Gln Ile Gly Leu Asn
145                 150                 155                 160
Met Cys Val Gln Cys Gly Glu Ile Ile Gly Leu Gln Ile Thr Pro Tyr
                165                 170                 175
Met Val Glu Phe Met Gly Asn Arg Tyr Thr Met Ile Thr Ala Leu Gly
                180                 185                 190
Leu Leu Thr Ala Tyr Val Phe Ile Leu Tyr Tyr Cys Lys Ser Leu Ala
                195                 200                 205
Met Ile Ala Val Gly Gln Val Leu Ser Ala Met Pro Trp Gly Cys Phe
210                 215                 220
Gln Gly Leu Thr Val Thr Tyr Ala Ser Glu Val Cys Pro Leu Ala Leu
225                 230                 235                 240
Arg Tyr Tyr Met Thr Ser Tyr Ser Asn Ile Cys Trp Leu Phe Gly Gln
                245                 250                 255
Ile Phe Ala Ser Gly Ile Met Lys Asn Ser Gln Glu Asn Leu Gly Asn
                260                 265                 270
Ser Asp Leu Gly Tyr Lys Leu Pro Phe Ala Leu Gln Trp Ile Trp Pro
                275                 280                 285
Ala Pro Leu Met Ile Gly Ile Phe Phe Ala Pro Glu Ser Pro Trp Trp
                290                 295                 300
Leu Val Arg Lys Asp Arg Val Ala Glu Ala Arg Lys Ser Leu Ser Arg
305                 310                 315                 320
Ile Leu Ser Gly Lys Gly Ala Glu Lys Asp Ile Gln Ile Asp Leu Thr
                325                 330                 335
Leu Lys Gln Ile Glu Leu Thr Ile Glu Lys Glu Arg Leu Leu Ala Ser
                340                 345                 350
Lys Ser Gly Ser Phe Phe Asp Cys Phe Lys Gly Val Asn Gly Arg Arg
                355                 360                 365
Thr Arg Leu Ala Cys Leu Thr Trp Val Ala Gln Asn Thr Ser Gly Ala
                370                 375                 380
Cys Leu Leu Gly Tyr Ser Thr Tyr Phe Glu Arg Ala Gly Met Ala
385                 390                 395                 400
Thr Asp Lys Ala Phe Thr Phe Ser Val Ile Gln Tyr Cys Leu Gly Leu
                405                 410                 415
Ala Gly Thr Leu Cys Ser Trp Val Ile Ser Gly Arg Val Gly Arg Trp
                420                 425                 430
```

```
Thr Ile Leu Thr Tyr Gly Leu Ala Phe Gln Met Val Cys Leu Phe Ile
        435                 440                 445

Ile Gly Gly Met Gly Phe Gly Ser Gly Ser Gly Ala Ser Asn Gly Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Thr Glu Ile Pro Ser Ala Glu Leu Arg
                485                 490                 495

Thr Lys Thr Ile Val Leu Ala Arg Ile Cys Tyr Asn Ile Met Ala Val
            500                 505                 510

Ile Asn Ala Ile Leu Thr Pro Tyr Met Leu Asn Val Ser Asp Trp Asn
        515                 520                 525

Trp Gly Ala Lys Thr Gly Leu Tyr Trp Gly Gly Phe Thr Ala Val Thr
    530                 535                 540

Leu Ala Trp Val Ile Ile Asp Leu Pro Glu Thr Ser Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Asp Asp Glu Ser Ile Ser Gln Ser Ser Ile Lys Gln Arg
        595                 600                 605

Glu Leu Asn Ala Ala Asp Lys Cys
610                 615
```

<210> SEQ ID NO 31
<211> LENGTH: 610
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 31

```
Met Lys Asn Ile Leu Ser Leu Val Gly Arg Lys Glu Asn Thr Pro Glu
1               5                   10                  15

Asp Val Thr Ala Asn Leu Ala Asp Thr Ser Ser Thr Thr Val Met Gln
            20                  25                  30

Ala Lys Asp Leu Val Ile Glu Asp Phe Glu Glu Arg Lys Lys Asn Asp
        35                  40                  45

Ala Phe Glu Leu Asn His Leu Glu Leu Thr Thr Asn Ala Thr Gln Leu
    50                  55                  60

Ser Asp Ser Asp Glu Asp Lys Glu Asn Val Ile Arg Val Ala Glu Ala
65                  70                  75                  80

Thr Asp Asp Ala Asn Glu Ala Asn Asn Glu Glu Lys Ser Met Thr Leu
                85                  90                  95

Arg Gln Ala Leu Arg Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Met Asn
    130                 135                 140

Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
```

```
            165                 170                 175
Met Val Glu Phe Met Gly Asn Arg Tyr Thr Met Ile Thr Ala Leu Ser
            180                 185                 190

Leu Leu Thr Ala Tyr Ile Phe Ile Leu Tyr Tyr Cys Lys Ser Leu Ala
            195                 200                 205

Met Ile Ala Val Gly Gln Ile Leu Ser Ala Met Pro Trp Gly Cys Phe
210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
                260                 265                 270

Ser Asp Leu Gly Tyr Lys Leu Pro Phe Ala Leu Gln Trp Ile Trp Pro
            275                 280                 285

Ala Pro Leu Ile Ile Gly Ile Phe Phe Ala Pro Glu Ser Pro Trp Trp
            290                 295                 300

Leu Val Arg Lys Asn Lys Ile Val Glu Ala Lys Lys Ser Leu Asn Arg
305                 310                 315                 320

Ile Leu Ser Gly Thr Val Thr Glu Lys Glu Ile Gln Val Asp Ile Thr
                325                 330                 335

Leu Lys Gln Ile Glu Met Thr Ile Glu Lys Glu Arg Leu Arg Ala Ser
            340                 345                 350

Lys Ser Gly Ser Phe Phe Ser Cys Phe Lys Gly Val Asp Gly Arg Arg
            355                 360                 365

Thr Arg Leu Ala Cys Leu Thr Trp Val Ala Gln Asn Ser Ser Gly Ala
370                 375                 380

Val Leu Leu Gly Tyr Ser Thr Tyr Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Gly Ser Trp Val Ile Ser Gly Arg Val Gly Arg Trp
            420                 425                 430

Thr Ile Leu Thr Tyr Gly Leu Ser Phe Gln Met Val Cys Leu Phe Ile
            435                 440                 445

Ile Gly Gly Met Gly Phe Ala Ser Gly Ser Ser Ala Ser Asn Ala Ala
            450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Phe Asn Ala Ile Leu Thr Pro Tyr Met Leu Asn Val Ser Asp Trp Asn
            515                 520                 525

Trp Gly Ala Lys Thr Gly Leu Tyr Trp Gly Gly Phe Thr Ala Leu Thr
            530                 535                 540

Leu Ala Trp Val Ile Ile Asp Leu Pro Glu Thr Thr Gly Arg Thr Phe
545                 550                 555                 560

Ser Glu Ile Asn Glu Leu Phe Ser Gln Gly Val Pro Ala Arg Lys Phe
                565                 570                 575

Ala Ser Thr Val Val Asp Pro Phe Gly Lys Arg Gly Leu Gln Asn Arg
            580                 585                 590
```

```
Pro Gln Val Asp Asn Ile Ile Asp Arg Phe Ser Ser Ala Ser Gln Gln
        595                 600                 605

Ala Leu
    610

<210> SEQ ID NO 32
<211> LENGTH: 610
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 32

Met Lys Asn Ile Leu Ser Leu Val Gly Arg Lys Glu Asn Thr Pro Glu
1               5                   10                  15

Asp Val Thr Ala Asn Leu Ala Asp Thr Ser Ser Thr Val Met Gln
            20                  25                  30

Ala Lys Asp Leu Val Ile Glu Asp Phe Glu Glu Arg Lys Lys Asn Asp
            35                  40                  45

Ala Phe Glu Leu Asn His Leu Glu Leu Thr Thr Asn Ala Thr Gln Leu
    50                  55                  60

Ser Asp Ser Asp Glu Asp Lys Glu Asn Val Ile Arg Val Ala Glu Ala
65                  70                  75                  80

Thr Asp Ala Asn Glu Ala Asn Asn Glu Lys Ser Met Thr Leu
                85                  90                  95

Arg Gln Ala Leu Arg Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
            115                 120                 125

Ala Leu Tyr Ala Leu Pro Val Phe Gln Arg Lys Phe Gly Thr Met Asn
    130                 135                 140

Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Ser
            180                 185                 190

Leu Leu Thr Ala Tyr Ile Phe Ile Leu Tyr Tyr Cys Lys Ser Leu Ala
    195                 200                 205

Met Ile Ala Val Gly Gln Ile Leu Ser Ala Met Pro Trp Gly Cys Phe
210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
    275                 280                 285

Ala Pro Leu Ile Ile Gly Ile Phe Phe Ala Pro Glu Ser Pro Trp Trp
            290                 295                 300

Leu Val Arg Lys Asn Lys Ile Val Glu Ala Lys Lys Ser Leu Asn Arg
305                 310                 315                 320

Ile Leu Ser Gly Thr Val Thr Glu Lys Glu Ile Gln Val Asp Ile Thr
```

```
                    325                 330                 335
Leu Lys Gln Ile Glu Met Thr Ile Glu Lys Glu Arg Leu Arg Ala Ser
                340                 345                 350
Lys Ser Gly Ser Phe Phe Ser Cys Phe Lys Gly Val Asp Gly Arg Arg
            355                 360                 365
Thr Arg Leu Ala Cys Leu Thr Trp Val Ala Gln Asn Ser Ser Gly Ala
        370                 375                 380
Val Leu Leu Gly Tyr Ser Thr Tyr Phe Glu Arg Ala Gly Met Ala
385                 390                 395                 400
Thr Asp Lys Ala Phe Thr Phe Ser Leu Ile Gln Tyr Cys Leu Gly Leu
                405                 410                 415
Ala Gly Thr Leu Gly Ser Trp Val Ile Ser Gly Arg Val Gly Arg Trp
                420                 425                 430
Thr Ile Leu Thr Tyr Gly Leu Ser Phe Gln Met Val Cys Leu Phe Ile
                435                 440                 445
Ile Gly Gly Met Gly Phe Ala Ser Gly Ser Ser Ala Ser Asn Ala Ala
            450                 455                 460
Gly Gly Leu Leu Leu Ala Leu Ser Phe Phe Tyr Asn Ala Gly Ile Gly
465                 470                 475                 480
Ala Val Val Tyr Cys Ile Val Ala Glu Ile Pro Ser Ala Glu Leu Arg
                485                 490                 495
Thr Lys Thr Ile Val Leu Ala Arg Ile Cys Tyr Asn Leu Met Ala Val
                500                 505                 510
Phe Asn Ala Ile Leu Thr Pro Tyr Met Leu Asn Val Ser Asp Trp Asn
                515                 520                 525
Trp Gly Ala Lys Thr Gly Leu Tyr Trp Gly Gly Phe Thr Ala Leu Thr
            530                 535                 540
Leu Ala Trp Val Ile Ile Asp Leu Pro Glu Thr Thr Gly Arg Thr Phe
545                 550                 555                 560
Gly Glu Ile Asn Glu Leu Phe Ser Gln Gly Val Pro Ala Arg Lys Phe
                565                 570                 575
Ala Ser Thr Val Val Asp Pro Phe Gly Lys Arg Gly Leu Gln Asn Arg
                580                 585                 590
Pro Gln Val Asp Asn Ile Ile Asp Arg Phe Ser Ser Ala Ser Gln Gln
                595                 600                 605
Ala Leu
    610

<210> SEQ ID NO 33
<211> LENGTH: 520
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 33

Met Gly Tyr Asp Ile Ala Asn Tyr Glu Lys Val Trp Pro Thr Tyr Gly
1               5                  10                  15
Thr Asn Glu Asp Cys Phe Ala Leu Ile Glu Lys Thr His Lys Leu Gly
            20                  25                  30
Met Lys Phe Ile Thr Asp Leu Val Ile Asn His Cys Ser Ser Glu His
        35                  40                  45
Glu Trp Phe Lys Glu Ser Arg Ser Ser Lys Thr Asn Pro Lys Arg Asp
    50                  55                  60
```

```
Trp Phe Phe Trp Arg Pro Pro Lys Gly Tyr Asp Ala Glu Gly Lys Pro
 65                  70                  75                  80

Ile Pro Pro Asn Asn Trp Lys Ser Tyr Phe Gly Gly Ser Ala Trp Thr
                 85                  90                  95

Phe Asp Glu Lys Thr Gln Glu Phe Tyr Leu Arg Leu Phe Cys Ser Thr
            100                 105                 110

Gln Pro Asp Leu Asn Trp Glu Asn Glu Asp Cys Arg Lys Ala Ile Tyr
        115                 120                 125

Glu Ser Ala Val Gly Tyr Trp Leu Asp His Gly Val Asp Gly Phe Arg
    130                 135                 140

Ile Asp Val Gly Ser Leu Tyr Ser Lys Val Val Gly Leu Pro Asp Ala
145                 150                 155                 160

Pro Val Val Asp Lys Asn Ser Thr Trp Gln Ser Ser Asp Pro Tyr Thr
                165                 170                 175

Leu Asn Gly Pro Arg Ile His Glu Phe His Gln Glu Met Asn Gln Phe
            180                 185                 190

Ile Arg Asn Arg Val Lys Asp Gly Arg Glu Ile Met Thr Val Gly Glu
        195                 200                 205

Met Gln His Ala Ser Asp Glu Thr Lys Arg Leu Tyr Thr Ser Ala Ser
    210                 215                 220

Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
                245                 250                 255

Trp Lys Ile Ala Leu Ala Glu Leu Phe Arg Phe Ile Asn Gly Thr Asp
            260                 265                 270

Cys Trp Ser Thr Ile Tyr Leu Glu Asn His Asp Gln Pro Arg Ser Ile
        275                 280                 285

Thr Arg Phe Gly Asp Asp Ser Pro Lys Asn Arg Val Ile Ser Gly Lys
    290                 295                 300

Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Ser Val Glu
                325                 330                 335

Lys Tyr Glu Asp Val Glu Ile Arg Asn Asn Tyr Arg Leu Ile Lys Glu
            340                 345                 350

Glu Cys Gly Glu Asn Ser Glu Met Lys Lys Phe Leu Glu Gly Ile
        355                 360                 365

Ala Leu Val Ser Arg Asp His Ala Arg Thr Pro Met Pro Trp Thr Pro
    370                 375                 380

Asn Glu Pro Asn Ala Gly Phe Ser Gly Pro Asn Thr Lys Pro Trp Phe
385                 390                 395                 400

Tyr Leu Asn Glu Ser Phe Arg Gln Gly Ile Asn Val Glu Glu Glu Gln
                405                 410                 415

Lys Asn Ser Asp Ser Val Leu Ala Phe Trp Lys Ala Leu Glu Phe
            420                 425                 430

Arg Lys Asn His Lys Asp Ile Ala Val Tyr Gly Phe Asp Phe Lys Phe
    435                 440                 445

Ile Asp Leu Asp Asn Lys Lys Leu Phe Ser Phe Thr Lys Arg Tyr Asn
        450                 455                 460

Asn Lys Thr Leu Phe Ala Ala Leu Asn Phe Ser Ser Asp Ala Thr Asp
465                 470                 475                 480

Phe Lys Ile Pro Asn Asp Gly Ser Ser Phe Lys Leu Glu Phe Gly Asn
```

-continued

```
                485                 490                 495
Tyr Pro Lys Asn Glu Val Asp Ala Ser Ser Arg Thr Leu Lys Pro Trp
            500                 505                 510
Glu Gly Arg Ile His Ile Asn Glu
            515                 520

<210> SEQ ID NO 34
<211> LENGTH: 581
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 34

Met Thr Ile Ile His Asn Pro Lys Trp Trp Lys Glu Ala Thr Val Tyr
  1               5                  10                  15

Gln Ile Tyr Pro Ala Ser Asn Lys Asp Ser Asn Asn Asp Gly Trp Gly
                 20                  25                  30

Asp Leu Ala Gly Ile Thr Ser Lys Leu Asp Tyr Val Lys Glu Leu Gly
             35                  40                  45

Val Asp Ala Ile Trp Val Cys Leu Phe Tyr Asp Ser Pro Gln Glu Asp
 50                  55                  60

Met Gly Tyr Asp Ile Ala Asn Tyr Glu Lys Val Trp Pro Arg Tyr Gly
 65                  70                  75                  80

Thr Asn Glu Asp Cys Phe Gln Met Ile Glu Glu Ala His Lys Arg Gly
                 85                  90                  95

Ile Lys Val Ile Val Asp Leu Val Ile Asn His Cys Ser Glu Glu His
            100                 105                 110

Glu Trp Phe Lys Glu Ser Lys Ser Ser Lys Thr Asn Pro Lys Arg Asp
        115                 120                 125

Trp Phe Phe Trp Arg Pro Pro Lys Gly Phe Asp Glu Lys Gly Asn Pro
130                 135                 140

Ile Pro Pro Asn Asn Trp Arg Ser Phe Phe Gly Gly Ser Ala Trp Arg
145                 150                 155                 160

Tyr Asp Glu Lys Thr Gly Glu Phe Phe Leu His Val Phe Ala Pro Gly
                165                 170                 175

Gln Pro Asp Phe Asn Trp Glu Asn Glu Glu Cys Arg Lys Ala Ile Tyr
            180                 185                 190

Asp Ser Ser Val Gly Tyr Trp Leu Arg His Asn Val Asp Gly Phe Arg
        195                 200                 205

Ile Asp Val Gly Ser Met Tyr Ser Lys Val Glu Gly Leu Pro Asp Ala
    210                 215                 220

Pro Ile Thr Asp Pro Thr Val Pro Tyr Gln Lys Gly Thr Glu Phe Phe
225                 230                 235                 240

Ile Asn Gly Pro Arg Ile His Glu Tyr His Lys Glu Met Arg Lys Tyr
                245                 250                 255

Met Leu Ser Gln Ile Pro Glu Gly Lys Glu Ile Met Thr Val Gly Glu
            260                 265                 270

Val Gly Val Gly Asn Glu Glu Asp Phe Arg Asp Tyr Thr Ser Ala Lys
        275                 280                 285

Glu Gly Glu Leu Asn Met Met Phe Asn Phe Lys His Thr Ser Val Gly
    290                 295                 300

Glu Ser Pro Glu Cys Lys Tyr Glu Leu Ile Pro Phe Thr Leu Lys Asp
305                 310                 315                 320
```

```
Phe Lys Leu Ala Leu Ala Glu Ser Phe Leu Phe Ile Glu Asn Thr Asp
                325                 330                 335

Cys Trp Ser Thr Ile Tyr Leu Glu Asn His Asp Gln Pro Arg Ser Val
            340                 345                 350

Ser Arg Phe Gly Ser Asp Ser Pro Lys Trp Arg Ala Ile Ser Ser Lys
        355                 360                 365

Met Leu Ala Thr Leu Ile Ile Ser Leu Thr Gly Thr Val Phe Ile Tyr
    370                 375                 380

Gln Gly Gln Glu Leu Gly Met Ser Asn Phe Lys Asn Arg Arg Ile Glu
385                 390                 395                 400

Gln Ile Lys Cys Val Glu Gly Thr Gly Thr Tyr Ala Ala Ile Lys Arg
                405                 410                 415

Asp Tyr Gly Glu Asp Ser Glu Lys Met Lys Lys Phe Glu Ala Leu
            420                 425                 430

Ala Leu Ile Ser Arg Asp His Gly Arg Thr Pro Phe Pro Trp Ser Ala
        435                 440                 445

Asp Glu Pro Ser Ala Gly Phe Ser Lys Asp Ala Lys Pro Trp Ile Asp
    450                 455                 460

Met Asn Glu Ser Phe Arg Asp Gly Ile Asn Ala Glu Ala Glu Leu Lys
465                 470                 475                 480

Asp Lys Asn Ser Val Phe Phe Trp Lys Lys Ala Leu Gln Val Arg
                485                 490                 495

Lys Glu His Lys Asp Ile Leu Val Tyr Gly His Asn Phe Gln Phe Ile
            500                 505                 510

Asp Leu Asp Asn Asp Lys Leu Phe Met Phe Thr Lys Asp Thr Asp Asn
        515                 520                 525

Lys Lys Met Phe Ala Val Phe Asn Phe Ser Ser Asp Asn Thr Asp Phe
    530                 535                 540

Ser Val Pro Asp Asn Glu Ala Ser Tyr Thr Met Phe Phe Gly Asn Tyr
545                 550                 555                 560

Ala Asn Ser Asn Gly Asp Ser Arg Thr Leu Gln Pro Trp Glu Gly Arg
                565                 570                 575

Leu Tyr Leu Leu Lys
            580

<210> SEQ ID NO 35
<211> LENGTH: 581
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 35

Met Thr Ile Ile His Asn Pro Lys Trp Trp Lys Glu Ala Thr Val Tyr
1               5                   10                  15

Gln Ile Tyr Pro Ala Ser Asn Lys Asp Ser Asn Asn Asp Gly Trp Gly
                20                  25                  30

Asp Leu Ala Gly Ile Thr Ser Lys Leu Asp Tyr Val Lys Glu Leu Gly
            35                  40                  45

Val Asp Ala Ile Trp Val Cys Leu Phe Tyr Asp Ser Pro Gln Glu Asp
        50                  55                  60

Met Gly Tyr Asp Ile Ala Asn Tyr Glu Lys Val Trp Pro Arg Tyr Gly
65                  70                  75                  80

Thr Asn Glu Asp Cys Phe Gln Met Ile Glu Glu Ala His Lys Arg Gly
                85                  90                  95
```

```
Ile Lys Val Ile Val Asp Leu Val Ile Asn His Cys Ser Glu Glu His
            100                 105                 110

Glu Trp Phe Lys Glu Ser Lys Ser Ser Lys Thr Asn Pro Lys Arg Asp
            115                 120                 125

Trp Phe Phe Trp Arg Pro Pro Lys Gly Phe Asp Glu Lys Gly Asn Pro
130                 135                 140

Ile Pro Pro Asn Asn Trp Arg Ser Phe Phe Gly Gly Ser Ala Trp Arg
145                 150                 155                 160

Tyr Asp Glu Lys Thr Gly Glu Phe Phe Leu His Val Phe Ala Pro Gly
                165                 170                 175

Gln Pro Asp Phe Asn Trp Glu Asn Glu Lys Cys Arg Lys Ala Ile Tyr
            180                 185                 190

Asp Ser Ser Val Gly Tyr Trp Leu Arg His Asn Val Asp Gly Phe Arg
            195                 200                 205

Ile Asp Val Gly Ser Met Tyr Ser Lys Val Glu Gly Leu Pro Asp Ala
            210                 215                 220

Pro Ile Thr Asp Pro Thr Val Pro Tyr Gln Lys Gly Thr Glu Phe Phe
225                 230                 235                 240

Ile Asn Gly Pro Arg Ile His Glu Tyr His Lys Glu Met Arg Lys Tyr
                245                 250                 255

Met Leu Ser Gln Ile Pro Glu Gly Lys Glu Ile Met Thr Val Gly Glu
            260                 265                 270

Val Gly Val Gly Asn Glu Glu Asp Phe Arg Asp Tyr Thr Ser Ala Lys
            275                 280                 285

Glu Gly Glu Leu Asn Met Met Phe Asn Phe Lys His Thr Ser Val Gly
            290                 295                 300

Glu Ser Pro Glu Cys Lys Tyr Glu Leu Ile Pro Phe Thr Leu Lys Asp
305                 310                 315                 320

Phe Lys Leu Ala Leu Ala Glu Ser Phe Leu Phe Ile Glu Asn Thr Asp
                325                 330                 335

Cys Trp Ser Thr Ile Tyr Leu Glu Asn His Asp Gln Pro Arg Ser Val
            340                 345                 350

Ser Arg Phe Gly Ser Asp Ser Pro Lys Trp Arg Ala Ile Ser Ser Lys
            355                 360                 365

Met Leu Ala Thr Leu Ile Ile Ser Leu Thr Gly Thr Val Phe Ile Tyr
            370                 375                 380

Gln Gly Gln Glu Leu Gly Met Ser Asn Phe Lys Asn Arg Arg Ile Glu
385                 390                 395                 400

Gln Ile Lys Cys Val Glu Gly Thr Gly Thr Tyr Ala Ala Ile Lys Arg
                405                 410                 415

Asp Tyr Gly Glu Asp Ser Glu Lys Met Lys Lys Phe Phe Glu Ala Leu
            420                 425                 430

Ala Leu Ile Ser Arg Asp His Gly Arg Thr Pro Phe Pro Trp Ser Ala
            435                 440                 445

Asp Glu Pro Ser Ala Gly Phe Ser Lys Asp Ala Lys Pro Trp Ile Asp
            450                 455                 460

Met Asn Glu Ser Phe Arg Asp Gly Ile Asn Ala Glu Ala Glu Leu Lys
465                 470                 475                 480

Asp Lys Asn Ser Val Phe Phe Trp Lys Lys Ala Leu Gln Val Arg
                485                 490                 495

Lys Glu His Lys Asp Ile Leu Val Tyr Gly His Asn Phe Gln Phe Ile
            500                 505                 510
```

```
Asp Leu Asp Asn Asp Lys Leu Phe Met Phe Thr Lys Asp Thr Asp Asn
            515                 520                 525

Lys Lys Met Phe Ala Val Phe Asn Phe Ser Ser Asp Asn Thr Asp Phe
530                 535                 540

Ser Val Pro Asp Asn Glu Ala Ser Tyr Thr Met Phe Phe Gly Asn Tyr
545                 550                 555                 560

Ala Asn Ser Asn Gly Asp Ser Arg Thr Leu Gln Pro Trp Glu Gly Arg
                565                 570                 575

Leu Tyr Leu Leu Lys
            580

<210> SEQ ID NO 36
<211> LENGTH: 575
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 36

Pro Lys Trp Trp Lys Glu Ala Thr Ile Tyr Gln Ile Tyr Pro Ala Ser
1               5                   10                  15

Phe Lys Asp Ser Asn Asn Asp Gly Trp Gly Asp Leu Ala Gly Ile Thr
            20                  25                  30

Ser Lys Leu Asp Tyr Ile Lys Glu Leu Gly Val Asp Ala Ile Trp Val
        35                  40                  45

Cys Pro Phe Tyr Asp Ser Pro Gln Glu Asp Met Gly Tyr Asp Ile Ala
    50                  55                  60

Asn Tyr Glu Lys Val Trp Pro Arg Tyr Gly Thr Ser Glu Asp Cys Phe
65                  70                  75                  80

Gln Met Ile Glu Glu Ser His Lys Arg Gly Ile Lys Val Ile Val Asp
                85                  90                  95

Leu Val Ile Asn His Cys Ser Glu Glu His Glu Trp Phe Lys Glu Ser
            100                 105                 110

Arg Ser Ser Lys Thr Asn Ala Lys Arg Asp Trp Phe Phe Trp Lys Pro
        115                 120                 125

Pro Lys Gly Tyr Glu Ile Asp Gly Thr Pro Ile Pro Pro Asn Asn Trp
    130                 135                 140

Arg Ser Phe Phe Gly Gly Ser Ala Trp Lys Tyr Asp Glu Asn Thr Glu
145                 150                 155                 160

Glu Phe Phe Leu His Val Phe Ala Pro Gly Gln Pro Asp Phe Asn Trp
                165                 170                 175

Glu Asn Lys Glu Cys Arg Gln Ala Ile Tyr Asp Ser Ser Val Gly Phe
            180                 185                 190

Trp Leu Arg His Asn Val Asp Gly Phe Arg Ile Asp Val Gly Ser Met
        195                 200                 205

Tyr Ser Lys Val Glu Gly Leu Pro Asp Ala Ser Ile Thr Asp Pro Thr
    210                 215                 220

Val Pro Tyr Gln Asp Gly Thr Asp Phe Phe Val Asn Gly Pro Arg Ile
225                 230                 235                 240

His Glu Tyr His Lys Glu Met Arg Gln Tyr Met Tyr Thr Gln Ile Pro
                245                 250                 255

Glu Gly Lys Glu Ile Met Thr Val Gly Glu Val Gly Ile Gly Asn Glu
            260                 265                 270

Lys Asp Phe Lys Asp Tyr Thr Ser Ser Lys Glu Glu Phe Asn Met
        275                 280                 285
```

```
Met Phe Asn Phe Lys His Thr Ser Val Gly Glu Ser Pro Glu Phe Lys
            290                 295                 300

Tyr Glu Leu Ile Pro Phe Thr Leu Lys Asp Phe Lys Leu Ala Leu Ala
305                 310                 315                 320

Glu Ser Phe Leu Phe Ile Glu Gly Thr Asp Cys Trp Ser Thr Ile Tyr
                325                 330                 335

Leu Glu Asn His Asp Gln Pro Arg Ser Val Ser Arg Phe Gly Ser Asp
            340                 345                 350

Ser Pro Glu Trp Arg Glu Ile Ser Ser Lys Met Leu Ala Thr Leu Ile
        355                 360                 365

Ile Ser Leu Thr Gly Thr Val Phe Ile Tyr Gln Gly Gln Glu Leu Gly
370                 375                 380

Met Pro Asn Phe Lys Asn Arg Lys Ile Glu Gln Ile Lys Cys Val Glu
385                 390                 395                 400

Gly Thr Gly Thr Tyr Gly Ala Ile Lys Arg Asp Tyr Gly Glu Asp Ser
                405                 410                 415

Glu Lys Met Lys Lys Phe Tyr Glu Ala Leu Ala Leu Ile Ser Arg Asp
            420                 425                 430

His Gly Arg Thr Pro Phe Pro Trp Ser Gly Lys Pro Tyr Ala Gly
        435                 440                 445

Phe Ser Lys Asn Ala Lys Pro Trp Ile Asp Ile Asn Glu Ser Phe Val
450                 455                 460

Glu Gly Ile Asn Ala Glu Ala Glu Leu Asn Asp Glu Asn Ser Val Phe
465                 470                 475                 480

Phe Phe Trp Lys Arg Ala Leu Gln Val Arg Lys Glu His Lys Asn Met
                485                 490                 495

Leu Val Tyr Gly Asp Asn Phe Gln Phe Tyr Asp Leu Asp Asn Glu Lys
            500                 505                 510

Leu Phe Met Phe Thr Lys Asp Ser Gly Asp Lys Lys Met Phe Ala Val
        515                 520                 525

Phe Asn Phe Cys Ser Asp Ser Thr Glu Phe Ser Val Pro Asp Asn Lys
530                 535                 540

Ala Ser Tyr Asp Met Phe Phe Gly Asn Tyr Ala Asn Ser Asp Gly Lys
545                 550                 555                 560

Ser Tyr Thr Leu Lys Pro Trp Glu Gly Arg Leu Tyr Tyr Ser Asn
                565                 570                 575

<210> SEQ ID NO 37
<211> LENGTH: 558
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 37

Asn Ser Thr Glu Arg Tyr Asn Leu Ser Pro Ser Pro Glu Asp Glu Asp
1               5                   10                  15

Phe Glu Ala Pro Thr Glu Glu Met Gln Thr Leu Arg His Val Gly
            20                  25                  30

Gly Lys Ile Pro Met Arg Cys Trp Leu Ile Ala Ile Val Glu Leu Ser
        35                  40                  45

Glu Arg Phe Ser Tyr Tyr Gly Leu Ser Ala Pro Phe Gln Asn Tyr Met
50                  55                  60

Glu Tyr Gly Pro Asn Asp Ser Pro Lys Gly Val Leu Ser Leu Asn Ser
```

```
                65                  70                  75                  80
Gln Gly Ala Thr Gly Leu Ser Tyr Phe Phe Gln Phe Trp Cys Tyr Val
                    85                  90                  95

Thr Pro Val Phe Gly Gly Tyr Val Ala Asp Thr Phe Trp Gly Lys Tyr
                    100                 105                 110

Asn Thr Ile Cys Cys Gly Thr Ala Ile Tyr Ile Ala Gly Ile Phe Ile
                    115                 120                 125

Leu Phe Ile Thr Ser Ile Pro Ser Val Gly Asn Arg Asp Ser Ala Ile
                    130                 135                 140

Gly Gly Phe Ile Ala Ala Ile Ile Leu Ile Gly Ile Ala Thr Gly Met
145                 150                 155                 160

Ile Lys Ala Asn Leu Ser Val Leu Ile Ala Asp Gln Leu Pro Lys Arg
                    165                 170                 175

Lys Pro Ser Ile Lys Val Leu Lys Ser Gly Glu Arg Val Ile Val Asp
                    180                 185                 190

Ser Asn Ile Thr Leu Gln Asn Val Phe Met Phe Phe Tyr Phe Met Ile
                    195                 200                 205

Asn Val Gly Ser Leu Ser Leu Met Ala Thr Thr Glu Leu Glu Tyr His
210                 215                 220

Lys Gly Phe Trp Ala Ala Tyr Leu Leu Pro Phe Cys Phe Phe Trp Ile
225                 230                 235                 240

Ala Val Val Thr Leu Ile Phe Gly Lys Lys Gln Tyr Ile Gln Arg Pro
                    245                 250                 255

Ile Gly Asp Lys Val Ile Ala Lys Ser Phe Lys Val Cys Trp Ile Leu
                    260                 265                 270

Thr Lys Asn Lys Phe Asp Phe Asn Ala Ala Lys Pro Ser Val His Pro
                    275                 280                 285

Glu Lys Asn Tyr Pro Trp Asn Asp Lys Phe Val Asp Glu Ile Lys Arg
                    290                 295                 300

Ala Leu Ala Ala Cys Lys Val Phe Ile Phe Tyr Pro Ile Tyr Trp Thr
305                 310                 315                 320

Gln Tyr Gly Thr Met Ile Ser Ser Phe Ile Thr Gln Ala Ser Met Met
                    325                 330                 335

Glu Leu His Gly Ile Pro Asn Asp Phe Leu Gln Ala Phe Asp Ser Ile
                    340                 345                 350

Ala Leu Ile Ile Phe Ile Pro Ile Phe Glu Lys Phe Val Tyr Pro Phe
                    355                 360                 365

Ile Arg Arg Tyr Thr Pro Leu Lys Pro Ile Thr Lys Ile Phe Phe Gly
                    370                 375                 380

Phe Met Phe Gly Ser Phe Ala Met Thr Trp Ala Ala Val Leu Gln Ser
385                 390                 395                 400

Phe Val Tyr Lys Ala Gly Pro Trp Tyr Asn Glu Pro Leu Gly His Asn
                    405                 410                 415

Thr Pro Asn His Val His Val Cys Trp Gln Ile Pro Ala Tyr Val Leu
                    420                 425                 430

Ile Ser Phe Ser Glu Ile Phe Ala Ser Ile Thr Gly Leu Glu Tyr Ala
                    435                 440                 445

Tyr Ser Lys Ala Pro Ala Ser Met Lys Ser Phe Ile Met Ser Ile Phe
                    450                 455                 460

Leu Leu Thr Asn Ala Phe Gly Ser Ala Ile Gly Cys Ala Leu Ser Pro
465                 470                 475                 480

Val Thr Val Asp Pro Lys Phe Thr Trp Leu Phe Thr Gly Leu Ala Val
                    485                 490                 495
```

-continued

```
Ala Cys Phe Ile Ser Gly Cys Leu Phe Trp Leu Cys Phe Arg Lys Tyr
            500                 505                 510

Asn Asp Thr Glu Glu Met Asn Ala Met Asp Tyr Glu Glu Asp
            515                 520                 525

Glu Phe Asp Leu Asn Pro Ile Ser Ala Pro Lys Ala Asn Asp Ile Glu
        530                 535                 540

Ile Leu Glu Pro Met Glu Ser Leu Arg Ser Thr Thr Lys Tyr
545                 550                 555

<210> SEQ ID NO 38
<211> LENGTH: 601
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 38

Met Leu Asn His Leu Ser Gln Gly Ser Asp Asp Ile Gln Asp Glu Lys
1               5                   10                  15

Gln Gly Asp Phe Pro Val Ile Glu Glu Lys Asn Gln Thr Val Thr
            20                  25                  30

Leu Lys Asp Ser Tyr Val Ser Asp Ala Ala Asn Ser Thr Glu His
        35                  40                  45

Tyr Asn Leu Ser Pro Ser Leu Glu Asp Glu Phe Glu Ala Pro Thr
 50                  55                  60

Asp Glu Glu Leu Arg Ser Leu Arg His Val Gly Gly Lys Ile Pro Met
65                  70                  75                  80

Arg Cys Trp Leu Ile Ala Ile Val Glu Leu Ser Glu Arg Phe Ser Tyr
                85                  90                  95

Tyr Gly Leu Ser Ala Pro Phe Gln Asn Tyr Met Glu Tyr Gly Pro Lys
            100                 105                 110

Asp Thr Pro Lys Gly Val Leu Ser Leu Asn Ser Gln Gly Ala Thr Gly
        115                 120                 125

Leu Ser Tyr Phe Phe Gln Phe Trp Cys Tyr Val Thr Pro Val Phe Gly
    130                 135                 140

Gly Tyr Val Ala Asp Thr Phe Trp Gly Lys Tyr Asn Thr Ile Cys Cys
145                 150                 155                 160

Gly Thr Ala Ile Tyr Ile Ala Gly Ile Phe Ile Leu Ile Thr Ser
                165                 170                 175

Ile Pro Ser Val Gly Asn Arg Asp Ser Ala Leu Gly Gly Phe Ile Ala
            180                 185                 190

Ser Ile Ile Leu Ile Gly Ile Ala Thr Gly Met Ile Lys Ala Asn Leu
        195                 200                 205

Ser Val Leu Ile Ala Asp Gln Leu Pro Lys Arg Lys Pro Ser Ile Lys
    210                 215                 220

Val Leu Lys Ser Gly Glu Arg Val Ile Val Asp Ser Asn Ile Thr Leu
225                 230                 235                 240

Gln Asn Val Phe Met Phe Phe Tyr Phe Met Ile Asn Val Gly Ser Leu
                245                 250                 255

Ser Leu Met Ala Thr Thr Glu Leu Glu Tyr His Lys Gly Phe Trp Ala
            260                 265                 270

Ala Tyr Leu Leu Pro Phe Cys Phe Phe Trp Val Ala Val Val Thr Leu
        275                 280                 285

Val Phe Gly Lys Lys Gln Tyr Ile Gln Arg Pro Ile Gly Asp Lys Val
```

```
                290                 295                 300
Ile Ala Lys Ser Phe Arg Val Cys Trp Ile Leu Thr Lys Asn Lys Phe
305                 310                 315                 320

Asp Phe Asn Ala Ala Lys Pro Ser Val His Pro Glu Lys Glu Tyr Pro
                325                 330                 335

Trp Asn Asp Lys Phe Val Asp Glu Ile Lys Arg Ala Leu Ala Ala Cys
                340                 345                 350

Lys Val Phe Val Phe Tyr Pro Ile Tyr Trp Thr Gln Tyr Gly Thr Met
                355                 360                 365

Ile Ser Ser Phe Ile Thr Gln Ala Gly Met Met Glu Leu His Gly Ile
                370                 375                 380

Pro Asn Asp Phe Leu Gln Ala Phe Asp Ser Ile Ala Leu Ile Ile Phe
385                 390                 395                 400

Ile Pro Ile Phe Glu Lys Phe Ile Tyr Pro Phe Ile Arg Arg Tyr Thr
                405                 410                 415

Pro Phe Lys Pro Ile Thr Lys Ile Phe Phe Gly Phe Met Phe Gly Ser
                420                 425                 430

Leu Ala Met Thr Trp Ala Ala Val Leu Gln Ser Phe Val Tyr Lys Ala
                435                 440                 445

Gly Pro Trp Tyr Ser Ala Pro Leu Gly His Asn Thr Pro Asn His Val
                450                 455                 460

His Val Cys Trp Gln Ile Pro Ala Tyr Val Leu Ile Ser Phe Ser Glu
465                 470                 475                 480

Ile Phe Ala Ser Ile Thr Gly Leu Glu Tyr Ala Tyr Ser Lys Ala Pro
                485                 490                 495

Ala Ser Met Lys Ser Phe Ile Met Ser Ile Phe Leu Leu Thr Asn Ala
                500                 505                 510

Phe Gly Ser Ala Ile Gly Cys Ala Leu Ser Pro Val Thr Val Asp Pro
                515                 520                 525

Lys Phe Thr Trp Leu Phe Thr Gly Leu Ala Val Ala Cys Phe Ile Ser
                530                 535                 540

Gly Cys Leu Phe Trp Phe Cys Phe Arg Lys Tyr Asn Asp Thr Glu Glu
545                 550                 555                 560

Glu Met Asn Ala Met Asp Tyr Glu Glu Glu Asp Glu Phe Asp Leu Asn
                565                 570                 575

Pro Ile Ser Gln Pro Lys Gly Asn Asp Ile Glu Ile Leu Glu Pro Met
                580                 585                 590

Gly Ser Leu Lys Ser Thr Thr Lys Tyr
                595                 600

<210> SEQ ID NO 39
<211> LENGTH: 543
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 39

Met Ser Ala Asp Ala Ser Thr Asn Ser Asn Ala Ser Leu Asp Glu Lys
1               5                   10                  15

Asn Leu Asn Ile Thr Ser Glu Ala Glu Ile Lys Asn Glu Asp Val Thr
                20                  25                  30

Ala Glu Pro Val Leu Ser Thr Val Leu Ser Pro Asn Gly Lys Ile Val
                35                  40                  45
```

```
Tyr Ile Ser Asp Lys Val Asp Glu Ala Met Lys Leu Ala Glu Ala
 50                  55                  60

Lys Glu Ile Glu Val Thr Pro Glu Glu Asp Arg Lys Leu Arg Trp Lys
 65                  70                  75                  80

Ile Asp Tyr Cys Met Phe Pro Leu Met Cys Ile Leu Tyr Ala Val Gln
                 85                  90                  95

Phe Met Asp Lys Ile Ser Thr Ser Ser Ala Ala Val Met Gly Leu Arg
            100                 105                 110

Thr Asp Leu Lys Met His Gly Asp Gln Tyr Ser Trp Val Thr Ser Ala
            115                 120                 125

Phe Tyr Phe Gly Tyr Leu Phe Met Asn Leu Gly Pro Val Gln Phe Ile
130                 135                 140

Phe Gln Arg Thr Ser His Met Ser Lys Met Leu Ala Val Phe Ile Val
145                 150                 155                 160

Ile Trp Gly Met Leu Leu Ala Leu His Ala Ala Pro Thr Val Lys Tyr
                165                 170                 175

Pro Ser Phe Ile Val Leu Arg Val Leu Leu Gly Cys Ala Glu Ser Val
            180                 185                 190

Val Thr Pro Cys Phe Thr Ile Ile Thr Ala Gln Tyr Trp Lys Thr Glu
            195                 200                 205

Glu Gln Phe Thr Arg Val Ser Ile Trp Phe Gly Met Asn Gly Leu Gly
210                 215                 220

Ser Ile Leu Ile Asn Ala Ile Ala Tyr Gly Val Tyr Ile His Gln Asp
225                 230                 235                 240

Ser Tyr Ala Ile Lys Gly Trp Arg Thr Leu Phe Val Ile Thr Gly Val
                245                 250                 255

Ile Thr Ile Phe Ile Gly Ile Leu Ile Phe Leu Trp Ile Pro Asp Asp
            260                 265                 270

Pro Ser Lys Ala Arg Phe Leu Ser Lys Arg Glu Lys Leu Met Val Val
            275                 280                 285

Gln Arg Ile Arg Ser Asn Gln Gln Gly Phe Gly Asn His Glu Ile Lys
290                 295                 300

Lys Tyr Gln Ile Ile Glu Ala Leu Lys Asp Val Arg Thr Trp Leu Tyr
305                 310                 315                 320

Phe Leu Phe Thr Val Ser Ser Asn Ile Pro Asn Gly Gly Ile Ser Ser
                325                 330                 335

Phe Met Ser Ile Leu Leu Asn Ser Asp Phe Gly Tyr Ser Ser Lys Glu
            340                 345                 350

Thr Leu Leu Met Gly Leu Pro Thr Gly Ala Val Glu Leu Val Gly Cys
            355                 360                 365

Pro Leu Phe Gly Ile Leu Ala Val Tyr Ala Ala Asn Lys Lys Ile Pro
370                 375                 380

Phe Trp Lys Tyr Lys Leu Ser Trp Ala Ile Phe Ala Ala Val Leu Ala
385                 390                 395                 400

Leu Ile Ala Ser Cys Met Leu Gly Phe Ala Thr Asn Ser Lys Lys Ala
                405                 410                 415

Arg Leu Ala Gly Ala Tyr Leu Trp Tyr Ile Ser Pro Val Ser Phe Ile
            420                 425                 430

Cys Val Leu Ser Asn Ile Ser Ala Asn Ser Ser Gly Tyr Ser Lys Lys
            435                 440                 445

Trp Thr Val Ser Ser Ile Asn Leu Val Ala Tyr Ala Ala Ala Asn Leu
450                 455                 460

Ala Gly Pro Gln Thr Phe Ile Ala Lys Gln Ala Pro Lys Tyr His Gly
```

```
                  465                 470                 475                 480
      Ala Lys Val Ala Met Val Val Cys Tyr Ala Val Met Ile Val Leu Leu
                          485                 490                 495

Ser Ile Leu Leu Ile Val Asn Leu Arg Glu Asn Lys Arg Arg Asp Lys
                          500                 505                 510

Ile Ala Ala Glu Arg Gly Phe Pro Glu Glu Thr Glu Asn Leu Glu Phe
                          515                 520                 525

Ser Asp Leu Thr Asp Phe Glu Asn Pro Asn Phe Arg Tyr Thr Leu
                          530                 535                 540

<210> SEQ ID NO 40
<211> LENGTH: 543
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 40

Met Ser Gly Gly Ala Ser Thr Asn Ser Asn Ala Ser Ile Asp Glu Lys
1               5                   10                  15

Asn Leu Asn Ile Thr Ser Glu Ala Glu Ile Lys Asn Glu Asp Val Tyr
                20                  25                  30

Ala Glu Pro Val Leu Ser Thr Val Leu Ser Pro Asn Gly Lys Val Val
                35                  40                  45

Tyr Ile Ser Asp Lys Val Asp Glu Ala Met Lys Leu Ala Asp Glu Ala
            50                  55                  60

Lys Glu Ile Glu Val Thr Pro Glu Glu Asp Arg Lys Leu Arg Trp Lys
65                  70                  75                  80

Ile Asp Tyr Cys Met Phe Pro Leu Met Cys Ile Leu Tyr Ala Val Gln
                85                  90                  95

Phe Met Asp Lys Ile Ser Thr Ser Ser Ala Ala Val Met Gly Leu Arg
                100                 105                 110

Thr Asp Leu Lys Met His Gly Asp Gln Tyr Ser Trp Val Thr Ser Ala
            115                 120                 125

Phe Tyr Phe Gly Tyr Leu Phe Met Asn Leu Gly Pro Val Gln Leu Ile
            130                 135                 140

Phe Gln Lys Ser Lys His Met Ser Lys Met Leu Ala Ile Phe Ile Ile
145                 150                 155                 160

Val Trp Gly Leu Leu Leu Ala Leu His Ala Val Pro Ser Val Lys Tyr
                165                 170                 175

Ser Ser Phe Ile Ala Leu Arg Val Leu Leu Gly Cys Ala Glu Ser Val
            180                 185                 190

Val Thr Pro Cys Phe Thr Ile Ile Thr Ala Gln Tyr Trp Lys Thr Glu
            195                 200                 205

Glu Gln Phe Thr Arg Ile Ser Ile Trp Phe Gly Met Asn Gly Leu Gly
            210                 215                 220

Ser Ile Leu Ile Asn Ala Ile Ala Tyr Gly Val Tyr Ile His Gln Glu
225                 230                 235                 240

Ser Tyr Ala Ile Lys Gly Trp Arg Ala Leu Phe Val Ile Thr Gly Val
                245                 250                 255

Ile Thr Ile Phe Val Gly Ala Leu Ile Phe Leu Trp Ile Pro Asp Asp
            260                 265                 270

Pro Ser Lys Ala Arg Phe Leu Ser Lys Arg Glu Lys Leu Met Val Val
            275                 280                 285
```

Gln Arg Ile Arg Ser Asn Gln Gln Gly Phe Gly Asn His Glu Ile Lys
290                 295                 300

Lys Tyr Gln Ile Val Glu Ala Leu Lys Asp Val Arg Thr Trp Leu Tyr
305                 310                 315                 320

Phe Leu Phe Thr Val Ser Ser Asn Ile Pro Asn Gly Gly Ile Ser Ser
            325                 330                 335

Phe Met Ser Ile Leu Leu Asn Ser Asp Phe Gly Tyr Leu Ser Lys Asp
            340                 345                 350

Thr Leu Leu Met Gly Leu Pro Thr Gly Ala Val Glu Leu Val Gly Cys
            355                 360                 365

Pro Leu Phe Gly Ile Leu Ala Val Tyr Ala Ala Asn Lys Lys Ile Pro
370                 375                 380

Phe Trp Lys Tyr Lys Leu Ala Trp Ala Ile Phe Ala Ala Val Leu Ala
385                 390                 395                 400

Leu Ile Ala Ser Cys Met Leu Gly Phe Ala Thr Ser Ser Lys Lys Ala
            405                 410                 415

Arg Leu Ala Gly Ala Tyr Leu Trp Tyr Ile Ser Pro Val Ser Phe Ile
            420                 425                 430

Cys Val Leu Ser Asn Ile Ser Ala Asn Ser Ser Gly Tyr Ser Lys Lys
            435                 440                 445

Trp Thr Val Ser Ser Ile Asn Leu Ala Ala Tyr Ala Ala Asn Leu
450                 455                 460

Ala Gly Pro Gln Thr Phe Ile Ala Lys Gln Ala Pro Lys Tyr His Gly
465                 470                 475                 480

Ala Lys Val Ala Met Val Val Cys Tyr Ala Val Met Ile Val Leu Leu
            485                 490                 495

Ser Ala Leu Leu Leu Ile Asn Met Arg Glu Asn Lys Arg Arg Asp Lys
            500                 505                 510

Ile Ala Ala Glu Arg Gly Tyr Pro Glu Glu Thr Ala Asn Leu Glu Phe
            515                 520                 525

Ser Asp Leu Thr Asp Phe Glu Asn Pro Asn Phe Arg Tyr Thr Leu
530                 535                 540

<210> SEQ ID NO 41
<211> LENGTH: 828
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 41

Met Ser Val Ala Asp Asp Leu Gly Ser Leu Gln Gly His Ile Arg
1               5                   10                  15

Arg Thr Leu Arg Ser Ile His Asn Leu Pro Tyr Phe Arg Tyr Thr Arg
                20                  25                  30

Gly Pro Thr Glu Arg Ala Asp Met Ser Arg Ala Leu Lys Glu Phe Ile
            35                  40                  45

Tyr Arg Tyr Leu Tyr Phe Val Ile Ser Asn Ser Gly Glu Asn Leu Pro
50                  55                  60

Thr Leu Phe Asn Ala His Pro Lys Gln Lys Leu Ser Asn Pro Glu Leu
65                  70                  75                  80

Thr Val Phe Pro Asp Ser Leu Glu Asp Ala Val Asp Ile Asp Lys Ile
            85                  90                  95

Thr Ser Gln Gln Thr Ile Pro Phe Tyr Lys Ile Asp Glu Ser Arg Ile
            100                 105                 110

```
Gly Asp Val His Lys His Thr Gly Arg Asn Cys Gly Arg Lys Phe Lys
            115                 120                 125

Ile Gly Glu Pro Leu Tyr Arg Cys His Glu Cys Gly Cys Asp Asp Thr
    130                 135                 140

Cys Val Leu Cys Ile His Cys Phe Asn Pro Lys Asp His Val Asn His
145                 150                 155                 160

His Val Cys Thr Asp Ile Cys Thr Glu Phe Thr Ser Gly Ile Cys Asp
                165                 170                 175

Cys Gly Asp Glu Glu Ala Trp Asn Ser Pro Leu His Cys Lys Ala Glu
            180                 185                 190

Glu Gln Glu Asn Asp Ile Ser Glu Asp Pro Ala Thr Asn Ala Asp Ile
            195                 200                 205

Lys Glu Glu Asp Val Trp Asn Asp Ser Val Asn Ile Ala Leu Val Glu
    210                 215                 220

Leu Val Leu Ala Glu Val Phe Asp Tyr Phe Ile Asp Val Phe Asn Gln
225                 230                 235                 240

Asn Ile Glu Pro Leu Pro Thr Ile Gln Lys Asp Ile Thr Ile Lys Leu
                245                 250                 255

Arg Glu Met Thr Gln Gln Gly Lys Met Tyr Glu Arg Ala Gln Phe Leu
            260                 265                 270

Asn Asp Leu Lys Tyr Glu Asn Asp Tyr Met Phe Asp Gly Thr Thr Thr
            275                 280                 285

Ala Lys Thr Ser Pro Ser Asn Ser Pro Glu Ala Ser Pro Ser Leu Ala
            290                 295                 300

Lys Ile Asp Pro Glu Asn Tyr Thr Val Ile Ile Tyr Asn Asp Glu Tyr
305                 310                 315                 320

His Asn Tyr Ser Gln Ala Thr Thr Ala Leu Arg Gln Gly Val Pro Asp
                325                 330                 335

Asn Val His Ile Asp Leu Leu Thr Ser Arg Ile Asp Gly Glu Gly Arg
            340                 345                 350

Ala Met Leu Lys Cys Ser Gln Asp Ser Ser Ser Val Leu Gly Gly Phe
            355                 360                 365

Phe Ala Val Gln Thr Asn Gly Leu Ser Ala Thr Leu Thr Ser Trp Ser
    370                 375                 380

Glu Tyr Leu His Gln Glu Thr Cys Lys Tyr Ile Ile Leu Trp Ile Thr
385                 390                 395                 400

His Cys Leu Asn Ile Pro Asn Ser Ser Phe Gln Thr Thr Phe Arg Asn
                405                 410                 415

Met Met Gly Lys Thr Leu Cys Ser Glu Tyr Leu Asn Ala Thr Glu Cys
            420                 425                 430

Arg Asp Met Thr Pro Val Val Glu Lys Tyr Phe Ser Asn Lys Phe Asp
            435                 440                 445

Lys Asn Asp Pro Tyr Arg Tyr Ile Asp Leu Ser Ile Leu Ala Asp Gly
    450                 455                 460

Asn Gln Ile Pro Leu Gly His His Lys Ile Leu Pro Glu Ser Ser Thr
465                 470                 475                 480

His Ser Leu Ser Pro Leu Ile Asn Asp Val Glu Thr Pro Thr Ser Arg
                485                 490                 495

Thr Tyr Ser Asn Thr Arg Leu Gln His Ile Leu Tyr Phe Asp Asn Arg
            500                 505                 510

Tyr Trp Lys Arg Leu Arg Lys Asp Ile Gln Asn Val Ile Ile Pro Thr
    515                 520                 525
```

```
Leu Ala Ser Ser Asn Leu Tyr Lys Pro Ile Phe Cys Gln Gln Val Val
        530                 535                 540

Glu Ile Phe Asn His Ile Thr Arg Ser Val Ala Tyr Met Asp Arg Glu
545                 550                 555                 560

Pro Gln Leu Thr Ala Ile Arg Glu Cys Val Val Gln Leu Phe Thr Cys
                565                 570                 575

Pro Thr Asn Ala Lys Asn Ile Phe Glu Asn Gln Ser Phe Leu Asp Ile
            580                 585                 590

Val Trp Ser Ile Ile Asp Ile Phe Lys Glu Phe Cys Lys Val Glu Gly
        595                 600                 605

Gly Val Leu Ile Trp Gln Arg Val Gln Lys Ser Asn Leu Thr Lys Ser
    610                 615                 620

Tyr Ser Ile Ser Phe Lys Gln Gly Leu Tyr Thr Val Glu Thr Leu Leu
625                 630                 635                 640

Ser Lys Val His Asp Pro Asn Ile Pro Leu Arg Pro Lys Glu Ile Ile
                645                 650                 655

Ser Leu Leu Thr Leu Cys Lys Leu Phe Asn Gly Ala Trp Lys Ile Lys
            660                 665                 670

Arg Lys Glu Gly Glu His Val Leu His Glu Asp Gln Asn Phe Ile Ser
        675                 680                 685

Tyr Leu Glu Tyr Thr Thr Ser Ile Tyr Ser Ile Ile Gln Thr Ala Glu
690                 695                 700

Lys Val Ser Glu Lys Ser Lys Asp Ser Ile Asp Ser Lys Leu Phe Leu
705                 710                 715                 720

Asn Ala Ile Arg Ile Ile Ser Ser Phe Leu Gly Asn Arg Ser Leu Thr
                725                 730                 735

Tyr Lys Leu Ile Tyr Asp Ser His Glu Val Ile Lys Phe Ser Val Ser
            740                 745                 750

His Glu Arg Val Ala Phe Met Asn Pro Leu Gln Thr Met Leu Ser Phe
        755                 760                 765

Leu Ile Glu Lys Val Ser Leu Lys Asp Ala Tyr Glu Ala Leu Glu Asp
770                 775                 780

Cys Ser Asp Phe Leu Lys Ile Ser Asp Phe Ser Leu Arg Ser Val Val
785                 790                 795                 800

Leu Cys Ser Gln Ile Asp Val Gly Phe Trp Val Arg Asn Gly Met Ser
                805                 810                 815

Val Leu His Gln Ala Ser Tyr Lys Asn Asn Pro
            820                 825

<210> SEQ ID NO 42
<211> LENGTH: 1950
<212> TYPE: PRT
<213> ORGANISM: Unknown
<220> FEATURE:
<223> OTHER INFORMATION: Hybrid between S. cerevisiae and S. pastorianus
      (Hybrid yeast 7)

<400> SEQUENCE: 42

Met Ser Phe Thr Asp Asn Gly Leu Gly Ser Leu Lys Ala His Ile Arg
1               5                   10                  15

Arg Thr Leu Arg Ser Ile His Asn Leu Pro Tyr Phe Arg Phe Thr Arg
            20                  25                  30

Gly Pro Thr Glu Arg Ala Asp Met Ser Arg Ala Leu Lys Glu Phe Ile
        35                  40                  45

Tyr Arg Tyr Leu Tyr Phe Ile Ile Ser Asn Asp Gly Glu Asn Leu Ser
    50                  55                  60
```

```
Thr Leu Phe Thr Ala His Pro Lys Gln Lys Ser Asn Gln Glu Leu
65                  70                  75                  80

Ala Val Phe Pro Glu Ser Leu Glu Asp Ala Leu Asp Val Asp Lys Ile
            85                  90                  95

Thr Ser Gln Gly Thr Phe Pro Phe Tyr Lys Ile Asp Glu Ser Lys Ile
                100                 105                 110

Gly Asp Val His Lys His Thr Gly Arg Asn Cys Gly Arg Lys Phe Lys
            115                 120                 125

Ile Gly Glu Pro Leu Tyr Arg Cys His Glu Cys Gly Cys Asp Asp Thr
            130                 135                 140

Cys Val Leu Cys Ile His Cys Phe Asn Pro Lys Asp His Ile Asn His
145                 150                 155                 160

His Val Cys Thr Asp Ile Cys Ser Glu Phe Thr Ser Gly Ile Cys Asp
                165                 170                 175

Cys Gly Asp Glu Glu Ala Trp Asn Ser Ser Leu His Cys Lys Ala Glu
            180                 185                 190

Glu Gln Gly Asn Asp Thr Ser Glu Asp Pro Ser Asn Phe Asp Ser Thr
            195                 200                 205

Lys Gln Lys Asp Val Trp Asn Asp Pro Glu Cys Ile Ala Leu Val Glu
210                 215                 220

Leu Val Leu Ser Glu Val Phe Asp Tyr Phe Ile Asp Val Phe Asn Gln
225                 230                 235                 240

Asn Ile Glu Pro Leu Pro Thr Ile Gln Lys Asp Ile Thr Ile Lys Leu
            245                 250                 255

Arg Glu Met Thr Gln Gln Gly Lys Met Tyr Glu Arg Ala Gln Phe Leu
            260                 265                 270

Asn Asp Leu Lys Tyr Glu Asn Asp Tyr Met Phe Asp Gly Thr Thr Thr
            275                 280                 285

Ala Lys Thr Ser Pro Ser Asn Ser Pro Glu Ala Ser Pro Ser Leu Ala
            290                 295                 300

Lys Ile Asp Pro Glu Asn Tyr Thr Val Ile Ile Tyr Asn Asp Glu Tyr
305                 310                 315                 320

His Asn Tyr Ser Gln Ala Thr Thr Ala Leu Arg Gln Gly Val Pro Asp
                325                 330                 335

Asn Val His Ile Asp Leu Leu Thr Ser Arg Ile Asp Gly Glu Gly Arg
            340                 345                 350

Ala Met Leu Lys Cys Ser Gln Asp Leu Ser Ser Val Leu Gly Gly Phe
            355                 360                 365

Phe Ala Val Gln Thr Asn Gly Leu Ser Ala Thr Leu Thr Ser Trp Ser
            370                 375                 380

Glu Tyr Leu His Gln Glu Ala Cys Lys Tyr Ile Ile Leu Trp Ile Thr
385                 390                 395                 400

His Cys Leu Asn Ile Pro Asn Pro Ser Phe Gln Ile Thr Phe Arg Asn
                405                 410                 415

Met Met Gly Lys Ser Leu Cys Ser Glu Tyr Leu Asn Ala Thr Glu Ser
            420                 425                 430

Arg Asp Met Thr Pro Val Val Glu Lys Tyr Phe Ser Thr Lys Phe Asp
            435                 440                 445

Lys Asp Asp Pro Tyr Arg Tyr Ile Asp Leu Ser Val Leu Ala Glu Gly
            450                 455                 460

Asn Gln Ile Pro Leu Gly His His Lys Val Leu Pro Glu Ser Ser Thr
465                 470                 475                 480
```

-continued

His Ser Leu Ser Thr Leu Ile Asn Asp Val Glu Asn Leu Thr Ser Lys
            485                 490                 495

Glu Tyr Ser Asn Thr Arg Leu Gln His Ile Leu Tyr Phe Asp Asn Arg
        500                 505                 510

Tyr Trp Lys Arg Leu Arg Lys Asp Ile Gln Asn Val Ile Ile Pro Thr
        515                 520                 525

Leu Ala Ser Ser Thr Leu Tyr Lys Pro Ile Phe Cys Gln Gln Val Val
530                 535                 540

Glu Ile Phe Asn His Ile Thr Arg Ser Val Ala Tyr Met Asp Arg Glu
545                 550                 555                 560

Pro Gln Leu Thr Ala Ile Arg Glu Cys Val Val Gln Leu Phe Thr Cys
                565                 570                 575

Pro Thr Asn Thr Arg Asn Ile Phe Glu Asn Gln Ser Phe Leu Asp Ile
            580                 585                 590

Leu Trp Ser Ile Ile Asp Ile Phe Lys Glu Phe Cys Lys Val Glu Ala
        595                 600                 605

Gly Val Leu Ile Trp Gln Arg Val Gln Lys Ser Asn Leu Thr Lys Ser
        610                 615                 620

Tyr Ser Leu Ser Phe Lys Gln Gly Leu Tyr Thr Val Glu Thr Leu Leu
625                 630                 635                 640

Ser Lys Val Asn Asp Pro Asn Ile Thr Ile Arg Pro Lys Val Phe Ile
                645                 650                 655

Ser Leu Leu Thr Leu Gly Lys Leu Phe Asn Gly Ala Trp Lys Ile Lys
            660                 665                 670

Arg Lys Glu Gly Glu His Val Leu His Glu Asp Gln Asn Phe Ile Ser
        675                 680                 685

Tyr Leu Glu Tyr Thr Thr Ser Ile Tyr Ser Ile Ile Gln Thr Ala Glu
        690                 695                 700

Lys Val Leu Glu Lys Ser His Asp Ser Leu Asp Leu Asn Leu Val Leu
705                 710                 715                 720

Asn Ala Ile Arg Ile Val Ser Ser Phe Leu Gly Asn Arg Ser Leu Thr
                725                 730                 735

Tyr Lys Leu Ile Tyr Asp Ser His Glu Ile Ile Lys Phe Ser Val Ser
            740                 745                 750

His Glu Arg Val Ala Phe Met Asn Pro Ile Gln Thr Met Leu Ser Phe
        755                 760                 765

Leu Ile Glu Lys Val Ser Leu Lys Asp Ala Tyr Glu Ser Leu Glu Asn
        770                 775                 780

Cys Pro Asp Phe Leu Lys Ile Ala Asp Phe Ser Leu Arg Ser Val Val
785                 790                 795                 800

Leu Cys Ser Gln Ile Asp Val Gly Phe Trp Val Arg Asn Gly Met Ser
                805                 810                 815

Val Leu His Gln Ala Ser Tyr Tyr Lys Asn Asn Pro Glu Leu Gly Ser
            820                 825                 830

Tyr Ser Arg Asp Ile His Leu Asn Gln Leu Ala Ile Ile Trp Glu Arg
        835                 840                 845

Asp Asp Leu Pro Arg Val Ile Tyr Asn Ile Leu Asp Arg Trp Glu Leu
        850                 855                 860

Leu Asp Trp Phe Met Gly Glu Ala Glu Tyr Gln His Thr Val Tyr Glu
865                 870                 875                 880

Asp Lys Ile Ser Phe Met Ile Gln Gln Phe Ile Ala Phe Ile Tyr Gln
                885                 890                 895

Ile Leu Thr Glu Arg Gln Tyr Phe Lys Thr Phe Ser Leu Leu Arg Asp

```
                900            905             910
Arg Arg Met Asp Met Ile Lys Asn Ser Ile Met Tyr Asn Leu Tyr Met
            915             920             925

Lys Pro Leu Ser Tyr Ser Lys Leu Leu Lys Ser Val Pro Asp Tyr Leu
            930             935             940

Thr Asp Asp Thr Thr Glu Phe Asp Glu Ala Leu Glu Glu Val Ser Val
945             950             955             960

Phe Val Glu Pro Lys Gly Leu Ala Asp Asn Gly Val Phe Lys Leu Lys
                965             970             975

Ala Ala Leu Tyr Ala Lys Ile Asp Pro Leu Lys Leu Leu Asn Leu Glu
            980             985             990

Asn Glu Phe Glu Ser Ser Ala Thr Ile Ile Lys Thr His Leu Ala Lys
            995             1000            1005

Asn Lys Asp Glu Val Ser Lys Val Val Leu Ile Pro Gln Val Ser
        1010            1015            1020

Thr Lys Leu Leu Asp Lys Gly Ala Met Asn Leu Gly Glu Phe Thr
        1025            1030            1035

Arg Asn Thr Val Phe Ala Lys Val Ile Tyr Lys Leu Leu Gln Val
        1040            1045            1050

Cys Leu Asp Met Glu Asp Ser Thr Phe Leu Asn Glu Leu Leu His
        1055            1060            1065

Leu Val His Gly Ile Phe Lys Asp Asp Glu Leu Ile Asn Gly Lys
        1070            1075            1080

Asp Ser Ile Pro Glu Ala Tyr Leu Ala Lys Pro Ile Cys Asn Leu
        1085            1090            1095

Leu Leu Ser Ile Ala Asn Ala Lys Ser Asp Ile Phe Ser Glu Ser
        1100            1105            1110

Ile Val Arg Lys Ala Asp Tyr Leu Leu Glu Lys Met Ile Met Lys
        1115            1120            1125

Lys Pro Asp Glu Ile Phe Glu Ser Leu Ile Ala Ser Phe Gly Asn
        1130            1135            1140

Gln Tyr Ile Asp Asn Tyr Lys Asp Lys Lys Leu Ser Gln Gly Val
        1145            1150            1155

Asn Leu Gln Glu Thr Glu Lys Glu Arg Lys Arg Arg Met Ala Lys
        1160            1165            1170

Lys His Gln Ala Arg Leu Leu Ala Lys Phe Asn Asn Gln Gln Ser
        1175            1180            1185

Lys Phe Met Lys Glu His Glu Ser Glu Phe Asp Glu Gln Asp Asn
        1190            1195            1200

Asp Val Asp Met Asp Gly Glu Lys Val Tyr Glu Ser Glu Asp Phe
        1205            1210            1215

Thr Cys Ala Leu Cys Gln Asp Ser Ser Ser Thr Asp Phe Phe Val
        1220            1225            1230

Ile Pro Ala Tyr His Asp His Thr Pro Ile Phe Arg Pro Gly Asn
        1235            1240            1245

Ile Phe Asn Pro Arg Glu Phe Met Ala Lys Trp Asp Gly Phe Tyr
        1250            1255            1260

Asn Asp Asp Asp Lys Gln Ala Tyr Ile Asp Asp Glu Val Leu Glu
        1265            1270            1275

Ser Leu Lys Glu Asn Gly Thr Arg Gly Ser Arg Lys Val Phe Val
        1280            1285            1290

Ser Cys Asn His His Ile His His Asn Cys Phe Lys Arg Tyr Val
        1295            1300            1305
```

-continued

```
Gln Lys Lys Arg Phe Ser Ser Asn Ala Phe Ile Cys Pro Leu Cys
    1310                1315                1320

Gln Thr Phe Ser Asn Cys Thr Leu Pro Ile Cys Pro Thr Ser Arg
    1325                1330                1335

Ala Asn Thr Gly Leu Ser Leu Asp Met Phe Leu Lys Ser Glu Leu
    1340                1345                1350

Ser Leu Asp Ile Leu Ser Arg Leu Phe Lys Pro Phe Thr Glu Asp
    1355                1360                1365

Asn Tyr Arg Thr Ile Asn Ser Ile Phe Ser Leu Met Val Ser Gln
    1370                1375                1380

Cys Gln Gly Phe Asp Lys Val Val Arg Lys His Val Asn Phe Thr
    1385                1390                1395

His Lys Asp Val Ser Leu Val Leu Ser Val His Trp Ala Asn Thr
    1400                1405                1410

Ile Ser Met Leu Glu Val Ala Ser Arg Leu Glu Lys Pro His Asn
    1415                1420                1425

Ile Ser Phe Phe Arg Ser Arg Glu Gln Lys Tyr Lys Thr Leu Lys
    1430                1435                1440

Asn Ile Leu Ile Cys Ile Met Leu Phe Thr Phe Val Ile Gly Lys
    1445                1450                1455

Pro Ser Met Glu Phe Glu Pro Tyr Pro Val Glu Ser Asp Ile Ile
    1460                1465                1470

Cys Asn Gln Asn Gln Leu Phe Gln Tyr Ile Val Arg Lys Ser Leu
    1475                1480                1485

Phe Ser Pro Ala Ser Leu Arg Glu Thr Ile Thr Glu Ala Leu Thr
    1490                1495                1500

Val Phe Cys Lys Gln Phe Leu Asp Asp Phe Val Gln Gly Leu Ser
    1505                1510                1515

Asp Ala Glu Gln Val Asp Lys Leu Tyr Thr Glu Ala Lys Lys Leu
    1520                1525                1530

Gly Asp Val Tyr Asn Val Asp Glu Ser Ile Leu Ile Thr Leu Met
    1535                1540                1545

Ser Ile Thr Val Val Lys Thr Glu Gly Leu Glu Ser Arg Ser Ile
    1550                1555                1560

Tyr Asp Leu Ala Tyr Thr Ser Leu Leu Lys Ser Leu Leu Pro Thr
    1565                1570                1575

Ile Arg Arg Cys Leu Val Met Val Lys Val Leu His Glu Leu Val
    1580                1585                1590

Lys Asp Ser Glu Asn Glu Thr Met Val Ile Asp Gly Phe Asp Val
    1595                1600                1605

Glu Glu Glu Leu Glu Phe Glu Gly Leu Pro Gly Phe Val Asp Lys
    1610                1615                1620

Ala Leu Lys Leu Ile Thr Asp Lys Glu Ser Phe Val Asp Leu Phe
    1625                1630                1635

Lys Thr Lys Gln Ala Ile Val Pro Ser His Pro Tyr Leu Glu Arg
    1640                1645                1650

Ile Pro Tyr Glu Tyr Cys Gly Ile Val Lys Leu Ile Asp Leu Ser
    1655                1660                1665

Lys Phe Leu Asn Thr Tyr Val Thr Gln Ser Lys Glu Ile Lys Leu
    1670                1675                1680

Arg Glu Glu Arg Ser Gln His Met Lys Asn Ala Asp Asn Arg Leu
    1685                1690                1695
```

-continued

```
Asp Phe Lys Ile Cys Leu Thr Cys Gly Val Lys Val His Leu Arg
    1700                1705                1710

Ala Asp Arg His Glu Met Thr Lys His Leu Asn Lys Asn Cys Phe
    1715                1720                1725

Lys Ser Phe Gly Ala Phe Leu Met Pro Asn Ser Ser Glu Val Cys
    1730                1735                1740

Leu His Leu Thr Gln Pro Pro Ser Asn Ile Phe Val Ser Ala Pro
    1745                1750                1755

Tyr Leu Asn Ser His Gly Glu Val Gly Arg Asn Ala Met Arg Arg
    1760                1765                1770

Gly Asp Leu Thr Thr Leu Asn Leu Lys Arg Tyr Glu His Leu Asn
    1775                1780                1785

Arg Leu Trp Ile Asn Asn Glu Ile Pro Gly Tyr Ile Ser Arg Val
    1790                1795                1800

Met Gly Asp Glu Phe Arg Val Thr Ile Leu Ser Asn Gly Phe Leu
    1805                1810                1815

Phe Ala Phe Asn Arg Glu Pro Arg Pro Arg Arg Val Pro Pro Thr
    1820                1825                1830

Asp Glu Asp Asp Glu Asp Met Glu Glu Gly Glu Gly Phe Phe
    1835                1840                1845

Thr Glu Glu Asn Asp Asp Met Asp Val Asp Asp Glu Thr Gly Gln
    1850                1855                1860

Ala Ala Asn Leu Phe Gly Val Gly Ala Glu Gly Ile Gly Asp Gly
    1865                1870                1875

Gly Val Arg Asn Phe Phe Gln Phe Phe Glu Asn Phe Arg Asn Thr
    1880                1885                1890

Leu Gln Pro Gln Gly Asn Asp Asp Glu Asp Ala Pro Gln Asn Pro
    1895                1900                1905

Pro Pro Ile Leu Gln Phe Leu Gly Pro Gln Phe Asp Gly Ala Thr
    1910                1915                1920

Ile Ile Arg Asn Thr Asn Gln Arg Asn Leu Asp Glu Asp Asp Ser
    1925                1930                1935

Ser Glu Asn Asp Asp Ser Asp Glu Arg Glu Ile Trp
    1940                1945                1950

<210> SEQ ID NO 43
<211> LENGTH: 601
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 43

Met Leu Asn His Pro Ser Gln Gly Ser Asp Asp Ala Gln Asp Glu Lys
1               5                   10                  15

Gln Gly Asp Phe Pro Val Ile Glu Glu Glu Lys Thr Gln Ala Val Met
                20                  25                  30

Leu Lys Asp Ser Tyr Val Ser Asp Val Ala Asn Ser Thr Glu Arg
            35                  40                  45

Tyr Asn Leu Ser Pro Ser Pro Glu Asp Glu Asp Phe Glu Ala Pro Thr
        50                  55                  60

Glu Glu Glu Met Gln Thr Leu Arg His Val Gly Gly Lys Ile Pro Met
65                  70                  75                  80

Arg Cys Trp Leu Ile Ala Ile Val Glu Leu Ser Glu Arg Phe Ser Tyr
                85                  90                  95
```

```
Tyr Gly Leu Ser Ala Pro Phe Gln Asn Tyr Met Glu Tyr Gly Pro Asn
            100                 105                 110

Asp Ser Pro Lys Gly Val Leu Ser Leu Asn Ser Gln Gly Ala Thr Gly
            115                 120                 125

Leu Ser Tyr Phe Phe Gln Phe Trp Cys Tyr Val Thr Pro Val Phe Gly
            130                 135                 140

Gly Tyr Val Ala Asp Thr Phe Trp Gly Lys Tyr Asn Thr Ile Cys Cys
145                 150                 155                 160

Gly Thr Ala Ile Tyr Ile Ala Gly Ile Phe Ile Leu Phe Ile Thr Ser
                165                 170                 175

Ile Pro Ser Val Gly Asn Arg Asp Ser Ala Ile Gly Gly Phe Ile Ala
            180                 185                 190

Ala Ile Ile Leu Ile Gly Ile Ala Thr Gly Met Ile Lys Ala Asn Leu
            195                 200                 205

Ser Val Leu Ile Ala Asp Gln Leu Pro Lys Arg Lys Pro Ser Ile Lys
            210                 215                 220

Val Leu Lys Ser Gly Glu Arg Val Ile Val Asp Ser Asn Ile Thr Leu
225                 230                 235                 240

Gln Asn Val Phe Met Phe Phe Tyr Phe Met Ile Asn Val Gly Ser Leu
                245                 250                 255

Ser Leu Met Ala Thr Thr Glu Leu Glu Tyr His Lys Gly Phe Trp Ala
            260                 265                 270

Ala Tyr Leu Leu Pro Phe Cys Phe Phe Trp Ile Ala Val Val Thr Leu
            275                 280                 285

Ile Phe Gly Lys Lys Gln Tyr Ile Gln Arg Pro Ile Gly Asp Lys Val
            290                 295                 300

Ile Ala Lys Ser Phe Lys Val Cys Trp Ile Leu Thr Lys Asn Lys Phe
305                 310                 315                 320

Asp Phe Asn Ala Ala Lys Pro Ser Val His Pro Glu Lys Asn Tyr Pro
                325                 330                 335

Trp Asn Asp Lys Phe Val Asp Glu Ile Lys Arg Ala Leu Ala Ala Cys
            340                 345                 350

Lys Val Phe Ile Phe Tyr Pro Ile Tyr Trp Thr Gln Tyr Gly Thr Met
            355                 360                 365

Ile Ser Ser Phe Ile Thr Gln Ala Ser Met Met Glu Leu His Gly Ile
            370                 375                 380

Pro Asn Asp Phe Leu Gln Ala Phe Asp Ser Ile Ala Leu Ile Ile Phe
385                 390                 395                 400

Ile Pro Ile Phe Glu Lys Phe Val Tyr Pro Phe Ile Arg Arg Tyr Thr
                405                 410                 415

Pro Leu Lys Pro Ile Thr Lys Ile Phe Val Gly Phe Met Phe Gly Ser
            420                 425                 430

Phe Ala Met Thr Trp Ala Ala Val Leu Gln Ser Phe Val Tyr Lys Ala
            435                 440                 445

Gly Pro Trp Tyr Asn Glu Pro Leu Gly His Asn Thr Pro Asn His Val
            450                 455                 460

His Val Cys Trp Gln Ile Pro Ala Tyr Val Leu Ile Ser Phe Ser Glu
465                 470                 475                 480

Ile Phe Ala Ser Ile Thr Gly Leu Glu Tyr Ala Tyr Ser Lys Ala Pro
                485                 490                 495

Ala Ser Met Lys Ser Phe Ile Met Ser Ile Phe Leu Leu Thr Asn Ala
            500                 505                 510
```

```
Phe Gly Ser Ala Ile Gly Cys Ala Leu Ser Pro Val Thr Val Asp Pro
            515                 520                 525

Lys Phe Thr Trp Leu Phe Thr Gly Leu Ala Val Ala Cys Phe Ile Ser
        530                 535                 540

Gly Cys Leu Phe Trp Leu Cys Phe Arg Lys Tyr Asn Asp Thr Glu Glu
545                 550                 555                 560

Glu Met Asn Ala Met Asp Tyr Glu Glu Glu Asn Glu Phe Asp Leu Asn
                565                 570                 575

Pro Ile Ser Ala Pro Lys Ala Asn Asp Ile Glu Ile Leu Glu Pro Met
            580                 585                 590

Asp Ser Leu Arg Ser Thr Thr Lys Tyr
        595                 600
```

<210> SEQ ID NO 44
<211> LENGTH: 601
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 44

```
Met Leu Asn His Leu Ser Gln Gly Ser Asp Asp Ile Gln Asp Glu Lys
1               5                   10                  15

Gln Gly Asp Phe Pro Val Ile Glu Glu Lys Asn Gln Thr Val Thr
            20                  25                  30

Leu Lys Asp Ser Tyr Val Ser Asp Ala Ala Asn Ser Thr Glu His
        35                  40                  45

Tyr Asn Leu Ser Pro Ser Leu Glu Asp Glu Phe Glu Ala Pro Thr
    50                  55                  60

Asp Glu Glu Leu Arg Ser Leu Arg His Val Gly Gly Lys Ile Pro Met
65                  70                  75                  80

Arg Cys Trp Leu Ile Ala Ile Val Glu Leu Ser Glu Arg Phe Ser Tyr
                85                  90                  95

Tyr Gly Leu Ser Ala Pro Phe Gln Asn Tyr Met Glu Tyr Gly Pro Lys
            100                 105                 110

Asp Thr Pro Lys Gly Val Leu Ser Leu Asn Ser Gln Gly Ala Thr Gly
        115                 120                 125

Leu Ser Tyr Phe Phe Gln Phe Trp Cys Tyr Val Thr Pro Val Phe Gly
    130                 135                 140

Gly Tyr Val Ala Asp Thr Phe Trp Gly Lys Tyr Asn Thr Ile Cys Cys
145                 150                 155                 160

Gly Thr Ala Ile Tyr Ile Ala Gly Ile Phe Ile Leu Ile Thr Ser
                165                 170                 175

Ile Pro Ser Val Gly Asn Arg Asp Ser Ala Leu Gly Gly Phe Ile Ala
            180                 185                 190

Ser Ile Ile Leu Ile Gly Ile Ala Thr Gly Met Ile Lys Ala Asn Leu
        195                 200                 205

Ser Val Leu Ile Ala Asp Gln Leu Pro Lys Arg Lys Pro Ser Ile Lys
    210                 215                 220

Val Leu Lys Ser Gly Glu Arg Val Ile Val Asp Ser Asn Ile Thr Leu
225                 230                 235                 240

Gln Asn Val Phe Met Phe Phe Tyr Phe Met Ile Asn Val Gly Ser Leu
                245                 250                 255

Ser Leu Met Ala Thr Thr Glu Leu Glu Tyr His Lys Gly Phe Trp Ala
            260                 265                 270
```

Ala Tyr Leu Leu Pro Phe Cys Phe Phe Trp Val Ala Val Val Thr Leu
            275                 280                 285

Val Phe Gly Lys Lys Gln Tyr Ile Gln Arg Pro Ile Gly Asp Lys Val
        290                 295                 300

Ile Ala Lys Ser Phe Arg Val Cys Trp Ile Leu Thr Lys Asn Lys Phe
305                 310                 315                 320

Asp Phe Asn Ala Ala Lys Pro Ser Val His Pro Glu Lys Glu Tyr Pro
                325                 330                 335

Trp Asn Asp Lys Phe Val Asp Glu Ile Lys Arg Ala Leu Ala Ala Cys
            340                 345                 350

Lys Val Phe Val Phe Tyr Pro Ile Tyr Trp Thr Gln Tyr Gly Thr Met
        355                 360                 365

Ile Ser Ser Phe Ile Thr Gln Ala Gly Met Met Glu Leu His Gly Ile
370                 375                 380

Pro Asn Asp Phe Leu Gln Ala Phe Asp Ser Ile Ala Leu Ile Ile Phe
385                 390                 395                 400

Ile Pro Ile Phe Glu Lys Phe Ile Tyr Pro Phe Ile Arg Arg Tyr Thr
                405                 410                 415

Pro Phe Lys Pro Ile Thr Lys Ile Phe Phe Gly Phe Met Phe Gly Ser
            420                 425                 430

Leu Ala Met Thr Trp Ala Ala Val Leu Gln Ser Phe Val Tyr Lys Ala
        435                 440                 445

Gly Pro Trp Tyr Ser Ala Pro Leu Gly His Asn Thr Pro Asn His Val
        450                 455                 460

His Val Cys Trp Gln Ile Pro Ala Tyr Val Leu Ile Ser Phe Ser Glu
465                 470                 475                 480

Ile Phe Ala Ser Ile Thr Gly Leu Glu Tyr Ala Tyr Ser Lys Ala Pro
                485                 490                 495

Ala Ser Met Lys Ser Phe Ile Met Ser Ile Phe Leu Leu Thr Asn Ala
            500                 505                 510

Phe Gly Ser Ala Ile Gly Cys Ala Leu Ser Pro Val Thr Val Asp Pro
        515                 520                 525

Lys Phe Thr Trp Leu Phe Thr Gly Leu Ala Val Ala Cys Phe Ile Ser
        530                 535                 540

Gly Cys Leu Phe Trp Phe Cys Phe Arg Lys Tyr Asn Asp Thr Glu Glu
545                 550                 555                 560

Glu Met Asn Ala Met Asp Tyr Glu Glu Glu Asp Phe Asp Leu Asn
                565                 570                 575

Pro Ile Ser Gln Pro Lys Gly Asn Asp Ile Glu Ile Leu Glu Pro Met
            580                 585                 590

Gly Ser Leu Lys Ser Thr Thr Lys Tyr
        595                 600

<210> SEQ ID NO 45
<211> LENGTH: 361
<212> TYPE: PRT
<213> ORGANISM: Unknown
<220> FEATURE:
<223> OTHER INFORMATION: Hybrid between S. cerevisiae and S. pastorianus
      (Hybrid yeast 1)

<400> SEQUENCE: 45

Met Ser Val Ala Asp Asp Leu Gly Ser Leu Gln Gly His Ile Arg
1               5                   10                  15

Arg Thr Leu Arg Ser Ile His Asn Leu Pro Tyr Phe Arg Tyr Thr Arg

```
            20                  25                  30
Gly Pro Thr Glu Arg Ala Asp Met Ser Arg Ala Leu Lys Glu Phe Ile
         35                  40                  45

Tyr Arg Tyr Leu Tyr Phe Val Ile Ser Asn Ser Gly Glu Asn Leu Pro
 50                  55                  60

Thr Leu Phe Asn Ala His Pro Lys Gln Lys Leu Ser Asn Pro Glu Leu
 65                  70                  75                  80

Thr Val Phe Pro Asp Ser Leu Glu Asp Ala Val Asp Ile Asp Lys Ile
                 85                  90                  95

Thr Ser Gln Gln Thr Ile Pro Phe Tyr Lys Ile Asp Glu Ser Arg Ile
                100                 105                 110

Gly Asp Val His Lys His Thr Gly Arg Asn Cys Gly Arg Lys Phe Lys
                115                 120                 125

Ile Gly Glu Pro Leu Tyr Arg Cys His Glu Cys Gly Cys Asp Asp Thr
                130                 135                 140

Cys Val Leu Cys Ile His Cys Phe Asn Pro Lys Asp His Val Asn His
145                 150                 155                 160

His Val Cys Thr Asp Ile Cys Thr Glu Phe Thr Ser Gly Ile Cys Asp
                165                 170                 175

Cys Gly Asp Glu Glu Ala Trp Asn Ser Pro Leu His Cys Lys Ala Glu
                180                 185                 190

Glu Gln Glu Asn Asp Ile Ser Glu Asp Pro Ala Thr Asn Ala Asp Ile
                195                 200                 205

Lys Glu Glu Asp Val Trp Asn Asp Ser Val Asn Ile Ala Leu Val Glu
                210                 215                 220

Leu Val Leu Ala Glu Val Phe Asp Tyr Phe Ile Asp Val Phe Asn Gln
225                 230                 235                 240

Asn Ile Glu Pro Leu Pro Thr Ile Gln Lys Asp Ile Thr Ile Lys Leu
                245                 250                 255

Arg Glu Met Thr Gln Gln Gly Lys Met Tyr Glu Arg Ala Gln Phe Leu
                260                 265                 270

Asn Asp Leu Lys Tyr Glu Asn Asp Tyr Met Phe Asp Gly Thr Thr Thr
                275                 280                 285

Ala Lys Thr Ser Pro Ser Asn Ser Pro Glu Ala Ser Pro Ser Leu Ala
                290                 295                 300

Lys Ile Asp Pro Glu Asn Tyr Thr Val Ile Ile Tyr Asn Asp Glu Tyr
305                 310                 315                 320

His Asn Tyr Ser Gln Ala Thr Thr Ala Leu Arg Gln Gly Val Pro Asp
                325                 330                 335

Asn Val His Ile Asp Leu Leu Thr Ser Arg Ile Asp Gly Glu Gly Arg
                340                 345                 350

Ala Met Leu Lys Cys Ser Gln Asp Leu
                355                 360

<210> SEQ ID NO 46
<211> LENGTH: 543
<212> TYPE: PRT
<213> ORGANISM: Saccharomyces cerevisiae

<400> SEQUENCE: 46

Met Ser Ala Asp Ala Ser Thr Asn Ser Asn Ala Ser Leu Asp Glu Lys
1               5                  10                  15

Asn Leu Asn Ile Thr Ser Glu Ala Glu Ile Lys Asn Glu Asp Val Thr
                20                  25                  30
```

```
Ala Glu Pro Val Leu Ser Thr Val Leu Ser Pro Asn Gly Lys Ile Val
         35                  40                  45

Tyr Ile Ser Asp Lys Val Asp Glu Ala Met Lys Leu Ala Glu Glu Ala
 50                  55                  60

Lys Glu Ile Glu Val Thr Pro Glu Glu Asp Arg Lys Leu Arg Trp Lys
 65                  70                  75                  80

Ile Asp Tyr Cys Met Phe Pro Leu Met Cys Ile Leu Tyr Ala Val Gln
                 85                  90                  95

Phe Met Asp Lys Ile Ser Thr Ser Ser Ala Ala Val Met Gly Leu Arg
            100                 105                 110

Thr Asp Leu Lys Met His Gly Asp Gln Tyr Ser Trp Val Thr Ser Ala
            115                 120                 125

Phe Tyr Phe Gly Tyr Leu Phe Met Asn Leu Gly Pro Val Gln Phe Ile
        130                 135                 140

Phe Gln Arg Thr Ser His Met Ser Lys Met Leu Ala Val Phe Ile Val
145                 150                 155                 160

Ile Trp Gly Met Leu Leu Ala Leu His Ala Ala Pro Thr Val Lys Tyr
                165                 170                 175

Pro Ser Phe Ile Val Leu Arg Val Leu Leu Gly Cys Ala Glu Ser Val
            180                 185                 190

Val Thr Pro Cys Phe Thr Ile Ile Thr Ala Gln Tyr Trp Lys Thr Glu
        195                 200                 205

Glu Gln Phe Thr Arg Val Ser Ile Trp Phe Gly Met Asn Gly Leu Gly
    210                 215                 220

Ser Ile Leu Ile Asn Ala Ile Ala Tyr Gly Val Tyr Ile His Gln Asp
225                 230                 235                 240

Ser Tyr Ala Ile Lys Gly Trp Arg Thr Leu Phe Val Ile Thr Gly Val
                245                 250                 255

Ile Thr Ile Phe Ile Gly Ile Leu Ile Phe Leu Trp Ile Pro Asp Asp
            260                 265                 270

Pro Ser Lys Ala Arg Phe Leu Ser Lys Arg Glu Lys Leu Met Val Val
        275                 280                 285

Gln Arg Ile Arg Ser Asn Gln Gln Gly Phe Gly Asn His Glu Ile Lys
    290                 295                 300

Lys Tyr Gln Ile Ile Glu Ala Leu Lys Asp Val Arg Thr Trp Leu Tyr
305                 310                 315                 320

Phe Leu Phe Thr Val Ser Ser Asn Ile Pro Asn Gly Gly Ile Ser Ser
                325                 330                 335

Phe Met Ser Ile Leu Leu Asn Ser Asp Phe Gly Tyr Ser Ser Lys Glu
            340                 345                 350

Thr Leu Leu Met Gly Leu Pro Thr Gly Ala Val Glu Leu Val Gly Cys
        355                 360                 365

Pro Leu Phe Gly Ile Leu Ala Val Tyr Ala Ala Asn Lys Lys Ile Pro
    370                 375                 380

Phe Trp Lys Tyr Lys Leu Ser Trp Ala Ile Phe Ala Ala Val Leu Ala
385                 390                 395                 400

Leu Ile Ala Ser Cys Met Leu Gly Phe Ala Thr Asn Ser Lys Lys Ala
                405                 410                 415

Arg Leu Ala Gly Ala Tyr Leu Trp Tyr Ile Ser Pro Val Ser Phe Ile
            420                 425                 430

Cys Val Leu Ser Asn Ile Ser Ala Asn Ser Ser Gly Tyr Ser Lys Lys
        435                 440                 445

Trp Thr Val Ser Ser Ile Asn Leu Val Ala Tyr Ala Ala Ala Asn Leu
```

450                 455                 460
Ala Gly Pro Gln Thr Phe Ile Ala Lys Gln Ala Pro Lys Tyr His Gly
465                 470                 475                 480

Ala Lys Val Ala Met Val Val Cys Tyr Ala Val Met Ile Val Leu Leu
                485                 490                 495

Ser Ile Leu Leu Ile Val Asn Leu Arg Glu Asn Lys Arg Arg Asp Lys
                500                 505                 510

Ile Ala Ala Glu Arg Gly Phe Pro Glu Glu Thr Glu Asn Leu Glu Phe
            515                 520                 525

Ser Asp Leu Thr Asp Phe Glu Asn Pro Asn Phe Arg Tyr Thr Leu
        530                 535                 540

<210> SEQ ID NO 47
<211> LENGTH: 543
<212> TYPE: PRT
<213> ORGANISM: Saccharomyces pastorianus

<400> SEQUENCE: 47

Met Ser Gly Gly Ala Ser Thr Asn Ser Asn Ala Ser Ile Asp Glu Lys
1               5                   10                  15

Asn Leu Asn Ile Thr Ser Glu Ala Glu Ile Lys Asn Glu Asp Val Tyr
            20                  25                  30

Ala Glu Pro Val Leu Ser Thr Val Leu Ser Pro Asn Gly Lys Val Val
        35                  40                  45

Tyr Ile Ser Asp Lys Val Asp Glu Ala Met Lys Leu Ala Asp Glu Ala
    50                  55                  60

Lys Glu Ile Glu Val Thr Pro Glu Glu Asp Arg Lys Leu Arg Trp Lys
65                  70                  75                  80

Ile Asp Tyr Cys Met Phe Pro Leu Met Cys Ile Leu Tyr Ala Val Gln
                85                  90                  95

Phe Met Asp Lys Ile Ser Thr Ser Ser Ala Ala Val Met Gly Leu Arg
            100                 105                 110

Thr Asp Leu Lys Met His Gly Asp Gln Tyr Ser Trp Val Thr Ser Ala
        115                 120                 125

Phe Tyr Phe Gly Tyr Leu Phe Met Asn Leu Gly Pro Val Gln Leu Ile
    130                 135                 140

Phe Gln Lys Ser Lys His Met Ser Lys Met Leu Ala Ile Phe Ile Ile
145                 150                 155                 160

Val Trp Gly Leu Leu Leu Ala Leu His Ala Val Pro Ser Val Lys Tyr
                165                 170                 175

Ser Ser Phe Ile Ala Leu Arg Val Leu Leu Gly Cys Ala Glu Ser Val
            180                 185                 190

Val Thr Pro Cys Phe Thr Ile Ile Thr Ala Gln Tyr Trp Lys Thr Glu
        195                 200                 205

Glu Gln Phe Thr Arg Ile Ser Ile Trp Phe Gly Met Asn Gly Leu Gly
    210                 215                 220

Ser Ile Leu Ile Asn Ala Ile Ala Tyr Gly Val Tyr Ile His Gln Glu
225                 230                 235                 240

Ser Tyr Ala Ile Lys Gly Trp Arg Ala Leu Phe Val Ile Thr Gly Val
                245                 250                 255

Ile Thr Ile Phe Val Gly Ala Leu Ile Phe Leu Trp Ile Pro Asp Asp
            260                 265                 270

Pro Ser Lys Ala Arg Phe Leu Ser Lys Arg Glu Lys Leu Met Val Val
        275                 280                 285

Gln Arg Ile Arg Ser Asn Gln Gln Gly Phe Gly Asn His Glu Ile Lys
            290                 295                 300

Lys Tyr Gln Ile Val Glu Ala Leu Lys Asp Val Arg Thr Trp Leu Tyr
305                 310                 315                 320

Phe Leu Phe Thr Val Ser Ser Asn Ile Pro Asn Gly Gly Ile Ser Ser
                325                 330                 335

Phe Met Ser Ile Leu Leu Asn Ser Asp Phe Gly Tyr Leu Ser Lys Asp
                340                 345                 350

Thr Leu Leu Met Gly Leu Pro Thr Gly Ala Val Glu Leu Val Gly Cys
            355                 360                 365

Pro Leu Phe Gly Ile Leu Ala Val Tyr Ala Ala Asn Lys Lys Ile Pro
370                 375                 380

Phe Trp Lys Tyr Lys Leu Ala Trp Ala Ile Phe Ala Ala Val Leu Ala
385                 390                 395                 400

Leu Ile Ala Ser Cys Met Leu Gly Phe Ala Thr Ser Ser Lys Lys Ala
                405                 410                 415

Arg Leu Ala Gly Ala Tyr Leu Trp Tyr Ile Ser Pro Val Ser Phe Ile
            420                 425                 430

Cys Val Leu Ser Asn Ile Ser Ala Asn Ser Ser Gly Tyr Ser Lys Lys
                435                 440                 445

Trp Thr Val Ser Ser Ile Asn Leu Ala Ala Tyr Ala Ala Ala Asn Leu
450                 455                 460

Ala Gly Pro Gln Thr Phe Ile Ala Lys Gln Ala Pro Lys Tyr His Gly
465                 470                 475                 480

Ala Lys Val Ala Met Val Val Cys Tyr Ala Val Met Ile Val Leu Leu
                485                 490                 495

Ser Ala Leu Leu Leu Ile Asn Met Arg Glu Asn Lys Arg Arg Asp Lys
            500                 505                 510

Ile Ala Ala Glu Arg Gly Tyr Pro Glu Glu Thr Ala Asn Leu Glu Phe
            515                 520                 525

Ser Asp Leu Thr Asp Phe Glu Asn Pro Asn Phe Arg Tyr Thr Leu
530                 535                 540

<210> SEQ ID NO 48
<211> LENGTH: 301
<212> TYPE: PRT
<213> ORGANISM: Saccharomyces cerevisiae
<220> FEATURE:
<221> NAME/KEY: MISC_FEATURE
<222> LOCATION: (40)..(40)
<223> OTHER INFORMATION: X: any amino acid
<220> FEATURE:
<221> NAME/KEY: MISC_FEATURE
<222> LOCATION: (298)..(298)
<223> OTHER INFORMATION: X: any amino acid

<400> SEQUENCE: 48

Phe Lys Glu Phe Cys Lys Val Glu Gly Gly Val Leu Ile Trp Gln Arg
1               5                   10                  15

Val Gln Lys Ser Asn Leu Thr Lys Ser Tyr Ser Ile Ser Phe Lys Gln
            20                  25                  30

Gly Leu Tyr Thr Val Glu Thr Xaa Leu Ser Lys Val His Asp Pro Asn
            35                  40                  45

Ile Pro Leu Arg Pro Lys Glu Ile Ser Leu Leu Thr Leu Cys Lys
50                  55                  60

Leu Phe Asn Gly Ala Trp Lys Ile Lys Arg Lys Glu Gly Glu His Val
65                  70                  75                  80

```
Leu His Glu Asp Gln Asn Phe Ile Ser Tyr Leu Glu Tyr Thr Thr Ser
                    85                  90                  95

Ile Tyr Ser Ile Ile Gln Thr Ala Glu Lys Val Ser Glu Lys Ser Lys
                100                 105                 110

Asp Ser Ile Asp Ser Lys Leu Phe Leu Asn Ala Ile Arg Ile Ile Ser
                115                 120                 125

Ser Phe Leu Gly Asn Arg Ser Leu Thr Tyr Lys Leu Ile Tyr Asp Ser
    130                 135                 140

His Glu Val Ile Lys Phe Ser Val Ser His Glu Arg Val Ala Phe Met
145                 150                 155                 160

Asn Pro Leu Gln Thr Met Leu Ser Phe Leu Ile Glu Lys Val Ser Leu
                165                 170                 175

Lys Asp Ala Tyr Glu Ala Leu Glu Asp Cys Ser Asp Phe Leu Lys Ile
                180                 185                 190

Ser Asp Phe Ser Leu Arg Ser Val Val Leu Cys Ser Gln Ile Asp Val
    195                 200                 205

Gly Phe Trp Val Arg Asn Gly Met Ser Val Leu His Gln Ala Ser Tyr
    210                 215                 220

Tyr Lys Asn Asn Pro Glu Leu Gly Ser Tyr Ser Arg Asp Ile His Leu
225                 230                 235                 240

Asn Gln Leu Ala Ile Leu Trp Glu Arg Asp Asp Ile Pro Arg Ile Ile
                245                 250                 255

Tyr Asn Ile Leu Asp Arg Trp Glu Leu Leu Asp Trp Phe Thr Gly Glu
                260                 265                 270

Val Asp Tyr Gln His Thr Val Tyr Glu Asp Lys Ile Ser Phe Ile Ile
    275                 280                 285

Gln Gln Phe Ile Ala Phe Ile Tyr Gln Xaa Ile Ser Leu
    290                 295                 300

<210> SEQ ID NO 49
<211> LENGTH: 399
<212> TYPE: PRT
<213> ORGANISM: Saccharomyces pastorianus
<220> FEATURE:
<221> NAME/KEY: MISC_FEATURE
<222> LOCATION: (232)..(232)
<223> OTHER INFORMATION: X: any amino acid
<220> FEATURE:
<221> NAME/KEY: MISC_FEATURE
<222> LOCATION: (368)..(368)
<223> OTHER INFORMATION: X: any amino acid

<400> SEQUENCE: 49

Phe Lys Glu Phe Cys Lys Val Glu Gly Gly Val Leu Ile Trp Gln Arg
1               5                   10                  15

Val Gln Lys Ser Asn Leu Thr Lys Ser Tyr Ser Ile Ser Phe Lys Gln
                20                  25                  30

Gly Leu Tyr Thr Val Glu Thr Leu Leu Ser Lys Val His Asp Pro Asn
            35                  40                  45

Ile Pro Leu Arg Pro Lys Glu Ile Ile Ser Leu Leu Thr Leu Cys Lys
        50                  55                  60

Leu Phe Asn Gly Ala Trp Lys Ile Lys Arg Lys Glu Gly Glu His Val
65                  70                  75                  80

Leu His Glu Asp Gln Asn Phe Ile Ser Tyr Leu Glu Tyr Thr Thr Ser
                85                  90                  95

Ile Tyr Ser Ile Ile Gln Thr Ala Glu Lys Val Ser Glu Lys Ser Lys
                100                 105                 110
```

-continued

Asp Ser Ile Asp Ser Lys Leu Phe Leu Asn Ala Ile Arg Ile Ile Ser
            115                 120                 125

Ser Phe Leu Gly Asn Arg Ser Leu Thr Tyr Lys Leu Ile Tyr Asp Ser
130                 135                 140

His Glu Val Ile Lys Phe Ser Val Ser His Glu Arg Val Ala Phe Met
145                 150                 155                 160

Asn Pro Leu Gln Thr Met Leu Ser Phe Leu Ile Glu Lys Val Ser Leu
                165                 170                 175

Lys Asp Ala Tyr Glu Ala Leu Glu Asp Cys Ser Asp Phe Leu Lys Ile
            180                 185                 190

Ser Asp Phe Ser Leu Arg Ser Val Val Leu Cys Ser Gln Ile Asp Val
        195                 200                 205

Gly Phe Trp Val Arg Asn Gly Met Ser Val Leu His Gln Ala Ser Tyr
210                 215                 220

Tyr Lys Asn Asn Pro Glu Leu Xaa Ser Tyr Ser Arg Asp Ile His Leu
225                 230                 235                 240

Asn Gln Leu Ala Ile Leu Trp Glu Arg Asp Ile Pro Arg Ile Ile
                245                 250                 255

Tyr Asn Ile Leu Asp Arg Trp Glu Leu Leu Asp Trp Phe Thr Gly Glu
            260                 265                 270

Val Asp Tyr Gln His Thr Val Tyr Glu Asp Lys Ile Ser Phe Ile Ile
        275                 280                 285

Gln Gln Phe Ile Ala Phe Ile Tyr Gln Ile Leu Thr Glu Arg Gln Tyr
    290                 295                 300

Phe Lys Thr Phe Ser Ser Leu Lys Asp Arg Arg Met Asp Gln Ile Lys
305                 310                 315                 320

Asn Ser Ile Ile Tyr Asn Leu Tyr Met Lys Pro Leu Ser Tyr Ser Lys
                325                 330                 335

Leu Leu Arg Ser Val Pro Asp Tyr Leu Thr Glu Asp Thr Thr Glu Phe
            340                 345                 350

Asp Glu Ala Leu Glu Glu Val Ser Val Phe Val Glu Pro Lys Gly Xaa
        355                 360                 365

Ala Asp Asn Gly Val Phe Lys Leu Lys Ala Ser Leu Tyr Ala Lys Val
370                 375                 380

Asp Pro Leu Lys Leu Leu Asn Leu Glu Asn Glu Phe Glu Ser Ser
385                 390                 395

<210> SEQ ID NO 50
<211> LENGTH: 1950
<212> TYPE: PRT
<213> ORGANISM: Saccharomyces pastorianus

<400> SEQUENCE: 50

Met Ser Phe Thr Asp Asn Gly Leu Gly Ser Leu Lys Ala His Ile Arg
1               5                   10                  15

Arg Thr Leu Arg Ser Ile His Asn Leu Pro Tyr Phe Arg Phe Thr Arg
            20                  25                  30

Gly Pro Thr Glu Arg Ala Asp Met Ser Arg Ala Leu Lys Glu Phe Ile
        35                  40                  45

Tyr Arg Tyr Leu Tyr Phe Ile Ile Ser Asn Asp Gly Glu Asn Leu Ser
    50                  55                  60

Thr Leu Phe Thr Ala His Pro Lys Gln Lys Ser Ser Asn Gln Glu Leu
65                  70                  75                  80

Ala Val Phe Pro Glu Ser Leu Glu Asp Ala Leu Asp Val Asp Lys Ile
                85                  90                  95

```
Thr Ser Gln Gly Thr Phe Pro Phe Tyr Lys Ile Asp Glu Ser Lys Ile
            100                 105                 110

Gly Asp Val His Lys His Thr Gly Arg Asn Cys Gly Arg Lys Phe Lys
            115                 120                 125

Ile Gly Glu Pro Leu Tyr Arg Cys His Glu Cys Gly Cys Asp Asp Thr
            130                 135                 140

Cys Val Leu Cys Ile His Cys Phe Asn Pro Lys Asp His Ile Asn His
145                 150                 155                 160

His Val Cys Thr Asp Ile Cys Ser Glu Phe Thr Ser Gly Ile Cys Asp
                165                 170                 175

Cys Gly Asp Glu Glu Ala Trp Asn Ser Ser Leu His Cys Lys Ala Glu
            180                 185                 190

Glu Gln Gly Asn Asp Thr Ser Glu Asp Pro Ser Asn Phe Asp Ser Thr
            195                 200                 205

Lys Gln Lys Asp Val Trp Asn Asp Pro Glu Cys Ile Ala Leu Val Glu
            210                 215                 220

Leu Val Leu Ser Glu Val Phe Asp Tyr Phe Ile Asp Val Phe Asn Gln
225                 230                 235                 240

Asn Ile Glu Pro Leu Pro Thr Ile Gln Lys Asp Ile Thr Ile Lys Leu
                245                 250                 255

Arg Glu Met Thr Gln Gln Gly Lys Met Tyr Glu Arg Ala Gln Phe Leu
            260                 265                 270

Asn Asp Leu Lys Tyr Glu Asn Asp Tyr Met Phe Asp Gly Thr Thr Thr
            275                 280                 285

Ala Lys Thr Ser Pro Ser Asn Ser Pro Glu Ala Ser Pro Ser Leu Ala
            290                 295                 300

Lys Ile Asp Pro Glu Asn Tyr Thr Val Ile Ile Tyr Asn Asp Glu Tyr
305                 310                 315                 320

His Asn Tyr Ser Gln Ala Thr Thr Ala Leu Arg Gln Gly Val Pro Asp
                325                 330                 335

Asn Val His Ile Asp Leu Leu Thr Ser Arg Ile Asp Gly Glu Gly Arg
            340                 345                 350

Ala Met Leu Lys Cys Ser Gln Asp Leu Ser Ser Val Leu Gly Gly Phe
            355                 360                 365

Phe Ala Val Gln Thr Asn Gly Leu Ser Ala Thr Leu Thr Ser Trp Ser
            370                 375                 380

Glu Tyr Leu His Gln Glu Ala Cys Lys Tyr Ile Ile Leu Trp Ile Thr
385                 390                 395                 400

His Cys Leu Asn Ile Pro Asn Pro Ser Phe Gln Ile Thr Phe Arg Asn
                405                 410                 415

Met Met Gly Lys Ser Leu Cys Ser Glu Tyr Leu Asn Ala Thr Glu Ser
            420                 425                 430

Arg Asp Met Thr Pro Val Val Glu Lys Tyr Phe Ser Thr Lys Phe Asp
            435                 440                 445

Lys Asp Asp Pro Tyr Arg Tyr Ile Asp Leu Ser Val Leu Ala Glu Gly
            450                 455                 460

Asn Gln Ile Pro Leu Gly His His Lys Val Leu Pro Glu Ser Ser Thr
465                 470                 475                 480

His Ser Leu Ser Thr Leu Ile Asn Asp Val Glu Asn Leu Thr Ser Lys
                485                 490                 495

Glu Tyr Ser Asn Thr Arg Leu Gln His Ile Leu Tyr Phe Asp Asn Arg
            500                 505                 510
```

-continued

```
Tyr Trp Lys Arg Leu Arg Lys Asp Ile Gln Asn Val Ile Pro Thr
            515                 520                 525
Leu Ala Ser Ser Thr Leu Tyr Lys Pro Ile Phe Cys Gln Gln Val Val
530                 535                 540
Glu Ile Phe Asn His Ile Thr Arg Ser Val Ala Tyr Met Asp Arg Glu
545                 550                 555                 560
Pro Gln Leu Thr Ala Ile Arg Glu Cys Val Val Gln Leu Phe Thr Cys
                565                 570                 575
Pro Thr Asn Thr Arg Asn Ile Phe Glu Asn Gln Ser Phe Leu Asp Ile
            580                 585                 590
Leu Trp Ser Ile Ile Asp Ile Phe Lys Glu Phe Cys Lys Val Glu Ala
            595                 600                 605
Gly Val Leu Ile Trp Gln Arg Val Gln Lys Ser Asn Leu Thr Lys Ser
        610                 615                 620
Tyr Ser Leu Ser Phe Lys Gln Gly Leu Tyr Thr Val Glu Thr Leu Leu
625                 630                 635                 640
Ser Lys Val Asn Asp Pro Asn Ile Thr Ile Arg Pro Lys Val Phe Ile
                645                 650                 655
Ser Leu Leu Thr Leu Gly Lys Leu Phe Asn Gly Ala Trp Lys Ile Lys
            660                 665                 670
Arg Lys Glu Gly Glu His Val Leu His Glu Asp Gln Asn Phe Ile Ser
        675                 680                 685
Tyr Leu Glu Tyr Thr Thr Ser Ile Tyr Ser Ile Ile Gln Thr Ala Glu
            690                 695                 700
Lys Val Leu Glu Lys Ser His Asp Ser Leu Asp Leu Asn Leu Val Leu
705                 710                 715                 720
Asn Ala Ile Arg Ile Val Ser Ser Phe Leu Gly Asn Arg Ser Leu Thr
                725                 730                 735
Tyr Lys Leu Ile Tyr Asp Ser His Glu Ile Ile Lys Phe Ser Val Ser
            740                 745                 750
His Glu Arg Val Ala Phe Met Asn Pro Ile Gln Thr Met Leu Ser Phe
        755                 760                 765
Leu Ile Glu Lys Val Ser Leu Lys Asp Ala Tyr Glu Ser Leu Glu Asn
770                 775                 780
Cys Pro Asp Phe Leu Lys Ile Ala Asp Phe Ser Leu Arg Ser Val Val
785                 790                 795                 800
Leu Cys Ser Gln Ile Asp Val Gly Phe Trp Val Arg Asn Gly Met Ser
                805                 810                 815
Val Leu His Gln Ala Ser Tyr Tyr Lys Asn Asn Pro Glu Leu Gly Ser
            820                 825                 830
Tyr Ser Arg Asp Ile His Leu Asn Gln Leu Ala Ile Ile Trp Glu Arg
        835                 840                 845
Asp Asp Leu Pro Arg Val Ile Tyr Asn Ile Leu Asp Arg Trp Glu Leu
850                 855                 860
Leu Asp Trp Phe Met Gly Glu Ala Glu Tyr Gln His Thr Val Tyr Glu
865                 870                 875                 880
Asp Lys Ile Ser Phe Met Ile Gln Gln Phe Ile Ala Phe Ile Tyr Gln
                885                 890                 895
Ile Leu Thr Glu Arg Gln Tyr Phe Lys Thr Phe Ser Leu Leu Arg Asp
            900                 905                 910
Arg Arg Met Asp Met Ile Lys Asn Ser Ile Met Tyr Asn Leu Tyr Met
        915                 920                 925
Lys Pro Leu Ser Tyr Ser Lys Leu Leu Lys Ser Val Pro Asp Tyr Leu
```

```
                930             935             940
Thr Asp Asp Thr Thr Glu Phe Asp Glu Ala Leu Glu Val Ser Val
945                 950             955             960
Phe Val Glu Pro Lys Gly Leu Ala Asp Asn Gly Val Phe Lys Leu Lys
                965             970             975
Ala Ala Leu Tyr Ala Lys Ile Asp Pro Leu Lys Leu Leu Asn Leu Glu
            980             985             990
Asn Glu Phe Glu Ser Ser Ala Thr Ile Ile Lys Thr His Leu Ala Lys
        995             1000            1005
Asn Lys Asp Glu Val Ser Lys Val Val Leu Ile Pro Gln Val Ser
    1010            1015            1020
Thr Lys Leu Leu Asp Lys Gly Ala Met Asn Leu Gly Glu Phe Thr
    1025            1030            1035
Arg Asn Thr Val Phe Ala Lys Val Val Tyr Lys Leu Leu Gln Val
    1040            1045            1050
Cys Leu Asp Met Glu Asp Ser Thr Phe Leu Asn Glu Leu Leu His
    1055            1060            1065
Leu Val His Gly Ile Phe Lys Asp Asp Glu Leu Ile Asn Gly Lys
    1070            1075            1080
Asp Ser Ile Pro Glu Ala Tyr Leu Ala Lys Pro Ile Cys Asn Leu
    1085            1090            1095
Leu Leu Ser Ile Ala Asn Ala Lys Ser Asp Ile Phe Ser Glu Ser
    1100            1105            1110
Ile Val Arg Lys Ala Asp Tyr Leu Leu Glu Lys Met Ile Met Lys
    1115            1120            1125
Lys Pro Asp Glu Ile Phe Glu Ser Leu Ile Ala Ser Phe Gly Asn
    1130            1135            1140
Gln Tyr Ile Asp Asn Tyr Lys Asp Lys Lys Leu Ser Gln Gly Val
    1145            1150            1155
Asn Leu Gln Glu Thr Glu Lys Glu Arg Lys Arg Arg Met Ala Lys
    1160            1165            1170
Lys His Gln Ala Arg Leu Leu Ala Lys Phe Asn Asn Gln Gln Ser
    1175            1180            1185
Lys Phe Met Lys Glu His Glu Ser Glu Phe Asp Glu Gln Asp Asn
    1190            1195            1200
Asp Val Asp Met Asp Gly Glu Lys Val Tyr Glu Ser Glu Asp Phe
    1205            1210            1215
Thr Cys Ala Leu Cys Gln Asp Ser Ser Ser Thr Asp Phe Phe Val
    1220            1225            1230
Ile Pro Ala Tyr His Asp His Thr Pro Ile Phe Arg Pro Gly Asn
    1235            1240            1245
Ile Phe Asn Pro Arg Glu Phe Met Ala Lys Trp Asp Gly Phe Tyr
    1250            1255            1260
Asn Asp Asp Lys Gln Ala Tyr Ile Asp Asp Glu Val Leu Glu
    1265            1270            1275
Ser Leu Lys Glu Asn Gly Thr Arg Gly Ser Arg Lys Val Phe Val
    1280            1285            1290
Ser Cys Asn His His Ile His His Asn Cys Phe Lys Arg Tyr Val
    1295            1300            1305
Gln Lys Lys Arg Phe Ser Ser Asn Ala Phe Ile Cys Pro Leu Cys
    1310            1315            1320
Gln Thr Phe Ser Asn Cys Thr Leu Pro Ile Cys Pro Thr Ser Arg
    1325            1330            1335
```

```
Ala Asn Thr Gly Leu Ser Leu Asp Met Phe Leu Lys Ser Glu Leu
1340                1345                1350

Ser Leu Asp Ile Leu Ser Arg Leu Phe Lys Pro Phe Thr Glu Asp
    1355                1360                1365

Asn Tyr Arg Thr Ile Asn Ser Ile Phe Ser Leu Met Val Ser Gln
    1370                1375                1380

Cys Gln Gly Phe Asp Lys Val Val Arg Lys His Val Asn Phe Thr
    1385                1390                1395

His Lys Asp Val Ser Leu Val Leu Ser Val His Trp Ala Asn Thr
    1400                1405                1410

Ile Ser Met Leu Glu Val Ala Ser Arg Leu Glu Lys Pro His Asn
    1415                1420                1425

Ile Ser Phe Phe Arg Ser Arg Glu Gln Lys Tyr Lys Thr Leu Lys
    1430                1435                1440

Asn Ile Leu Ile Cys Ile Met Leu Phe Thr Phe Val Ile Gly Lys
    1445                1450                1455

Pro Ser Met Glu Phe Glu Pro Tyr Pro Val Glu Ser Asp Ile Ile
    1460                1465                1470

Cys Asn Gln Asn Gln Leu Phe Gln Tyr Ile Val Arg Lys Ser Leu
    1475                1480                1485

Phe Ser Pro Ala Ser Leu Arg Glu Thr Ile Thr Glu Ala Leu Thr
    1490                1495                1500

Val Phe Cys Lys Gln Phe Leu Asp Asp Phe Val Gln Gly Leu Ser
    1505                1510                1515

Asp Ala Glu Gln Val Asp Lys Leu Tyr Thr Glu Ala Lys Lys Leu
    1520                1525                1530

Gly Asp Val Tyr Asn Val Asp Glu Ser Ile Leu Ile Thr Leu Met
    1535                1540                1545

Ser Ile Thr Val Val Lys Thr Glu Gly Leu Glu Ser Arg Ser Ile
    1550                1555                1560

Tyr Asp Leu Ala Tyr Thr Ser Leu Leu Lys Ser Leu Leu Pro Thr
    1565                1570                1575

Ile Arg Arg Cys Leu Val Met Val Lys Val Leu His Glu Leu Val
    1580                1585                1590

Lys Asp Ser Glu Asn Glu Thr Met Val Ile Asp Gly Phe Asp Val
    1595                1600                1605

Glu Glu Glu Leu Glu Phe Glu Gly Leu Pro Gly Phe Val Asp Lys
    1610                1615                1620

Ala Leu Lys Leu Ile Thr Asp Lys Glu Ser Phe Val Asp Leu Phe
    1625                1630                1635

Lys Thr Lys Gln Ala Ile Val Pro Ser His Pro Tyr Leu Glu Arg
    1640                1645                1650

Ile Pro Tyr Glu Tyr Cys Gly Ile Val Lys Leu Ile Asp Leu Ser
    1655                1660                1665

Lys Phe Leu Asn Thr Tyr Val Thr Gln Ser Lys Glu Ile Lys Leu
    1670                1675                1680

Arg Glu Glu Arg Ser Gln His Met Lys Asn Ala Asp Asn Arg Leu
    1685                1690                1695

Asp Phe Lys Ile Cys Leu Thr Cys Gly Val Lys Val His Leu Arg
    1700                1705                1710

Ala Asp Arg His Glu Met Thr Lys His Leu Asn Lys Asn Cys Phe
    1715                1720                1725
```

-continued

```
Lys Ser Phe Gly Ala Phe Leu Met Pro Asn Ser Ser Glu Val Cys
    1730                1735                1740

Leu His Leu Thr Gln Pro Pro Ser Asn Ile Phe Val Ser Ala Pro
    1745                1750                1755

Tyr Leu Asn Ser His Gly Glu Val Gly Arg Asn Ala Met Arg Arg
    1760                1765                1770

Gly Asp Leu Thr Thr Leu Asn Leu Lys Arg Tyr Glu His Leu Asn
    1775                1780                1785

Arg Leu Trp Ile Asn Asn Glu Ile Pro Gly Tyr Ile Ser Arg Val
    1790                1795                1800

Met Gly Asp Glu Phe Arg Val Thr Ile Leu Ser Asn Gly Phe Leu
    1805                1810                1815

Phe Ala Phe Asn Arg Glu Pro Arg Pro Arg Arg Val Pro Pro Thr
    1820                1825                1830

Asp Glu Asp Asp Glu Asp Met Glu Glu Gly Glu Glu Gly Phe Phe
    1835                1840                1845

Thr Glu Glu Asn Asp Asp Met Asp Val Asp Asp Glu Thr Gly Gln
    1850                1855                1860

Ala Ala Asn Leu Phe Gly Val Gly Ala Glu Gly Ile Gly Asp Gly
    1865                1870                1875

Gly Val Arg Asn Phe Phe Gln Phe Phe Glu Asn Phe Arg Asn Thr
    1880                1885                1890

Leu Gln Pro Gln Gly Asn Asp Asp Glu Asp Ala Pro Gln Asn Pro
    1895                1900                1905

Pro Pro Ile Leu Gln Phe Leu Gly Pro Gln Phe Asp Gly Ala Thr
    1910                1915                1920

Ile Ile Arg Asn Thr Asn Gln Arg Asn Leu Asp Glu Asp Asp Ser
    1925                1930                1935

Ser Glu Asn Asp Asp Ser Asp Glu Arg Glu Ile Trp
    1940                1945                1950

<210> SEQ ID NO 51
<211> LENGTH: 520
<212> TYPE: PRT
<213> ORGANISM: Saccharomyces cerevisiae
<220> FEATURE:
<221> NAME/KEY: MISC_FEATURE
<222> LOCATION: (96)..(96)
<223> OTHER INFORMATION: X: any amino acid
<220> FEATURE:
<221> NAME/KEY: MISC_FEATURE
<222> LOCATION: (218)..(218)
<223> OTHER INFORMATION: X: any amino acid
<220> FEATURE:
<221> NAME/KEY: MISC_FEATURE
<222> LOCATION: (267)..(267)
<223> OTHER INFORMATION: X: any amino acid

<400> SEQUENCE: 51

Met Gly Tyr Asp Ile Ala Asn Tyr Glu Lys Val Trp Pro Thr Tyr Gly
1               5                   10                  15

Thr Asn Glu Asp Cys Phe Ala Leu Ile Glu Lys Thr His Lys Leu Gly
                20                  25                  30

Met Lys Phe Ile Thr Asp Leu Val Ile Asn His Cys Ser Ser Glu His
            35                  40                  45

Glu Trp Phe Lys Glu Ser Arg Ser Ser Lys Thr Asn Pro Lys Arg Asp
        50                  55                  60

Trp Phe Phe Trp Arg Pro Pro Lys Gly Tyr Asp Ala Glu Gly Lys Pro
65                  70                  75                  80
```

```
Ile Pro Pro Asn Asn Trp Lys Ser Tyr Phe Gly Gly Ser Ala Trp Xaa
            85                  90                  95

Phe Asp Glu Lys Thr Gln Glu Phe Tyr Leu Arg Leu Phe Cys Ser Thr
        100                 105                 110

Gln Pro Asp Leu Asn Trp Glu Asn Glu Asp Cys Arg Lys Ala Ile Tyr
        115                 120                 125

Glu Ser Ala Val Gly Tyr Trp Leu Asp His Gly Val Asp Gly Phe Arg
    130                 135                 140

Ile Asp Val Gly Ser Leu Tyr Ser Lys Val Val Gly Leu Pro Asp Ala
145                 150                 155                 160

Pro Val Val Asp Lys Asn Ser Thr Trp Gln Ser Ser Pro Tyr Thr
                165                 170                 175

Leu Asn Gly Pro Arg Ile His Glu Phe His Gln Glu Met Asn Gln Phe
            180                 185                 190

Ile Arg Asn Arg Val Lys Asp Gly Arg Glu Ile Met Thr Val Gly Glu
        195                 200                 205

Met Gln His Ala Ser Asp Glu Thr Lys Xaa Leu Tyr Thr Ser Ala Ser
    210                 215                 220

Arg His Glu Leu Ser Glu Leu Phe Asn Phe Ser His Thr Asp Val Gly
225                 230                 235                 240

Thr Ser Pro Leu Phe Arg Tyr Asn Leu Val Pro Phe Glu Leu Lys Asp
            245                 250                 255

Trp Lys Ile Ala Leu Ala Glu Leu Phe Arg Xaa Ile Asn Gly Thr Asp
                260                 265                 270

Cys Trp Ser Thr Ile Tyr Leu Glu Asn His Asp Gln Pro Arg Ser Ile
            275                 280                 285

Thr Arg Phe Gly Asp Asp Ser Pro Lys Asn Arg Val Ile Ser Gly Lys
    290                 295                 300

Leu Leu Ser Val Leu Leu Ser Ala Leu Thr Gly Thr Leu Tyr Val Tyr
305                 310                 315                 320

Gln Gly Gln Glu Leu Gly Gln Ile Asn Phe Lys Asn Trp Ser Val Glu
                325                 330                 335

Lys Tyr Glu Asp Val Glu Ile Arg Asn Asn Tyr Arg Leu Ile Lys Glu
        340                 345                 350

Glu Cys Gly Glu Asn Ser Glu Glu Met Lys Lys Phe Leu Glu Gly Ile
    355                 360                 365

Ala Leu Val Ser Arg Asp His Ala Arg Thr Pro Met Pro Trp Thr Pro
370                 375                 380

Asn Glu Pro Asn Ala Gly Phe Ser Gly Pro Asn Thr Lys Pro Trp Phe
385                 390                 395                 400

Tyr Leu Asn Glu Ser Phe Arg Gln Gly Ile Asn Val Glu Glu Glu Gln
            405                 410                 415

Lys Asn Ser Asp Ser Val Leu Ala Phe Trp Lys Lys Ala Leu Glu Phe
            420                 425                 430

Arg Lys Asn His Lys Asp Ile Ala Val Tyr Gly Phe Asp Phe Lys Phe
        435                 440                 445

Ile Asp Leu Asp Asn Lys Lys Leu Phe Ser Phe Thr Lys Arg Tyr Asn
450                 455                 460

Asn Lys Thr Leu Phe Ala Ala Leu Asn Phe Ser Ser Asp Ala Thr Asp
465                 470                 475                 480

Phe Lys Ile Pro Asn Asp Gly Ser Ser Phe Lys Leu Glu Phe Gly Asn
                485                 490                 495
```

```
Tyr Pro Lys Asn Glu Val Asp Ala Ser Ser Arg Thr Leu Lys Pro Trp
            500                 505                 510

Glu Gly Arg Ile His Ile Asn Glu
        515                 520

<210> SEQ ID NO 52
<211> LENGTH: 589
<212> TYPE: PRT
<213> ORGANISM: Saccharomyces cerevisiae
<220> FEATURE:
<221> NAME/KEY: MISC_FEATURE
<222> LOCATION: (165)..(165)
<223> OTHER INFORMATION: X: any amino acid
<220> FEATURE:
<221> NAME/KEY: MISC_FEATURE
<222> LOCATION: (224)..(224)
<223> OTHER INFORMATION: X: any amino acid
<220> FEATURE:
<221> NAME/KEY: MISC_FEATURE
<222> LOCATION: (287)..(287)
<223> OTHER INFORMATION: X: any amino acid
<220> FEATURE:
<221> NAME/KEY: MISC_FEATURE
<222> LOCATION: (336)..(336)
<223> OTHER INFORMATION: X: any amino acid
<220> FEATURE:
<221> NAME/KEY: MISC_FEATURE
<222> LOCATION: (439)..(439)
<223> OTHER INFORMATION: X: any amino acid

<400> SEQUENCE: 52

Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
            20                  25                  30

Asp Asp Gly Trp Gly Asp Met Lys Gly Ile Ser Ser Lys Leu Glu Tyr
        35                  40                  45

Ile Lys Glu Leu Gly Val Asp Ala Ile Trp Ile Ser Pro Phe Tyr Asp
    50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
            100                 105                 110

Cys Ser Ser Glu His Glu Trp Phe Lys Glu Ser Arg Ser Ser Lys Thr
        115                 120                 125

Asn Pro Lys Arg Asp Trp Phe Phe Trp Arg Pro Pro Lys Gly Tyr Asp
    130                 135                 140

Ala Glu Gly Lys Pro Ile Pro Pro Asn Asn Trp Lys Ser Tyr Phe Gly
145                 150                 155                 160

Gly Ser Ala Trp Xaa Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Xaa
    210                 215                 220

Gly Leu Pro Asp Ala Pro Val Val Asp Lys Asn Ser Thr Trp Gln Ser
225                 230                 235                 240
```

```
Ser Asp Pro Tyr Thr Leu Asn Gly Pro Arg Ile His Glu Phe His Gln
            245                 250                 255

Glu Met Asn Gln Phe Ile Arg Asn Arg Val Lys Asp Gly Arg Glu Ile
        260                 265                 270

Met Thr Val Gly Glu Met Gln His Ala Ser Asp Glu Thr Lys Xaa Leu
    275                 280                 285

Tyr Thr Ser Ala Ser Arg His Glu Leu Ser Glu Leu Phe Asn Phe Ser
290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Xaa
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
    370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Ala Ile Ala Xaa Ile Ser Arg Asp His Ala Arg Thr Pro
        435                 440                 445

Met Gln Trp Ser Arg Glu Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
    530                 535                 540

Ser Asp Ala Thr Asp Phe Lys Ile Pro Asn Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585

<210> SEQ ID NO 53
<211> LENGTH: 589
<212> TYPE: PRT
<213> ORGANISM: Saccharomyces cerevisiae

<400> SEQUENCE: 53

Met Thr Ile Ser Ser Ala His Pro Glu Thr Glu Pro Lys Trp Trp Lys
1               5                   10                  15

Glu Ala Thr Phe Cys Gln Ile Tyr Pro Ala Ser Phe Lys Asp Ser Asn
            20                  25                  30
```

Asp Asp Gly Trp Gly Asp Met Glu Gly Ile Ser Ser Lys Leu Glu Tyr
            35                  40                  45

Ile Lys Glu Leu Gly Val Asp Ala Ile Trp Ile Ser Pro Phe Tyr Asp
 50                  55                  60

Ser Pro Gln Asp Met Gly Tyr Asp Ile Ala Asn Tyr Glu Lys Val
 65                  70                  75                  80

Trp Pro Thr Tyr Gly Thr Asn Glu Asp Cys Phe Ala Leu Ile Glu Lys
                 85                  90                  95

Thr His Lys Leu Gly Met Lys Phe Ile Thr Asp Leu Val Ile Asn His
                100                 105                 110

Cys Ser Ser Glu His Glu Trp Phe Lys Glu Ser Arg Ser Ser Lys Thr
            115                 120                 125

Asn Pro Lys Arg Asp Trp Phe Phe Trp Arg Pro Pro Lys Gly Tyr Asp
130                 135                 140

Ala Glu Gly Lys Pro Ile Pro Pro Asn Asn Trp Lys Ser Tyr Phe Gly
145                 150                 155                 160

Gly Ser Ala Trp Ile Phe Asp Glu Lys Thr Gln Glu Phe His Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
            195                 200                 205

Val Asp Gly Phe Arg Ile Asp Val Gly Ser Leu Tyr Ser Lys Val Val
210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe Tyr Gln
                245                 250                 255

Glu Met Asn Gln Phe Ile Arg Asn Arg Val Lys Asp Gly Arg Glu Ile
            260                 265                 270

Met Thr Val Gly Glu Met Gln His Ala Ser Asp Glu Thr Lys Arg Leu
            275                 280                 285

Tyr Thr Ser Ala Ser Arg His Glu Leu Ser Glu Leu Phe Asn Phe Ser
            290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Phe
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
            355                 360                 365

Val Ile Ser Gly Lys Leu Leu Ser Val Leu Leu Ser Ala Leu Thr Gly
370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Ala Ile Ala Leu Ile Ser Arg Asp His Ala Arg Thr Pro
            435                 440                 445

Met Gln Trp Ser Arg Glu Glu Pro Asn Ala Gly Phe Ser Gly Pro Ser
450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
    530                 535                 540

Ser Asp Ala Thr Asp Phe Lys Ile Pro Asn Asp Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585

<210> SEQ ID NO 54
<211> LENGTH: 589
<212> TYPE: PRT
<213> ORGANISM: Saccharomyces pastorianus

<400> SEQUENCE: 54

Met Thr Ile Ser Ser Ala His Pro Gly Thr Glu Pro Lys Trp Trp Lys
1               5                   10                  15

Glu Ala Thr Phe Tyr Gln Ile Tyr Pro Ala Ser Phe Lys Asp Ser Asn
            20                  25                  30

Asp Asp Gly Trp Gly Asp Met Lys Gly Ile Ser Ser Lys Leu Glu Tyr
        35                  40                  45

Ile Lys Glu Leu Gly Val Asp Ala Ile Trp Ile Ser Pro Phe Tyr Asp
    50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
            100                 105                 110

Cys Ser Ser Glu His Glu Trp Phe Lys Glu Ser Arg Ser Ser Lys Thr
        115                 120                 125

Asn Pro Lys Arg Asp Trp Ser Phe Trp Arg Pro Pro Lys Gly Tyr Asp
    130                 135                 140

Ala Glu Gly Lys Pro Ile Pro Pro Asn Asn Trp Lys Ser Tyr Phe Gly
145                 150                 155                 160

Gly Ser Ala Trp Thr Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Val
    210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
            245                 250                 255

Glu Met Asn Gln Phe Ile Arg Asn Arg Val Lys Asp Gly Arg Glu Ile
        260                 265                 270

Met Thr Val Gly Glu Met Gln His Ala Ser Asp Glu Thr Lys Arg Leu
    275                 280                 285

Tyr Thr Ser Ala Ser Arg His Glu Leu Ser Glu Leu Phe Asn Phe Ser
290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Tyr
                325                 330                 335

Ile Asn Gly Thr Asp Cys Trp Ser Thr Ile Tyr Leu Gly Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
    370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Gly Ile Ala Leu Val Ser Arg Asp His Ala Arg Thr Pro
        435                 440                 445

Met Pro Trp Thr Pro Asn Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
    530                 535                 540

Ser Asp Ala Thr Asp Phe Lys Ile Pro Asn Asp Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585

<210> SEQ ID NO 55
<211> LENGTH: 589
<212> TYPE: PRT
<213> ORGANISM: Saccharomyces cerevisiae
<220> FEATURE:
<221> NAME/KEY: MISC_FEATURE
<222> LOCATION: (287)..(287)
<223> OTHER INFORMATION: X: any amino acid

<400> SEQUENCE: 55

-continued

```
Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
            20                  25                  30

Asp Asp Gly Trp Gly Asp Met Lys Gly Ile Ser Ser Lys Leu Glu Tyr
        35                  40                  45

Ile Lys Glu Leu Gly Val Asp Ala Ile Trp Ile Ser Pro Phe Tyr Asp
50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
                100                 105                 110

Cys Ser Ser Glu His Glu Trp Phe Lys Glu Ser Arg Ser Ser Lys Thr
            115                 120                 125

Asn Pro Lys Arg Asp Trp Phe Phe Trp Arg Pro Pro Lys Gly Tyr Asp
        130                 135                 140

Ala Glu Gly Lys Pro Ile Pro Pro Asn Asn Trp Lys Ser Tyr Phe Gly
145                 150                 155                 160

Gly Ser Ala Trp Ile Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Val
210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
                245                 250                 255

Glu Met Asn Gln Phe Ile Arg Asn Arg Val Lys Asp Gly Arg Glu Ile
            260                 265                 270

Met Thr Val Gly Glu Met Gln His Ala Ser Asp Glu Thr Lys Xaa Leu
        275                 280                 285

Tyr Thr Ser Ala Ser Arg His Glu Leu Ser Glu Leu Phe Asn Phe Ser
290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Phe
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Ser Ala Leu Thr Gly
370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
```

```
                420           425           430
Phe Leu Glu Ala Ile Ala Leu Ile Ser Arg Asp His Ala Arg Thr Pro
            435               440               445
Met Gln Trp Ser Arg Glu Glu Pro Asn Ala Gly Phe Ser Gly Pro Ser
    450               455               460
Ala Lys Pro Trp Phe Tyr Leu Asn Asp Ser Phe Arg Glu Gly Ile Asn
465               470               475               480
Val Glu Asp Glu Ile Lys Asp Pro Asn Ser Val Leu Asn Phe Trp Lys
                485               490               495
Glu Ala Leu Lys Phe Arg Lys Ala His Lys Asp Ile Thr Val Tyr Gly
            500               505               510
Tyr Asp Phe Glu Phe Ile Asp Leu Asp Asn Lys Lys Leu Phe Ser Phe
        515               520               525
Thr Lys Lys Tyr Asn Asn Lys Thr Leu Phe Ala Ala Leu Asn Phe Ser
    530               535               540
Ser Asp Ala Thr Asp Phe Lys Ile Pro Asn Asp Asp Ser Ser Phe Lys
545               550               555               560
Leu Glu Phe Gly Asn Tyr Pro Lys Lys Glu Val Asp Ala Ser Ser Arg
                565               570               575
Thr Leu Lys Pro Trp Glu Gly Arg Ile Tyr Ile Ser Glu
            580               585
```

<210> SEQ ID NO 56
<211> LENGTH: 589
<212> TYPE: PRT
<213> ORGANISM: Saccharomyces cerevisiae

<400> SEQUENCE: 56

```
Met Thr Ile Ser Ser Ala His Pro Glu Thr Glu Pro Lys Trp Trp Lys
1               5                  10                  15
Glu Ala Thr Phe Tyr Gln Ile Tyr Pro Ala Ser Phe Lys Asp Ser Asn
            20                  25                  30
Asp Asp Gly Trp Gly Asp Met Lys Gly Ile Ser Ser Lys Leu Glu Tyr
        35                  40                  45
Ile Lys Glu Leu Gly Val Asp Ala Ile Trp Ile Ser Pro Phe Tyr Asp
    50                  55                  60
Ser Pro Gln Asp Asp Met Gly Tyr Asp Ile Ala Asn Tyr Glu Lys Val
65                  70                  75                  80
Trp Pro Thr Tyr Gly Thr Asn Glu Asp Cys Phe Ala Leu Ile Glu Lys
                85                  90                  95
Thr His Lys Leu Gly Met Lys Phe Ile Thr Asp Leu Val Ile Asn His
            100                 105                 110
Cys Ser Ser Glu His Glu Trp Phe Lys Glu Ser Arg Ser Ser Lys Thr
        115                 120                 125
Asn Pro Lys Arg Asp Trp Phe Phe Trp Arg Pro Pro Lys Gly Tyr Asp
    130                 135                 140
Ala Glu Gly Lys Pro Ile Pro Pro Asn Asn Trp Lys Ser Tyr Phe Gly
145                 150                 155                 160
Gly Ser Ala Trp Ile Phe Asp Glu Lys Thr Gln Glu Phe Tyr Leu Arg
                165                 170                 175
Leu Phe Cys Ser Thr Gln Pro Asp Leu Asn Trp Glu Asn Glu Asp Cys
            180                 185                 190
Arg Lys Ala Ile Tyr Glu Ser Ala Val Gly Tyr Trp Leu Asp His Gly
        195                 200                 205
```

```
Val Asp Gly Phe Arg Ile Asp Val Gly Ser Leu Tyr Ser Lys Val Val
210                 215                 220
Gly Leu Pro Asp Ala Pro Val Val Asp Lys Asn Ser Thr Trp Gln Ser
225                 230                 235                 240
Ser Asp Pro Tyr Thr Leu Asn Gly Pro Arg Ile His Glu Phe His Gln
            245                 250                 255
Glu Met Asn Gln Phe Ile Arg Asn Arg Val Lys Asp Gly Arg Glu Ile
        260                 265                 270
Met Thr Val Gly Glu Met Gln His Ala Ser Asp Glu Thr Lys Arg Leu
    275                 280                 285
Tyr Thr Ser Ala Ser Arg His Glu Leu Ser Glu Leu Phe Asn Phe Ser
290                 295                 300
His Thr Asp Val Gly Thr Ser Pro Leu Phe Arg Tyr Asn Leu Val Pro
305                 310                 315                 320
Phe Glu Leu Lys Asp Trp Lys Ile Ala Leu Ala Glu Leu Phe Arg Phe
            325                 330                 335
Ile Asn Gly Thr Asp Cys Trp Ser Thr Ile Tyr Leu Glu Asn His Asp
        340                 345                 350
Gln Pro Arg Ser Ile Thr Arg Phe Gly Asp Asp Ser Pro Lys Asn Arg
    355                 360                 365
Val Ile Ser Gly Lys Leu Leu Ser Val Leu Leu Ser Ala Leu Thr Gly
370                 375                 380
Thr Leu Tyr Val Tyr Gln Gly Gln Glu Leu Gly Gln Ile Asn Phe Lys
385                 390                 395                 400
Asn Trp Pro Val Glu Lys Tyr Glu Asp Val Glu Ile Arg Asn Asn Tyr
            405                 410                 415
Asn Ala Ile Lys Glu Glu His Gly Glu Asn Ser Glu Glu Met Lys Lys
        420                 425                 430
Phe Leu Glu Ala Ile Ala Leu Ile Ser Arg Asp His Ala Arg Thr Pro
    435                 440                 445
Met Gln Trp Ser Arg Glu Glu Pro Asn Ala Gly Phe Ser Gly Pro Ser
450                 455                 460
Ala Lys Pro Trp Phe Tyr Leu Asn Asp Ser Phe Arg Glu Gly Ile Asn
465                 470                 475                 480
Val Glu Asp Glu Ile Lys Asp Pro Asn Ser Val Leu Asn Phe Trp Lys
            485                 490                 495
Glu Ala Leu Lys Phe Arg Lys Ala His Lys Asp Ile Thr Val Tyr Gly
        500                 505                 510
Tyr Asp Phe Glu Phe Ile Asp Leu Asp Asn Lys Lys Leu Phe Ser Phe
    515                 520                 525
Thr Lys Lys Tyr Asn Asn Lys Thr Leu Phe Ala Ala Leu Asn Phe Ser
530                 535                 540
Ser Asp Ala Thr Asp Phe Lys Ile Pro Asn Asp Asp Ser Ser Phe Lys
545                 550                 555                 560
Leu Glu Phe Gly Asn Tyr Pro Lys Lys Glu Val Asp Ala Ser Ser Arg
            565                 570                 575
Thr Leu Lys Pro Trp Glu Gly Arg Ile Tyr Ile Ser Glu
        580                 585
```

<210> SEQ ID NO 57
<211> LENGTH: 589
<212> TYPE: PRT
<213> ORGANISM: Saccharomyces pastorianus

<400> SEQUENCE: 57

```
Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
                20                  25                  30

Asp Asp Gly Trp Gly Asp Met Lys Gly Ile Ser Ser Lys Leu Glu Tyr
            35                  40                  45

Ile Lys Glu Leu Gly Val Asp Ala Ile Trp Ile Ser Pro Phe Tyr Asp
50                  55                  60

Ser Pro Gln Asp Asp Met Gly Tyr Asp Ile Ala Asn Tyr Glu Lys Val
65              70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
                100                 105                 110

Cys Ser Ser Glu His Glu Trp Phe Lys Glu Ser Arg Ser Ser Lys Thr
            115                 120                 125

Asn Pro Lys Arg Asp Trp Phe Phe Trp Arg Pro Pro Lys Gly Tyr Asp
            130                 135                 140

Ala Glu Gly Lys Pro Ile Pro Pro Asn Asn Trp Lys Ser Tyr Phe Gly
145                 150                 155                 160

Gly Ser Ala Trp Thr Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
            195                 200                 205

Val Asp Gly Phe Arg Ile Asp Val Gly Ser Leu Tyr Ser Lys Val Val
210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
                245                 250                 255

Glu Met Asn Gln Phe Ile Arg Asn Arg Val Lys Asp Gly Arg Glu Ile
            260                 265                 270

Met Thr Val Gly Glu Met Gln His Ala Ser Asp Glu Thr Lys Arg Leu
            275                 280                 285

Tyr Thr Ser Ala Ser Arg His Glu Leu Ser Glu Leu Phe Asn Phe Ser
            290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Tyr
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
            355                 360                 365

Val Ile Ser Gly Lys Leu Leu Ser Val Leu Leu Ser Ala Leu Thr Gly
370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415
```

```
Asn Ala Ile Lys Glu His Gly Glu Asn Ser Glu Met Lys Lys
            420                 425                 430

Phe Leu Glu Ala Ile Ala Leu Ile Ser Arg Asp His Ala Arg Thr Pro
            435                 440                 445

Met Gln Trp Ser Arg Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
            515                 520                 525

Thr Lys Lys Tyr Asn Asn Lys Thr Leu Phe Ala Ala Leu Asn Phe Ser
    530                 535                 540

Ser Asp Ala Thr Asp Phe Lys Ile Pro Asn Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585

<210> SEQ ID NO 58
<211> LENGTH: 581
<212> TYPE: PRT
<213> ORGANISM: Saccharomyces cerevisiae

<400> SEQUENCE: 58

Met Thr Ile Ile His Asn Pro Lys Trp Trp Lys Glu Ala Thr Val Tyr
1               5                   10                  15

Gln Ile Tyr Pro Ala Ser Asn Lys Asp Ser Asn Asn Asp Gly Trp Gly
            20                  25                  30

Asp Leu Ala Gly Ile Thr Ser Lys Leu Asp Tyr Val Lys Glu Leu Gly
        35                  40                  45

Val Asp Ala Ile Trp Val Cys Leu Phe Tyr Asp Ser Pro Gln Glu Asp
    50                  55                  60

Met Gly Tyr Asp Ile Ala Asn Tyr Glu Lys Val Trp Pro Arg Tyr Gly
65                  70                  75                  80

Thr Asn Glu Asp Cys Phe Gln Met Ile Glu Glu Ala His Lys Arg Gly
                85                  90                  95

Ile Lys Val Ile Val Asp Leu Val Ile Asn His Cys Ser Glu Glu His
            100                 105                 110

Glu Trp Phe Lys Glu Ser Lys Ser Ser Lys Thr Asn Pro Lys Arg Asp
        115                 120                 125

Trp Phe Phe Trp Arg Pro Pro Lys Gly Phe Asp Glu Lys Gly Asn Pro
    130                 135                 140

Ile Pro Pro Asn Asn Trp Arg Ser Phe Phe Gly Gly Ser Ala Trp Arg
145                 150                 155                 160

Tyr Asp Glu Lys Thr Gly Glu Phe Phe Leu His Val Phe Ala Pro Gly
                165                 170                 175

Gln Pro Asp Phe Asn Trp Glu Asn Glu Glu Cys Arg Lys Ala Ile Tyr
            180                 185                 190

Asp Ser Ser Val Gly Tyr Trp Leu Arg His Asn Val Asp Gly Phe Arg
        195                 200                 205
```

Ile Asp Val Gly Ser Met Tyr Ser Lys Val Glu Gly Leu Pro Asp Ala
210                 215                 220

Pro Ile Thr Asp Pro Thr Val Pro Tyr Gln Lys Gly Thr Glu Phe Phe
225                 230                 235                 240

Ile Asn Gly Pro Arg Ile His Glu Tyr His Lys Glu Met Arg Lys Tyr
                245                 250                 255

Met Leu Ser Gln Ile Pro Glu Gly Lys Glu Ile Met Thr Val Gly Glu
            260                 265                 270

Val Gly Val Gly Asn Glu Glu Asp Phe Arg Asp Tyr Thr Ser Ala Lys
        275                 280                 285

Glu Gly Glu Leu Asn Met Met Phe Asn Phe Lys His Thr Ser Val Gly
290                 295                 300

Glu Ser Pro Glu Cys Lys Tyr Glu Leu Ile Pro Phe Thr Leu Lys Asp
305                 310                 315                 320

Phe Lys Leu Ala Leu Ala Glu Ser Phe Leu Phe Ile Glu Asn Thr Asp
                325                 330                 335

Cys Trp Ser Thr Ile Tyr Leu Glu Asn His Asp Gln Pro Arg Ser Val
            340                 345                 350

Ser Arg Phe Gly Ser Asp Ser Pro Lys Trp Arg Ala Ile Ser Ser Lys
        355                 360                 365

Met Leu Ala Thr Leu Ile Ile Ser Leu Thr Gly Thr Val Phe Ile Tyr
370                 375                 380

Gln Gly Gln Glu Leu Gly Met Ser Asn Phe Lys Asn Arg Arg Ile Glu
385                 390                 395                 400

Gln Ile Lys Cys Val Glu Gly Thr Gly Thr Tyr Ala Ala Ile Lys Arg
                405                 410                 415

Asp Tyr Gly Glu Asp Ser Glu Lys Met Lys Lys Phe Phe Glu Ala Leu
            420                 425                 430

Ala Leu Ile Ser Arg Asp His Gly Arg Thr Pro Phe Pro Trp Ser Ala
        435                 440                 445

Asp Glu Pro Ser Ala Gly Phe Ser Lys Asp Ala Lys Pro Trp Ile Asp
450                 455                 460

Met Asn Glu Ser Phe Arg Asp Gly Ile Asn Ala Glu Ala Glu Leu Lys
465                 470                 475                 480

Asp Lys Asn Ser Val Phe Phe Trp Lys Lys Ala Leu Gln Val Arg
                485                 490                 495

Lys Glu His Lys Asp Ile Leu Val Tyr Gly His Asn Phe Gln Phe Ile
            500                 505                 510

Asp Leu Asp Asn Asp Lys Leu Phe Met Phe Thr Lys Asp Thr Asp Asn
        515                 520                 525

Lys Lys Met Phe Ala Val Phe Asn Phe Ser Ser Asp Asn Thr Asp Phe
530                 535                 540

Ser Val Pro Asp Asn Glu Ala Ser Tyr Thr Met Phe Phe Gly Asn Tyr
545                 550                 555                 560

Ala Asn Ser Asn Gly Asp Ser Arg Thr Leu Gln Pro Trp Glu Gly Arg
                565                 570                 575

Leu Tyr Leu Leu Lys
            580

<210> SEQ ID NO 59
<211> LENGTH: 581
<212> TYPE: PRT
<213> ORGANISM: Saccharomyces pastorianus

<400> SEQUENCE: 59

```
Met Thr Ile Ile His Asn Pro Lys Trp Trp Lys Glu Ala Thr Val Tyr
1               5                   10                  15

Gln Ile Tyr Pro Ala Ser Phe Lys Asp Ser Asn Asn Asp Gly Trp Gly
                20                  25                  30

Asp Leu Ala Gly Ile Thr Ser Lys Leu Asp Tyr Val Lys Glu Leu Gly
            35                  40                  45

Val Asp Ala Ile Trp Val Cys Pro Phe Tyr Asp Ser Pro Gln Glu Asp
    50                  55                  60

Met Gly Tyr Asp Ile Ala Asn Tyr Glu Lys Val Trp Pro Arg Tyr Gly
65                  70                  75                  80

Thr Asn Glu Asp Cys Phe Gln Met Ile Glu Glu Ala His Lys Arg Gly
                85                  90                  95

Ile Lys Val Ile Val Asp Leu Val Ile Asn His Cys Ser Glu Glu His
                100                 105                 110

Glu Trp Phe Lys Glu Ser Lys Ser Ser Lys Thr Asn Pro Lys Arg Asp
                115                 120                 125

Trp Phe Phe Trp Arg Pro Pro Lys Gly Phe Asp Glu Lys Gly Asn Pro
            130                 135                 140

Ile Pro Pro Asn Asn Trp Arg Ser Phe Phe Gly Gly Ser Ala Trp Arg
145                 150                 155                 160

Tyr Asp Glu Lys Thr Gly Glu Phe Phe Leu His Val Phe Ala Pro Gly
                165                 170                 175

Gln Pro Asp Phe Asn Trp Glu Asn Glu Lys Cys Arg Lys Ala Ile Tyr
            180                 185                 190

Asp Ser Ser Val Gly Tyr Trp Leu Arg His Asn Val Asp Gly Phe Arg
        195                 200                 205

Ile Asp Val Gly Ser Met Tyr Ser Lys Val Glu Gly Leu Pro Asp Ala
210                 215                 220

Pro Ile Thr Asp Pro Thr Val Pro Tyr Gln Lys Gly Thr Glu Phe Phe
225                 230                 235                 240

Ile Asn Gly Pro Arg Ile His Glu Tyr His Lys Glu Met Arg Lys Tyr
                245                 250                 255

Met Leu Ser Gln Ile Pro Glu Gly Lys Glu Ile Met Thr Val Gly Glu
            260                 265                 270

Val Gly Val Gly Asn Glu Glu Asp Phe Arg Asp Tyr Thr Ser Ala Lys
        275                 280                 285

Glu Gly Glu Leu Asn Met Met Phe Asn Phe Lys His Thr Ser Val Gly
290                 295                 300

Glu Ser Pro Glu Cys Lys Tyr Glu Leu Ile Pro Phe Thr Leu Lys Asp
305                 310                 315                 320

Phe Lys Leu Ala Leu Ala Glu Ser Phe Leu Phe Ile Glu Asn Thr Asp
                325                 330                 335

Cys Trp Ser Thr Ile Tyr Leu Glu Asn His Asp Gln Pro Arg Ser Val
            340                 345                 350

Ser Arg Phe Gly Ser Asp Ser Pro Lys Trp Arg Ala Ile Ser Ser Lys
        355                 360                 365

Met Leu Ala Thr Leu Ile Ile Ser Leu Thr Gly Thr Val Phe Ile Tyr
370                 375                 380

Gln Gly Gln Glu Leu Gly Met Ser Asn Phe Lys Asn Arg Arg Ile Glu
385                 390                 395                 400

Gln Ile Lys Cys Val Glu Gly Thr Gly Thr Tyr Ala Ala Ile Lys Arg
                405                 410                 415
```

Asp Tyr Gly Glu Asp Ser Glu Lys Met Lys Lys Phe Glu Ala Leu
            420                 425                 430

Ala Leu Ile Ser Arg Asp His Gly Arg Thr Pro Phe Pro Trp Ser Ala
        435                 440                 445

Asp Glu Pro Ser Ala Gly Phe Ser Lys Asp Ala Lys Pro Trp Ile Asp
    450                 455                 460

Met Asn Glu Ser Phe Arg Asp Gly Ile Asn Ala Glu Ala Glu Leu Lys
465                 470                 475                 480

Asp Lys Asn Ser Val Phe Phe Trp Lys Lys Ala Leu Gln Val Arg
            485                 490                 495

Lys Glu His Lys Asp Ile Leu Val Tyr Gly His Asn Phe Gln Phe Ile
            500                 505                 510

Asp Leu Asp Asn Asp Lys Leu Phe Met Phe Thr Lys Asp Thr Asp Asn
        515                 520                 525

Lys Lys Met Phe Ala Val Phe Asn Phe Ser Ser Asp Asn Thr Asp Phe
    530                 535                 540

Ser Val Pro Asp Asn Glu Ala Ser Tyr Thr Met Phe Phe Gly Asn Tyr
545                 550                 555                 560

Ala Asn Ser Asn Gly Asp Ser Arg Thr Leu Gln Pro Trp Glu Gly Arg
            565                 570                 575

Leu Tyr Leu Leu Lys
            580

<210> SEQ ID NO 60
<211> LENGTH: 581
<212> TYPE: PRT
<213> ORGANISM: Saccharomyces pastorianus

<400> SEQUENCE: 60

Met Thr Ile Ile His Asn Pro Lys Trp Trp Lys Glu Ala Thr Ile Tyr
1               5                   10                  15

Gln Ile Tyr Pro Ala Ser Phe Lys Asp Ser Asn Asn Asp Gly Trp Gly
            20                  25                  30

Asp Leu Ala Gly Ile Thr Ser Lys Leu Asp Tyr Ile Lys Glu Leu Gly
        35                  40                  45

Val Asp Ala Ile Trp Val Cys Pro Phe Tyr Asp Ser Pro Gln Glu Asp
    50                  55                  60

Met Gly Tyr Asp Ile Ala Asn Tyr Glu Lys Val Trp Pro Arg Tyr Gly
65                  70                  75                  80

Thr Ser Glu Asp Cys Phe Gln Met Ile Glu Glu Ser His Lys Arg Gly
            85                  90                  95

Ile Lys Val Ile Val Asp Leu Val Ile Asn His Cys Ser Glu Glu His
            100                 105                 110

Glu Trp Phe Lys Glu Ser Arg Ser Ser Lys Thr Asn Ala Lys Arg Asp
        115                 120                 125

Trp Phe Phe Trp Lys Pro Pro Lys Gly Tyr Glu Ile Asp Gly Thr Pro
    130                 135                 140

Ile Pro Pro Asn Asn Trp Arg Ser Phe Phe Gly Gly Ser Ala Trp Lys
145                 150                 155                 160

Tyr Asp Glu Asn Thr Glu Glu Phe Phe Leu His Val Phe Ala Pro Gly
            165                 170                 175

Gln Pro Asp Phe Asn Trp Glu Asn Lys Glu Cys Arg Gln Ala Ile Tyr
            180                 185                 190

Asp Ser Ser Val Gly Phe Trp Leu Arg His Asn Val Asp Gly Phe Arg

```
            195                 200                 205
Ile Asp Val Gly Ser Met Tyr Ser Lys Val Glu Gly Leu Pro Asp Ala
210                 215                 220

Ser Ile Thr Asp Pro Thr Val Pro Tyr Gln Asp Gly Thr Asp Phe Phe
225                 230                 235                 240

Val Asn Gly Pro Arg Ile His Glu Tyr His Lys Glu Met Arg Gln Tyr
                245                 250                 255

Met Tyr Thr Gln Ile Pro Glu Gly Lys Glu Ile Met Thr Val Gly Glu
                260                 265                 270

Val Gly Ile Gly Asn Glu Lys Asp Phe Lys Asp Tyr Thr Ser Ser Lys
            275                 280                 285

Glu Glu Glu Phe Asn Met Met Phe Asn Phe Lys His Thr Ser Val Gly
290                 295                 300

Glu Ser Pro Glu Phe Lys Tyr Glu Leu Ile Pro Phe Thr Leu Lys Asp
305                 310                 315                 320

Phe Lys Leu Ala Leu Ala Glu Ser Phe Leu Phe Ile Glu Gly Thr Asp
                325                 330                 335

Cys Trp Ser Thr Ile Tyr Leu Glu Asn His Asp Gln Pro Arg Ser Val
                340                 345                 350

Ser Arg Phe Gly Ser Asp Ser Pro Glu Trp Arg Glu Ile Ser Ser Lys
            355                 360                 365

Met Leu Ala Thr Leu Ile Ile Ser Leu Thr Gly Thr Val Phe Ile Tyr
370                 375                 380

Gln Gly Gln Glu Leu Gly Met Pro Asn Phe Lys Asn Arg Lys Ile Glu
385                 390                 395                 400

Gln Ile Lys Cys Val Glu Gly Thr Gly Thr Tyr Gly Ala Ile Lys Arg
                405                 410                 415

Asp Tyr Gly Glu Asp Ser Glu Lys Met Lys Lys Phe Tyr Glu Ala Leu
                420                 425                 430

Ala Leu Ile Ser Arg Asp His Gly Arg Thr Pro Phe Pro Trp Ser Gly
            435                 440                 445

Glu Lys Pro Tyr Ala Gly Phe Ser Lys Asn Ala Lys Pro Trp Ile Asp
450                 455                 460

Ile Asn Glu Ser Phe Val Glu Gly Ile Asn Ala Glu Ala Glu Leu Asn
465                 470                 475                 480

Asp Glu Asn Ser Val Phe Phe Trp Lys Arg Ala Leu Gln Val Arg
                485                 490                 495

Lys Glu His Lys Asn Met Leu Val Tyr Gly Asp Asn Phe Gln Phe Tyr
                500                 505                 510

Asp Leu Asp Asn Glu Lys Leu Phe Met Phe Thr Lys Asp Ser Gly Asp
            515                 520                 525

Lys Lys Met Phe Ala Val Phe Asn Phe Cys Ser Asp Ser Thr Glu Phe
530                 535                 540

Ser Val Pro Asp Asn Lys Ala Ser Tyr Asp Met Phe Phe Gly Asn Tyr
545                 550                 555                 560

Ala Asn Ser Asp Gly Lys Ser Tyr Thr Leu Lys Pro Trp Glu Gly Arg
                565                 570                 575

Leu Tyr Tyr Ser Asn
                580

<210> SEQ ID NO 61
<211> LENGTH: 394
<212> TYPE: PRT
<213> ORGANISM: Saccharomyces pastorianus
```

<400> SEQUENCE: 61

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asn Phe Glu Glu Gly Lys Lys Asp Ser
        35                  40                  45

Ala Phe Glu Leu Asp His Leu Glu Phe Thr Thr Asn Ser Ala Gln Leu
    50                  55                  60

Gly Asp Ser Asp Glu Asp Asn Glu Asn Met Ile Asn Glu Met Asn Ala
65                  70                  75                  80

Thr Asp Glu Ala Asn Glu Ala Asn Ser Glu Glu Lys Ser Met Thr Leu
                85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Asn
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Gln Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
            180                 185                 190

Leu Leu Thr Ala Tyr Ile Phe Ile Leu Tyr Tyr Cys Lys Ser Leu Ala
        195                 200                 205

Met Ile Ala Val Gly Gln Val Leu Ser Ala Met Pro Trp Gly Cys Phe
    210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
            245                 250                 255

Ile Phe Ala Ser Gly Ile Met Lys Asn Ser Gln Glu Asn Leu Gly Asn
        260                 265                 270

Ser Asp Leu Asp Tyr Lys Leu Pro Phe Ala Leu Gln Trp Ile Trp Pro
    275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
            325                 330                 335

Leu Lys Gln Ile Glu Leu Thr Ile Glu Lys Arg Leu Leu Ala Ser
        340                 345                 350

Lys Ser Gly Ser Phe Phe Asp Cys Phe Lys Gly Val Asn Gly Arg Arg
    355                 360                 365

Thr Arg Leu Ala Cys Leu Ala Trp Val Ala Gln Asn Thr Ser Gly Ala
    370                 375                 380

Cys Leu Leu Gly Tyr Ser Thr Tyr Phe Phe
385                 390

<210> SEQ ID NO 62
<211> LENGTH: 616
<212> TYPE: PRT
<213> ORGANISM: Saccharomyces cerevisiae

<400> SEQUENCE: 62

```
Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asn Phe Glu Glu Gly Arg Lys Asp Ser
        35                  40                  45

Ala Phe Glu Leu Asp His Leu Glu Phe Thr Ile Asn Ser Ala Gln Leu
    50                  55                  60

Gly Asp Ser Asp Glu Asp Asn Glu Asn Val Ile Asn Glu Thr Asn Thr
65                  70                  75                  80

Thr Asp Asp Ala Asn Glu Ala Asn Ser Glu Glu Lys Ser Met Thr Leu
                85                  90                  95

Lys Gln Ala Leu Leu Ile Tyr Pro Lys Ala Ala Leu Trp Ser Ile Leu
            100                 105                 110

Val Ser Thr Thr Leu Val Met Glu Gly Tyr Asp Thr Ala Leu Leu Asn
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Gln Cys Gly Glu Ile Ile Gly Leu Gln Ile Thr Pro Tyr
                165                 170                 175

Met Val Glu Phe Met Gly Asn Arg Tyr Thr Met Ile Thr Ala Leu Gly
            180                 185                 190

Leu Leu Thr Ala Tyr Val Phe Ile Leu Tyr Tyr Cys Lys Ser Leu Ala
        195                 200                 205

Met Ile Ala Val Gly Gln Val Leu Ser Ala Met Pro Trp Gly Cys Phe
    210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Ile Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asp Cys Phe Lys Gly Val Asn Gly Arg Arg
        355                 360                 365

Thr Arg Leu Ala Cys Leu Thr Trp Val Ala Gln Asn Thr Ser Gly Ala
    370                 375                 380
```

-continued

Cys Leu Leu Gly Tyr Ser Thr Tyr Phe Phe Glu Arg Ala Gly Met Ala
385                 390                 395                 400

Thr Asp Lys Ala Phe Thr Phe Ser Val Ile Gln Tyr Cys Leu Gly Leu
            405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
            435                 440                 445

Ile Gly Gly Met Gly Phe Ser Gly Ser Gly Ala Ser Asn Gly Ala
            450                 455                 460

Gly Gly Leu Leu Leu Ala Leu Ser Phe Phe Tyr Asn Ala Gly Ile Gly
465                 470                 475                 480

Ala Val Val Tyr Cys Ile Val Thr Glu Ile Pro Ser Ala Glu Leu Arg
            485                 490                 495

Thr Lys Thr Ile Val Leu Ala Arg Ile Cys Tyr Asn Ile Met Ala Val
            500                 505                 510

Ile Asn Ala Ile Leu Thr Pro Tyr Met Leu Asn Val Ser Asp Trp Asn
            515                 520                 525

Trp Gly Ala Lys Thr Gly Leu Tyr Trp Gly Gly Phe Thr Ala Val Thr
530                 535                 540

Leu Ala Trp Val Ile Ile Asp Leu Pro Glu Thr Ser Gly Arg Thr Phe
545                 550                 555                 560

Ser Glu Ile Asn Glu Leu Phe Asn Gln Gly Val Pro Ala Arg Lys Phe
            565                 570                 575

Ala Ser Thr Val Val Asp Pro Phe Gly Lys Gly Lys Thr Gln His Asp
            580                 585                 590

Ser Leu Asp Asp Glu Ser Ile Ser Gln Ser Ser Ile Lys Gln Arg
            595                 600                 605

Glu Leu Asn Ala Ala Asp Lys Cys
610                 615

```
<210> SEQ ID NO 63
<211> LENGTH: 408
<212> TYPE: PRT
<213> ORGANISM: Unknown
<220> FEATURE:
<223> OTHER INFORMATION: Hybrid between S. cerevisiae and S. pastorianus
      (Hybrid yeast 1)
<220> FEATURE:
<221> NAME/KEY: MISC_FEATURE
<222> LOCATION: (1)..(408)
<223> OTHER INFORMATION: hybrid

<400> SEQUENCE: 63
```

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asn Phe Glu Gly Arg Lys Asp Ser
            35                  40                  45

Ala Phe Glu Leu Asp His Leu Glu Phe Thr Ile Asn Ser Ala Gln Leu
50                  55                  60

Gly Asp Ser Asp Glu Asp Glu Asn Val Ile Asn Glu Thr Asn Thr
65                  70                  75                  80

Thr Asp Asp Ala Asn Glu Ala Asn Ser Glu Glu Lys Ser Met Thr Leu
            85                  90                  95

Lys Gln Ala Leu Leu Ile Tyr Pro Lys Ala Ala Leu Trp Ser Ile Leu

```
            100                 105                 110
Val Ser Thr Thr Leu Val Met Glu Gly Tyr Asp Thr Ala Leu Leu Asn
        115                 120                 125

Ala Leu Tyr Ala Leu Pro Val Phe Gln Arg Lys Phe Gly Thr Leu Asn
        130                 135                 140

Gly Glu Gly Ser Tyr Glu Ile Thr Ser Gln Trp Gln Ile Gly Leu Asn
145                 150                 155                 160

Met Cys Val Gln Cys Gly Glu Ile Ile Gly Leu Gln Ile Thr Pro Tyr
                165                 170                 175

Met Val Glu Phe Met Gly Asn Arg Tyr Thr Met Ile Thr Ala Leu Gly
            180                 185                 190

Leu Leu Thr Ala Tyr Val Phe Ile Leu Tyr Tyr Cys Lys Ser Leu Ala
        195                 200                 205

Met Ile Ala Val Gly Gln Val Leu Ser Ala Met Pro Trp Gly Cys Phe
210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Ala Pro Glu Ser Pro Trp Trp
        290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Ile Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asp Cys Phe Lys Gly Val Asn Gly Arg Arg
        355                 360                 365

Thr Arg Leu Ala Cys Leu Thr Trp Val Ala Gln Asn Thr Ser Gly Ala
        370                 375                 380

Cys Leu Leu Gly Tyr Ser Thr Tyr Phe Leu Lys Glu Gln Val Trp Pro
385                 390                 395                 400

Pro Thr Arg Arg Leu Leu Phe Leu
                405

<210> SEQ ID NO 64
<211> LENGTH: 394
<212> TYPE: PRT
<213> ORGANISM: Saccharomyces pastorianus

<400> SEQUENCE: 64

Met Lys Asn Ile Ile Ser Leu Val Ser Lys Lys Ala Ala Ser Lys
1               5                   10                  15

Asn Glu Asp Lys Asn Ile Ser Glu Ser Ser Arg Asp Ile Val Asn Gln
            20                  25                  30

Gln Glu Val Phe Asn Thr Glu Asn Phe Glu Glu Gly Lys Lys Asp Ser
        35                  40                  45

Ala Phe Glu Leu Asp His Leu Glu Phe Thr Thr Asn Ser Ala Gln Leu
    50                  55                  60
```

```
Gly Asp Ser Asp Glu Asp Asn Glu Asn Met Ile Asn Glu Met Asn Ala
 65                  70                  75                  80

Thr Asp Glu Ala Asn Glu Ala Asn Ser Glu Glu Lys Ser Met Thr Leu
                 85                  90                  95

Lys Gln Ala Leu Leu Lys Tyr Pro Lys Ala Ala Leu Trp Ser Ile Leu
            100                 105                 110

Val Ser Thr Thr Leu Val Met Glu Gly Tyr Asp Thr Ala Leu Leu Asn
        115                 120                 125

Ala Leu Tyr Ala Leu Pro Val Phe Gln Arg Lys Phe Gly Thr Leu Asn
    130                 135                 140

Gly Glu Gly Ser Tyr Glu Ile Thr Ser Gln Trp Gln Ile Gly Leu Asn
145                 150                 155                 160

Met Cys Val Gln Cys Gly Glu Met Ile Gly Leu Gln Ile Thr Thr Tyr
                165                 170                 175

Met Val Glu Phe Met Gly Asn Arg Tyr Thr Met Ile Thr Ala Leu Gly
                180                 185                 190

Leu Leu Thr Ala Tyr Ile Phe Ile Leu Tyr Tyr Cys Lys Ser Leu Ala
            195                 200                 205

Met Ile Ala Val Gly Gln Val Leu Ser Ala Met Pro Trp Gly Cys Phe
    210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
                260                 265                 270

Ser Asp Leu Asp Tyr Lys Leu Pro Phe Ala Leu Gln Trp Ile Trp Pro
            275                 280                 285

Ala Pro Leu Met Ile Gly Ile Phe Phe Ala Pro Glu Ser Pro Trp Trp
    290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Val Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asp Cys Phe Lys Gly Val Asn Gly Arg Arg
        355                 360                 365

Thr Arg Leu Ala Cys Leu Ala Trp Val Ala Gln Asn Thr Ser Gly Ala
    370                 375                 380

Cys Leu Leu Gly Tyr Ser Thr Tyr Phe Phe
385                 390

<210> SEQ ID NO 65
<211> LENGTH: 616
<212> TYPE: PRT
<213> ORGANISM: Saccharomyces cerevisiae

<400> SEQUENCE: 65

Met Lys Asn Ile Ile Ser Leu Val Ser Lys Lys Ala Ala Ser Lys
 1               5                  10                  15

Asn Glu Asp Lys Asn Ile Ser Glu Ser Ser Arg Asp Ile Val Asn Gln
                 20                  25                  30

Gln Glu Val Phe Asn Thr Glu Asn Phe Glu Gly Arg Lys Asp Ser
             35                  40                  45
```

```
Ala Phe Glu Leu Asp His Leu Glu Phe Thr Ile Asn Ser Ala Gln Leu
     50                  55                  60

Gly Asp Ser Asp Glu Asp Asn Glu Asn Val Ile Asn Glu Thr Asn Thr
 65                  70                  75                  80

Thr Asp Asp Ala Asn Glu Ala Asn Ser Glu Glu Lys Ser Met Thr Leu
                 85                  90                  95

Lys Gln Ala Leu Leu Ile Tyr Pro Lys Ala Ala Leu Trp Ser Ile Leu
                100                 105                 110

Val Ser Thr Thr Leu Val Met Glu Gly Tyr Asp Thr Ala Leu Leu Asn
            115                 120                 125

Ala Leu Tyr Ala Leu Pro Val Phe Gln Arg Lys Phe Gly Thr Leu Asn
        130                 135                 140

Gly Glu Gly Ser Tyr Glu Ile Thr Ser Gln Trp Gln Ile Gly Leu Asn
145                 150                 155                 160

Met Cys Val Gln Cys Gly Glu Ile Ile Gly Leu Gln Ile Thr Pro Tyr
                165                 170                 175

Met Val Glu Phe Met Gly Asn Arg Tyr Thr Met Ile Thr Ala Leu Gly
            180                 185                 190

Leu Leu Thr Ala Tyr Val Phe Ile Leu Tyr Tyr Cys Lys Ser Leu Ala
        195                 200                 205

Met Ile Ala Val Gly Gln Val Leu Ser Ala Met Pro Trp Gly Cys Phe
210                 215                 220

Gln Gly Leu Thr Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Met Ile Gly Ile Phe Phe Ala Pro Glu Ser Pro Trp Trp
290                 295                 300

Leu Val Arg Lys Asp Arg Val Ala Glu Ala Arg Lys Ser Leu Ser Arg
305                 310                 315                 320

Ile Leu Ser Gly Lys Gly Ala Glu Lys Asp Ile Gln Ile Asp Leu Thr
                325                 330                 335

Leu Lys Gln Ile Glu Leu Thr Ile Glu Lys Glu Arg Leu Leu Ala Ser
            340                 345                 350

Lys Ser Gly Ser Phe Phe Asp Cys Phe Lys Gly Val Asn Gly Arg Arg
        355                 360                 365

Thr Arg Leu Ala Cys Leu Thr Trp Val Ala Gln Asn Thr Ser Gly Ala
    370                 375                 380

Cys Leu Leu Gly Tyr Ser Thr Tyr Phe Phe Glu Arg Ala Gly Met Ala
385                 390                 395                 400

Thr Asp Lys Ala Phe Thr Phe Ser Val Ile Gln Tyr Cys Leu Gly Leu
                405                 410                 415

Ala Gly Thr Leu Cys Ser Trp Val Ile Ser Gly Arg Val Gly Arg Trp
            420                 425                 430

Thr Ile Leu Thr Tyr Gly Leu Ala Phe Gln Met Val Cys Leu Phe Ile
        435                 440                 445

Ile Gly Gly Met Gly Phe Gly Ser Gly Ser Gly Ala Ser Asn Gly Ala
450                 455                 460
```

```
Gly Gly Leu Leu Leu Ala Leu Ser Phe Phe Tyr Asn Ala Gly Ile Gly
465                 470                 475                 480

Ala Val Val Tyr Cys Ile Val Thr Glu Ile Pro Ser Ala Glu Leu Arg
                485                 490                 495

Thr Lys Thr Ile Val Leu Ala Arg Ile Cys Tyr Asn Ile Met Ala Val
            500                 505                 510

Ile Asn Ala Ile Leu Thr Pro Tyr Met Leu Asn Val Ser Asp Trp Asn
                515                 520                 525

Trp Gly Ala Lys Thr Gly Leu Tyr Trp Gly Gly Phe Thr Ala Val Thr
        530                 535                 540

Leu Ala Trp Val Ile Ile Asp Leu Pro Glu Thr Ser Gly Arg Thr Phe
545                 550                 555                 560

Ser Glu Ile Asn Glu Leu Phe Asn Gln Gly Val Pro Ala Arg Lys Phe
                565                 570                 575

Ala Ser Thr Val Val Asp Pro Phe Gly Lys Gly Lys Thr Gln His Asp
            580                 585                 590

Ser Leu Asp Asp Glu Ser Ile Ser Gln Ser Ser Ile Lys Gln Arg
        595                 600                 605

Glu Leu Asn Ala Ala Asp Lys Cys
    610                 615

<210> SEQ ID NO 66
<211> LENGTH: 610
<212> TYPE: PRT
<213> ORGANISM: Saccharomyces pastorianus

<400> SEQUENCE: 66

Met Lys Asn Ile Leu Ser Leu Val Gly Arg Lys Glu Asn Thr Pro Glu
1               5                   10                  15

Asp Val Thr Ala Asn Leu Ala Asp Thr Ser Ser Thr Thr Val Met Gln
            20                  25                  30

Ala Lys Asp Leu Val Ile Glu Asp Phe Glu Glu Arg Lys Lys Asn Asp
        35                  40                  45

Ala Phe Glu Leu Asn His Leu Glu Leu Thr Thr Asn Ala Thr Gln Leu
    50                  55                  60

Ser Asp Ser Asp Glu Asp Lys Glu Asn Val Ile Arg Val Ala Glu Ala
65                  70                  75                  80

Thr Asp Asp Ala Asn Glu Ala Asn Asn Glu Glu Lys Ser Met Thr Leu
                85                  90                  95

Arg Gln Ala Leu Arg Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Met Asn
    130                 135                 140

Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Ser
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Met Pro Trp Gly Cys Phe
    210                 215                 220
```

```
Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Ile Ile Gly Ile Phe Phe Ala Pro Glu Ser Pro Trp Trp
    290                 295                 300

Leu Val Arg Lys Asn Lys Ile Val Glu Ala Lys Lys Ser Leu Asn Arg
305                 310                 315                 320

Ile Leu Ser Gly Thr Val Thr Glu Lys Glu Ile Gln Val Asp Ile Thr
                325                 330                 335

Leu Lys Gln Ile Glu Met Thr Ile Glu Lys Glu Arg Leu Arg Ala Ser
                340                 345                 350

Lys Ser Gly Ser Phe Phe Ser Cys Phe Lys Gly Val Asp Gly Arg Arg
            355                 360                 365

Thr Arg Leu Ala Cys Leu Thr Trp Val Ala Gln Asn Ser Ser Gly Ala
    370                 375                 380

Val Leu Leu Gly Tyr Ser Thr Tyr Phe Phe Glu Arg Ala Gly Met Ala
385                 390                 395                 400

Thr Asp Lys Ala Phe Thr Phe Ser Leu Ile Gln Tyr Cys Leu Gly Leu
                405                 410                 415

Ala Gly Thr Leu Gly Ser Trp Val Ile Ser Gly Arg Val Gly Arg Trp
            420                 425                 430

Thr Ile Leu Thr Tyr Gly Leu Ser Phe Gln Met Val Cys Leu Phe Ile
        435                 440                 445

Ile Gly Gly Met Gly Phe Ala Ser Gly Ser Ser Ala Ser Asn Ala Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
                500                 505                 510

Phe Asn Ala Ile Leu Thr Pro Tyr Met Leu Asn Val Ser Asp Trp Asn
            515                 520                 525

Trp Gly Ala Lys Thr Gly Leu Tyr Trp Gly Gly Phe Thr Ala Leu Thr
    530                 535                 540

Leu Ala Trp Val Ile Ile Asp Leu Pro Glu Thr Thr Gly Arg Thr Phe
545                 550                 555                 560

Ser Glu Ile Asn Glu Leu Phe Ser Gln Gly Val Pro Ala Arg Lys Phe
                565                 570                 575

Ala Ser Thr Val Val Asp Pro Phe Gly Lys Arg Gly Leu Gln Asn Arg
            580                 585                 590

Pro Gln Val Asp Asn Ile Ile Asp Arg Phe Ser Ser Ala Ser Gln Gln
        595                 600                 605

Ala Leu
    610

<210> SEQ ID NO 67
<211> LENGTH: 610
```

<212> TYPE: PRT
<213> ORGANISM: Saccharomyces pastorianus

<400> SEQUENCE: 67

```
Met Lys Asn Ile Leu Ser Leu Val Gly Arg Lys Glu Asn Thr Pro Glu
1               5                   10                  15

Asp Val Thr Ala Asn Leu Ala Asp Thr Ser Ser Thr Thr Val Met Gln
            20                  25                  30

Ala Lys Asp Leu Val Ile Glu Asp Phe Glu Glu Arg Lys Lys Asn Asp
        35                  40                  45

Ala Phe Glu Leu Asn His Leu Glu Leu Thr Thr Asn Ala Thr Gln Leu
    50                  55                  60

Ser Asp Ser Asp Glu Asp Lys Glu Asn Val Ile Arg Val Ala Glu Ala
65                  70                  75                  80

Thr Asp Asp Ala Asn Glu Ala Asn Asn Glu Glu Lys Ser Met Thr Leu
                85                  90                  95

Arg Gln Ala Leu Arg Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Met Asn
    130                 135                 140

Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Ser
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Met Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285

Ala Pro Leu Ile Ile Gly Ile Phe Phe Ala Pro Glu Ser Pro Trp Trp
    290                 295                 300

Leu Val Arg Lys Asn Lys Ile Val Glu Ala Lys Lys Ser Leu Asn Arg
305                 310                 315                 320

Ile Leu Ser Gly Thr Val Thr Glu Lys Glu Ile Gln Val Asp Ile Thr
                325                 330                 335

Leu Lys Gln Ile Glu Met Thr Ile Glu Lys Glu Arg Leu Arg Ala Ser
            340                 345                 350

Lys Ser Gly Ser Phe Phe Ser Cys Phe Lys Gly Val Asp Gly Arg Arg
        355                 360                 365

Thr Arg Leu Ala Cys Leu Thr Trp Val Ala Gln Asn Ser Ser Gly Ala
    370                 375                 380

Val Leu Leu Gly Tyr Ser Thr Tyr Phe Phe Glu Arg Ala Gly Met Ala
385                 390                 395                 400
```

```
Thr Asp Lys Ala Phe Thr Phe Ser Leu Ile Gln Tyr Cys Leu Gly Leu
            405                 410                 415

Ala Gly Thr Leu Gly Ser Trp Val Ile Ser Gly Arg Val Gly Arg Trp
        420                 425                 430

Thr Ile Leu Thr Tyr Gly Leu Ser Phe Gln Met Val Cys Leu Phe Ile
            435                 440                 445

Ile Gly Gly Met Gly Phe Ala Ser Gly Ser Ser Ala Ser Asn Ala Ala
    450                 455                 460

Gly Gly Leu Leu Leu Ala Leu Ser Phe Phe Tyr Asn Ala Gly Ile Gly
465                 470                 475                 480

Ala Val Val Tyr Cys Ile Val Ala Glu Ile Pro Ser Ala Glu Leu Arg
                485                 490                 495

Thr Lys Thr Ile Val Leu Ala Arg Ile Cys Tyr Asn Leu Met Ala Val
            500                 505                 510

Phe Asn Ala Ile Leu Thr Pro Tyr Met Leu Asn Val Ser Asp Trp Asn
        515                 520                 525

Trp Gly Ala Lys Thr Gly Leu Tyr Trp Gly Gly Phe Thr Ala Leu Thr
    530                 535                 540

Leu Ala Trp Val Ile Ile Asp Leu Pro Glu Thr Thr Gly Arg Thr Phe
545                 550                 555                 560

Ser Glu Ile Asn Glu Leu Phe Ser Gln Gly Val Pro Ala Arg Lys Phe
                565                 570                 575

Ala Ser Thr Val Val Asp Pro Phe Gly Lys Arg Gly Leu Gln Asn Arg
            580                 585                 590

Pro Gln Val Asp Asn Ile Ile Asp Arg Phe Ser Ser Ala Ser Gln Gln
        595                 600                 605

Ala Leu
    610

<210> SEQ ID NO 68
<211> LENGTH: 610
<212> TYPE: PRT
<213> ORGANISM: Saccharomyces pastorianus

<400> SEQUENCE: 68

Met Lys Asn Ile Leu Ser Leu Val Gly Arg Lys Glu Asn Thr Pro Glu
1               5                   10                  15

Asp Val Thr Ala Asn Leu Ala Asp Thr Ser Ser Thr Thr Val Met Gln
            20                  25                  30

Ala Lys Asp Leu Val Ile Glu Asp Phe Glu Glu Arg Lys Lys Asn Asp
        35                  40                  45

Ala Phe Glu Leu Asn His Leu Glu Leu Thr Thr Asn Ala Thr Gln Leu
    50                  55                  60

Ser Asp Ser Asp Glu Asp Lys Glu Asn Val Ile Arg Val Ala Glu Ala
65                  70                  75                  80

Thr Asp Asp Ala Asn Glu Ala Asn Asn Glu Lys Ser Met Thr Leu
                85                  90                  95

Arg Gln Ala Leu Arg Lys Tyr Pro Lys Ala Ala Leu Trp Ser Ile Leu
            100                 105                 110

Val Ser Thr Thr Leu Val Met Glu Gly Tyr Asp Thr Ala Leu Leu Ser
        115                 120                 125

Ala Leu Tyr Ala Leu Pro Val Phe Gln Arg Lys Phe Gly Thr Met Asn
    130                 135                 140

Ala Glu Gly Ser Tyr Glu Ile Thr Ser Gln Trp Gln Ile Gly Leu Asn
```

-continued

```
145                 150                 155                 160
Met Cys Val Leu Cys Gly Glu Met Ile Gly Leu Gln Ile Thr Thr Tyr
                165                 170                 175
Met Val Glu Phe Met Gly Asn Arg Tyr Thr Met Ile Thr Ala Leu Ser
                180                 185                 190
Leu Leu Thr Ala Tyr Ile Phe Ile Leu Tyr Tyr Cys Lys Ser Leu Ala
                195                 200                 205
Met Ile Ala Val Gly Gln Ile Leu Ser Ala Met Pro Trp Gly Cys Phe
            210                 215                 220
Gln Ser Leu Ala Val Thr Tyr Ala Ser Glu Val Cys Pro Leu Ala Leu
225                 230                 235                 240
Arg Tyr Tyr Met Thr Ser Tyr Ser Asn Ile Cys Trp Leu Phe Gly Gln
                245                 250                 255
Ile Phe Ala Ser Gly Ile Met Lys Asn Ser Gln Glu Asn Leu Gly Asn
                260                 265                 270
Ser Asp Leu Gly Tyr Lys Leu Pro Phe Ala Leu Gln Trp Ile Trp Pro
                275                 280                 285
Ala Pro Leu Ile Ile Gly Ile Phe Phe Ala Pro Glu Ser Pro Trp Trp
            290                 295                 300
Leu Val Arg Lys Asn Lys Ile Val Glu Ala Lys Lys Ser Leu Asn Arg
305                 310                 315                 320
Ile Leu Ser Gly Thr Val Thr Glu Lys Glu Ile Gln Val Asp Ile Thr
                325                 330                 335
Leu Lys Gln Ile Glu Met Thr Ile Glu Lys Glu Arg Leu Arg Ala Ser
                340                 345                 350
Lys Ser Gly Ser Phe Phe Ser Cys Phe Lys Gly Val Asp Gly Arg Arg
                355                 360                 365
Thr Arg Leu Ala Cys Leu Thr Trp Val Ala Gln Asn Ser Ser Gly Ala
            370                 375                 380
Val Leu Gly Tyr Ser Thr Tyr Phe Glu Arg Ala Gly Met Ala
385                 390                 395                 400
Thr Asp Lys Ala Phe Thr Phe Ser Leu Ile Gln Tyr Cys Leu Gly Leu
                405                 410                 415
Ala Gly Thr Leu Gly Ser Trp Val Ile Ser Gly Arg Val Gly Arg Trp
                420                 425                 430
Thr Ile Leu Thr Tyr Gly Leu Ser Phe Gln Met Val Cys Leu Phe Ile
                435                 440                 445
Ile Gly Gly Met Gly Phe Ala Ser Gly Ser Ser Ala Ser Asn Ala Ala
            450                 455                 460
Gly Gly Leu Leu Leu Ala Leu Ser Phe Phe Tyr Asn Ala Gly Ile Gly
465                 470                 475                 480
Ala Val Val Tyr Cys Ile Val Ala Glu Ile Pro Ser Ala Glu Leu Arg
                485                 490                 495
Thr Lys Thr Ile Val Leu Ala Arg Ile Cys Tyr Asn Leu Met Ala Val
                500                 505                 510
Phe Asn Ala Ile Leu Thr Pro Tyr Met Leu Asn Val Ser Asp Trp Asn
                515                 520                 525
Trp Gly Ala Lys Thr Gly Leu Tyr Trp Gly Phe Thr Ala Leu Thr
            530                 535                 540
Leu Ala Trp Val Ile Ile Asp Leu Pro Glu Thr Thr Gly Arg Thr Phe
545                 550                 555                 560
Ser Glu Ile Asn Glu Leu Phe Ser Gln Gly Val Pro Ala Arg Lys Phe
                565                 570                 575
```

```
Ala Ser Thr Val Val Asp Pro Phe Gly Lys Arg Gly Leu Gln Asn Arg
            580                 585                 590

Pro Gln Val Asp Asn Ile Ile Asp Arg Phe Ser Ser Ala Ser Gln Gln
        595                 600                 605

Ala Leu
    610

<210> SEQ ID NO 69
<211> LENGTH: 610
<212> TYPE: PRT
<213> ORGANISM: Unknown
<220> FEATURE:
<223> OTHER INFORMATION: Hybrid between S. cerevisiae and S. pastorianus
      (Hybrid yeast 1)
<220> FEATURE:
<221> NAME/KEY: MISC_FEATURE
<222> LOCATION: (1)..(610)
<223> OTHER INFORMATION: Hybrid

<400> SEQUENCE: 69

Met Lys Asn Ile Leu Ser Leu Val Gly Arg Lys Glu Asn Thr Pro Glu
1               5                   10                  15

Asp Val Thr Ala Asn Leu Ala Asp Thr Ser Ser Thr Val Met Gln
            20                  25                  30

Ala Lys Asp Leu Val Ile Glu Asp Phe Glu Glu Arg Lys Lys Asn Asp
        35                  40                  45

Ala Phe Glu Leu Asn His Leu Glu Leu Thr Thr Asn Ala Thr Gln Leu
    50                  55                  60

Ser Asp Ser Asp Glu Asp Lys Glu Asn Val Ile Arg Val Ala Glu Ala
65                  70                  75                  80

Thr Asp Asp Ala Asn Glu Ala Asn Asn Glu Lys Ser Met Thr Leu
            85                  90                  95

Arg Gln Ala Leu Arg Lys Tyr Pro Lys Ala Ala Leu Trp Ser Ile Leu
                100                 105                 110

Val Ser Thr Thr Leu Val Met Glu Gly Tyr Asp Thr Ala Leu Leu Ser
            115                 120                 125

Ala Leu Tyr Ala Leu Pro Val Phe Gln Arg Lys Phe Gly Thr Met Asn
        130                 135                 140

Ala Glu Gly Ser Tyr Glu Ile Thr Ser Gln Trp Gln Ile Gly Leu Asn
145                 150                 155                 160

Met Cys Val Leu Cys Gly Glu Met Ile Gly Leu Gln Ile Thr Thr Tyr
                165                 170                 175

Met Val Glu Phe Met Gly Asn Arg Tyr Thr Met Ile Thr Ala Leu Ser
            180                 185                 190

Leu Leu Thr Ala Tyr Ile Phe Ile Leu Tyr Tyr Cys Lys Ser Leu Ala
        195                 200                 205

Met Ile Ala Val Gly Gln Ile Leu Ser Ala Met Pro Trp Gly Cys Phe
    210                 215                 220

Gln Ser Leu Ala Val Thr Tyr Ala Ser Glu Val Cys Pro Leu Ala Leu
225                 230                 235                 240

Arg Tyr Tyr Met Thr Ser Tyr Ser Asn Ile Cys Trp Leu Phe Gly Gln
                245                 250                 255

Ile Phe Ala Ser Gly Ile Met Lys Asn Ser Gln Glu Asn Leu Gly Asn
            260                 265                 270

Ser Asp Leu Gly Tyr Lys Leu Pro Phe Ala Leu Gln Trp Ile Trp Pro
        275                 280                 285
```

```
Ala Pro Leu Ile Ile Gly Ile Phe Phe Ala Pro Glu Ser Pro Trp Trp
    290             295                 300
Leu Val Arg Lys Asn Lys Ile Val Glu Ala Lys Lys Ser Leu Asn Arg
305             310                 315                 320
Ile Leu Ser Gly Thr Val Thr Glu Lys Glu Ile Gln Val Asp Ile Thr
                325                 330                 335
Leu Lys Gln Ile Glu Met Thr Ile Glu Lys Glu Arg Leu Arg Ala Ser
                340                 345                 350
Lys Ser Gly Ser Phe Phe Ser Cys Phe Lys Gly Val Asp Gly Arg Arg
            355                 360                 365
Thr Arg Leu Ala Cys Leu Thr Trp Val Ala Gln Asn Ser Ser Gly Ala
    370                 375                 380
Val Leu Leu Gly Tyr Ser Thr Tyr Phe Phe Glu Arg Ala Gly Met Ala
385                 390                 395                 400
Thr Asp Lys Ala Phe Thr Phe Ser Leu Ile Gln Tyr Cys Leu Gly Leu
                405                 410                 415
Ala Gly Thr Leu Gly Ser Trp Val Ile Ser Gly Arg Val Gly Arg Trp
            420                 425                 430
Thr Ile Leu Thr Tyr Gly Leu Ser Phe Gln Met Val Cys Leu Phe Ile
                435                 440                 445
Ile Gly Gly Met Gly Phe Ala Ser Gly Ser Ser Ala Ser Asn Ala Ala
    450                 455                 460
Gly Gly Leu Leu Leu Ala Leu Ser Phe Phe Tyr Asn Ala Gly Ile Gly
465                 470                 475                 480
Ala Val Val Tyr Cys Ile Val Ala Glu Ile Pro Ser Ala Glu Leu Arg
                485                 490                 495
Thr Lys Thr Ile Val Leu Ala Arg Ile Cys Tyr Asn Leu Met Ala Val
                500                 505                 510
Phe Asn Ala Ile Leu Thr Pro Tyr Met Leu Asn Val Ser Asp Trp Asn
            515                 520                 525
Trp Gly Ala Lys Thr Gly Leu Tyr Trp Gly Gly Phe Thr Ala Leu Thr
    530                 535                 540
Leu Ala Trp Val Ile Ile Asp Leu Pro Glu Thr Thr Gly Arg Thr Phe
545                 550                 555                 560
Ser Glu Ile Asn Glu Leu Phe Ser Gln Gly Val Pro Ala Arg Lys Phe
                565                 570                 575
Ala Ser Thr Val Val Asp Pro Phe Gly Lys Arg Gly Leu Gln Asn Arg
                580                 585                 590
Pro Gln Val Asp Asn Ile Ile Asp Arg Phe Ser Ser Ala Ser Gln Gln
            595                 600                 605
Ala Leu
    610
```